US011141184B2

(12) United States Patent
Conlon et al.

(10) Patent No.: US 11,141,184 B2
(45) Date of Patent: Oct. 12, 2021

(54) ULTRASONIC SURGICAL INSTRUMENT WITH REMOVABLE SHAFT ASSEMBLY PORTION

(71) Applicant: Ethicon LLC, Guaynabo, PR (US)

(72) Inventors: Sean P. Conlon, Loveland, OH (US); Ellen Burkart, Cincinnati, OH (US); Rafael J. Ruiz Ortiz, Mason, OH (US); Matthew S. Corbin, Loveland, OH (US); Matthew C. Miller, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 138 days.

(21) Appl. No.: 16/368,969

(22) Filed: Mar. 29, 2019

(65) Prior Publication Data

US 2019/0290319 A1   Sep. 26, 2019

Related U.S. Application Data

(63) Continuation of application No. 15/270,540, filed on Sep. 20, 2016, now Pat. No. 10,327,797.

(Continued)

(51) Int. Cl.
*A61B 17/32* (2006.01)
*A61B 17/29* (2006.01)

(52) U.S. Cl.
CPC ......... *A61B 17/320092* (2013.01); *A61B 17/320068* (2013.01); *A61B 2017/2902* (2013.01);

(Continued)

(58) Field of Classification Search
CPC .... A61B 17/320068; A61B 17/320092; A61B 2017/320071; A61B 2017/320072;

(Continued)

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

| CN | 1676107 A | 10/2005 |
| CN | 101141922 A | 3/2008 |

(Continued)

OTHER PUBLICATIONS

Chinese Search Report dated Sep. 6, 2019 for Application No. 201780002074.0, 1 page.

(Continued)

*Primary Examiner* — Melanie R Tyson
(74) *Attorney, Agent, or Firm* — Frost Brown Todd LLC

(57) ABSTRACT

An apparatus includes a body, a shaft assembly, and an end effector. The shaft assembly includes an outer tube, a proximal inner tube member, a distal inner tube member, and an acoustic waveguide. The end effector includes an ultrasonic blade and a clamp arm. A first portion of the clamp arm is pivotably coupled with a distal end of the outer tube. A second portion of the clamp arm is pivotably coupled with a distal end of the distal inner tube member. The outer tube is configured to removably couple with the body and the distal inner tube member is configured to removably couple with the proximal inner tube member such that the outer tube, the distal inner tube member, and the clamp arm are configured to removably couple with the body and the remainder of the shaft assembly and end effector as a unit.

20 Claims, 122 Drawing Sheets

Related U.S. Application Data

(60) Provisional application No. 62/242,440, filed on Oct. 16, 2015, provisional application No. 62/263,102, filed on Dec. 4, 2015, provisional application No. 62/329,981, filed on Apr. 29, 2016.

(52) U.S. Cl.
CPC ............... *A61B 2017/2931* (2013.01); *A61B 2017/320071* (2017.08); *A61B 2017/320072* (2013.01); *A61B 2017/320075* (2017.08); *A61B 2017/320093* (2017.08); *A61B 2017/320094* (2017.08)

(58) Field of Classification Search
CPC ....... A61B 2017/320074; A61B 2017/320078; A61B 2017/320093; A61B 2017/320094
See application file for complete search history.

(56) References Cited

U.S. PATENT DOCUMENTS

| | | | |
|---|---|---|---|
| 5,873,873 | A | 2/1999 | Smith et al. |
| 5,897,523 | A | 4/1999 | Wright et al. |
| 5,980,510 | A | 11/1999 | Tsonton et al. |
| 5,989,264 | A | 11/1999 | Wright |
| 6,063,098 | A | 5/2000 | Houser et al. |
| 6,090,120 | A | 7/2000 | Wright et al. |
| 6,165,191 | A | 12/2000 | Shibata et al. |
| 6,283,981 | B1 | 9/2001 | Beaupré |
| 6,309,400 | B2 | 10/2001 | Beaupré |
| 6,325,811 | B1 | 12/2001 | Messerly |
| 6,423,082 | B1 | 7/2002 | Houser et al. |
| 6,454,782 | B1 | 9/2002 | Schwemberger |
| 6,458,142 | B1 | 10/2002 | Faller et al. |
| 6,500,176 | B1 | 12/2002 | Truckai et al. |
| 6,589,200 | B1 | 7/2003 | Schwemberger et al. |
| 6,752,815 | B2 | 6/2004 | Beaupré |
| 6,773,444 | B2 | 8/2004 | Messerly |
| 6,783,524 | B2 | 8/2004 | Anderson et al. |
| 6,887,252 | B1 | 5/2005 | Okada et al. |
| 7,052,506 | B2 | 5/2006 | Young et al. |
| 7,112,201 | B2 | 9/2006 | Truckai et al. |
| 7,125,409 | B2 | 10/2006 | Truckai et al. |
| 7,135,030 | B2 | 11/2006 | Schwemberger et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 7,621,930 | B2 | 11/2009 | Houser |
| 8,057,498 | B2 | 11/2011 | Robertson |
| 8,142,461 | B2 | 3/2012 | Houser et al. |
| 8,461,744 | B2 | 6/2013 | Wiener et al. |
| 8,591,536 | B2 | 11/2013 | Robertson |
| 8,623,027 | B2 | 1/2014 | Price et al. |
| 8,663,220 | B2 | 3/2014 | Wiener et al. |
| 8,911,460 | B2 | 12/2014 | Neurohr et al. |
| 8,986,302 | B2 | 3/2015 | Aldridge et al. |
| 9,023,071 | B2 | 5/2015 | Miller et al. |
| 9,095,367 | B2 | 8/2015 | Olson et al. |
| 9,107,690 | B2 | 8/2015 | Bales, Jr. et al. |
| 9,308,009 | B2 | 4/2016 | Madan et al. |
| 10,050,453 | B2 | 8/2018 | Miller et al. |
| 10,172,684 | B2 | 1/2019 | Conlon et al. |
| 10,327,797 | B2 | 6/2019 | Conlon et al. |
| 10,492,820 | B2 | 12/2019 | Hibner et al. |
| 2004/0097911 | A1 | 5/2004 | Murakami et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2008/0234708 | A1* | 9/2008 | Houser .......... A61B 17/320092 606/169 |
| 2010/0063528 | A1 | 3/2010 | Beaupré |
| 2012/0078278 | A1 | 3/2012 | Bales, Jr. et al. |
| 2012/0112687 | A1 | 5/2012 | Houser et al. |
| 2012/0116265 | A1 | 5/2012 | Houser et al. |
| 2014/0005701 | A1 | 1/2014 | Olson et al. |
| 2014/0005703 | A1 | 1/2014 | Stulen et al. |
| 2014/0151079 | A1 | 6/2014 | Furui et al. |
| 2015/0080924 | A1 | 3/2015 | Stulen et al. |
| 2015/0141981 | A1 | 5/2015 | Price et al. |
| 2015/0148832 | A1 | 5/2015 | Boudreaux et al. |
| 2015/0164532 | A1 | 6/2015 | Faller et al. |
| 2015/0245850 | A1 | 9/2015 | Hibner et al. |
| 2016/0015419 | A1 | 1/2016 | Hibner et al. |
| 2020/0078042 | A1 | 3/2020 | Hibner et al. |

FOREIGN PATENT DOCUMENTS

| | | |
|---|---|---|
| CN | 103052362 A | 4/2013 |
| CN | 103313672 A | 9/2013 |
| CN | 103315807 A | 9/2013 |
| CN | 103442658 A | 12/2013 |
| CN | 103703651 A | 4/2014 |
| EP | 2042112 A2 | 4/2009 |
| EP | 2510891 A1 | 10/2012 |
| EP | 2641552 A2 | 9/2013 |
| EP | 2692297 A2 | 2/2014 |
| EP | 2992842 A1 | 3/2016 |
| JP | 2002-200094 A | 7/2002 |
| JP | 2004-154256 A | 6/2004 |
| JP | 2005-278934 A | 10/2005 |
| JP | 2010-167084 A | 8/2010 |
| JP | 2013-545535 A | 12/2013 |
| WO | WO 2000/078237 A1 | 12/2000 |
| WO | WO 2010/150618 A1 | 12/2010 |
| WO | WO 2016/036656 A1 | 3/2016 |

OTHER PUBLICATIONS

Chinese Office Action dated Sep. 19, 2019 for Application No. 201780002074.0, 12 pages.
International Search Report and Written Opinion dated Jan. 25, 2017 for Application No. PCT/US2016/055923, 11 pages.
International Search Report and Written Opinion dated Mar. 8, 2017 for Application No. PCT/US2016/055926, 18 pages.
International Search Report and Written Opinion dated Aug. 22, 2017 for Application No. PCT/US2017/029274, 15 pages.
U.S. Appl. No. 61/410,603, filed Nov. 5, 2010.
U.S. Appl. No. 62/242,440, filed Oct. 16, 2015.
U.S. Appl. No. 62/263,102, filed Dec. 4, 2015.
U.S. Appl. No. 62/329,381, filed Apr. 29, 2016.
U.S. Appl. No. 14/258,179, filed Apr. 22, 2014.
Brazilian Search Report dated Jun. 16, 2020 for Application No. BR 112018007524-8, 4 pgs.
Brazilian Search Report dated Jun. 16, 2020 for Application No. BR 112018007533-7, 4 pgs.
Chinese Office Action, The Second Office Action, dated Jun. 17, 2020 for Application No. CN 201780002074.0, 5 pgs.
Chinese Office Action, The First Office Action, and First Search, dated Dec. 11, 2019 for Application No. CN 201680035752.9, 17 pgs.
Chinese Office Action, The Second Office Action dated Jun. 12, 2020 for Application No. CN 201680035752.9, 5 pgs.
Chinese Office Action, The Third Office Action dated Oct. 23, 2020 for Application No. CN 201680035752.9, 7 pgs.
Chinese Office Action, Notification of the First Office Action, and First Search, dated Dec. 25, 2019 for Application No. CN 201680035754.8, 15 pgs.
Chinese Office Action, Notification of the Second Office Action, dated Sep. 9, 2020 for Application No. CN 201680035754.8, 7 pgs.
European Search Report, Extended, and Written Opinion dated Oct. 22, 2020 for Application No. EP 20185283.7, 10 pgs.
Japanese Office Action, Notice of Reasons for Refusal, dated Mar. 2, 2021 for Application No. JP 2018-556369, 7 pgs.

(56) References Cited

OTHER PUBLICATIONS

Japanese Office Action, Notice of Reasons for Refusal, and First Search, dated Oct. 27, 2020 for Application No. JP 2018-519283, 32 pgs.
Japanese Office Action, Notice of Reasons for Refusal, and First Search, dated Nov. 24, 2020 for Application No. JP 2018-519287, 25 pgs.

* cited by examiner

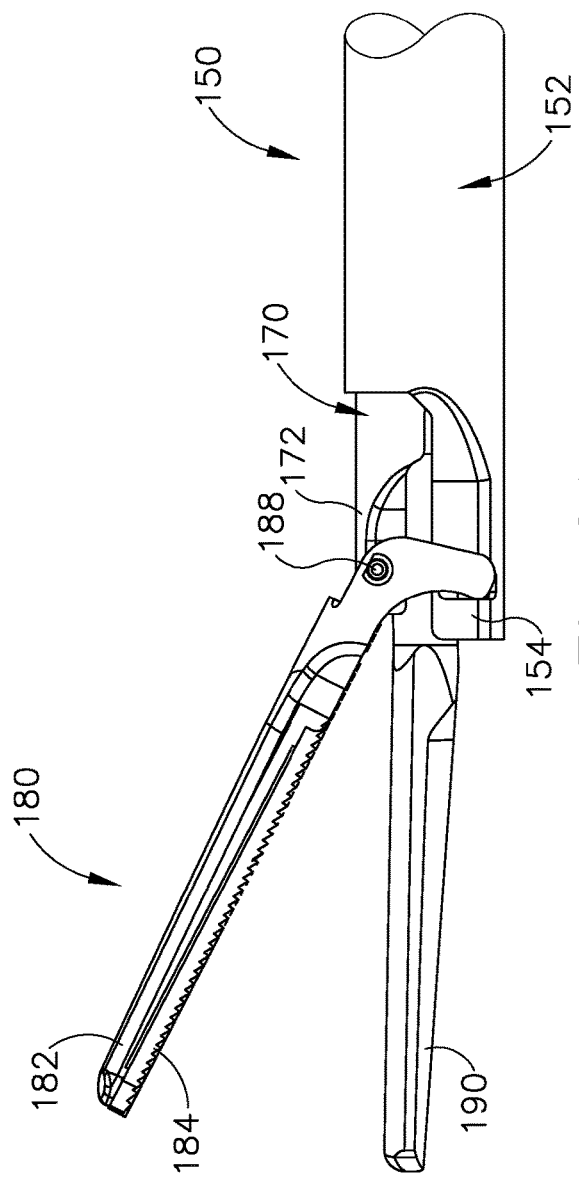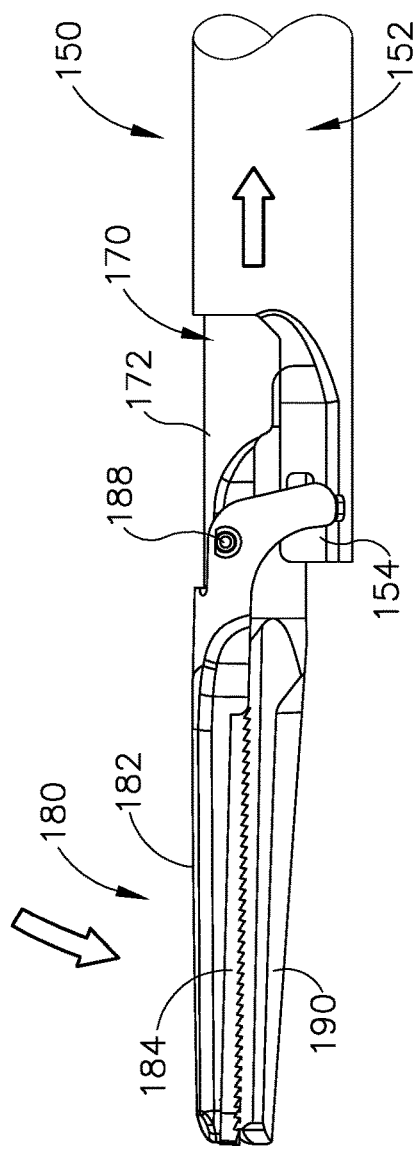

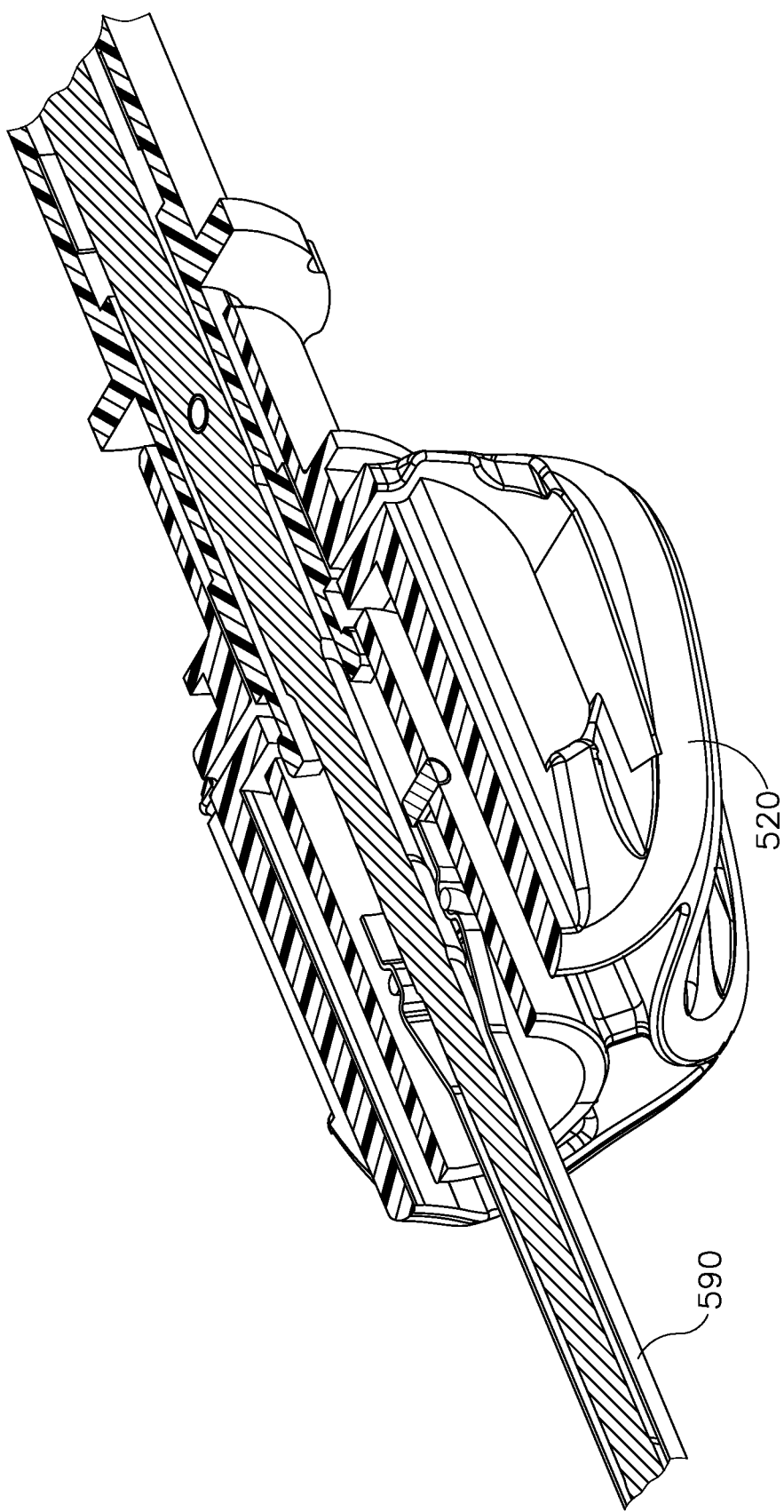

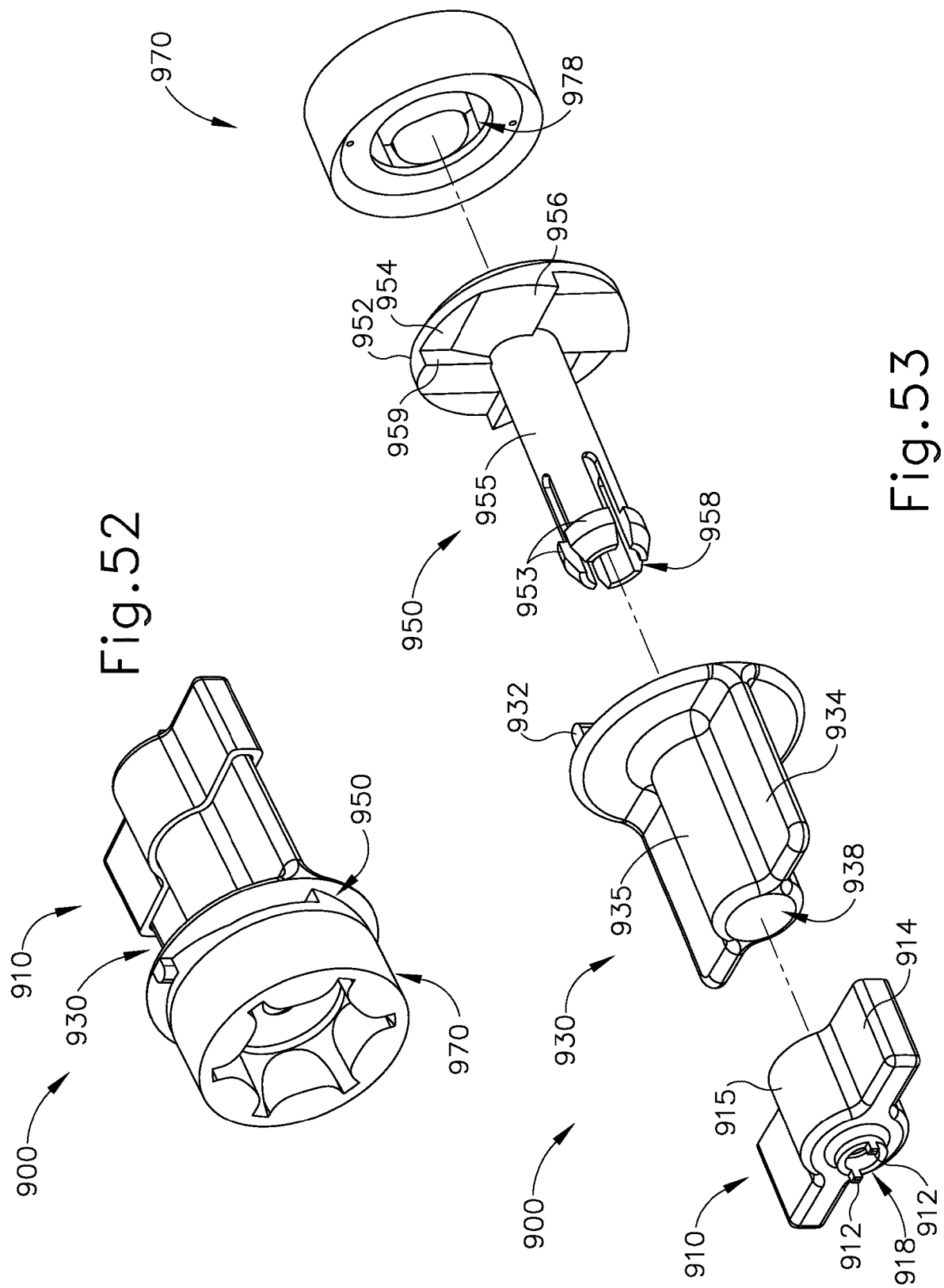

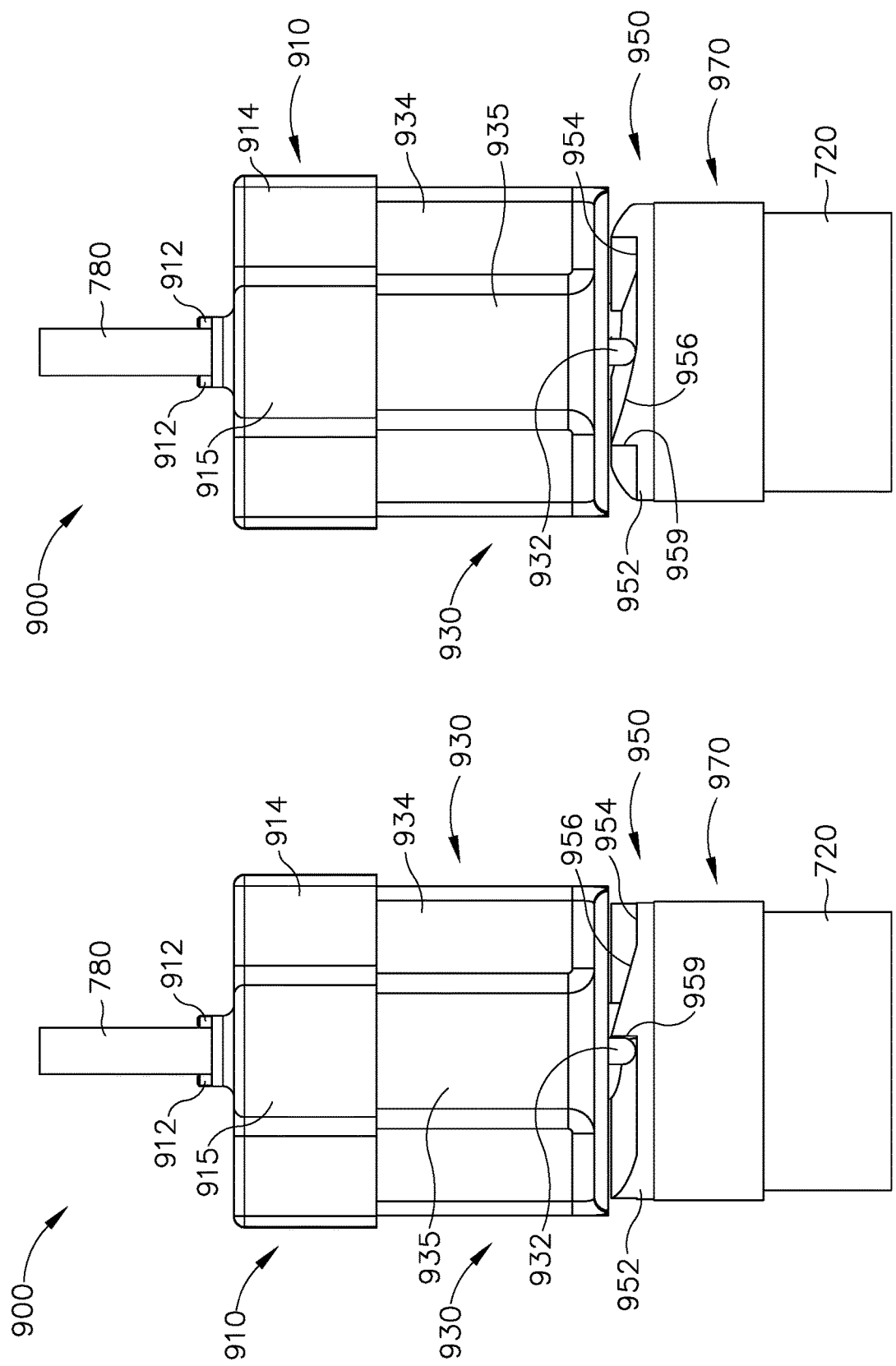

ULTRASONIC SURGICAL INSTRUMENT WITH REMOVABLE SHAFT ASSEMBLY PORTION

PRIORITY

This application is a continuation of U.S. patent application Ser. No. 15/270,540, entitled "Ultrasonic Surgical Instrument with Removable Shaft Assembly Portion," filed Sep. 20, 2016, issued as U.S. Pat. No. 10,327,797 on Jun. 25, 2019; which claims priority to U.S. Provisional Pat. App. No. 62/242,440, entitled "Ultrasonic Surgical Instrument with Disposable Outer Tube," filed Oct. 16, 2015, which also claims priority to U.S. Provisional Pat. App. No. 62/263,102, entitled "Ultrasonic Surgical Instrument with Disposable Tube Assembly and Clamp Pad," filed Dec. 4, 2015, which also claims priority to U.S. Provisional Pat. App. No. 62/329,381, entitled "Apparatus to Provide Reusability of Ultrasonic Surgical Instrument Feature," filed Apr. 29, 2016, the disclosures of which are incorporated by reference herein.

BACKGROUND

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008 now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012 now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," issued as U.S. Pat. No. 9,393,037 on Jul. 19, 2016, the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. Pat. App. No. 62/176,880, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6A depicts a side elevational view of the end effector of FIG. 4, in the open configuration;

FIG. 6B depicts a side elevational view of the end effector of FIG. 4, in a closed configuration;

FIG. 35E depicts a cross-sectional perspective view of the disposable portion of FIG. 8, with the first disposable sub-assembly removed from the second disposable sub-assembly upon completion of the process of disassembly;

FIG. 52 depicts a perspective rear view of the assembly tool of FIG. 51;

FIG. 53 depicts an exploded front perspective view of the assembly tool of FIG. 51;

FIG. 65A depicts a top plan view of the assembly tool of FIG. 51 rotationally secured to the knob member of the second sub-assembly of FIG. 38, where the reusable assembly of FIG. 37 is sufficiently coupled with the disposable assembly of FIG. 37;

FIG. 65B depicts a top plan view of the assembly tool of FIG. 51 rotationally secured to the knob member of the second sub-assembly of FIG. 38, where the reusable assembly of FIG. 37 is sufficiently coupled with the disposable assembly of FIG. 37 and the reusable assembly is further rotated relative to the disposable assembly;

FIG. 84 depicts a cross-sectional perspective view of the base member of FIG. 81, taken along line 84-84 of FIG. 81;

FIG. 85 depicts a front perspective view of a rotating member of the assembly tool of FIG. 78A;

FIG. 86 depicts a rear perspective view of the rotating member of FIG. 85;

FIG. 87A depicts a cross-sectional perspective view of the assembly tool of FIG. 78A in an open configuration, taken along line 87A-87A of FIG. 78A;

FIG. 87B depicts a cross-sectional perspective view of the assembly tool of FIG. 78A in a closed configuration, taken along line 87B-87B of FIG. 78B;

FIG. 88A depicts a cross-sectional side view of the assembly tool of FIG. 78A in an open configuration to receive the first disposable sub-assembly of FIG. 67, taken along line 87A-87A of FIG. 78A;

FIG. 88B depicts a cross-sectional side view of the assembly tool of FIG. 78A in an open configuration housing the first disposable sub-assembly of FIG. 67, taken along line 87A-87A of FIG. 78A;

FIG. 88C depicts a cross-sectional side view of the assembly tool of FIG. 78A in a closed configuration fixing the first disposable sub-assembly of FIG. 67 relative to the assembly tool, taken along line 87B-87B of FIG. 78B;

FIG. 89A depicts a cross-sectional perspective view of the assembly tool of FIG. 78A in an open configuration to receive the first disposable sub-assembly of FIG. 67, taken along line 87A-87A of FIG. 78A;

FIG. 89B depicts a cross-sectional perspective view of the assembly tool of FIG. 78A in an open configuration housing the first disposable sub-assembly of FIG. 67, taken along line 87A-87A of FIG. 78A;

FIG. 89C depicts a cross-sectional perspective view of the assembly tool of FIG. 78A in a closed configuration fixing the first disposable sub-assembly of FIG. 67 relative to the assembly tool, taken along line 87B-87B of FIG. 78B:

FIG. 90 depicts a perspective view of an alternative assembly tool that may be utilized to assemble the first disposable sub-assembly of FIG. 67 and the second disposable sub-assembly of FIG. 67, where the assembly tool is in a closed configuration;

Figure 66:
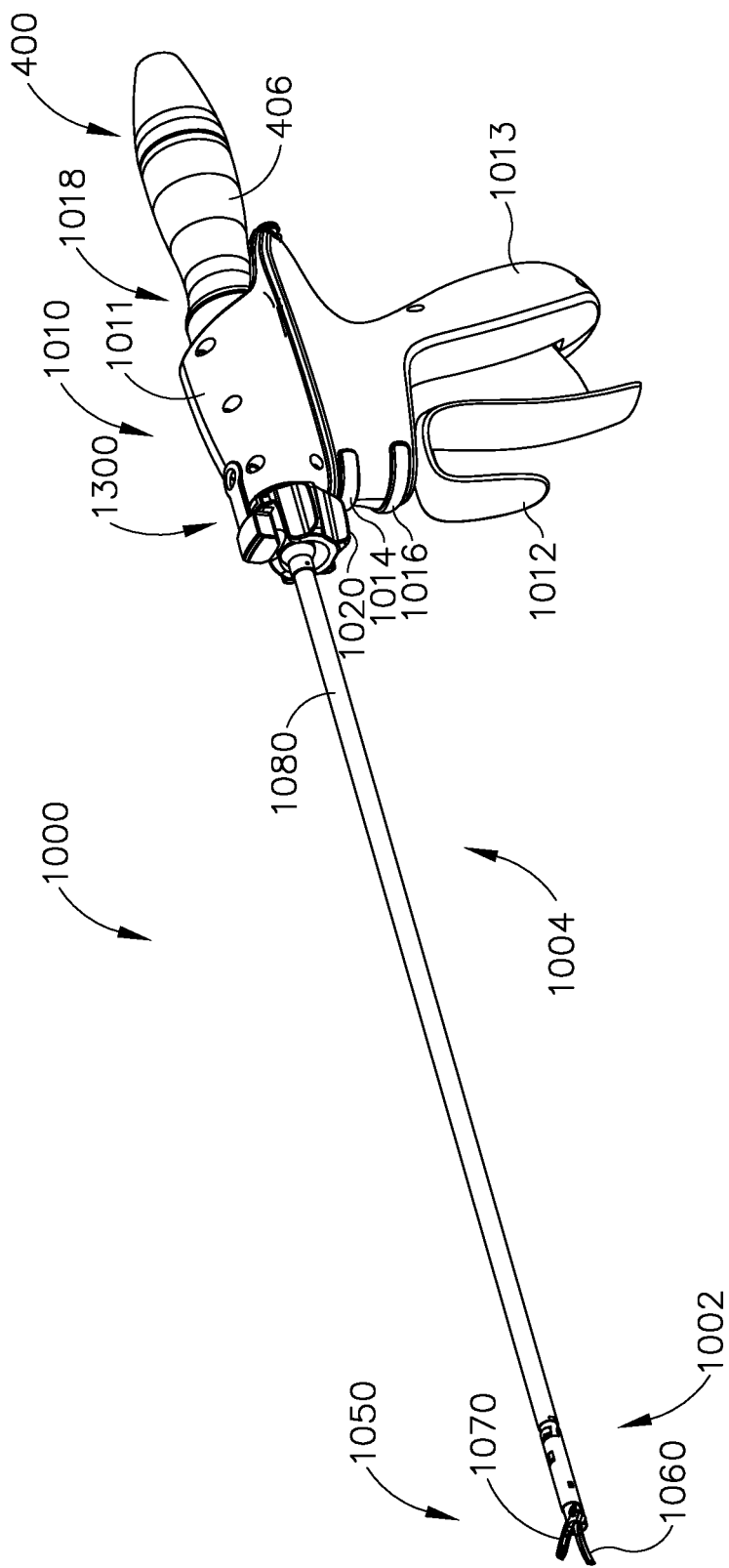
FIG. 66 depicts a perspective view of another alternative ultrasonic surgical instrument having a disposable assembly and a reusable assembly.
Figure 67:
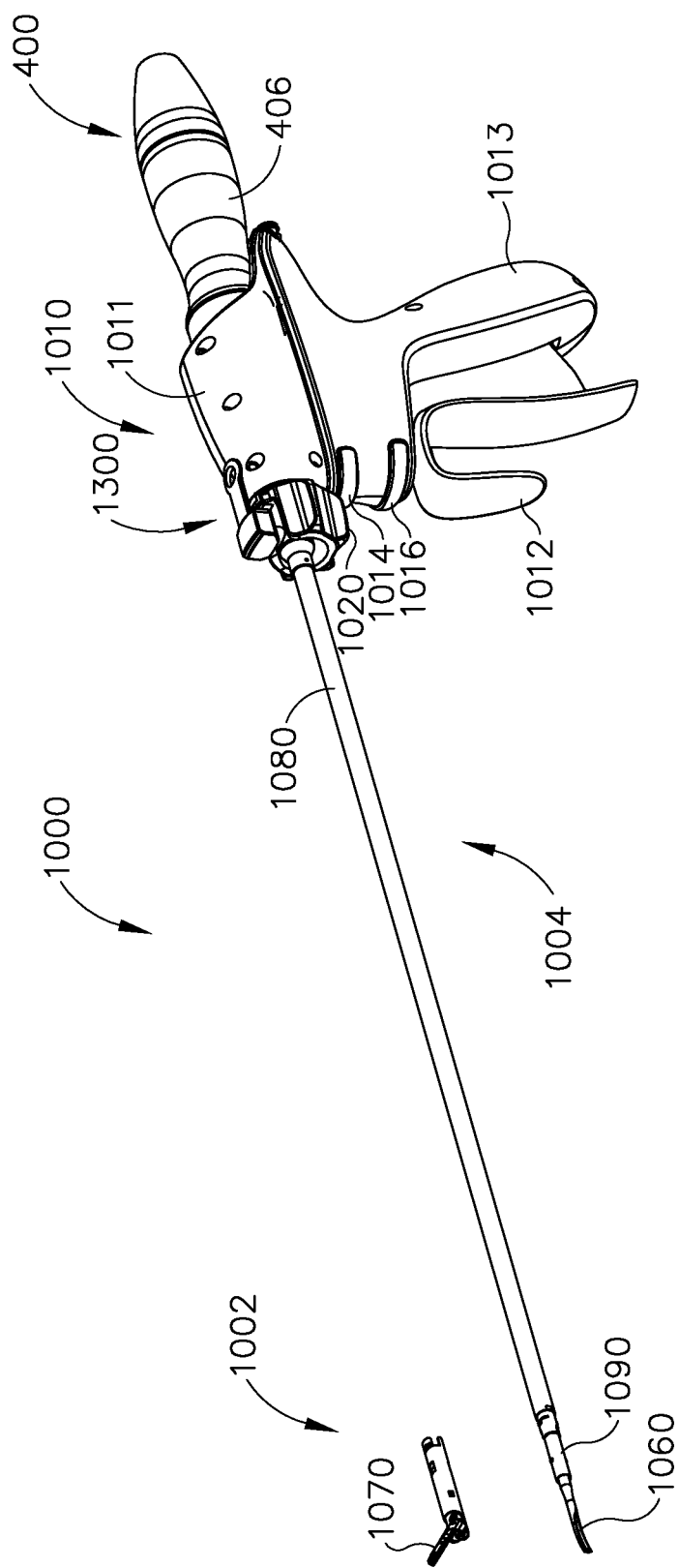
FIG. 67 depicts a partially exploded view of the ultrasonic surgical instrument of FIG. 66, with a first disposable sub-assembly separated from a second disposable sub-assembly.
Figures 78A, 78B:
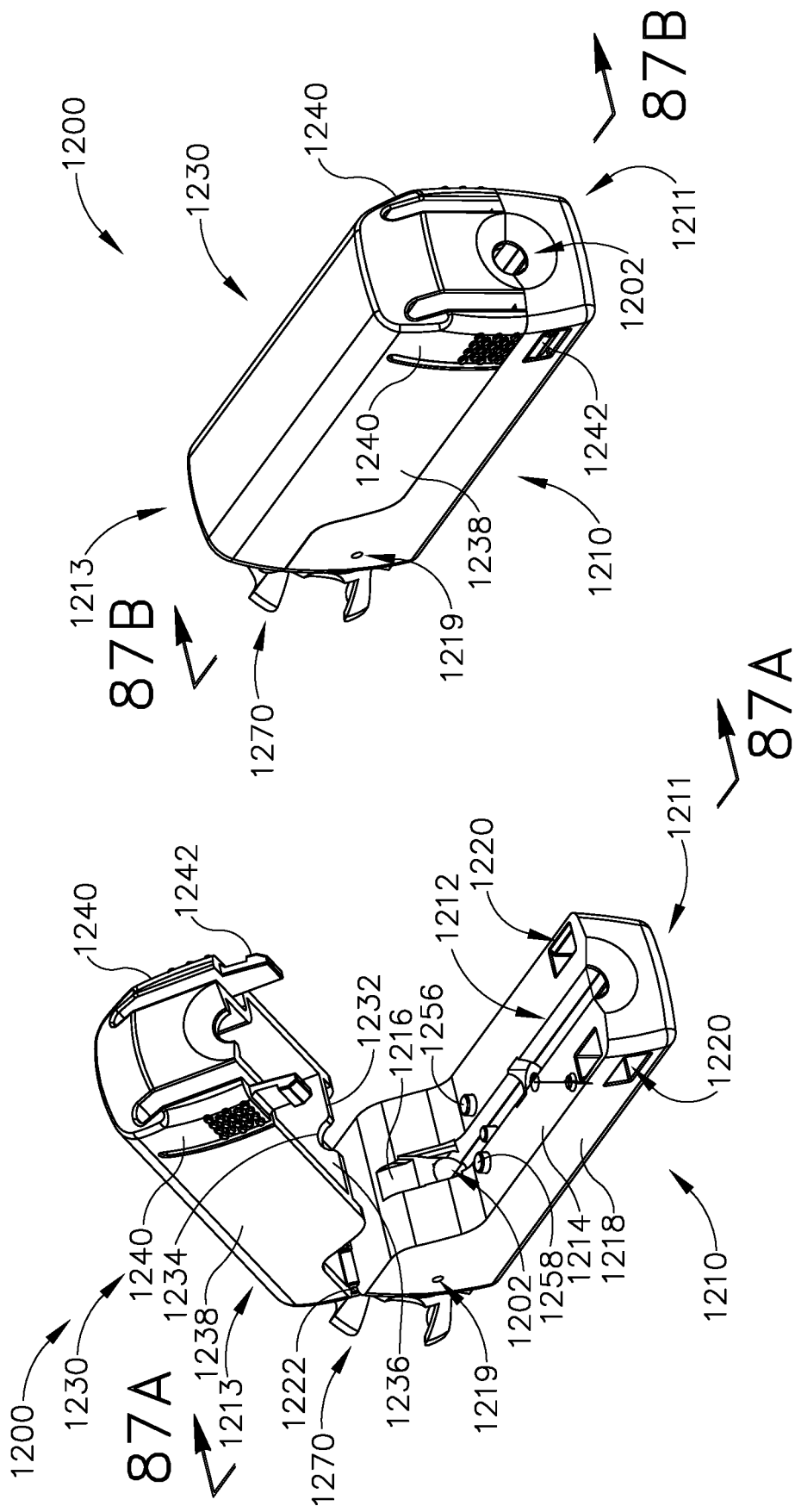
FIG. 78A depicts a perspective view of an assembly tool that may be utilized to assemble the reusable assembly of FIG. 66 with the disposable assembly of FIG. 66, as well as assemble the first disposable sub-assembly of FIG. 67 and the second disposable sub-assembly of FIG. 67, where the assembly tool is in an open configuration.
FIG. 78B depicts another perspective view of the assembly tool of FIG. 78A, where the assembly tool is in a closed configuration.
Figure 79:
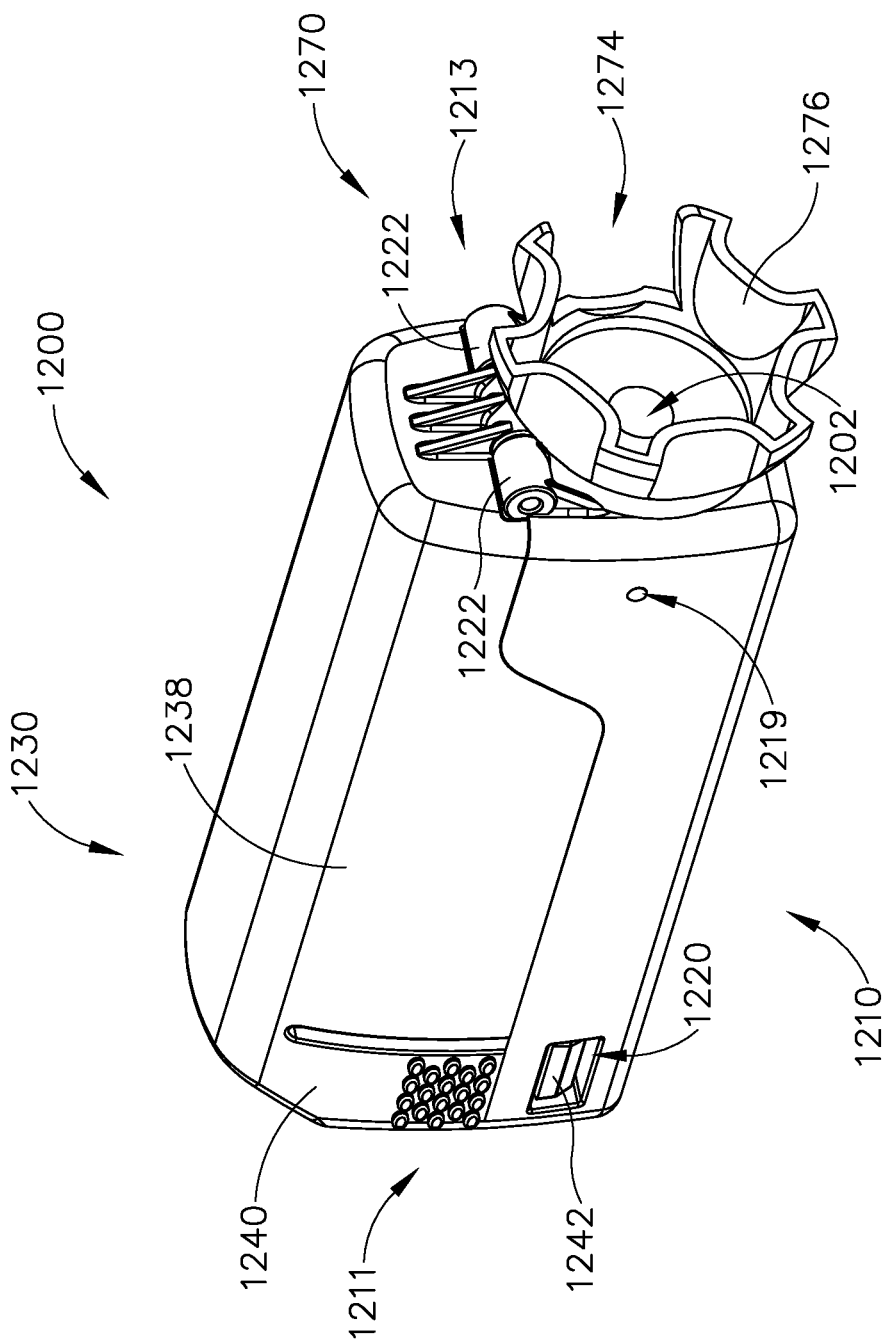
FIG. 79 depicts a perspective view of the assembly tool of FIG. 78A.
Figure 90:
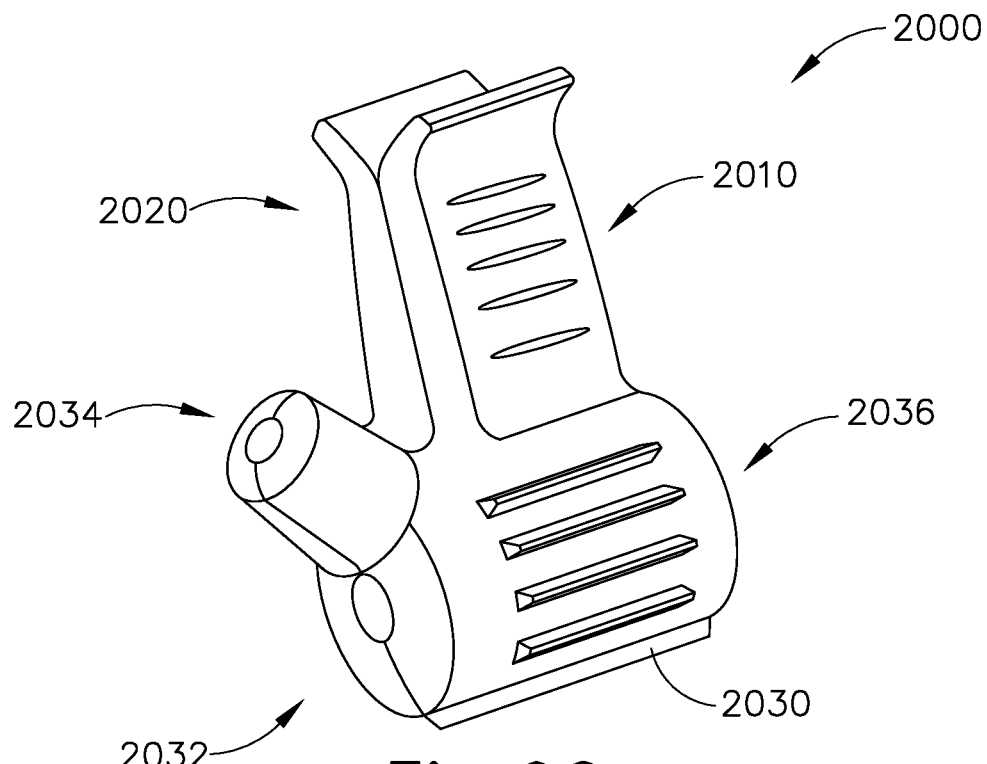
Figure 91:
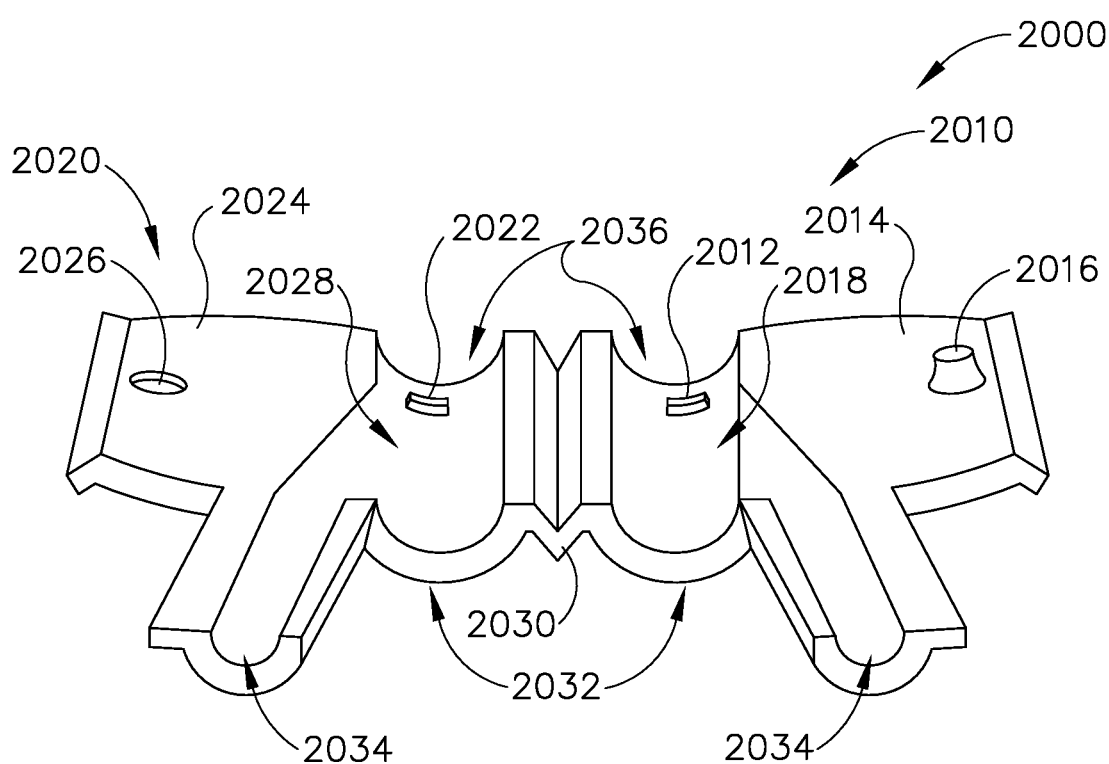
Figure 92:
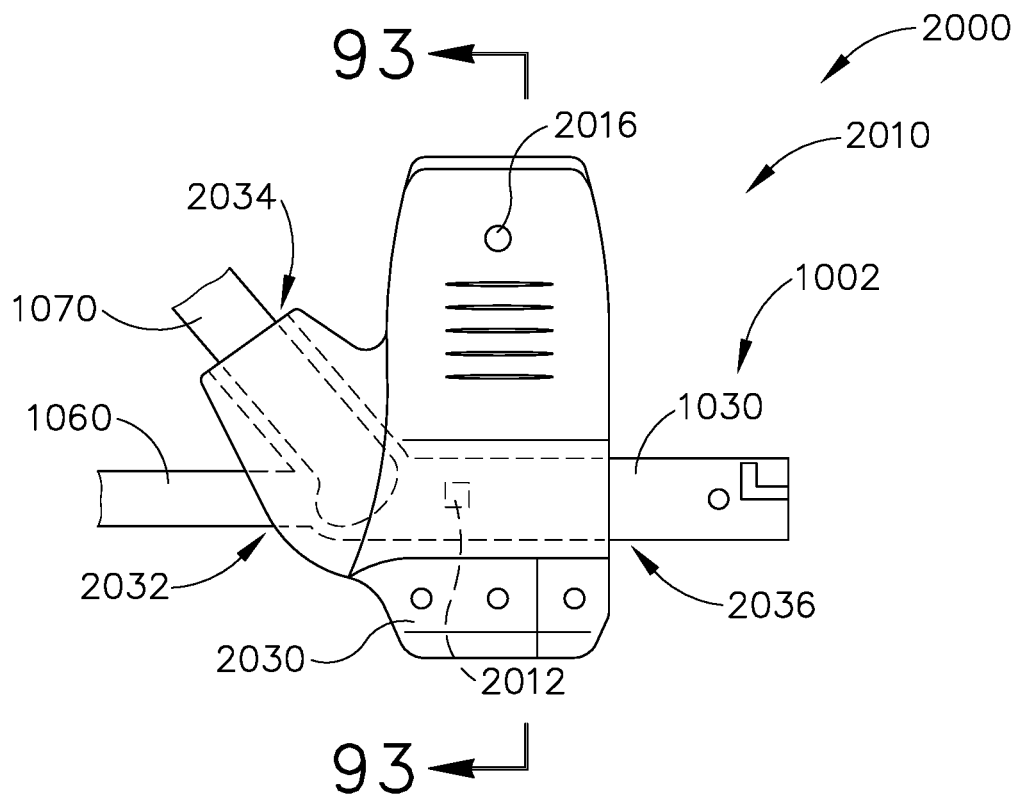
Figure 93:
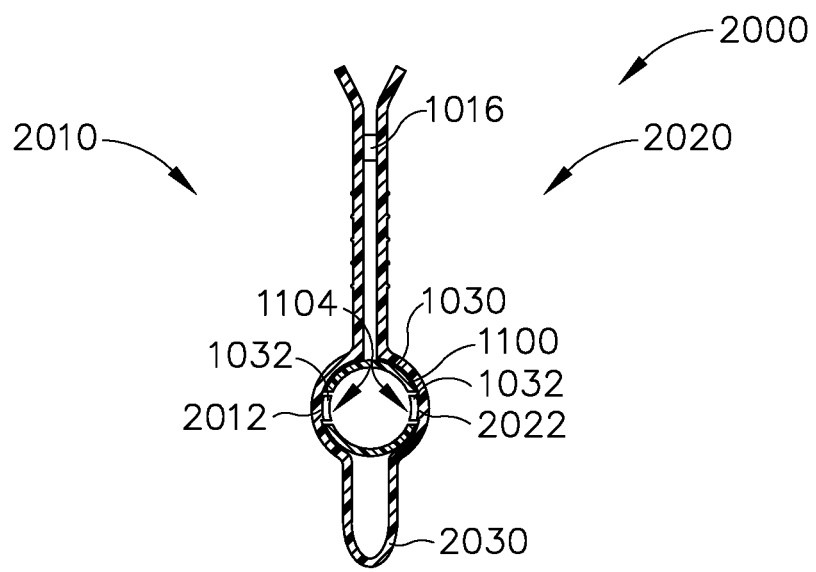
Figure 94A:
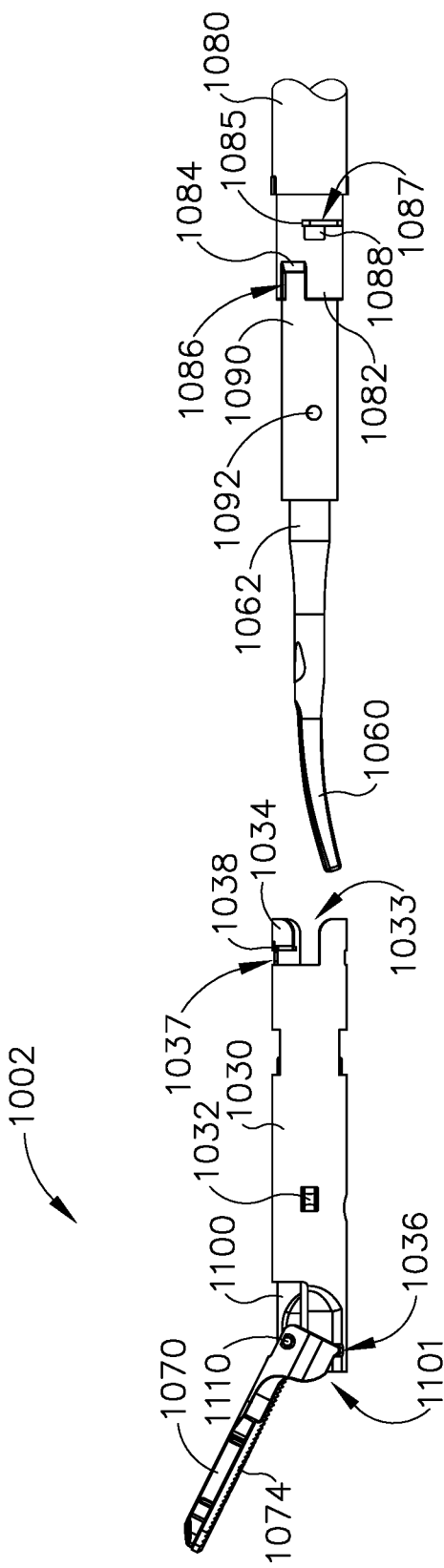
Figure 94B:
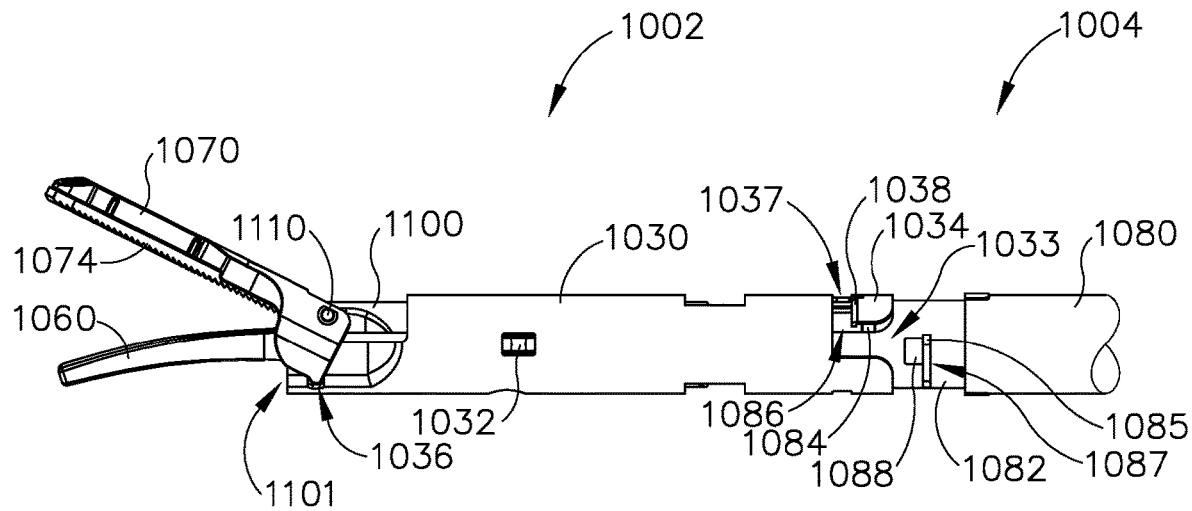
Figure 94C:
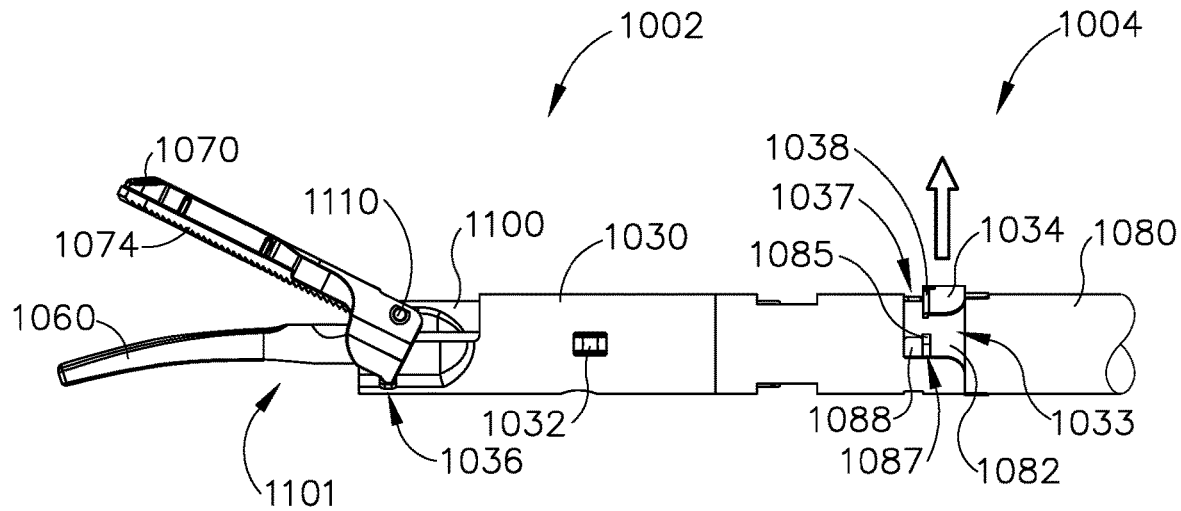
Figure 94D:
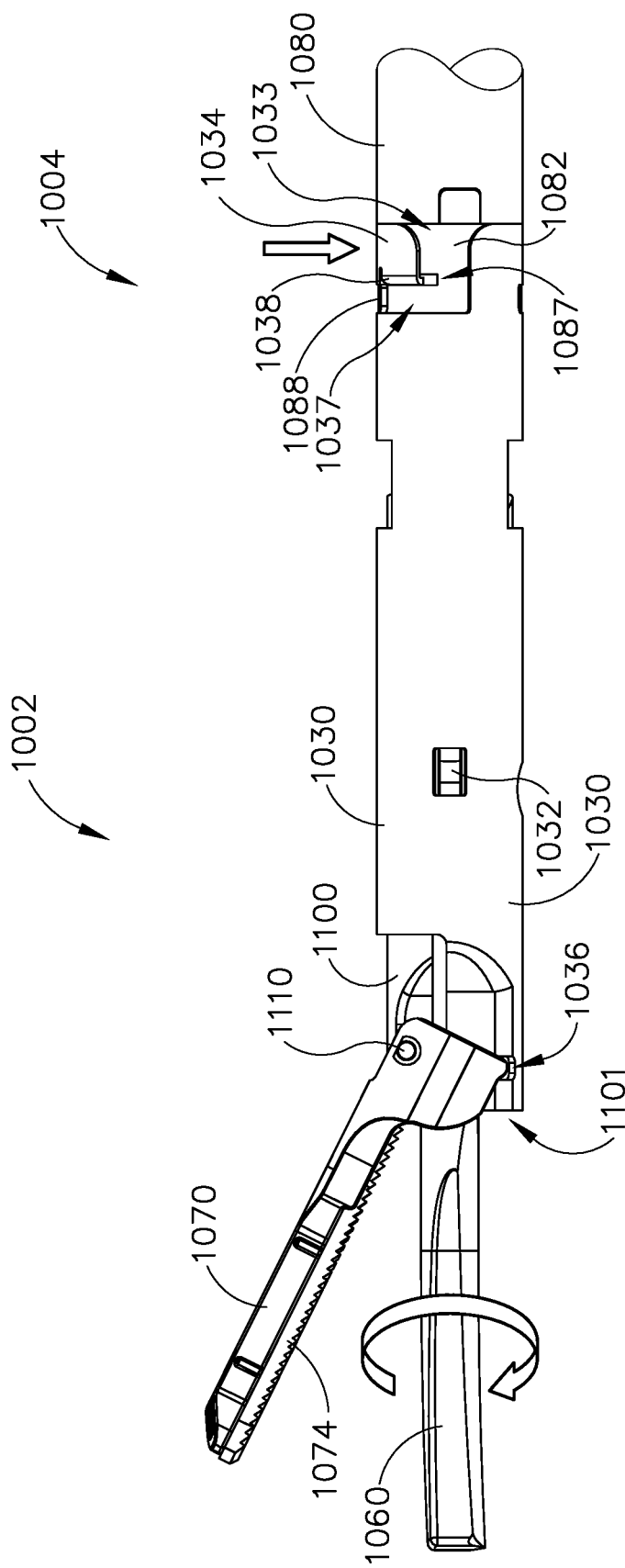
Figure 95A:
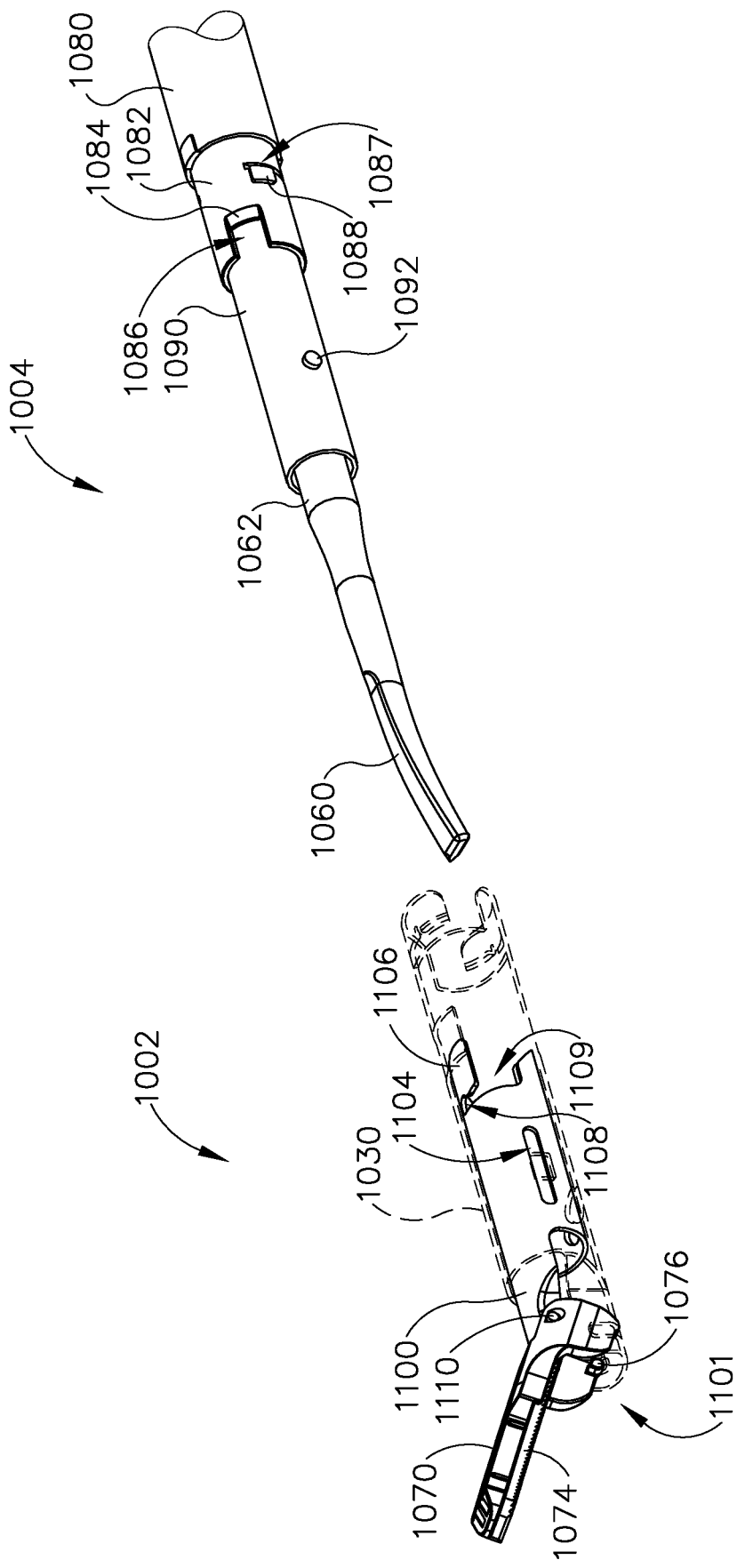
Figure 95B:
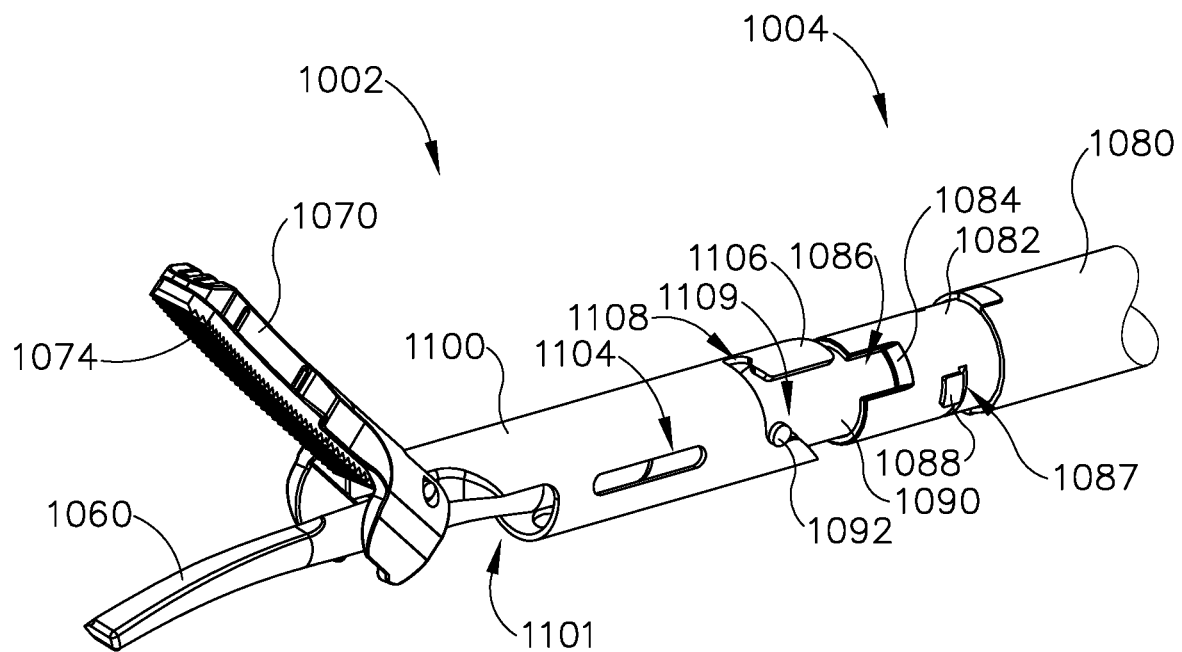
Figure 95C:
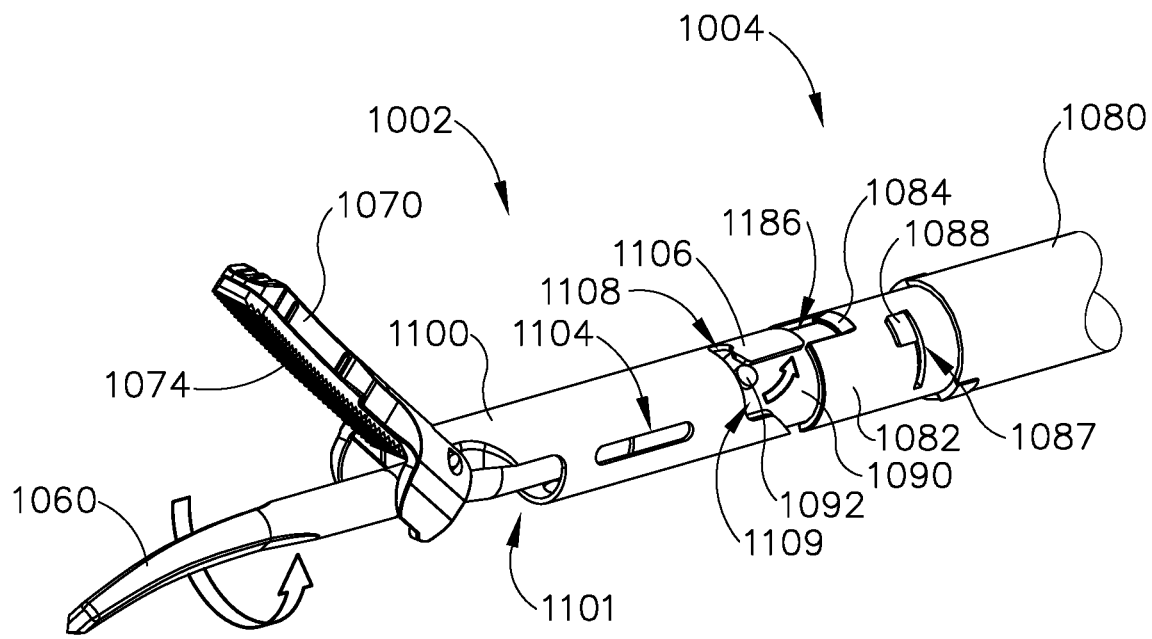
Figure 95D:
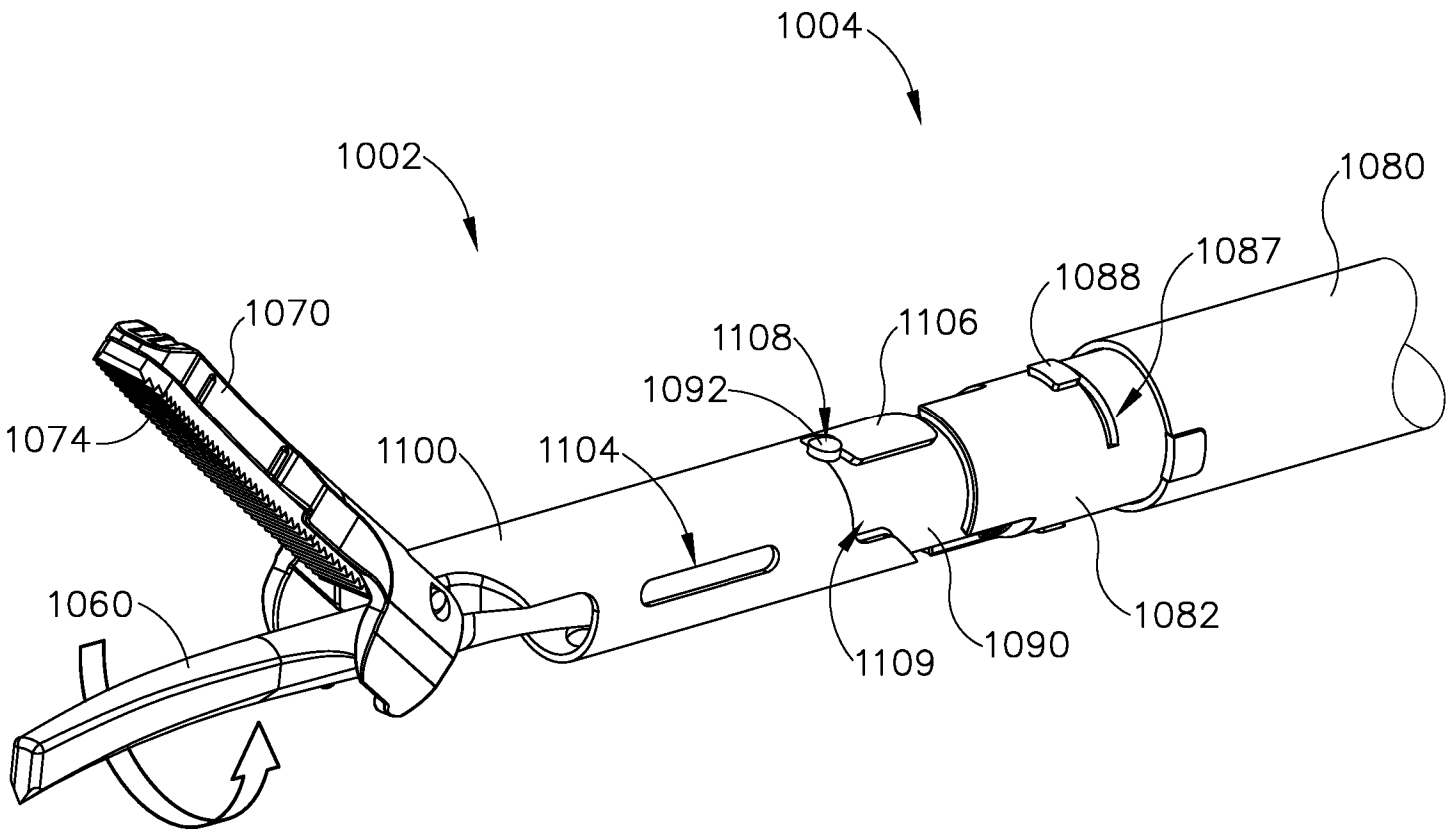
Figure 96A:
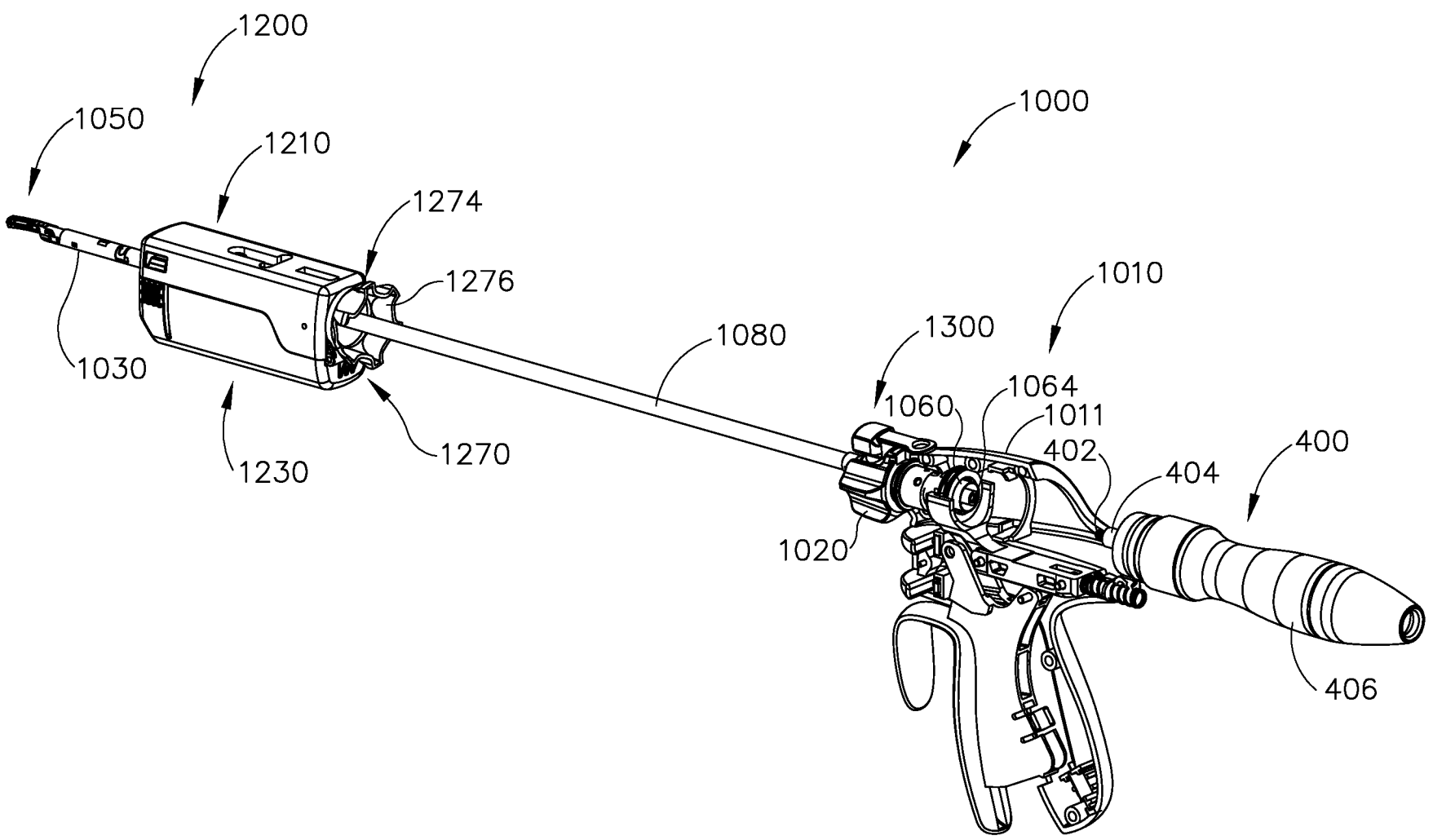
Figure 96B:
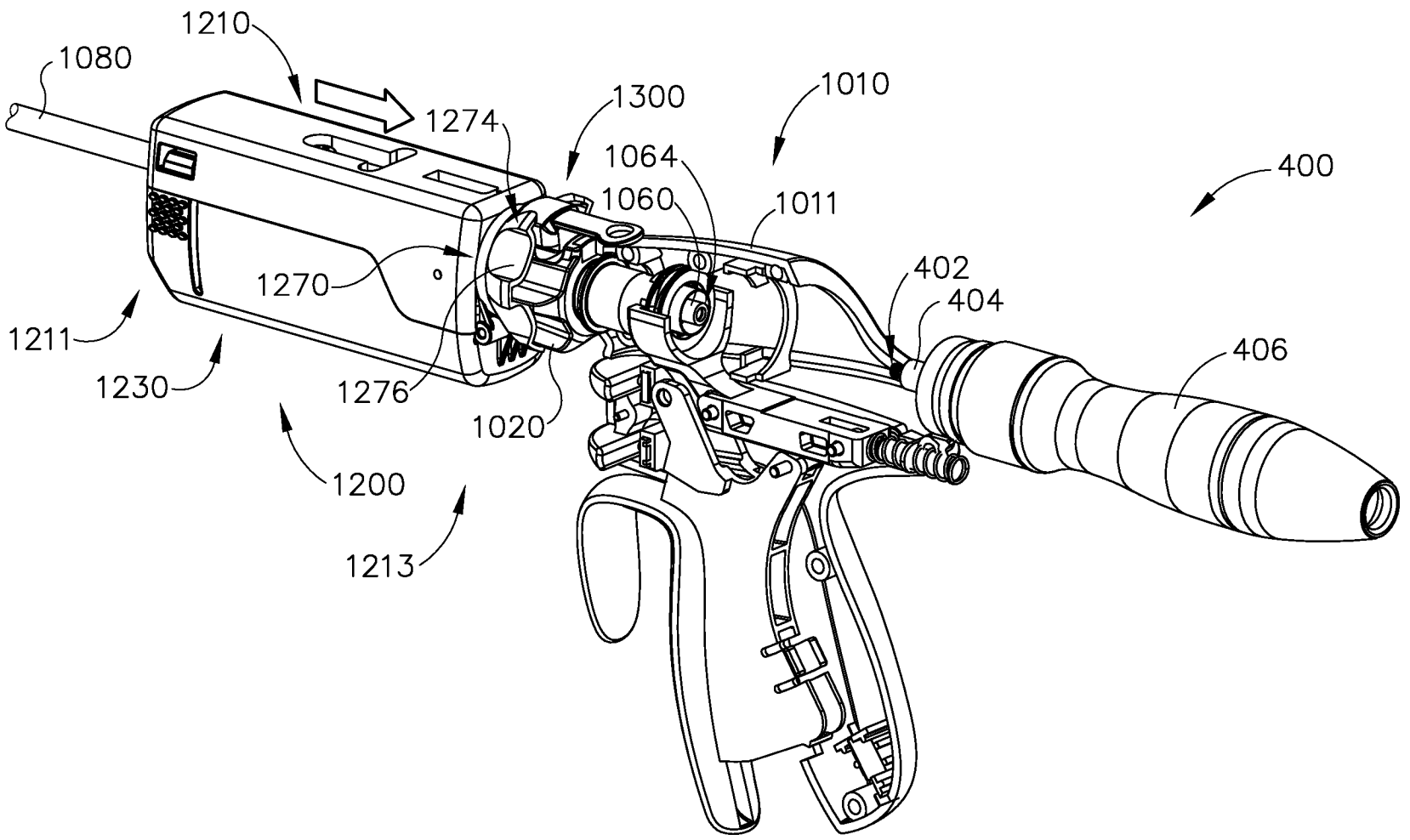
Figure 96C:
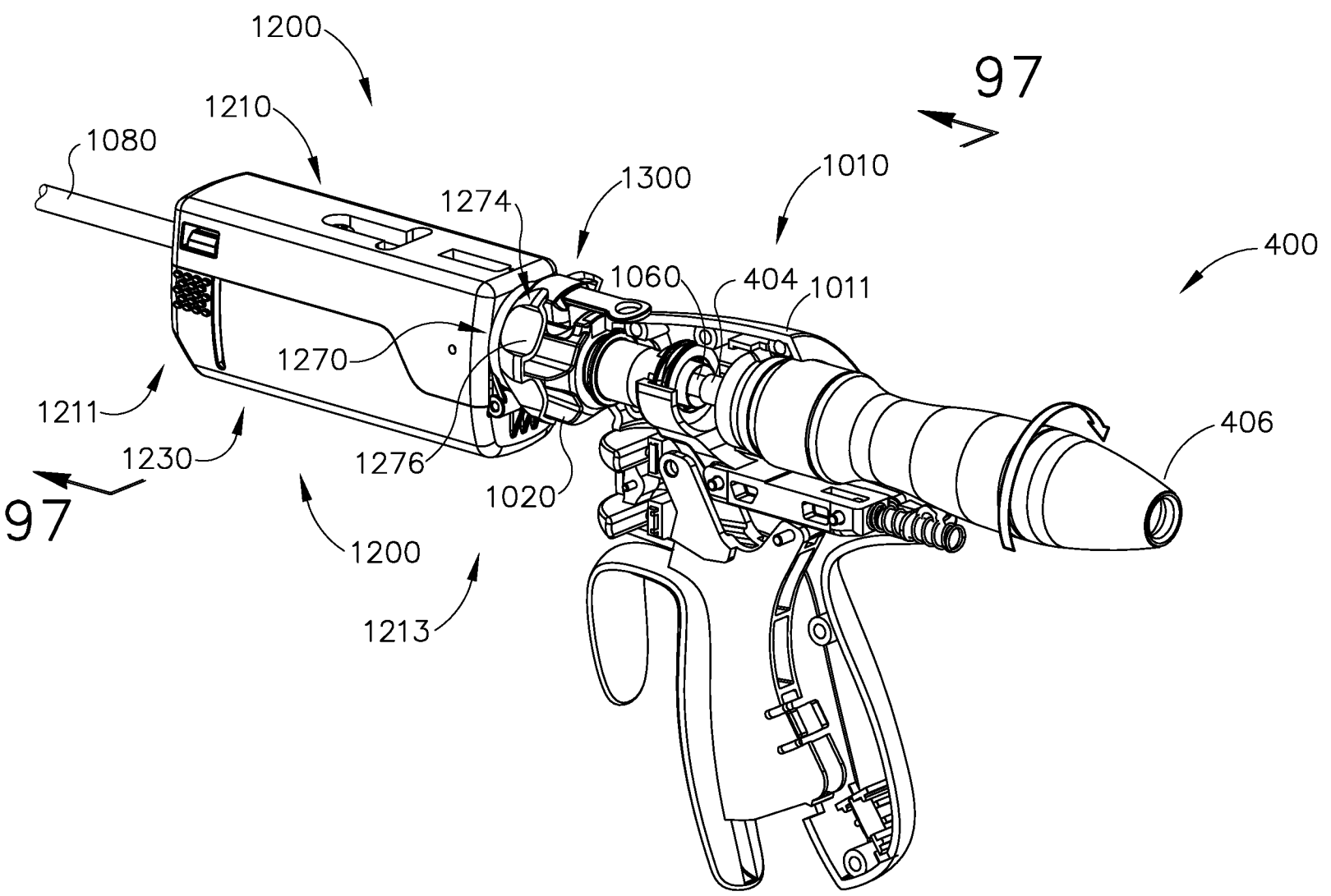
Figure 97A:
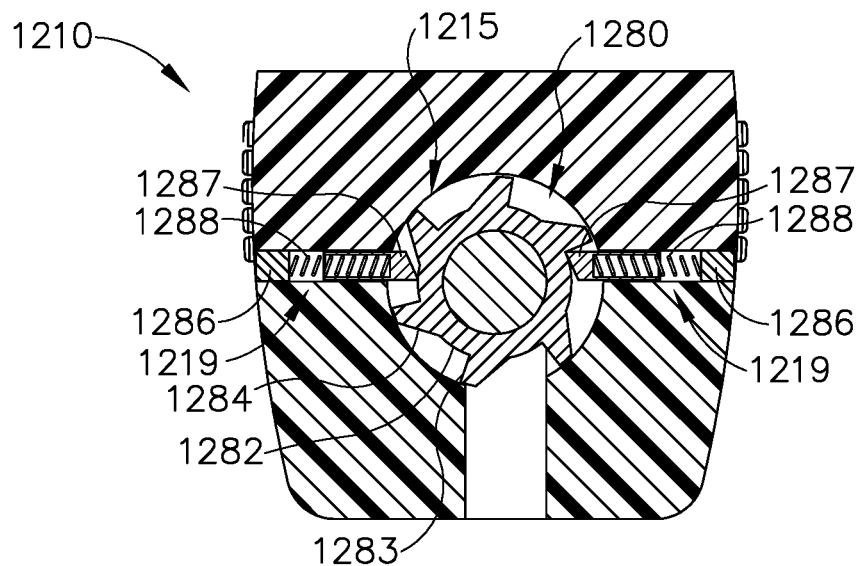
Figure 97B:
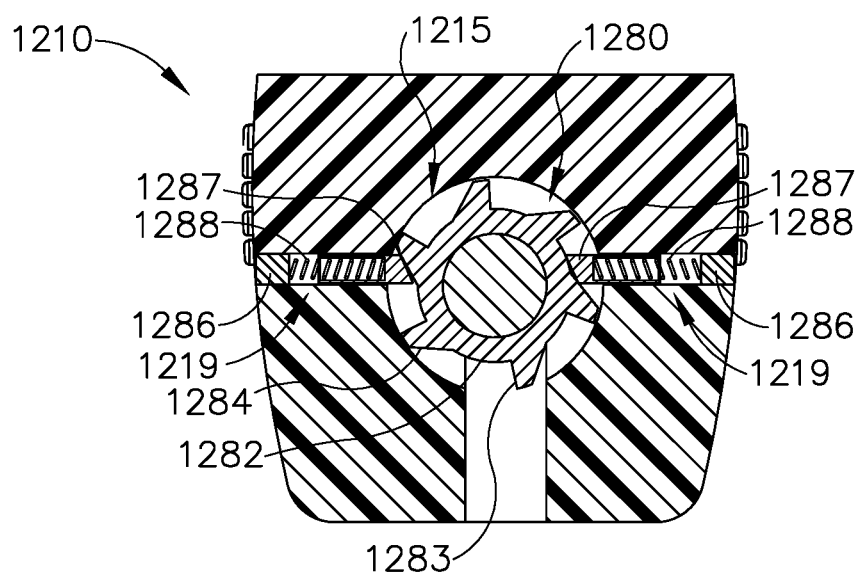
Figure 97C:
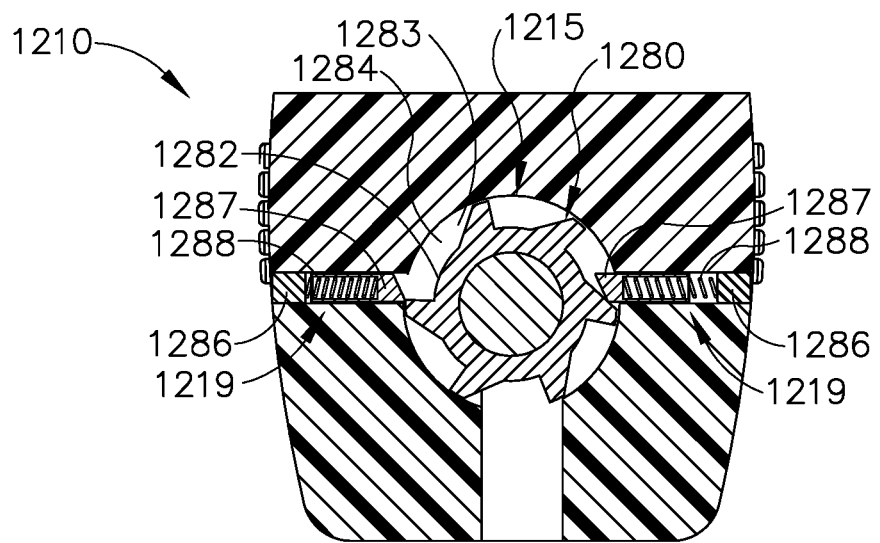
Figure 97D:
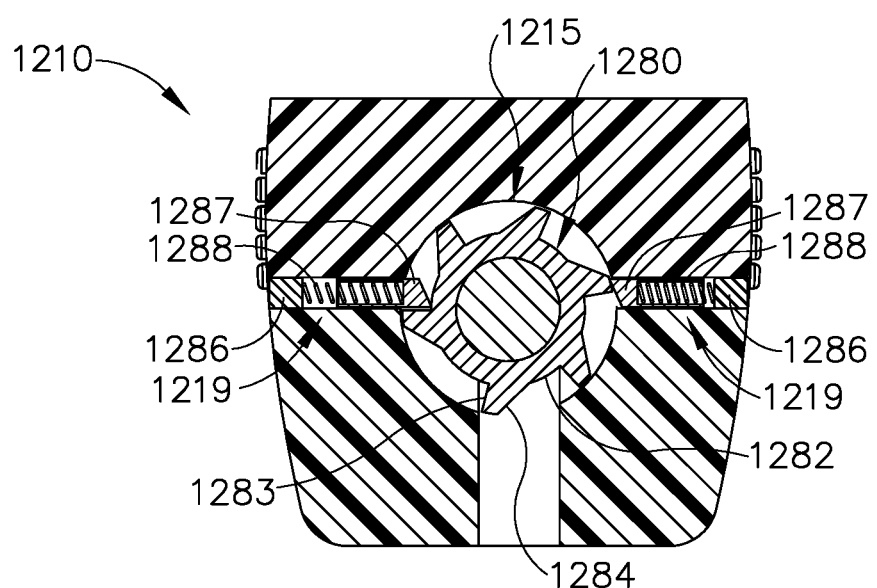
Figure 98:
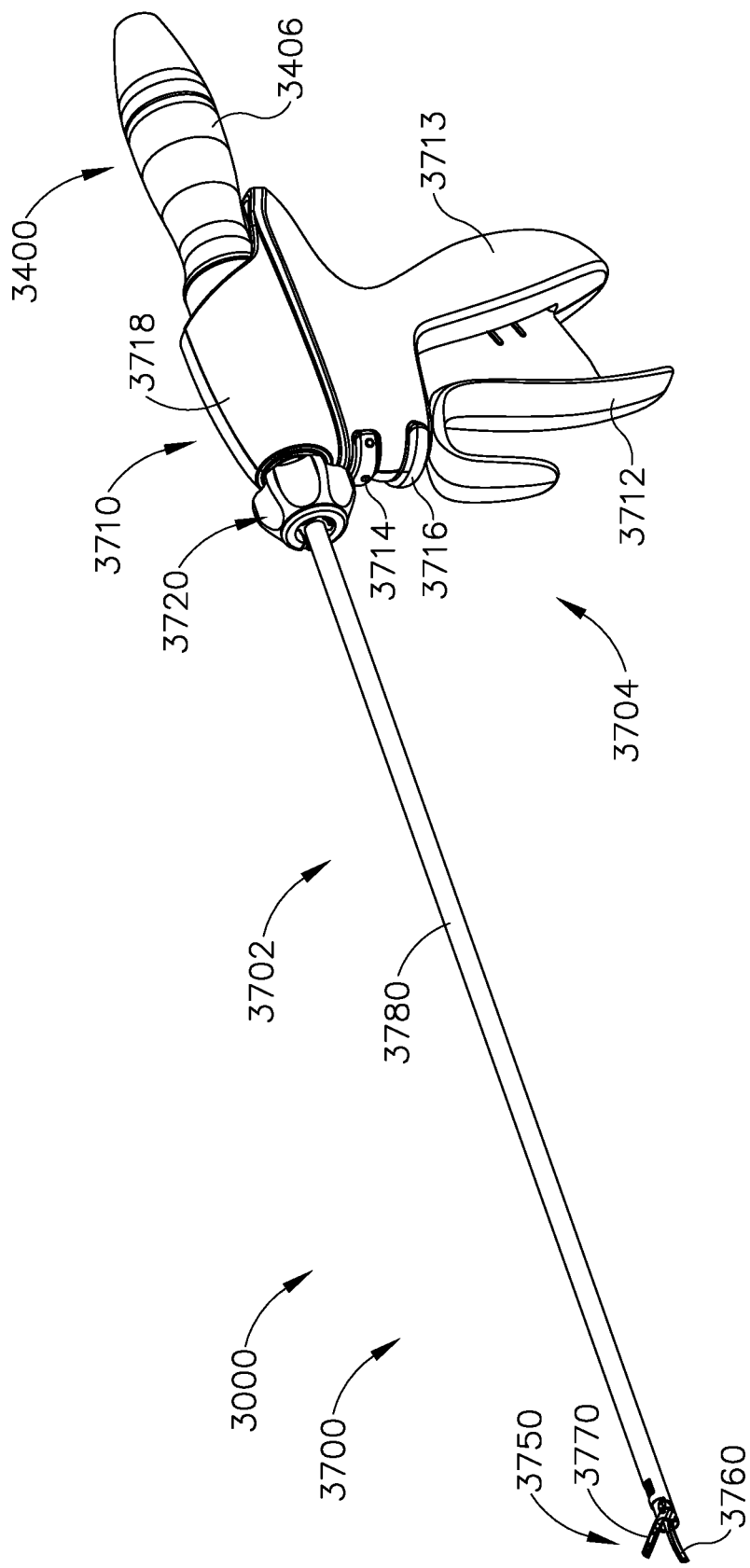
Figure 99:
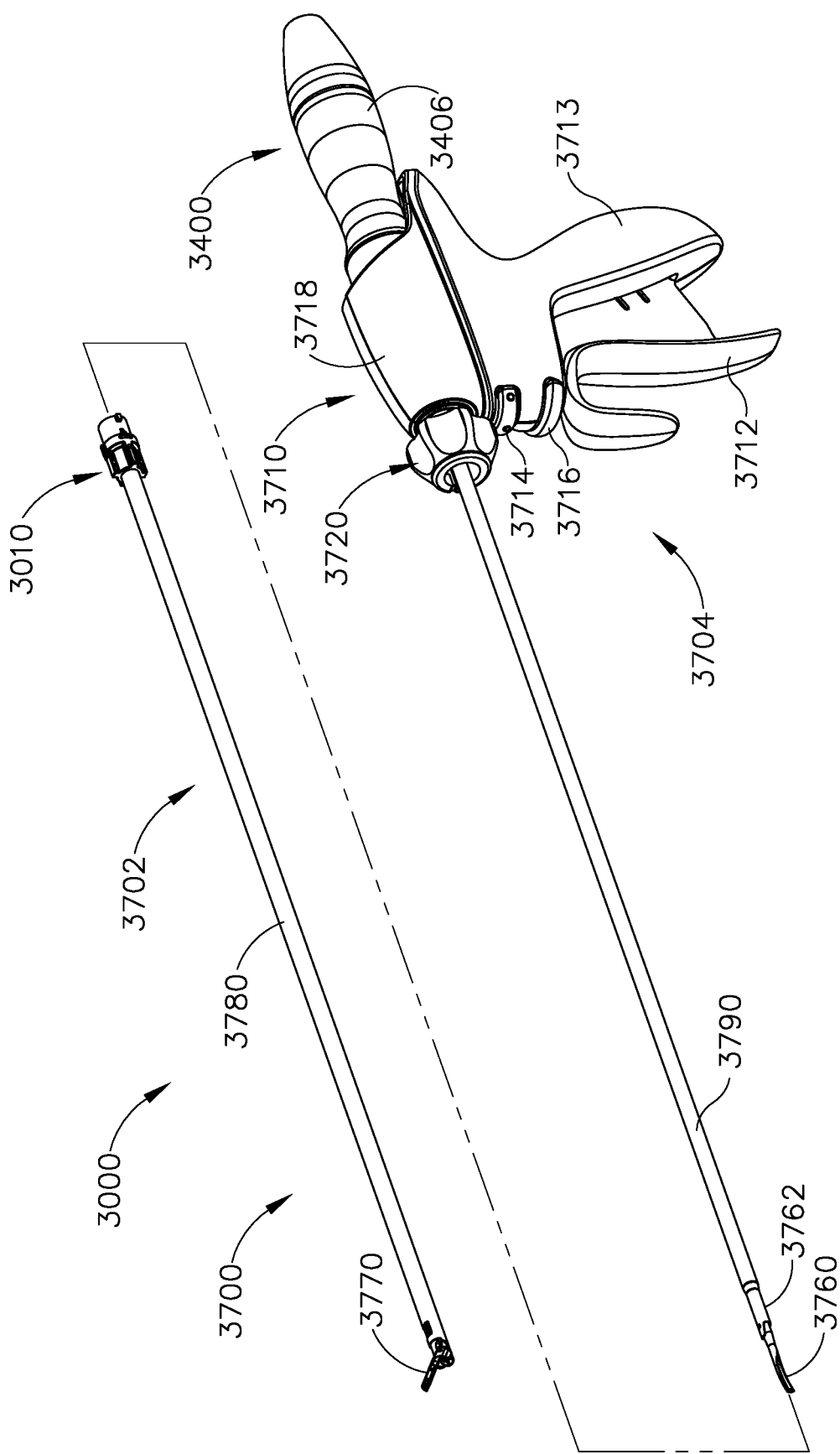
Figure 100:
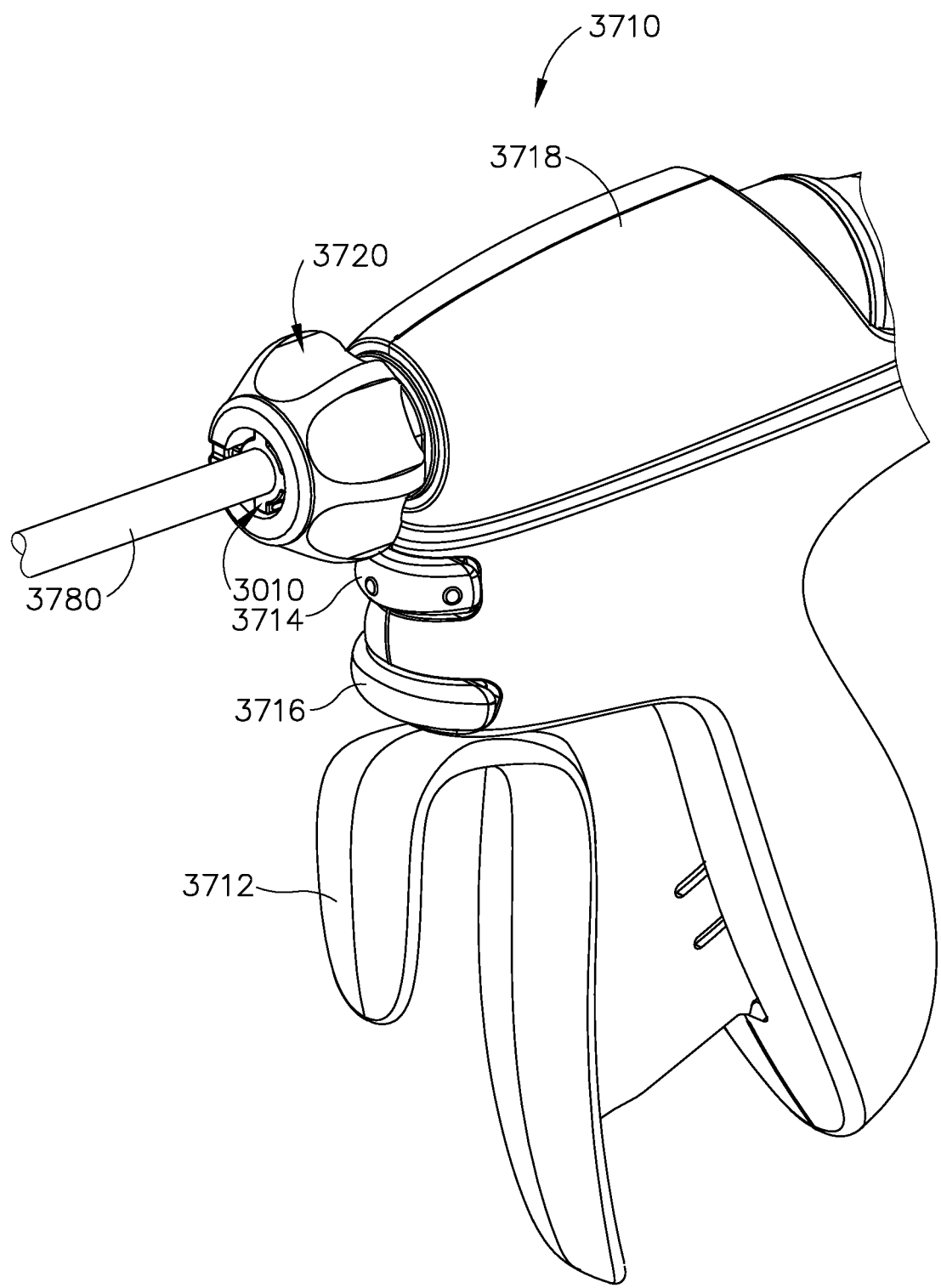
Figure 101:
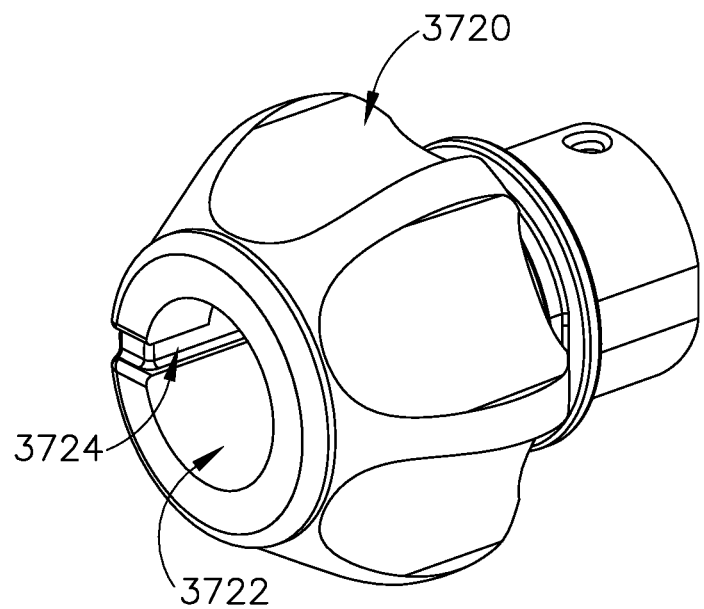
Figure 102:
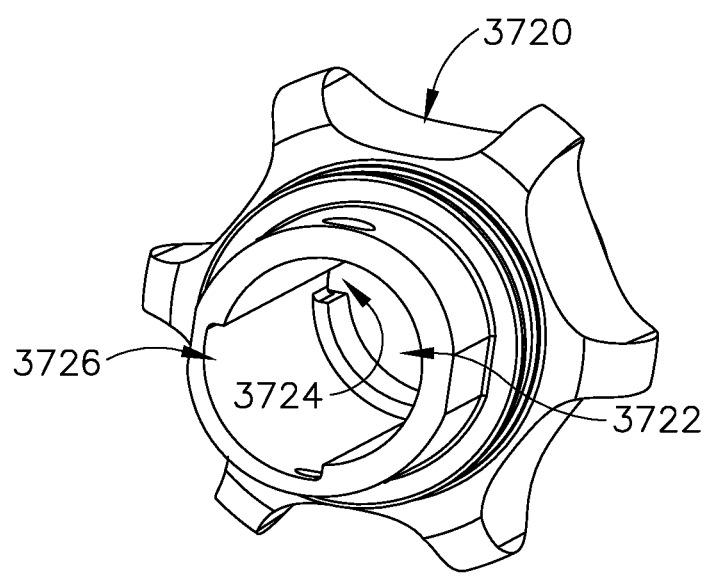
Figure 103:
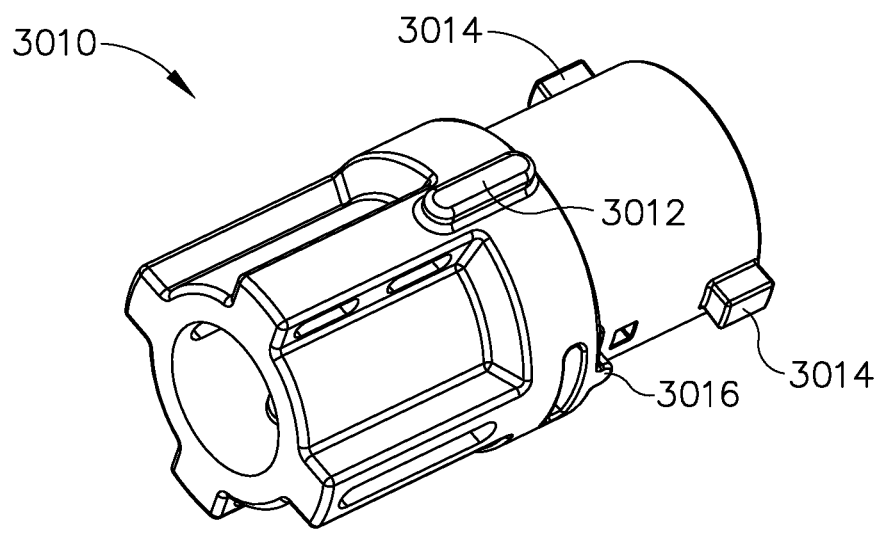
Figure 104:
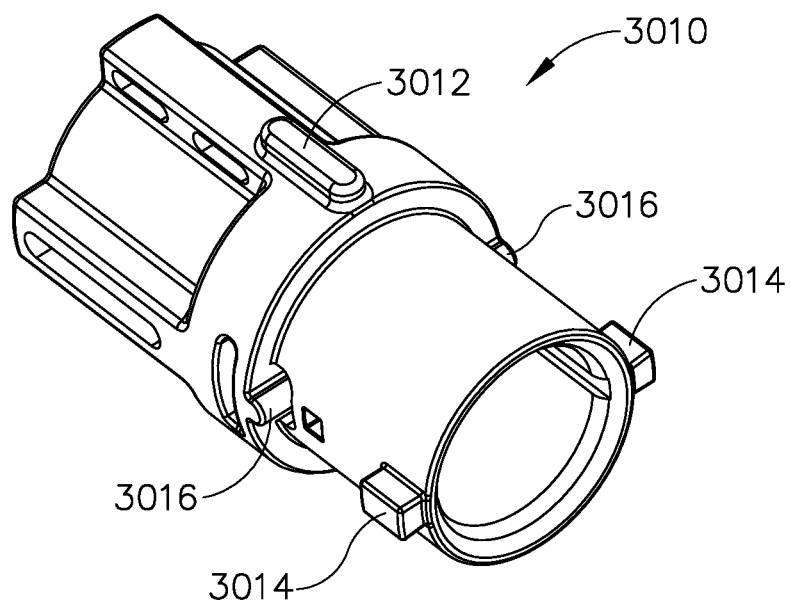
Figure 105:
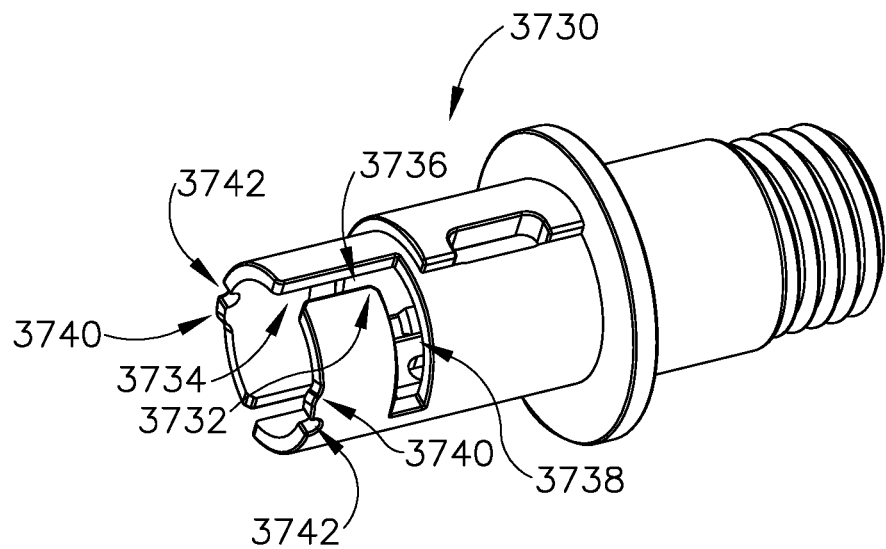
Figure 106:
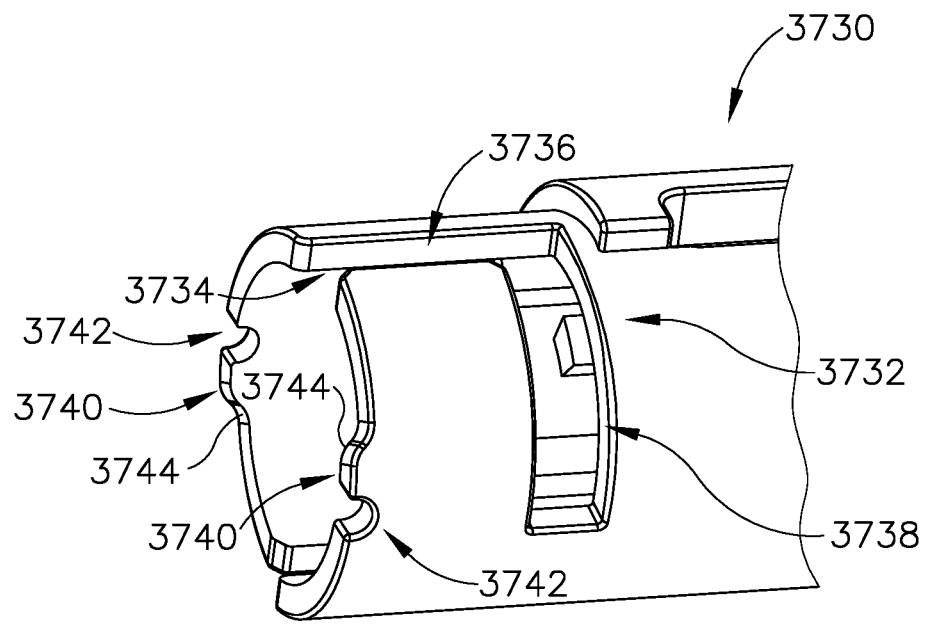
Figure 107A:
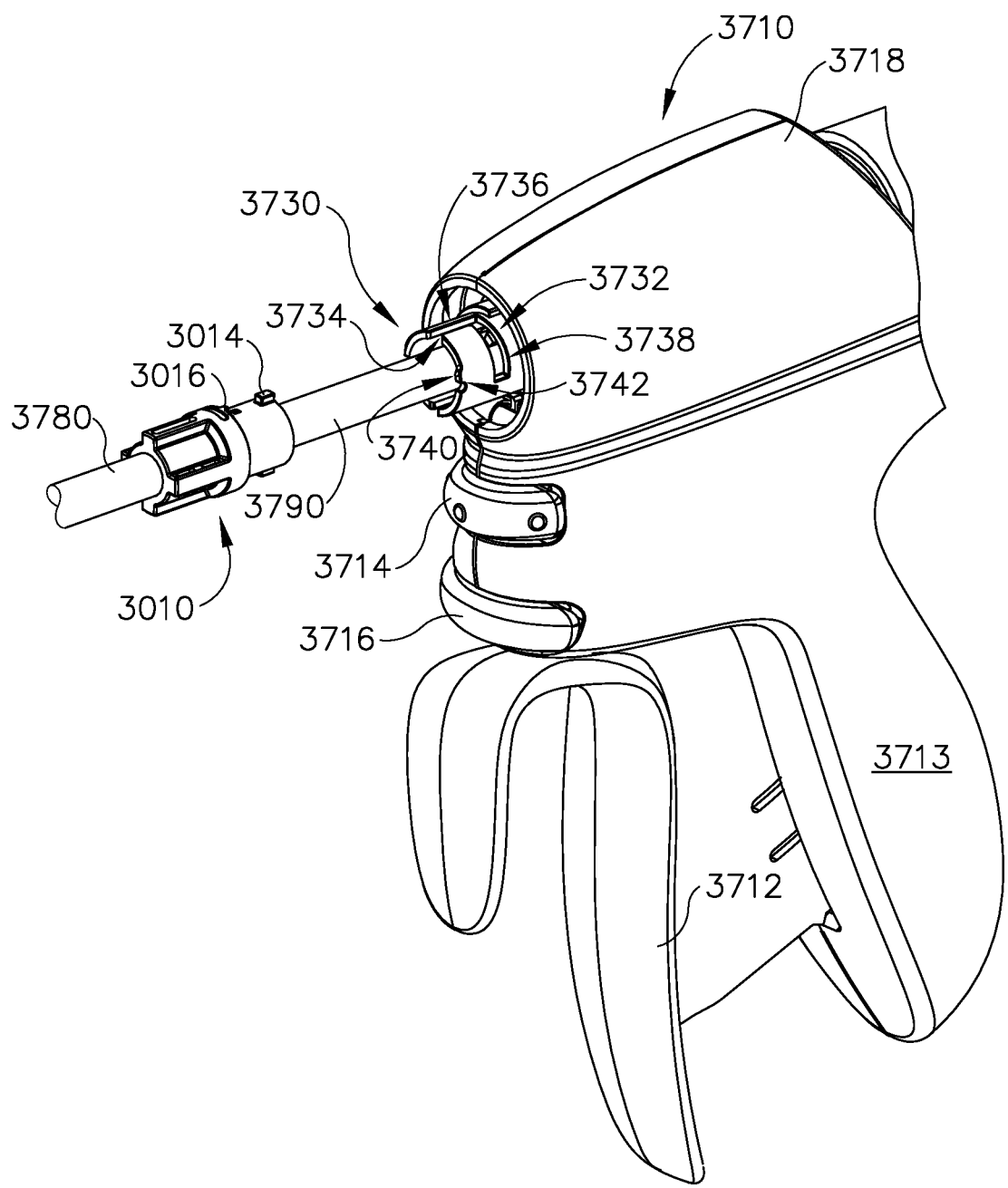
Figure 107B:
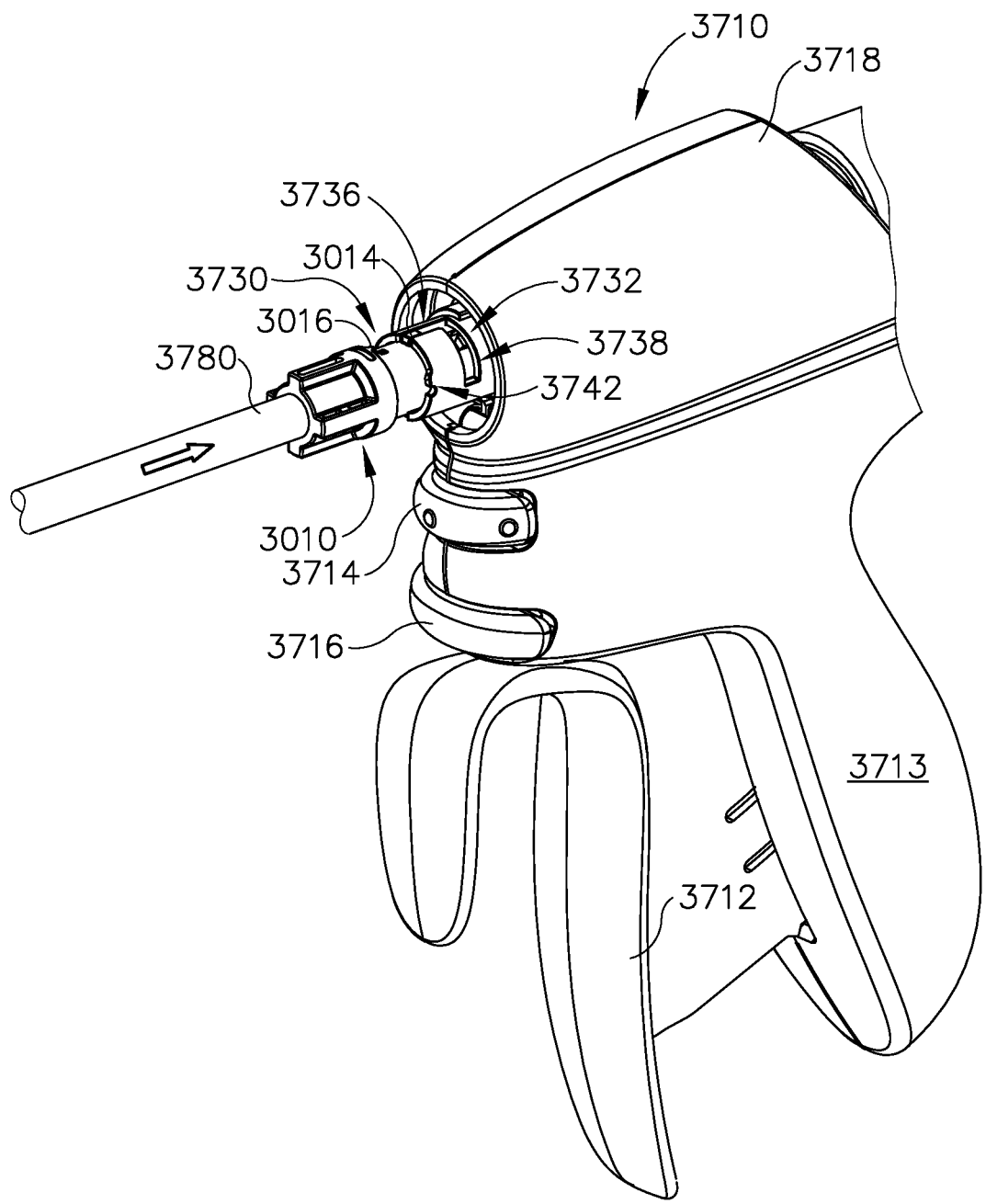
Figure 107C:
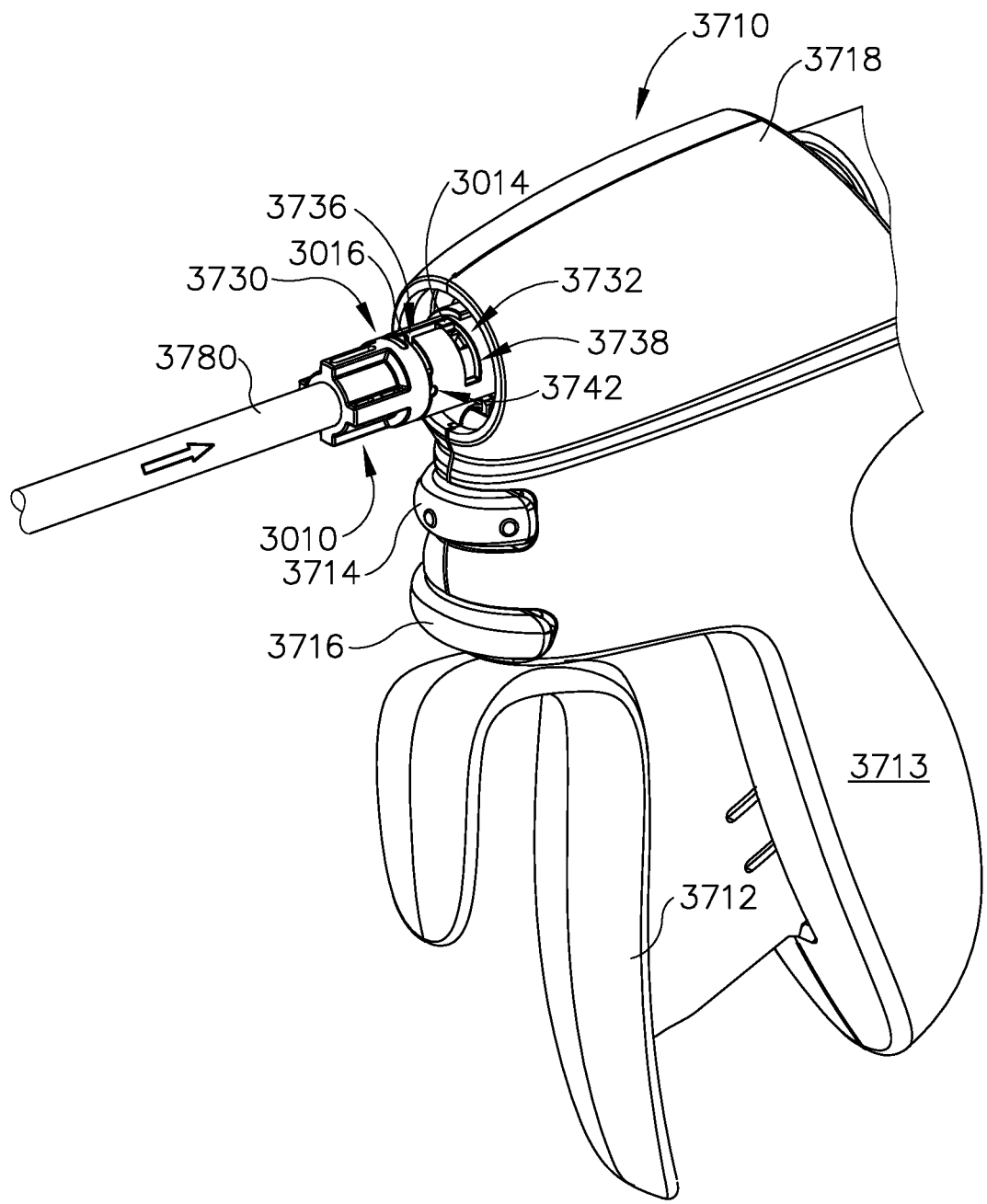
Figure 107D:
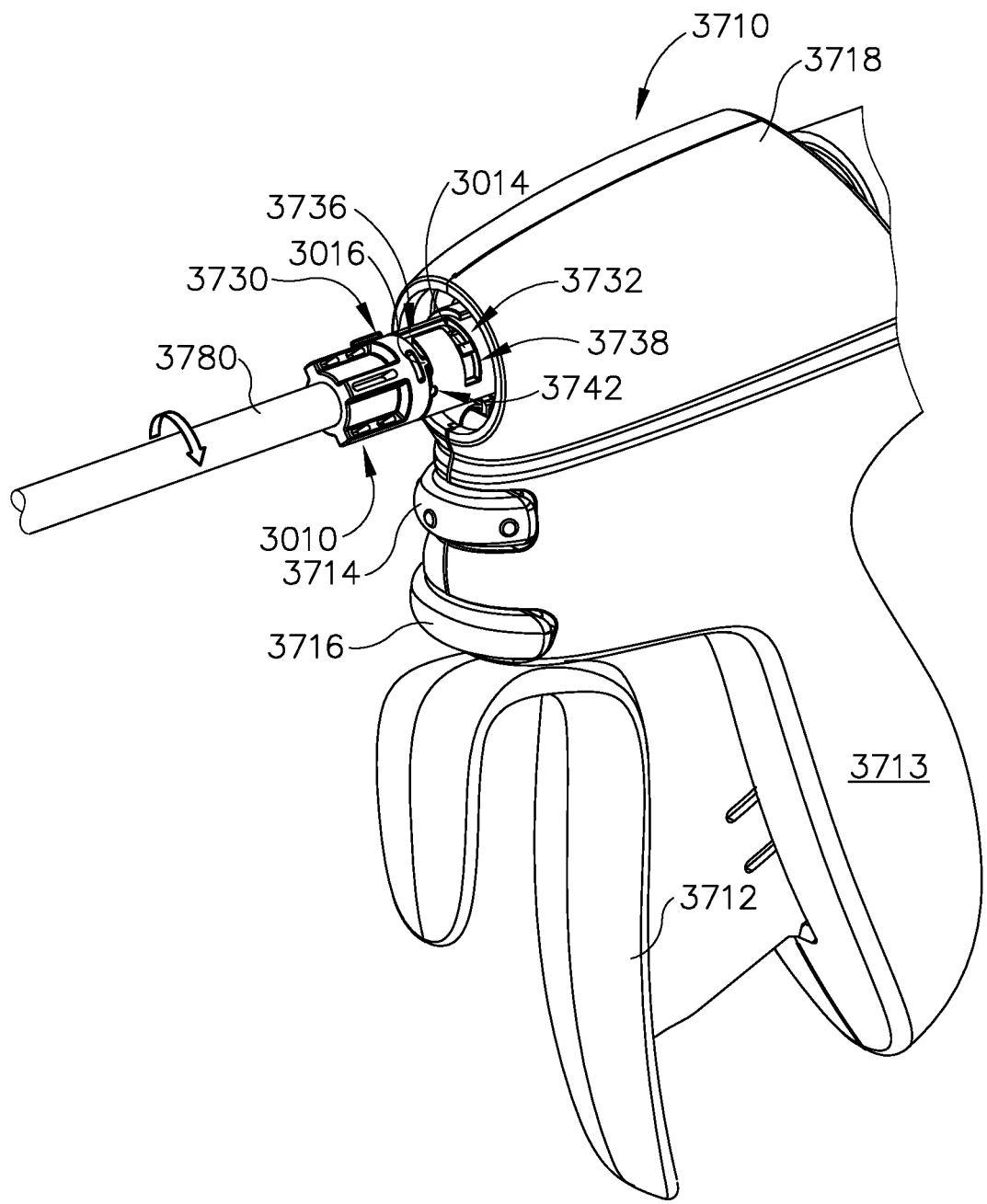
Figure 107E:
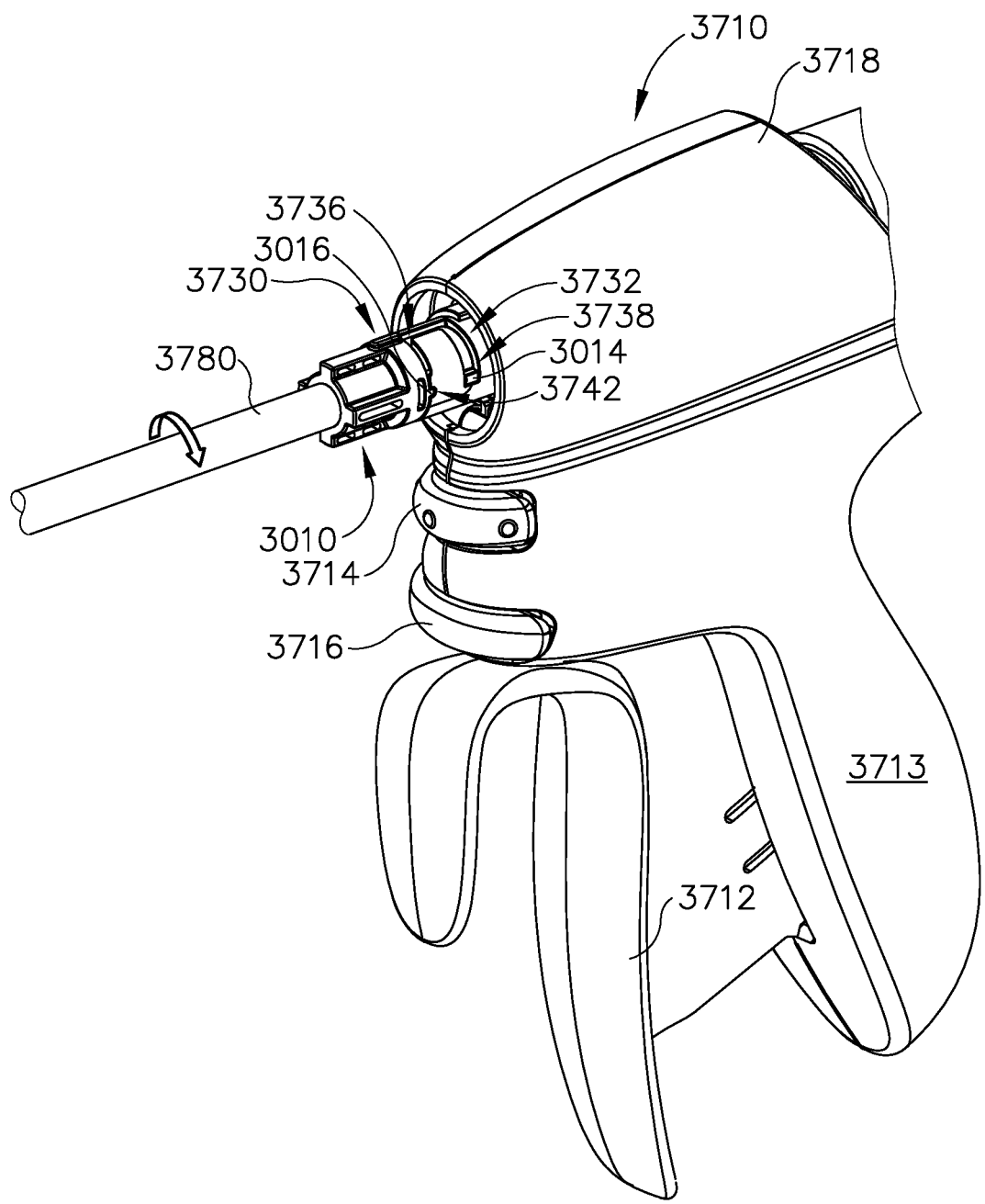
Figure 108:
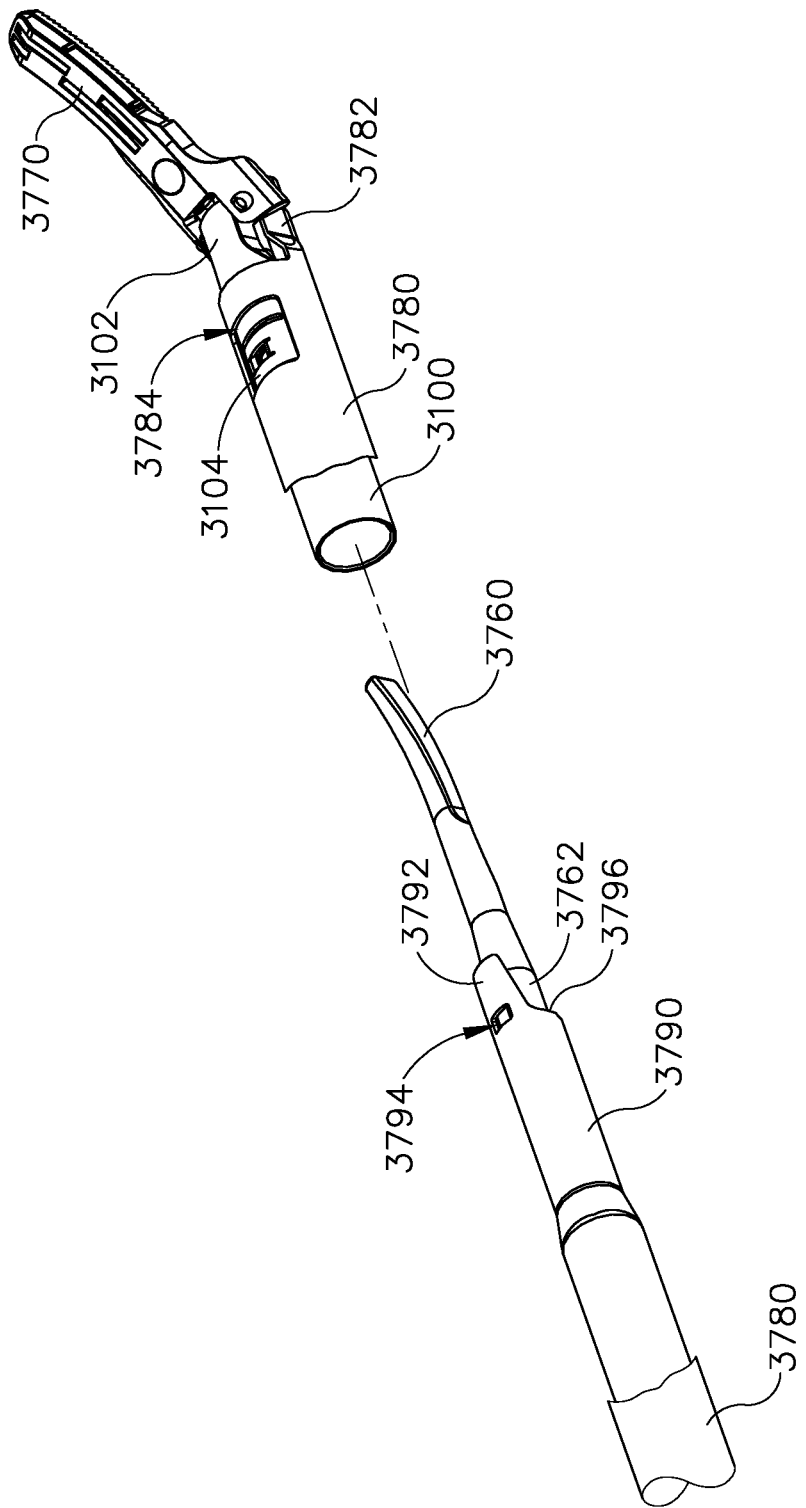
Figure 109:
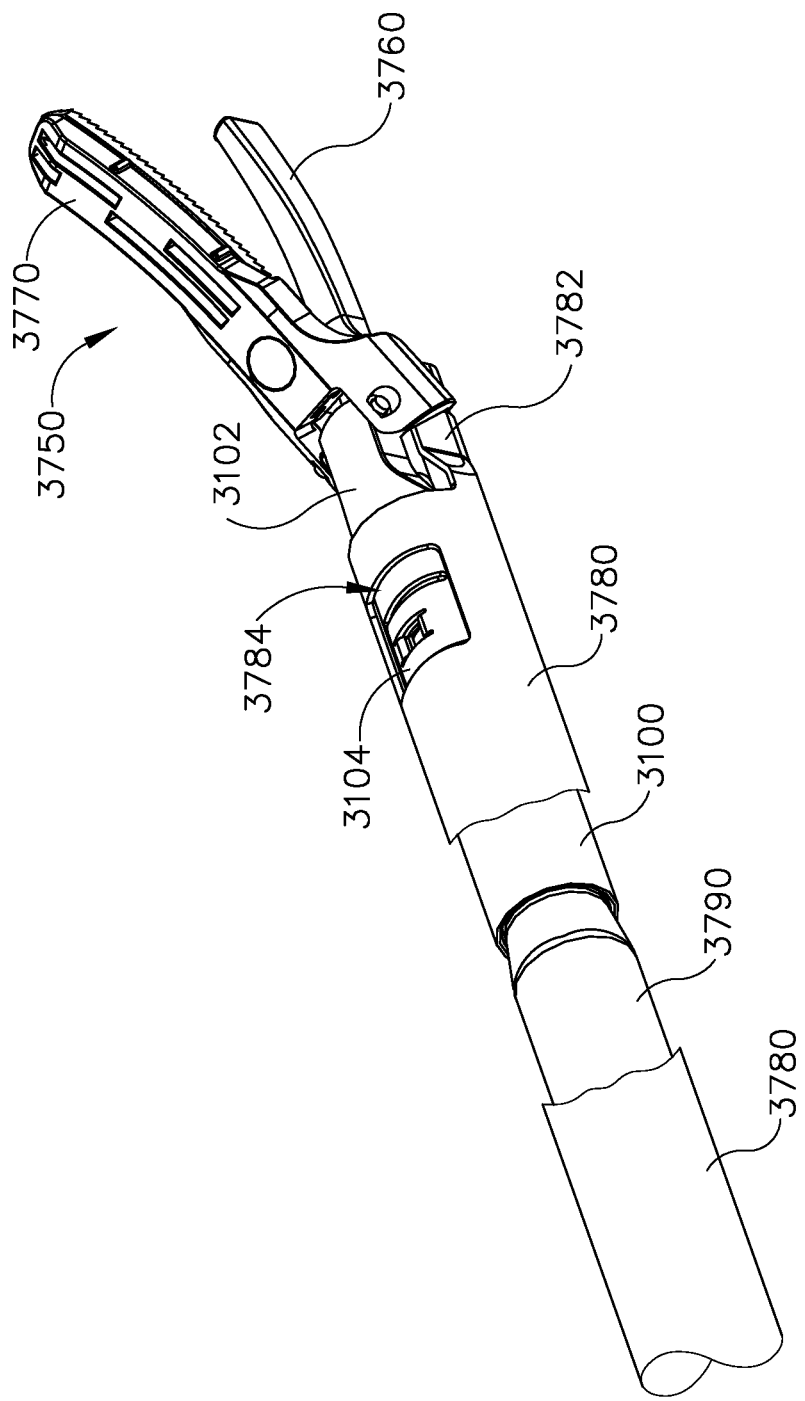
Figure 110:
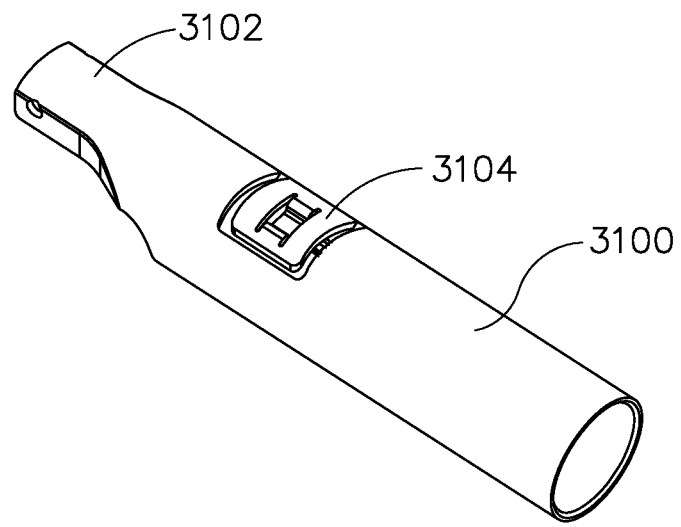
Figure 111:
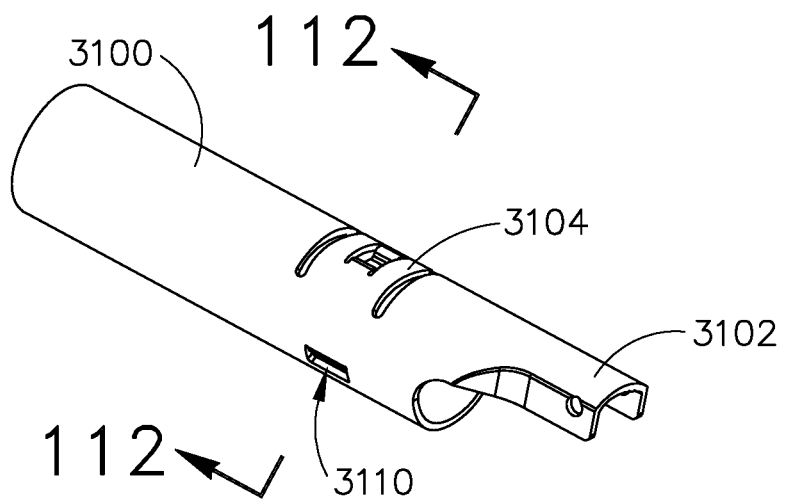
Figure 112:
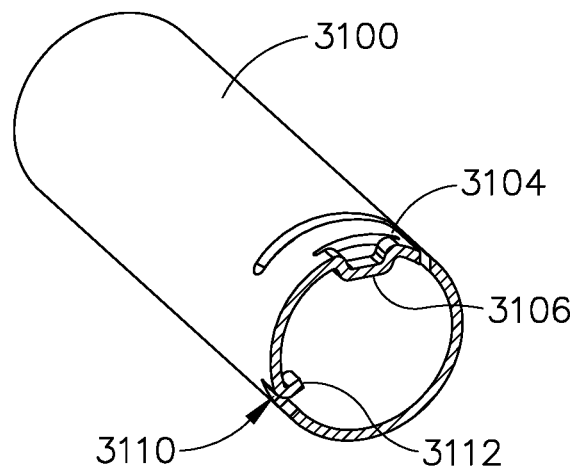
Figure 113:
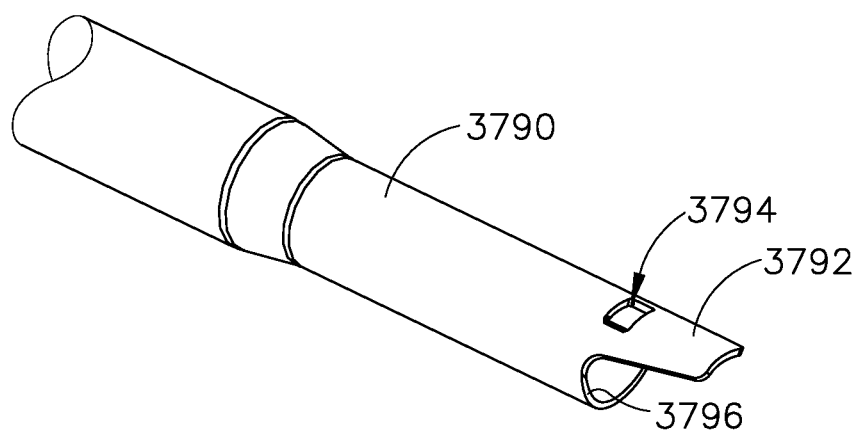
Figure 114:
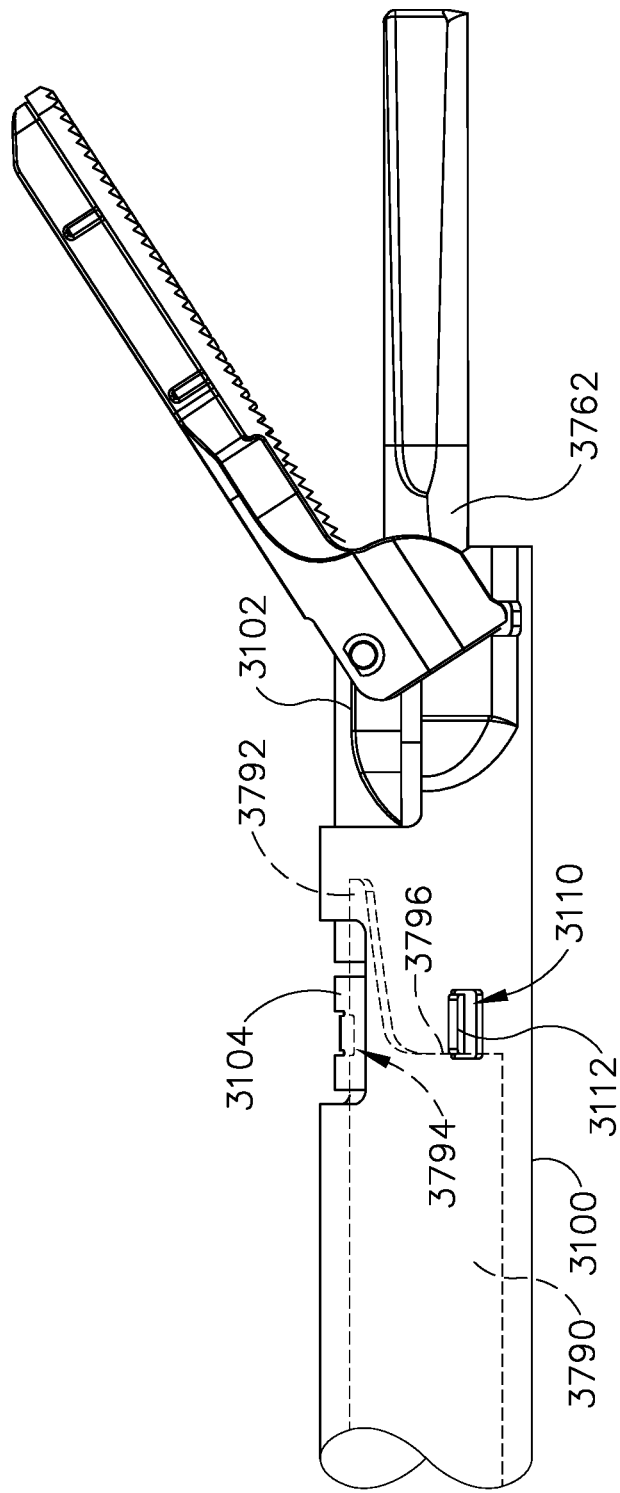

FIG. 91 depicts a perspective view of the assembly tool of FIG. 90 in an open configuration;

FIG. 92 depicts a side elevational view of the assembly tool of FIG. 90 in a closed position and fixed to the first disposable sub-assembly of FIG. 67;

FIG. 93 depicts a cross-sectional rear view, taken along line 93-93 of FIG. 92, where the assembly tool of FIG. 90 is in a closed position and fixed to the first disposable sub-assembly of FIG. 67;

FIG. 94A depicts a side elevational view of the first sub-assembly of FIG. 67 right before being inserted over the distal end of the second sub-assembly of FIG. 67;

FIG. 94B depicts a side elevational view of the first sub-assembly of FIG. 67 partially inserted over the distal end of the second sub-assembly of FIG. 67;

FIG. 94C depicts a side elevational view of the first sub-assembly of FIG. 67 inserted to a most proximal position over the distal end of the second sub-assembly of FIG. 67;

FIG. 94D depicts a side elevational view of the first sub-assembly of FIG. 67 inserted to a most proximal position over the distal end of the second sub-assembly of FIG. 67, where the second sub-assembly is rotated relative to the first sub-assembly such that the first sub-assembly is coupled to the second sub-assembly;

FIG. 95A depicts a perspective view of the first sub-assembly of FIG. 67 inserted over the distal end of the second sub-assembly of FIG. 67, where the distal outer tube member of the first sub-assembly is shown in phantom for clarity;

FIG. 95B depicts a perspective view of the first sub-assembly of FIG. 67 further inserted to a most proximal position over the distal end of the second sub-assembly of FIG. 67, where the distal outer tube member of the first sub-assembly is omitted for clarity;

FIG. 95C depicts a perspective view of the first sub-assembly of FIG. 67 inserted to a most proximal position over the distal end of the second sub-assembly of FIG. 67, where the first sub-assembly is rotated relative to the second sub-assembly, where the distal outer tube member of the first sub-assembly is omitted for clarity;

FIG. 95D depicts a perspective view of the first sub-assembly of FIG. 67 inserted to a most proximal position over the distal end of the second sub-assembly of FIG. 67, where the second sub-assembly is rotated relative to the second sub-assembly such that the first sub-assembly is coupled to the second sub-assembly;

FIG. 96A depicts a perspective view of the assembly tool of FIG. 78A utilized to couple the reusable assembly of FIG. 66 with the disposable assembly of FIG. 66, with a housing portion of the reusable assembly omitted for clarity, where the reusable assembly is decoupled with the disposable assembly, where the assembly tool is distal in relation to the knob member of the second sub-assembly of FIG. 67;

FIG. 96B depicts a perspective view of the assembly tool of FIG. 78A utilized to couple the reusable assembly of FIG. 66 with the disposable assembly of FIG. 66, with a housing portion of the reusable assembly omitted for clarity, where the reusable assembly is decoupled with the disposable assembly, where the assembly tool is rotationally secured to the knob member of the second sub-assembly of FIG. 67;

FIG. 96C depicts a perspective view of the assembly tool of FIG. 78A utilized to couple the reusable assembly of FIG. 66 with the disposable assembly of FIG. 66, with a housing portion of the reusable assembly omitted for clarity, where the reusable assembly is coupled with the disposable assembly, where the assembly tool is rotationally secured to the knob member of the second sub-assembly of FIG. 67;

FIG. 97A depicts a cross-sectional rear view of the assembly tool of FIG. 78A rotationally secured to the knob member of the second sub-assembly of FIG. 67, where the reusable assembly of FIG. 66 is sufficiently coupled with the disposable assembly of FIG. 66, taken along line 97-97 of FIG. 96C;

FIG. 97B depicts a cross-sectional rear view of the assembly tool of FIG. 78A rotationally secured to the knob member of the second sub-assembly of FIG. 67, where the reusable assembly of FIG. 66 is sufficiently coupled with the disposable assembly of FIG. 66 and the reusable assembly is further rotated relative to the disposable assembly, taken along line 97-97 of FIG. 96C;

FIG. 97C depicts a cross-sectional rear view of the assembly tool of FIG. 78A rotationally secured to the knob member of the second sub-assembly of FIG. 67, where the reusable assembly of FIG. 66 is sufficiently coupled with the disposable assembly of FIG. 66 and the reusable assembly is further rotated relative to the disposable assembly, taken along line 97-97 of FIG. 96C;

FIG. 97D depicts a cross-sectional rear view of the assembly tool of FIG. 78A rotationally secured to the knob member of the second sub-assembly of FIG. 67, where the reusable assembly of FIG. 66 is sufficiently coupled with the disposable assembly of FIG. 66 and the reusable assembly is further rotated relative to the disposable assembly, taken along line 97-97 of FIG. 96C;

FIG. 98 depicts a perspective view of another alternative ultrasonic surgical instrument having a disposable assembly and a reusable assembly;

FIG. 99 depicts a partially exploded view of the ultrasonic surgical instrument of FIG. 98, with a first disposable sub-assembly separated from a second disposable sub-assembly;

FIG. 100 depicts a partial perspective view of the distal portion of a handle assembly of the ultrasonic surgical instrument of FIG. 98 and the proximal portion of a shaft assembly of the ultrasonic surgical instrument of FIG. 98;

FIG. 101 depicts a perspective view of a knob member of the handle assembly of FIG. 100;

FIG. 102 depicts another perspective view of the knob member of FIG. 101;

FIG. 103 depicts a perspective view of a coupling feature of a first disposable sub-assembly of the disposable assembly of FIG. 98;

FIG. 104 depicts another perspective view of the coupling feature of FIG. 103;

FIG. 105 depicts a perspective view of a coupling feature of the handle assembly of FIG. 100;

FIG. 106 depicts a partial perspective view of the coupling feature of FIG. 105;

FIG. 107A depicts a partial perspective view of the distal portion of the handle assembly of FIG. 100 and the proximal portion of the shaft assembly of FIG. 100, with the knob member of FIG. 101 omitted, and with the first disposable sub-assembly of FIG. 98 at a first longitudinal position and at a first angular position;

FIG. 107B depicts a partial perspective view of the distal portion of the handle assembly of FIG. 100 and the proximal portion of the shaft assembly of FIG. 100, with the knob member of FIG. 101 omitted, and with the first disposable sub-assembly of FIG. 98 at a second longitudinal position and at the first angular position;

FIG. 107C depicts a partial perspective view of the distal portion of the handle assembly of FIG. 100 and the proximal portion of the shaft assembly of FIG. 100, with the knob member of FIG. 101 omitted, and with the first disposable sub-assembly of FIG. 98 at a third longitudinal position and at the first angular position;

FIG. 107D depicts a partial perspective view of the distal portion of the handle assembly of FIG. 100 and the proximal portion of the shaft assembly of FIG. 100, with the knob member of FIG. 101 omitted, and with the first disposable sub-assembly of FIG. 98 at the third longitudinal position and at a second angular position;

FIG. 107E depicts a partial perspective view of the distal portion of the handle assembly of FIG. 100 and the proximal portion of the shaft assembly of FIG. 100, with the knob member of FIG. 101 omitted, and with the first disposable sub-assembly of FIG. 98 at the third longitudinal position and at a third angular position;

FIG. 108 depicts a partial exploded view of the distal portion of the shaft assembly of FIG. 100, with the first disposable sub-assembly of FIG. 98 at a distal position, and with portions of an outer tube omitted;

FIG. 109 depicts a partial view of the distal portion of the shaft assembly of FIG. 100, with the first disposable sub-assembly of FIG. 98 at a proximal position, and with portions of the outer tube omitted;

FIG. 110 depicts a perspective view of a distal inner tube member of the first disposable sub-assembly of FIG. 98;

FIG. 111 depicts another perspective view of the distal inner tube member of FIG. 110;

FIG. 112 depicts a cross-sectional view of the distal inner tube member of FIG. 110, taken along line 112-112 of FIG. 111;

FIG. 113 depicts a partial perspective view of a distal end of a proximal inner tube member of the first disposable sub-assembly of FIG. 98; and FIG. 114 depicts a partial view of the distal end of the shaft assembly of FIG. 100, with the outer tube omitted, and with the proximal inner tube member of FIG. 113 shown in broken lines.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. OVERVIEW OF EXEMPLARY ULTRASONIC SURGICAL INSTRUMENT

Figure 1:
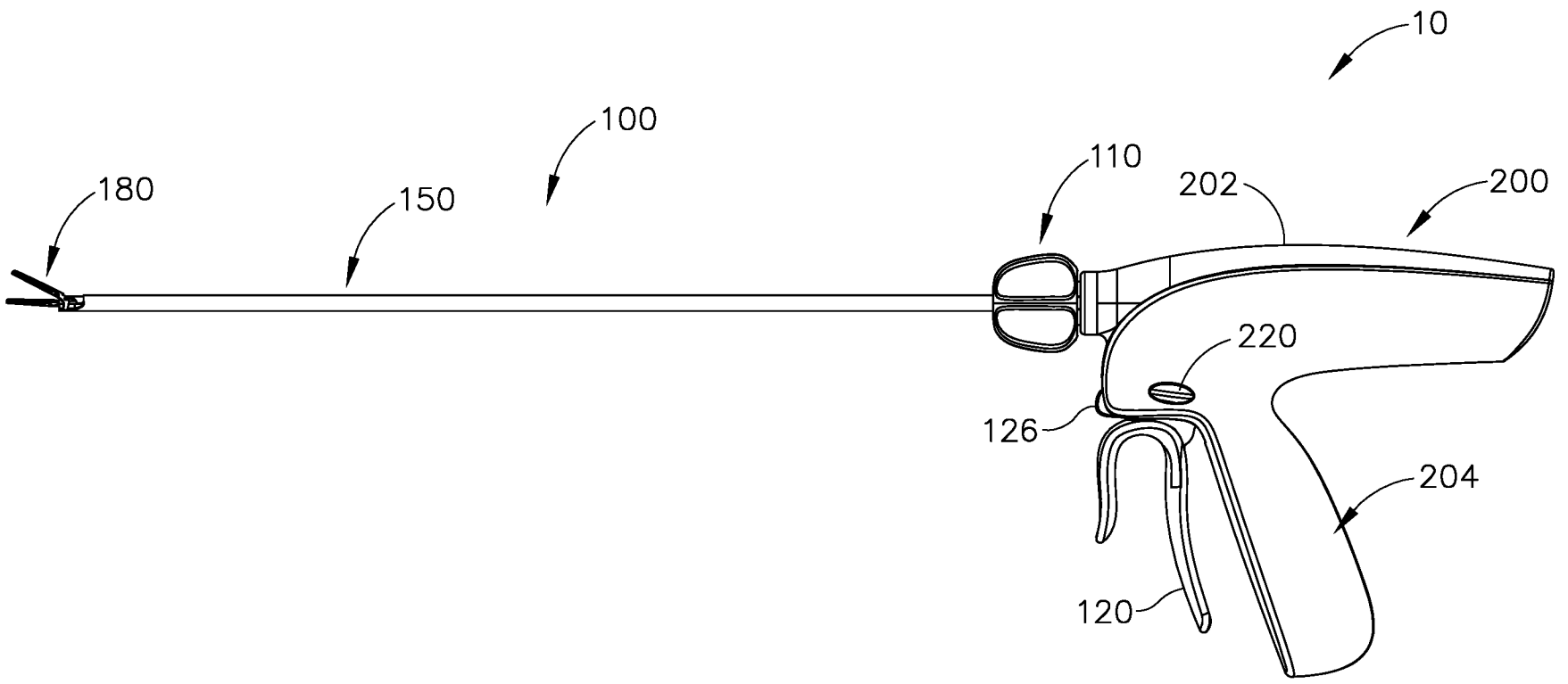
FIG. 1 depicts a side elevational view of an exemplary ultrasonic surgical instrument.
Figure 2:

FIG. 2 depicts a perspective view of the instrument of FIG. 1.
Figure 3:
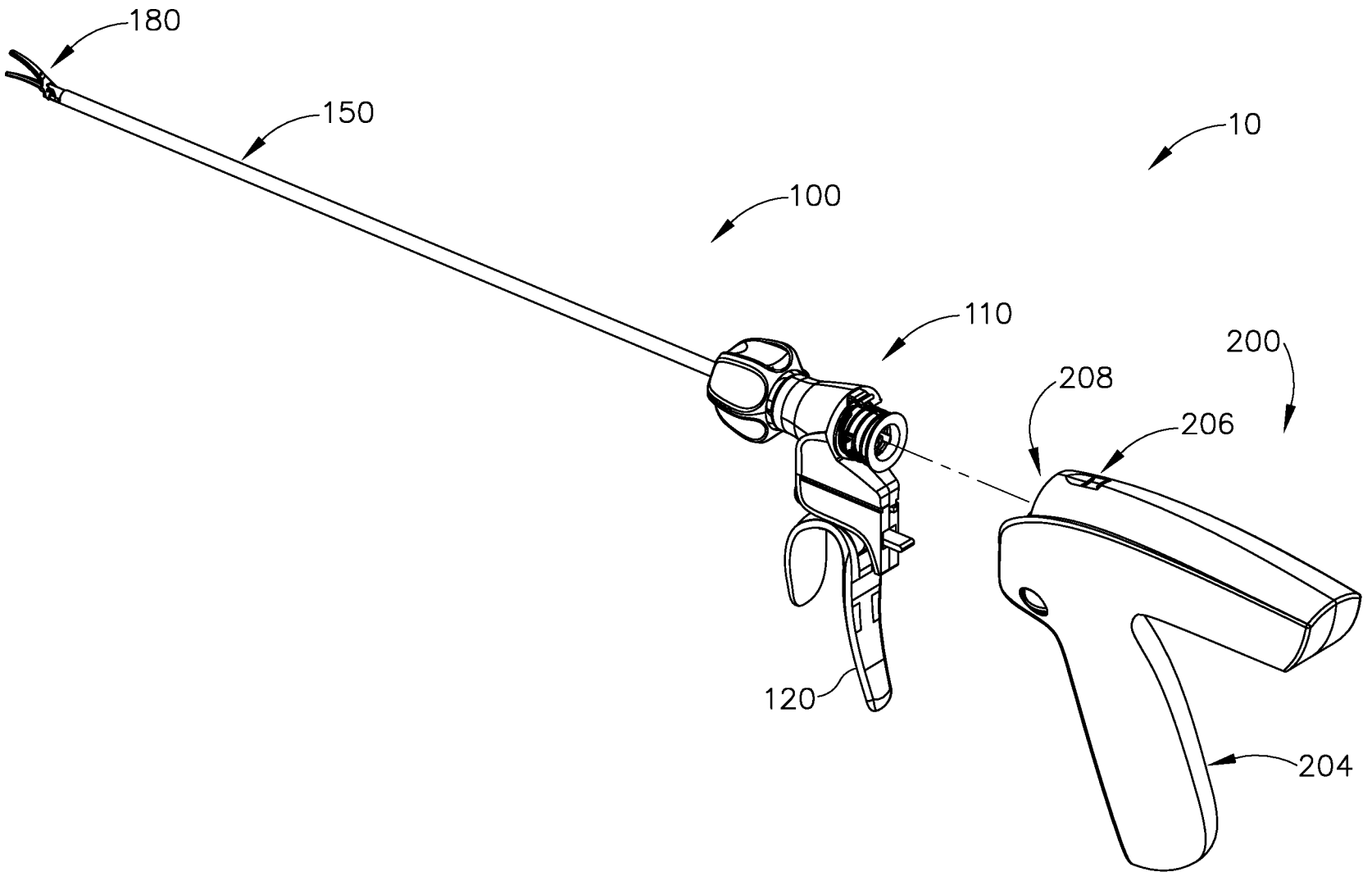
FIG. 3 depicts a perspective view of the instrument of FIG. 1, with a disposable portion separated from a reusable portion.
Figure 4:
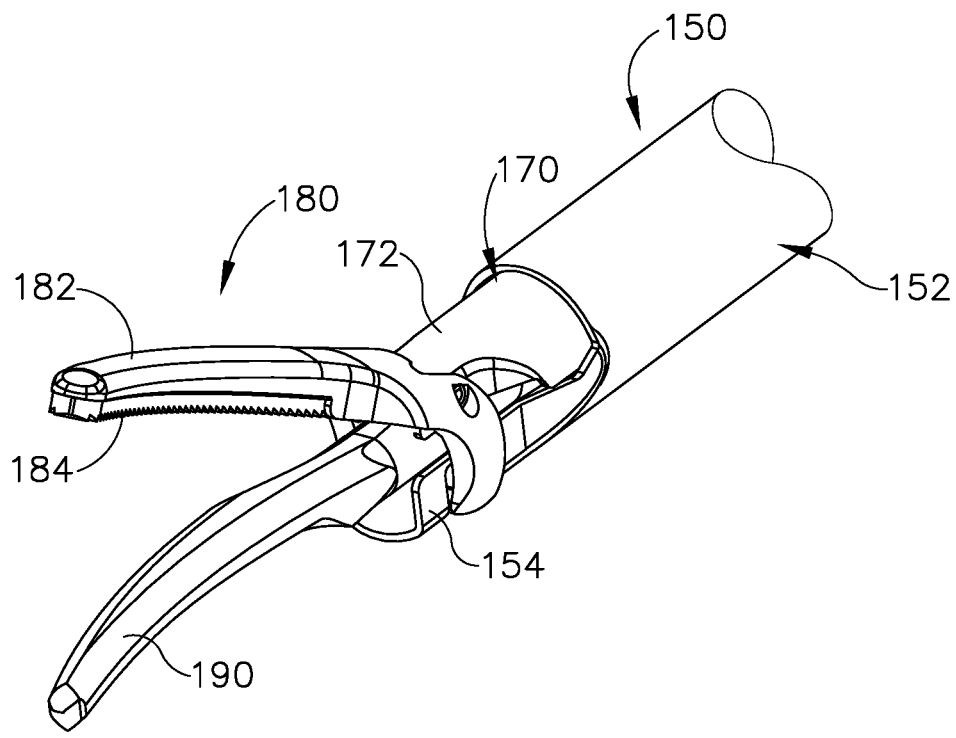
FIG. 4 depicts a perspective view of an end effector of the instrument of FIG. 1, in an open configuration.

FIGS. 1-3 show an exemplary ultrasonic surgical instrument (10) that is configured to be used in minimally invasive surgical procedures (e.g., via a trocar or other small diameter access port, etc.). As will be described in greater detail below, instrument (10) is operable to cut tissue and seal or weld tissue (e.g., a blood vessel, etc.) substantially simultaneously. Instrument (10) of this example comprises a disposable assembly (100) and a reusable assembly (200). The distal portion of reusable assembly (200) is configured to removably receive the proximal portion of disposable assembly (100), as seen in FIGS. 2-3, to form instrument (10).

In an exemplary use, assemblies (100, 200) are coupled together to form instrument (10) before a surgical procedure, the assembled instrument (10) is used to perform the surgical procedure, and then assemblies (100, 200) are decoupled from each other for further processing. In some instances, after the surgical procedure is complete, disposable assembly (100) is immediately disposed of while reusable assembly (200) is sterilized and otherwise processed for re-use. By way of example only, reusable assembly (200) may be sterilized in a conventional relatively low temperature, relatively low pressure, hydrogen peroxide sterilization process. Alternatively, reusable assembly (200) may be sterilized using any other suitable systems and techniques (e.g., autoclave, etc.). In some versions, reusable assembly (200) may be sterilized and reused approximately 100 times. Alternatively, reusable assembly (200) may be subject to any other suitable life cycle. For instance, reusable assembly (200) may be disposed of after a single use, if desired. While disposable assembly (100) is referred to herein as being "disposable," it should be understood that, in some instances, disposable assembly (100) may also be sterilized and otherwise processed for re-use. By way of example only, disposable assembly (100) may be sterilized and reused approximately 2-30 times, using any suitable systems and techniques. Alternatively, disposable assembly (100) may be subject to any other suitable life cycle.

In some versions, disposable assembly (100) and/or reusable assembly (200) includes one or more features that are operable to track usage of the corresponding assembly (100, 200), and selectively restrict operability of the corresponding assembly (100, 200) based on use. For instance, disposable assembly (100) and/or reusable assembly (200) may include one or more counting sensors and a control logic (e.g., microprocessor, etc.) that is in communication with the counting sensor(s). The counting sensor(s) may be able to detect the number of times the ultrasonic transducer of instrument (10) is activated, the number of surgical procedures the corresponding assembly (100, 200) is used in, the number of trigger closures, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (100, 200). In instances where the control logic stores two or more threshold values (e.g., a first threshold for number of activations and a second threshold for number of surgical procedures, etc.), the control logic may disable operability of one or more components in the corresponding assembly (100, 200) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10).

Figure 7:
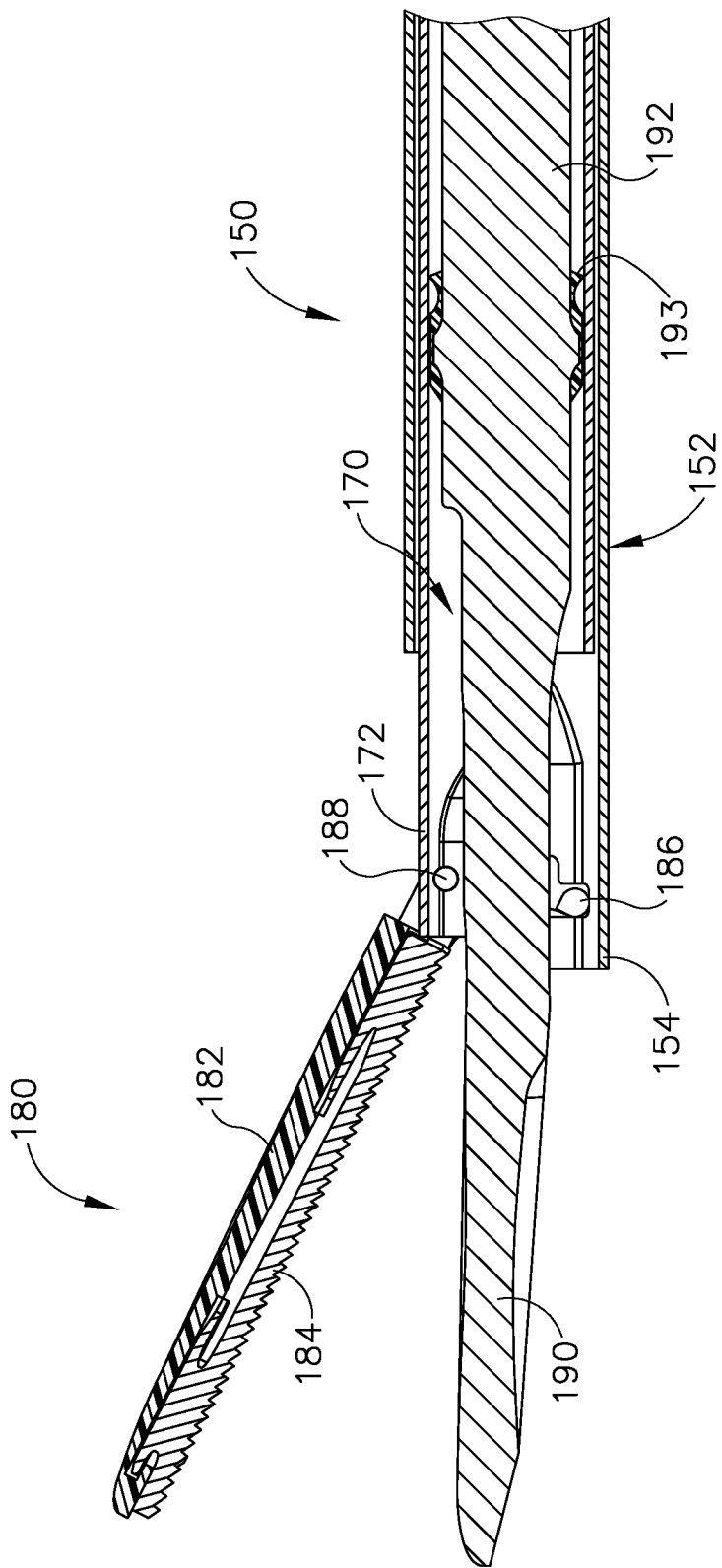
FIG. 7 depicts a side cross-sectional view of the end effector of FIG. 4, in the open configuration.
Figure 8:
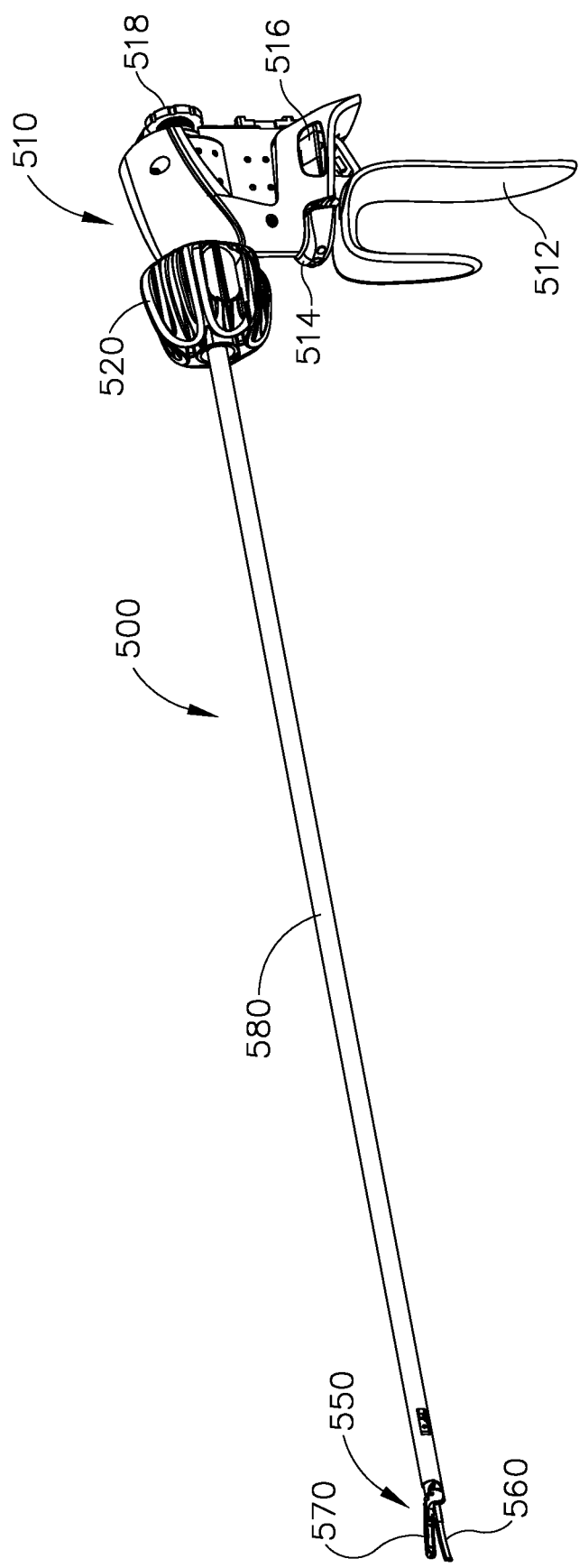
FIG. 8 depicts a perspective view of an exemplary alternative disposable portion of an ultrasonic surgical instrument that may be used with a variation of the reusable portion of the instrument of FIG. 1.
Figure 9:
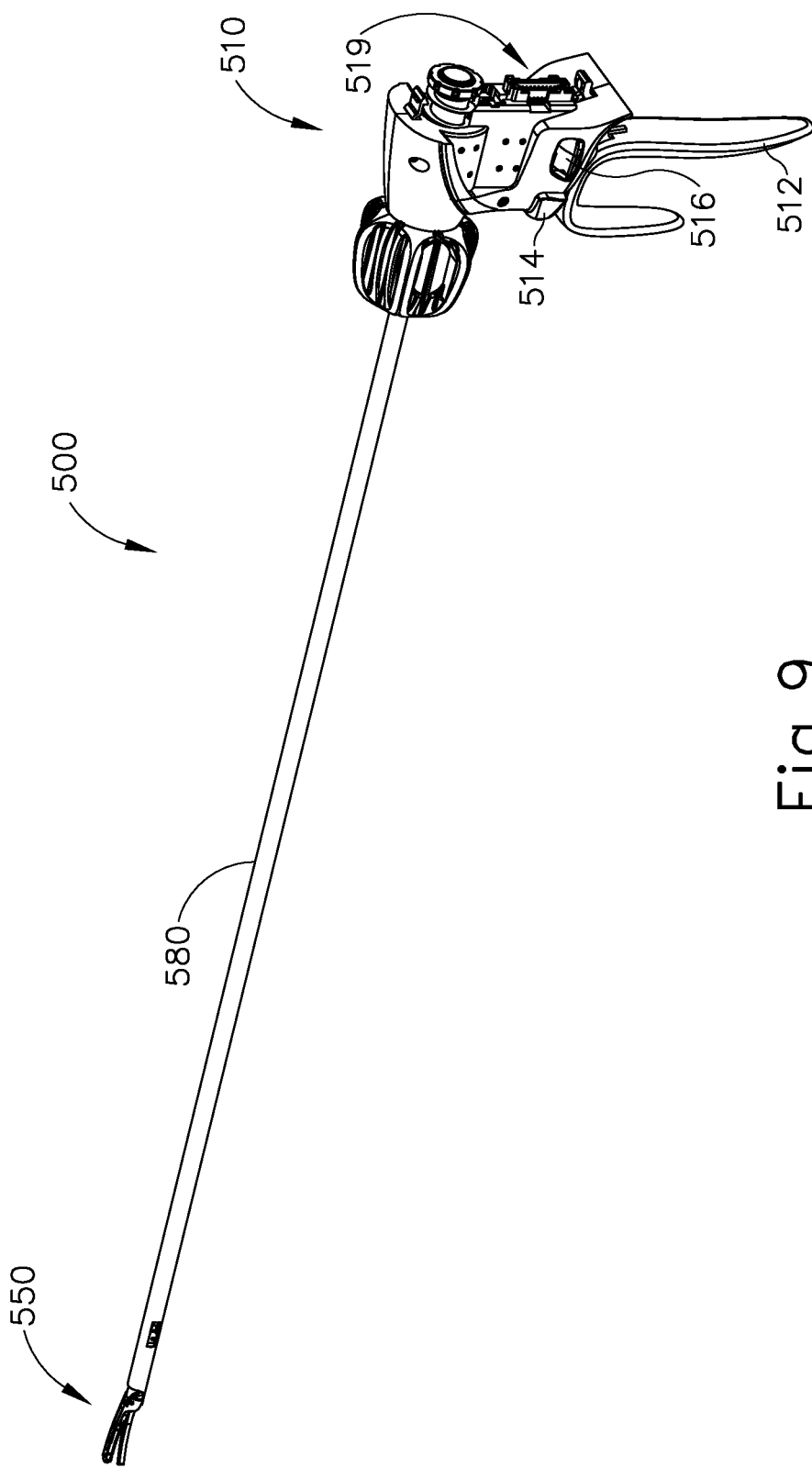
FIG. 9 depicts another perspective view of the disposable portion of FIG. 8.
Figure 10A:
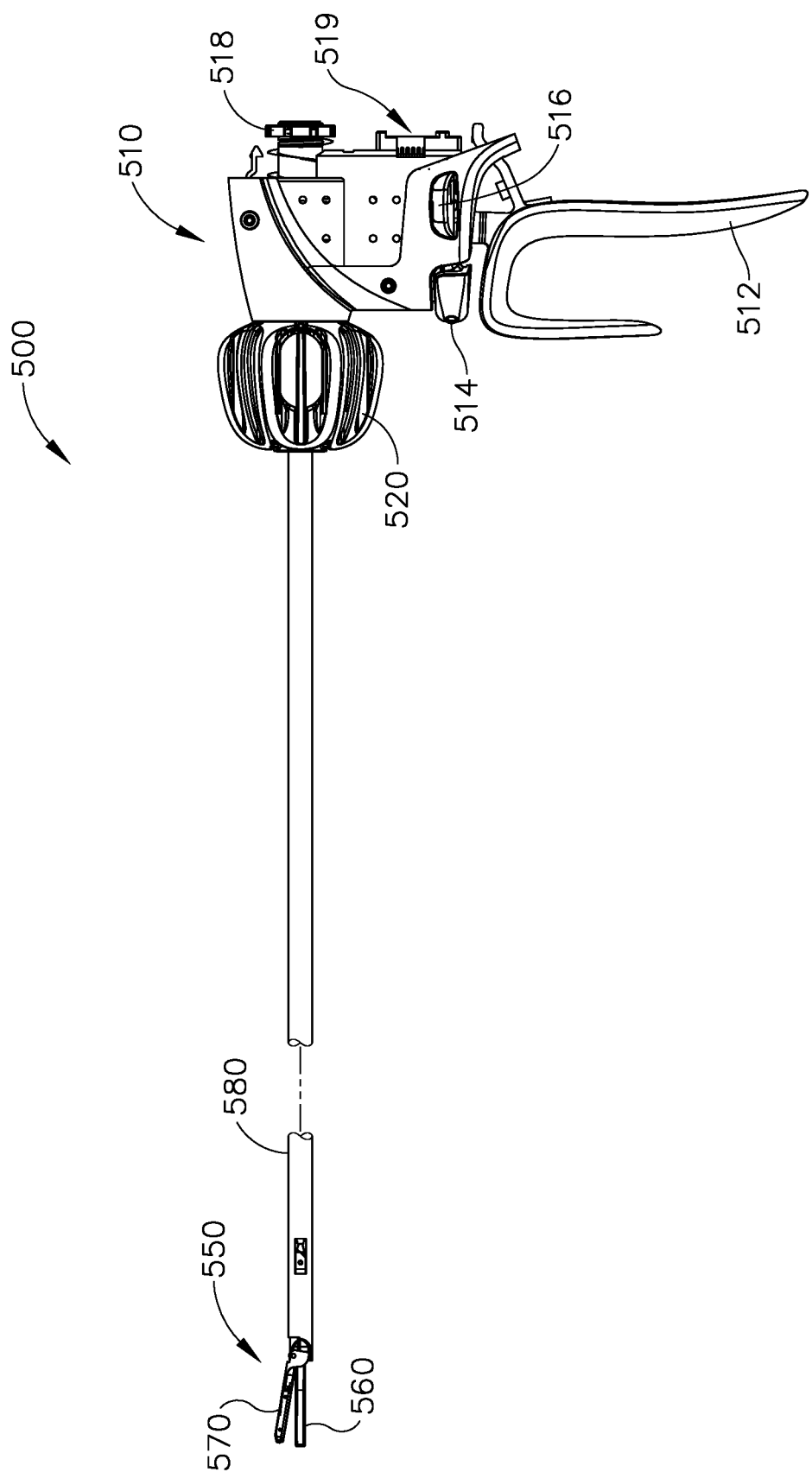
FIG. 10A depicts a side elevational view of the disposable portion of FIG. 8, with a portion of the shaft assembly omitted, and with the end effector in an open configuration.
Figure 10B:
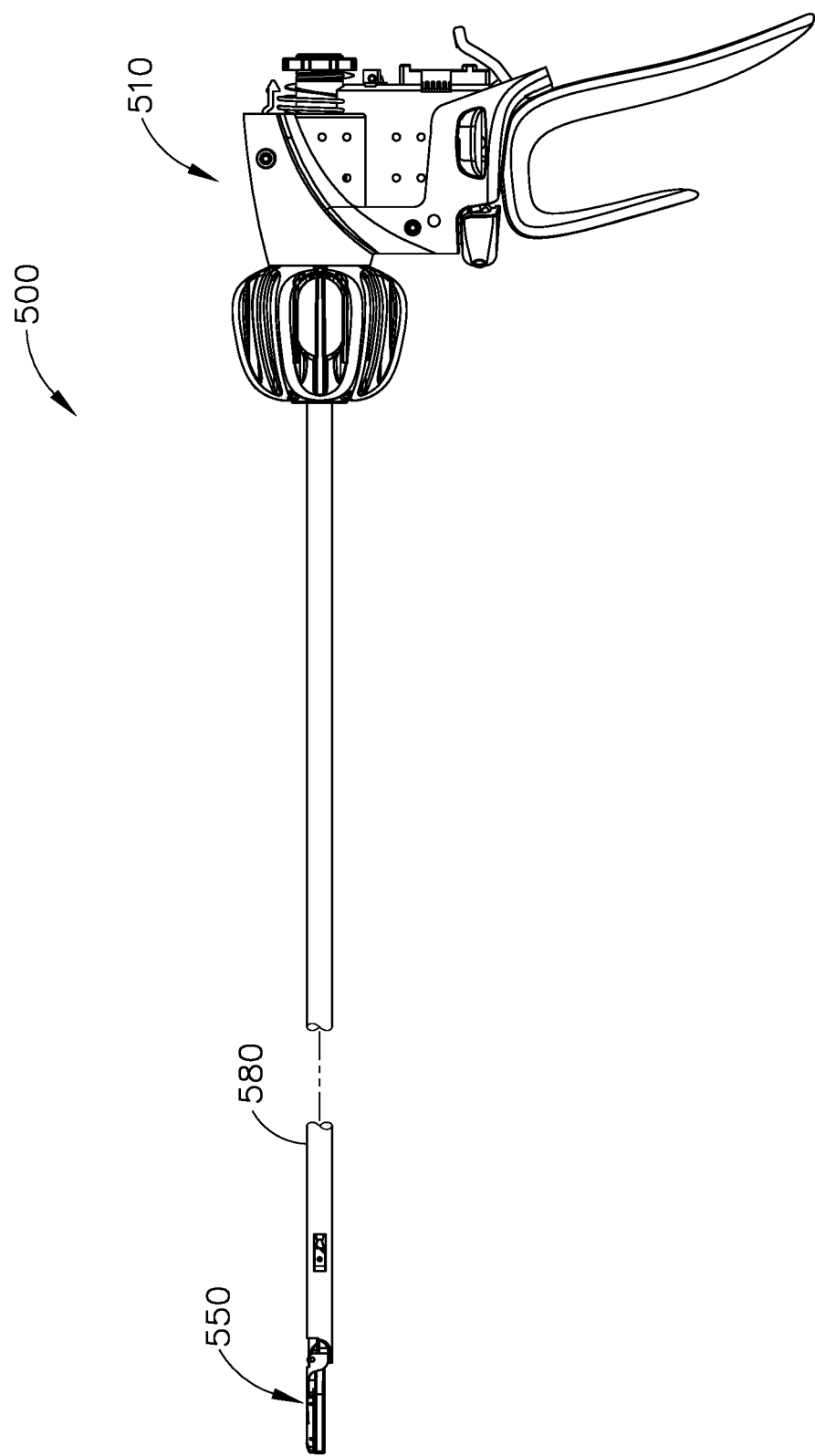
FIG. 10B depicts a side elevational view of the disposable portion of FIG. 8, with a portion of the shaft assembly omitted, and with the end effector in a closed configuration.

Disposable assembly (100) of the present example comprises a body portion (110), a shaft assembly (150) extending distally from body portion (110), and an end effector (180) located at the distal end of shaft assembly (150). As best seen in FIGS. 4-7, end effector (180) of this example comprises a clamp arm (182) and an ultrasonic blade (190). Clamp arm (182) includes a clamp pad (184), which faces blade (190). As shown in FIGS. 6A-6B and as will be described in greater detail below, clamp arm (182) is pivotable toward and away from blade (190) to selectively compress tissue between clamp pad (184) and blade (190). As seen in FIG. 7, blade (190) is an integral feature of the distal end of an acoustic waveguide (192), which extends coaxially through tubes (152, 170), and which is configured to communicate ultrasonic vibrations to blade (190) as will be described in greater detail below.

Figure 5:
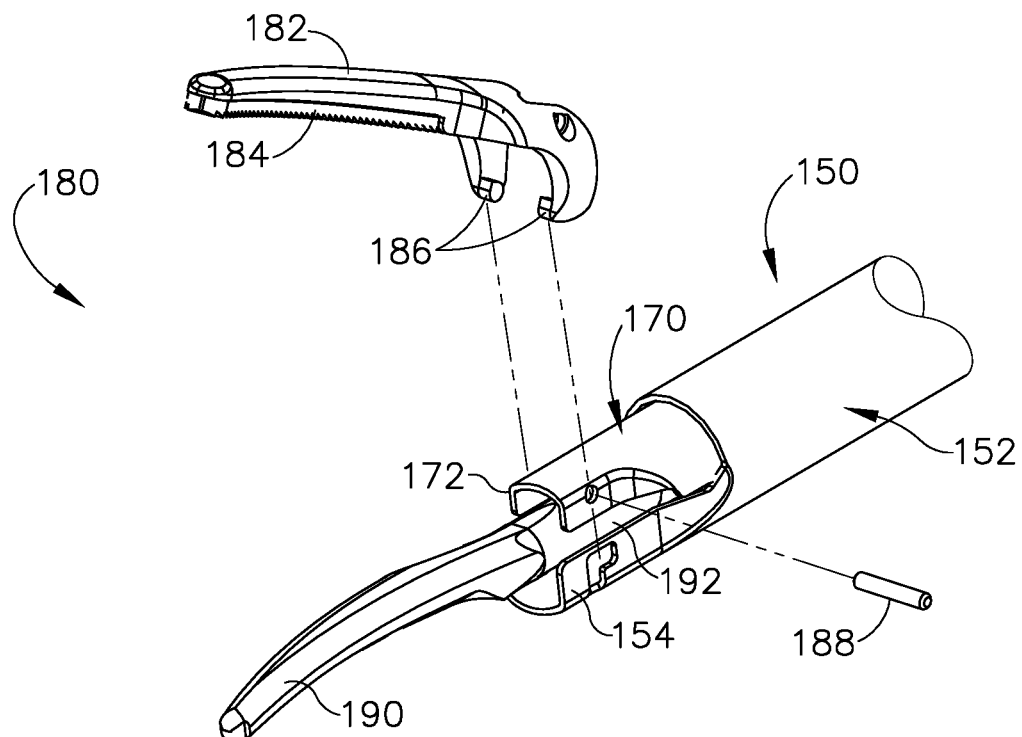
FIG. 5 depicts a partially exploded view of the end effector of FIG. 4.

Shaft assembly (150) comprises an outer tube (152) and an inner tube (170). Outer tube (152) is operable to translate longitudinally relative to inner tube (170) to selectively pivot clamp arm (182) toward and away from blade (190). To accomplish this, and as best seen in FIGS. 5 and 7, integral pin features (186) of clamp arm (182) pivotally secure a first portion of clamp arm (182) to a distally projecting tongue (154) of outer tube (152); while an inserted pin (188) pivotally secures a second portion of clamp arm (182) to a distally projecting tongue (172) of inner tube (170). Thus, as can be seen in the transition from FIG. 6A to FIG. 6B, tubes (152, 170) cooperate to pivot clamp arm (182) toward blade (190) when outer tube (152) is retracted proximally relative to inner tube (170). It should be understood that clamp arm (182) may be pivoted back away from blade (190) (e.g., from the position shown in FIG. 6B to the position shown in FIG. 6A) by translating outer tube (152) distally relative to inner tube (170), in reverse of the operation shown in FIGS. 6A-6B. In an exemplary use, clamp arm (182) may be pivoted toward blade (190) to grasp, compress, seal, and sever tissue captured between clamp pad (184) and blade (190). Clamp arm (182) may be pivoted away from blade (190) to release tissue from between clamp pad (184) and blade (190); and/or to perform blunt dissection of tissue engaging opposing outer surfaces of clamp arm (182) and blade (190).

Reusable assembly (200) comprises various features that are operable to activate blade, including a battery and an ultrasonic transducer. Reusable assembly (200) further includes features that are operable to couple the ultrasonic transducer with waveguide to thereby couple the ultrasonic transducer with blade (190). In the present example, the distal end of blade (190) is located at a position corresponding to an anti-node associated with resonant ultrasonic vibrations communicated through waveguide (192), in order to tune the acoustic assembly to a preferred resonant frequency $f_o$ when the acoustic assembly is not loaded by tissue. When the transducer assembly is energized, the distal end of blade (190) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly of the present example is activated, these mechanical oscillations are transmitted through waveguide (192) to reach blade (190), thereby providing oscillation of blade (190) at the resonant ultrasonic frequency. Thus, when tissue is secured between blade (190) and clamp pad (184), the ultrasonic oscillation of blade (190) may simultaneously sever the tissue and denature the proteins in adjacent tissue cells, thereby providing a coagulative effect with relatively little thermal spread. In some versions, an electrical current may also be provided through blade (190) and/or clamp pad (184) to also seal the tissue.

In addition to the foregoing, disposable assembly (100) and/or reusable assembly (200) may be constructed and operable in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition, or in the alternative, disposable assembly (100) and/or reusable assembly (200) may be constructed and operable in accordance with at least some of the teachings of U.S. Pub. No. 2016/0015419, entitled "Ultrasonic Surgical Instrument with Removable Handle Assembly," published Jan. 21, 2016, issued as U.S. Pat. No. 10,349,967 on Jul. 16, 2019, the disclosure of which is incorporated by reference herein. Other suitable components, features, and operabilities that may be incorporated into disposable assembly (100) and/or reusable assembly (200) and variations thereof will be apparent to those of ordinary skill in the art in view of the teachings herein.

II. EXEMPLARY ALTERNATIVE DISPOSABLE ASSEMBLY FOR ULTRASONIC SURGICAL INSTRUMENT WITH REMOVABLE ACOUSTIC WAVEGUIDE

FIGS. 8-11 show an exemplary alternative disposable assembly (500) that may be used with a variation of reusable assembly (200). To the extent that the following discussion omits various details of disposable assembly (500), it should be understood that disposable assembly (500) may incorporate the various details described above and/or details described in any of the various references that are cited herein. Other suitable details will be apparent to those of ordinary skill in the art in view of the teachings herein.

Disposable assembly (500) of the present example comprises a first disposable sub-assembly (502) and a second disposable sub-assembly (504). Sub-assemblies (502, 504) are configured to be coupled together in order to form disposable assembly (500), which may then be coupled with a variation of reusable assembly (200) to form a complete ultrasonic surgical instrument. After the ultrasonic surgical instrument is used in a surgical procedure, disposable assembly (500) may be removed from the variation of reusable assembly (200); and then first disposable sub-assembly (502) may be removed from second disposable sub-assembly (504). In some such instances, the variation of reusable assembly (200) may be cleaned, sterilized, and re-used up to 100 times (by way of example only). First disposable sub-assembly (502) may be disposed of, such that first disposable sub-assembly (502) is only used one single time. Second disposable sub-assembly (504) may be cleaned, sterilized, and re-used between 2 to 20 times (by way of example only). Of course, these re-use scenarios are merely illustrative examples. It should nevertheless be understood that the configuration of disposable assembly (500) may minimize the amount of single-use material that is disposed of after each surgical procedure. This may reduce cost and overall waste as compared to conventional instrumentation.

A. Exemplary First Disposable Sub-Assembly

As shown in FIGS. 8-12, first disposable sub-assembly (502) of the present example comprises an outer tube (580), a clamp arm (570), and a distal inner tube member (600). Clamp arm (570) is configured to form an end effector (550) with an ultrasonic blade (560), which is part of second disposable sub-assembly (504) as will be described in greater detail below. Clamp arm (570) is pivotably coupled with outer tube (580) and with distal inner tube member (600). Outer tube (580) is configured to translate longitudinally while distal inner tube member (600) remains stationary, which drives clamp arm (570) to pivot between an open position (FIG. 10A) and a closed position (FIG. 10B). In the closed position, clamp arm (570) is operable to clamp tissue against blade (560), which may then be ultrasonically activated to sever and/or seal the tissue as described herein and in various references cited herein.

Figure 12:
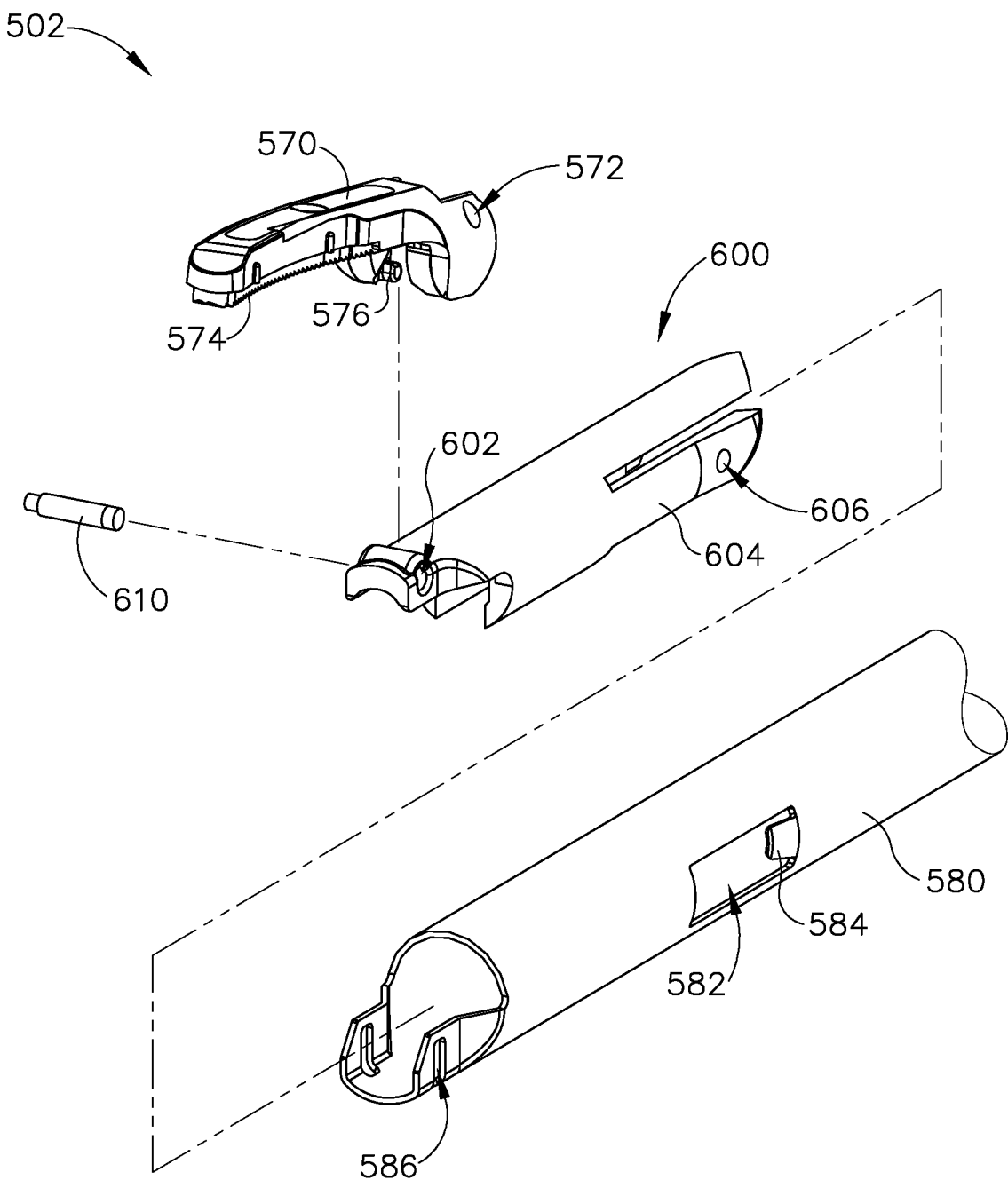
FIG. 12 depicts an exploded view of the distal end of the first disposable sub-assembly of FIG. 11.
Figure 13:
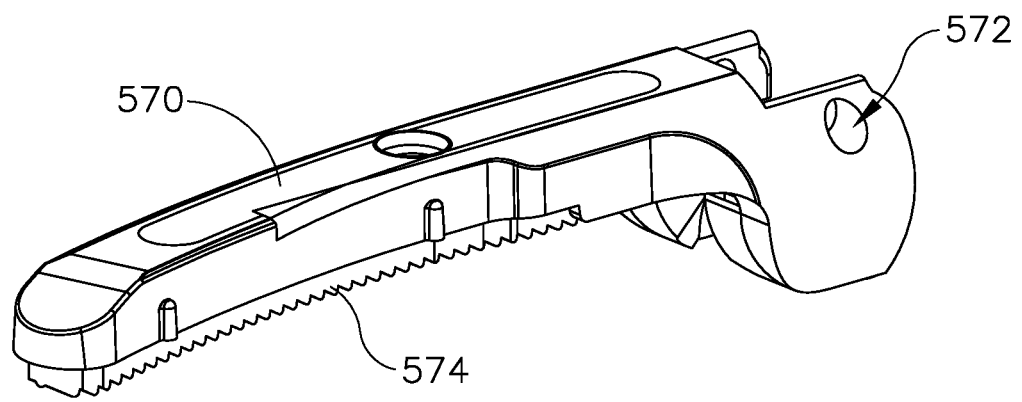
FIG. 13 depicts a perspective view of a clamp arm of the first disposable sub-assembly of FIG. 11.
Figure 14:
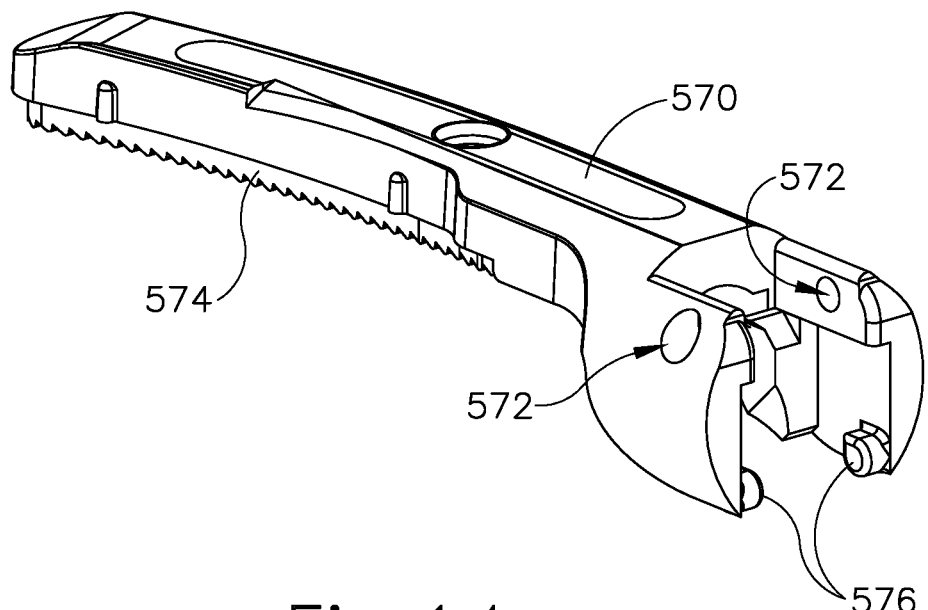
FIG. 14 depicts another perspective view of the clamp arm of FIG. 13.

As shown in FIGS. 12-14, clamp arm (570) of the present example comprises a pair of pin openings (572), a clamp pad (574), and a pair of pivot studs (576). Pin openings (572) are configured to receive a pin (610), which is also disposed in a pin opening (602) of distal inner tube member (600). Clamp pad (574) of the present example comprises polytetrafluoroethylene (PTFE) and includes surface features (e.g., teeth or ridges, etc.) that are configured to promote gripping of tissue. Various suitable materials and configurations that may be used to form clamp pad (574) will be apparent to those of ordinary skill in the art in view of the teachings herein. Pivot studs (576) are received in openings (586) of outer tube (580). Clamp arm (570) is pivotable about axes defined by pivot studs (576) and by pin (610), which enables clamp arm (570) to transition between the open position (FIG. 10A) and the closed position (FIG. 10B) in response to translation of outer tube (580) relative to distal inner tube member (600).

Figure 15:
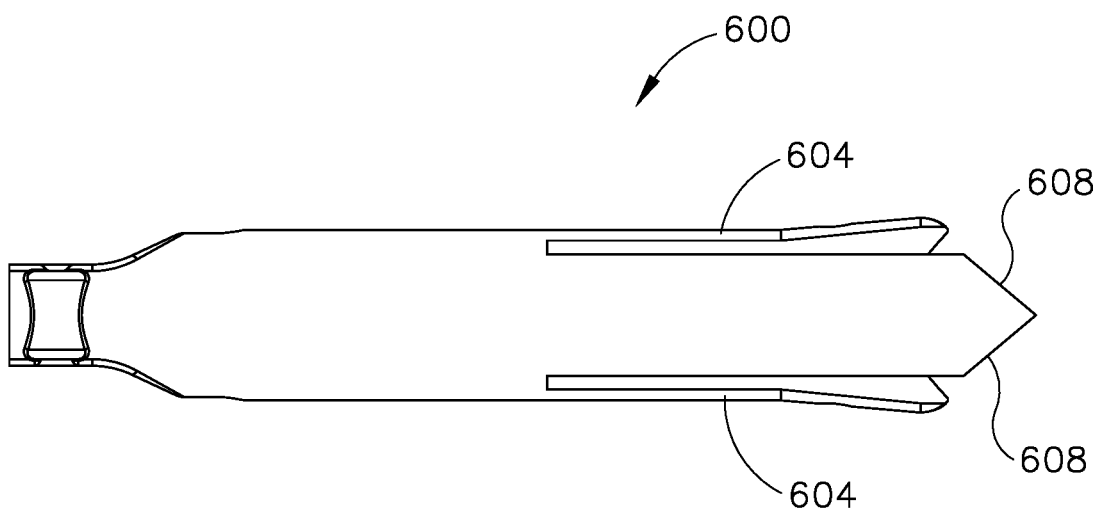
FIG. 15 depicts a top plan view of a distal inner tube member of the first disposable sub-assembly of FIG. 11.
Figure 16:
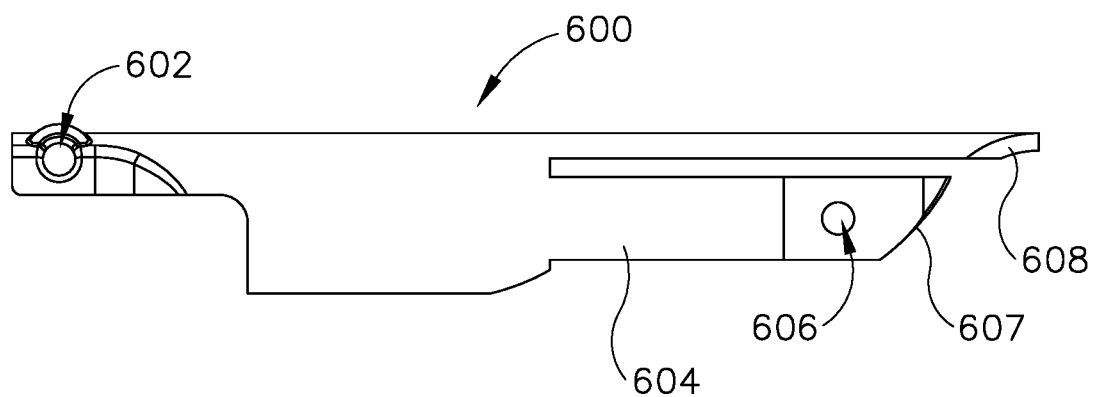
FIG. 16 depicts a side elevational view of the distal inner tube member of FIG. 15.
Figure 17:
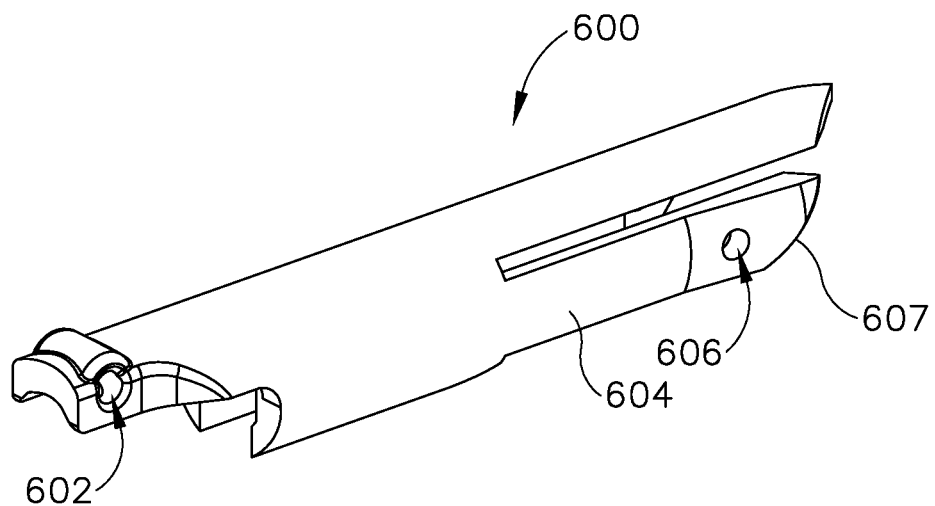
FIG. 17 depicts a perspective view of the distal inner tube member of FIG. 15.
Figure 18:
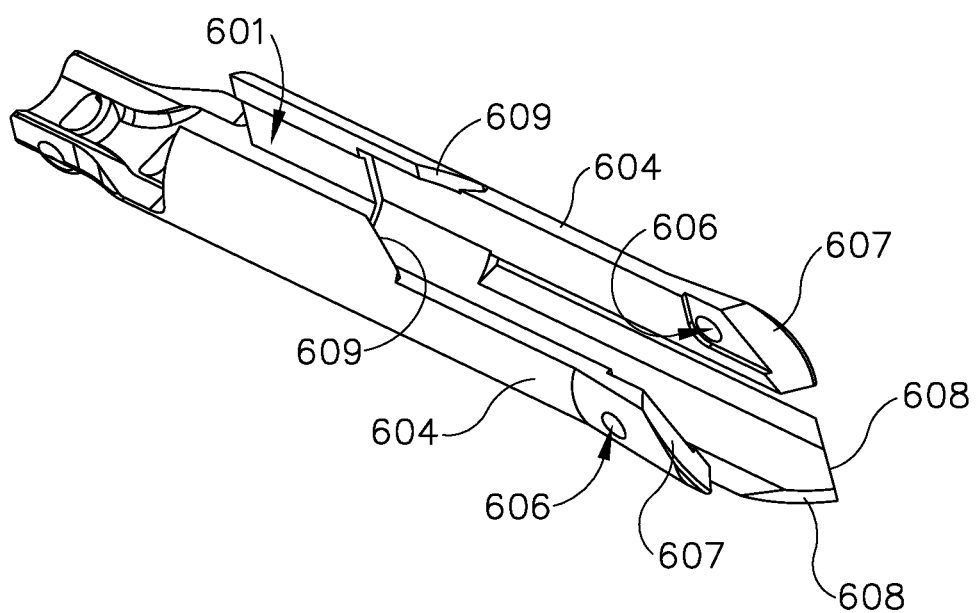
FIG. 18 depicts another perspective view of the distal inner tube member of FIG. 15.

As shown in FIGS. 12 and 15-18, distal inner tube member (600) of the present example comprises pin opening (602) and a pair of proximally projecting, resilient coupling arms (604). Each coupling arm (604) defines a laterally presented opening (606) and a proximally facing, obliquely angled bearing surface (607). As best seen in FIG. 15, each coupling arm (604) also flares outwardly. As also best seen in FIG. 16, the proximal end of distal inner tube member (600) also includes a pair of proximally facing, obliquely angled bearing surfaces (608) that converge proximally at a proximal-most point. As best seen in FIG. 18, distal inner tube member (600) further includes additional proximally facing, obliquely angled bearing surfaces (609). Bearing surfaces (607, 608, 609) are all oriented to generally provide a lead-in toward a gap (601) that is defined in the underside of distal inner tube member (600). This gap (601) is configured to accommodate longitudinal travel of the distal end of ultrasonic blade (560) during assembly of first disposable sub-assembly (502) with second disposable sub-assembly (504), as will be described in greater detail below.

As will be also described in greater detail below, distal inner tube member (600) is configured to be removably secured to a proximal inner tube member (590) during assembly of first disposable sub-assembly (502) with second disposable sub-assembly (504). This coupling provides a longitudinal mechanical grounding for distal inner tube member (600), such that distal inner tube member (600) does not translate longitudinally relative to other components of disposable assembly (500) when inner tube members (590, 600) are coupled together.

Figure 19:
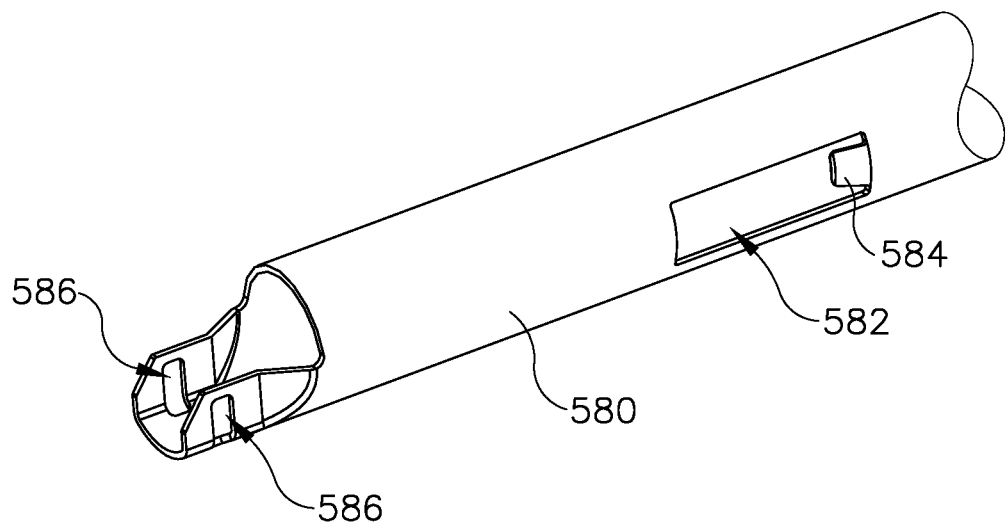
FIG. 19 depicts a perspective view of the distal end of an outer tube of the first disposable sub-assembly of FIG. 11.
Figure 20:
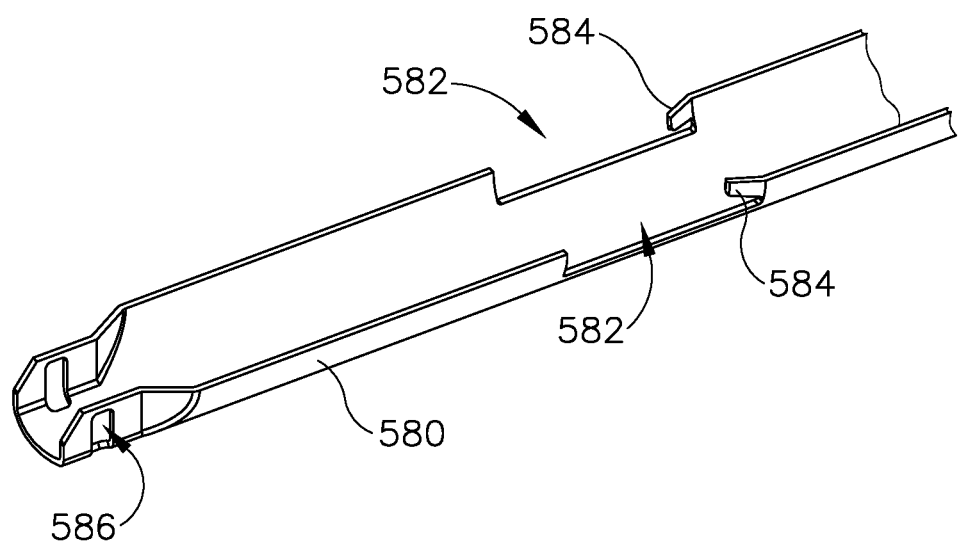
FIG. 20 depicts a cross-sectional perspective view of the distal end of the outer tube of FIG. 19.

As shown in FIGS. 12 and 19-20, the distal end of outer tube (580) of the present example comprises openings (586) that pivotably receive pivot studs (576) as noted above. The distal end of outer tube (580) further includes a pair of elongate lateral openings (582) that are located proximal to openings (586). Openings (582) are angularly offset from each other by 180° about the longitudinal axis of outer tube (580). A tab (584) is located at the proximal end of each opening (586). Each tab (584) is directed inwardly and is substantially rigid. In particular, each tab (584) is rigid enough to not deform during disassembly of first disposable sub-assembly (502) from second disposable sub-assembly (504) as will be described in greater detail below. Outer tube (580) is slidably disposed about distal inner tube member (600), such that outer tube (580) is operable to translate longitudinally relative to distal inner tube member (600).

Figure 21:
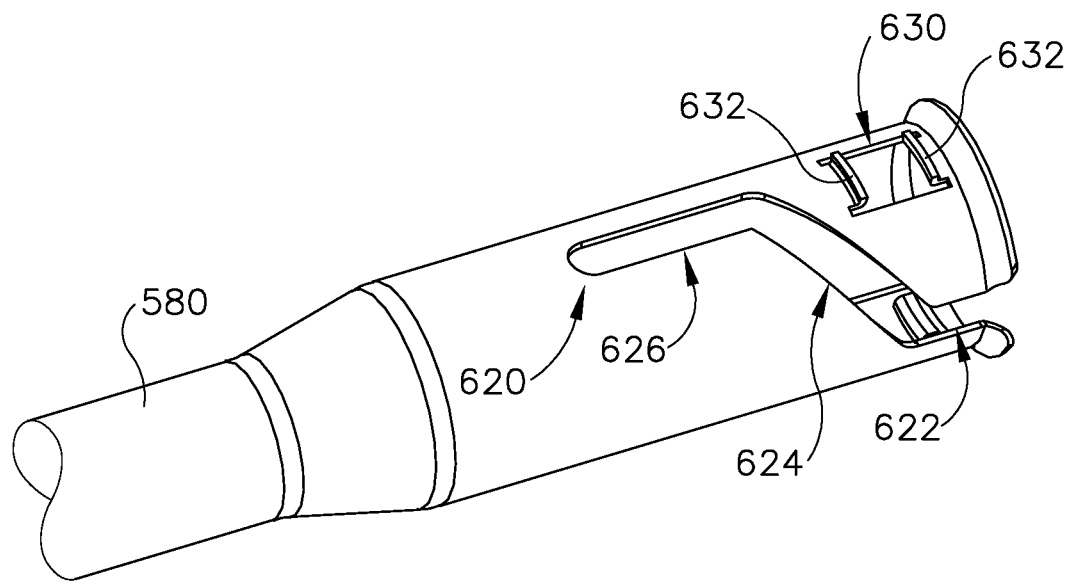
FIG. 21 depicts a perspective view of the proximal end of the outer tube of FIG. 19.
Figure 22:
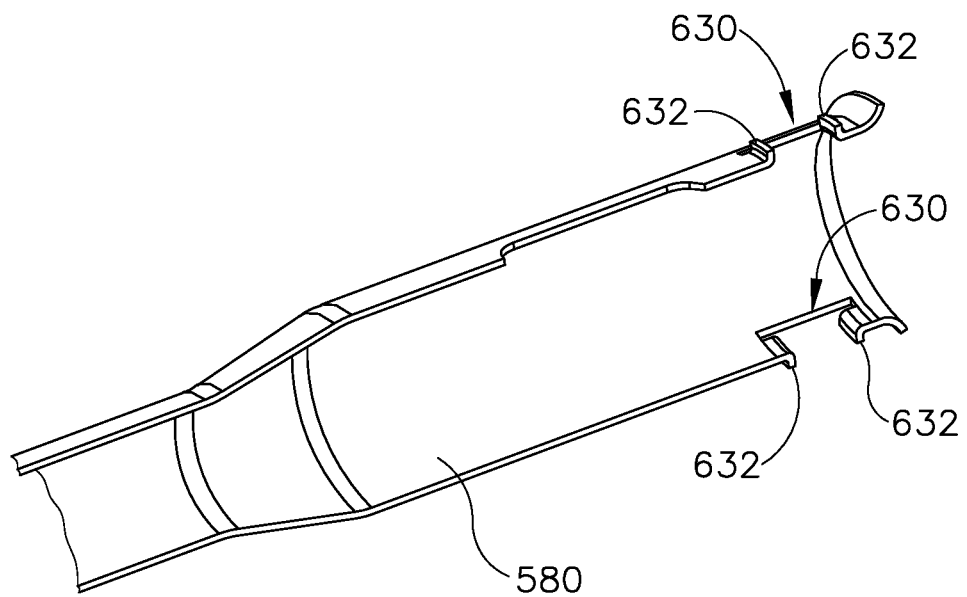
FIG. 22 depicts a cross-sectional perspective view of the proximal end of the outer tube of FIG. 19.

As shown in FIGS. 21-22, the proximal end of outer tube (580) of the present example comprises a guide slot (620) and a pair of lateral openings (630). Guide slot (620) includes a first portion (622), a second portion (624), and a third portion (626). First and third portions (622, 626) extend longitudinally while second portion (624) extends helically. First and third portions (622, 626) are angularly offset from each other by approximately 90° about the longitudinal axis of outer tube (580). Guide slot (620) thus has a dogleg configuration in the present example. Other suitable forms that guide slot (620) may take will be apparent to those of ordinary skill in the art in view of the teachings herein. Each lateral opening (630) includes a respective pair of distal and proximal flange features (632) in the present example.

As will be described in further detail below, outer tube (580) is configured to couple with a tube actuator (650) of second disposable sub-assembly (504) when first disposable sub-assembly (502) is coupled with second disposable sub-assembly (504). Tube actuator (650) is configured to drive outer tube (580) longitudinally, to thereby drive clamp arm (570) toward and away from blade (560) as described above.

B. Exemplary Second Disposable Sub-Assembly

Figure 11:
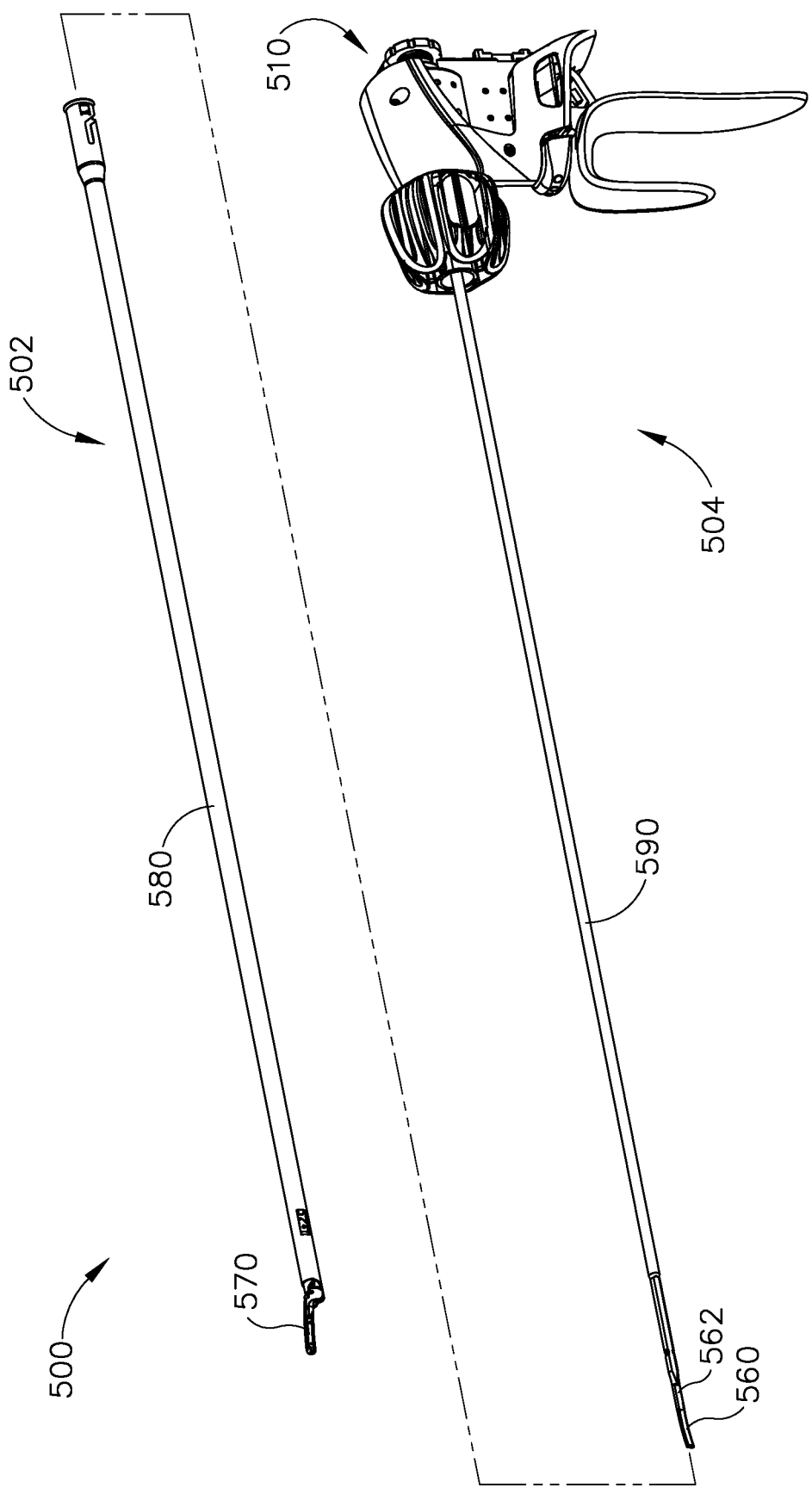
FIG. 11 depicts an exploded view of the disposable portion of FIG. 8, with a first disposable sub-assembly separated from a second disposable sub-assembly.

As shown in FIGS. 8-11, second disposable sub-assembly (504) of the present example comprises a partial handle assembly (510) having a pivoting trigger (512), a set of buttons (514, 516), a coupling feature (518), a communication feature (519), and a knob member (520). As best seen in FIG. 11 proximal inner tube member (590) extends distally from partial handle assembly (510). An acoustic waveguide (562) is coaxially disposed in proximal inner tube member (590) and distally terminates in ultrasonic blade (560). Waveguide (562) and blade (560) may be configured and operable just like waveguide (192) and blade (190) described above; and/or as described in any of the various references cited herein.

Trigger (512) is operable to drive tube actuator (650) longitudinally, to thereby drive outer tube (580) longitudinally, to thereby drive clamp arm (570) toward and away from blade (560), when first disposable sub-assembly (502) is coupled with second disposable sub-assembly (504). Structural features of tube actuator (650) will be described in greater detail below. Various suitable components that may be used to provide longitudinal movement of tube actuator (650) in response to pivotal movement of trigger (512) will be apparent to those of ordinary skill in the art in view of the teachings herein. By way of example only, trigger (512) may be operatively coupled with tube actuator (650) in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition or in the alternative, trigger (512) may be operatively coupled with tube actuator (650) in accordance with at least some of the teachings of U.S. Pub. No. 2016/0015419, entitled "Ultrasonic Surgical Instrument with Removable Handle Assembly," published Jan. 21, 2016, issued as U.S. Pat. No. 10,349,967 on Jul. 16, 2019, the disclosure of which is incorporated by reference herein.

Buttons (514, 516) are operable to activate ultrasonic blade (560). In particular, buttons (514, 516) are operable to activate the ultrasonic transducer assembly in the variation of reusable assembly (200), which in turn generates ultrasonic vibrations, which are communicated along waveguide (562) to reach blade (560). In some versions, button (514) activates ultrasonic blade (560) with ultrasonic energy at a first set of parameters (e.g., high power); while button (516) activates ultrasonic blade (560) with ultrasonic energy at a second set of parameters (e.g., low power). As another merely illustrative alternative, button (514) may activate ultrasonic blade (560) with ultrasonic energy; while button (516) activates end effector (550) to apply RF electrosurgical energy. Various suitable ways in which this may be carried out, as well as various other suitable ways in which buttons (514, 516) may be configured, arranged, and operable will be apparent to those of ordinary skill in the art in view of the teachings herein.

Coupling feature (518) is operable to couple with one or more complementary coupling features in the variation of reusable assembly (200) in accordance with at least some of the teachings of U.S. Pub. No. 2015/0245850, issued as U.S.

Pat. No. 10,010,340, and/or in accordance with at least some of the teachings of U.S. Pub. No. 2016/0015419, issued as U.S. Pat. No. 10,349,967 on Jul. 16, 2019. In addition, or in the alternative, coupling feature (518) may be actuated to transition disposable assembly (500) into a cleaning mode in accordance with at least some of the teachings of U.S. Pub. No. 2015/0245850, issued as U.S. Pat. No. 10,010,340, and/or in accordance with at least some of the teachings of U.S. Pub. No. 2016/0015419, issued as U.S. Pat. No. 10,349, 967 on Jul. 16, 2019. Various suitable components, features, and operabilities that may be incorporated into and/or otherwise associated with coupling feature (518) will be apparent to those of ordinary skill in the art in view of the teachings herein.

Communication feature (519) is operable to couple with one or more complementary coupling features in the variation of reusable assembly (200) in accordance with at least some of the teachings of U.S. Pub. No. 2015/0245850, issued as U.S. Pat. No. 10,010,340, and/or in accordance with at least some of the teachings of U.S. Pub. No. 2016/0015419, issued as U.S. Pat. No. 10,349,967 on Jul. 16, 2019. By way of example only, communication feature (519) may comprise one or more electrical contacts that are operable to provide data communication and/or other electrical related operability when coupled with one or more complementary coupling features in the variation of reusable assembly (200). By way of example only, partial handle assembly (510) may include sensors and/or various other kinds of features from which data may be provided to the variation of reusable assembly (200) via communication feature (519). Various suitable components, features, and operabilities that may be incorporated into and/or otherwise associated with communication feature (519) will be apparent to those of ordinary skill in the art in view of the teachings herein.

Figure 23:
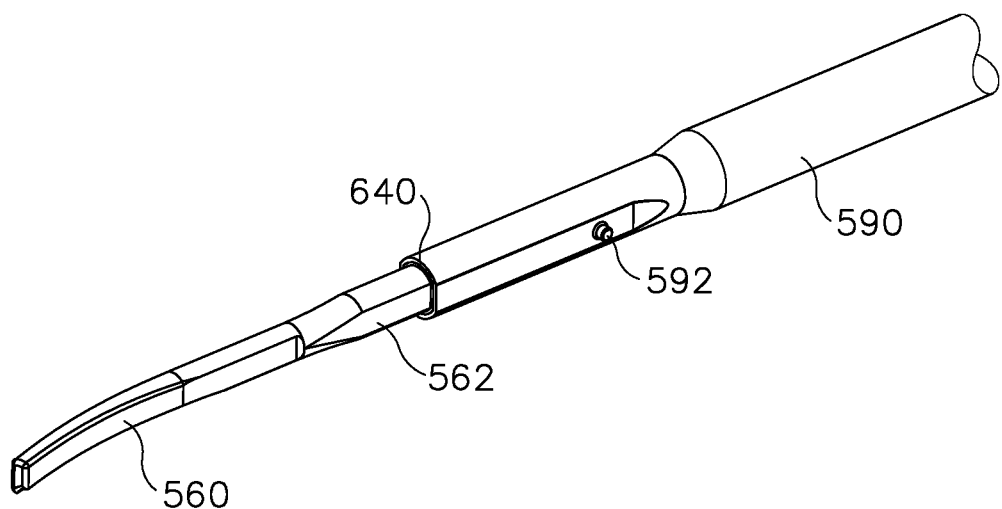
FIG. 23 depicts a perspective view of the distal end of the second disposable sub-assembly of FIG. 11.
Figure 24:
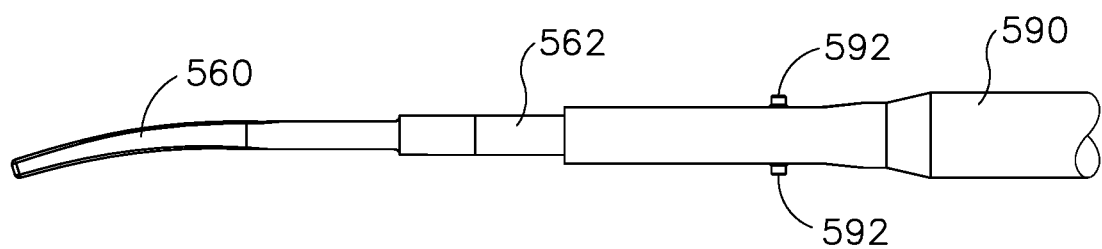
FIG. 24 depicts a top plan view of the distal end of the second disposable sub-assembly of FIG. 11.
Figure 25:
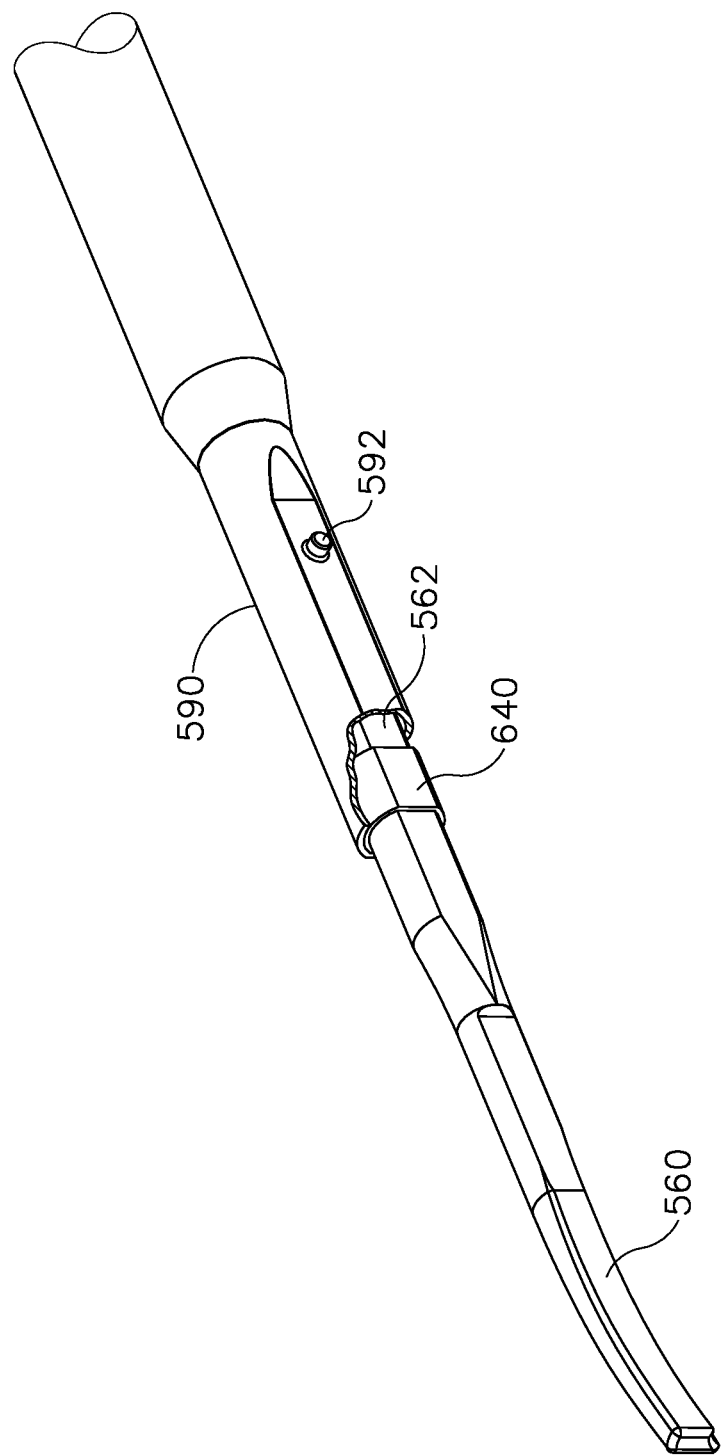
FIG. 25 depicts a perspective view of the distal end of the second disposable sub-assembly of FIG. 11, with a portion of a proximal inner tube member broken away to reveal a seal member disposed between the inner tube member and an acoustic waveguide.
Figure 26:
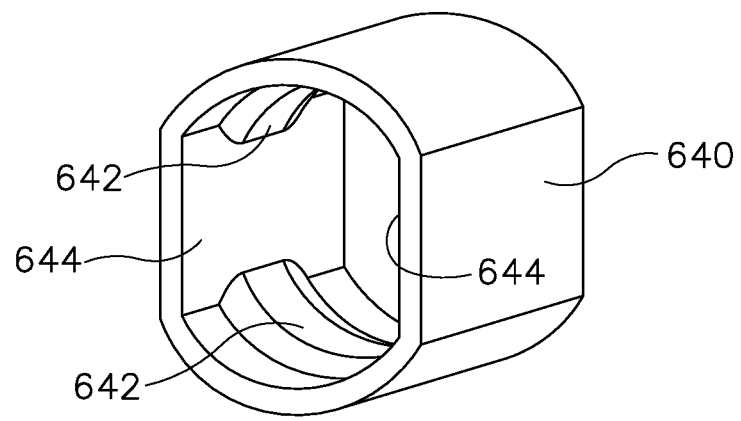
FIG. 26 depicts a perspective view of the seal member of FIG. 25.
Figure 27:
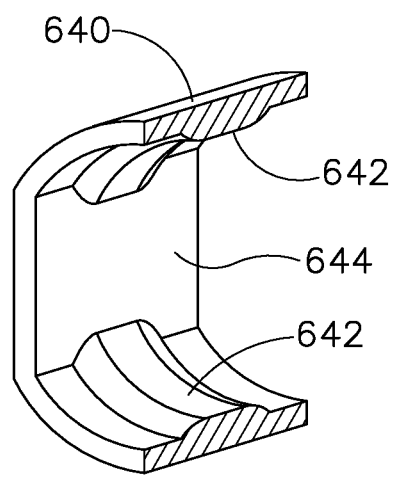
FIG. 27 depicts a cross-sectional perspective view of the seal member of FIG. 25.

As best seen in FIGS. 23-25, proximal inner tube member (590) is disposed coaxially about waveguide (562) yet is radially spaced apart from waveguide (562) such that inner tube member (590) does not contact waveguide (562). As best seen in FIG. 25, a seal member (640) is coaxially interposed between the distal end of proximal inner tube member (590) and waveguide (562). As best seen in FIGS. 26-27, seal member (640) comprises a pair of inner ridges (642) and laterally positioned flats (644) that complement flats formed in waveguide (562). Seal member (640) is formed of an elastomeric material and is located on waveguide (562) at a longitudinal position corresponding to a node associated with resonant ultrasonic vibrations communicated through waveguide (562). Seal member (640) thus provides structural support between waveguide (562) and proximal inner tube member (590) without substantially interfering with ultrasonic vibrations through waveguide (562). Seal member (640) also prevents the ingress of fluids into the gap that is defined between proximal inner tube member (590) and waveguide (562). It should be understood that a series of elastomeric members may be interposed between proximal inner tube member (590) and waveguide (562), at longitudinal positions corresponding to a nodes associated with resonant ultrasonic vibrations communicated through waveguide (562), though such elastomeric members may be configured differently from seal member (640).

Proximal inner tube member (590) also comprises a pair of integral, outwardly projecting studs (592) in this example. Studs (592) are configured to fit in openings (606) of distal inner tube member (600), to thereby couple inner tube members (590, 600) together as will be described in greater detail below.

Figure 28:
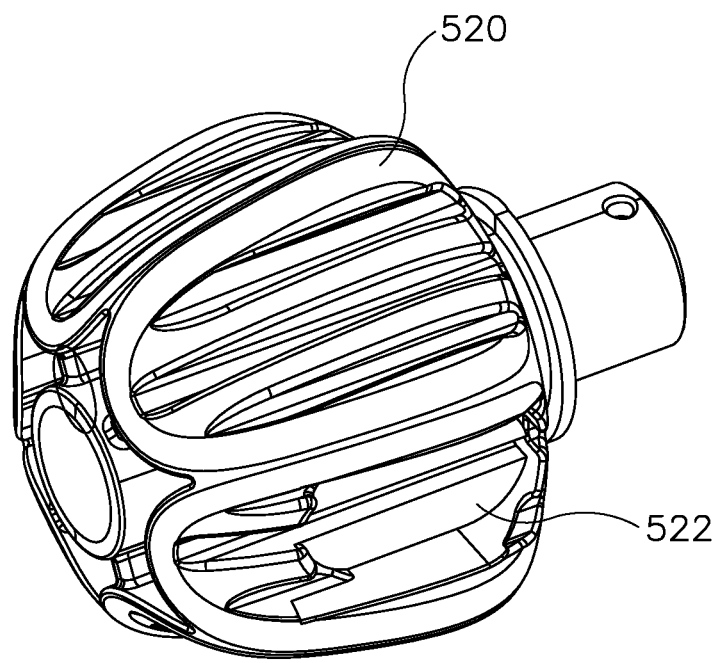
FIG. 28 depicts a perspective view of a knob member of the second disposable sub-assembly of FIG. 11.
Figure 29:
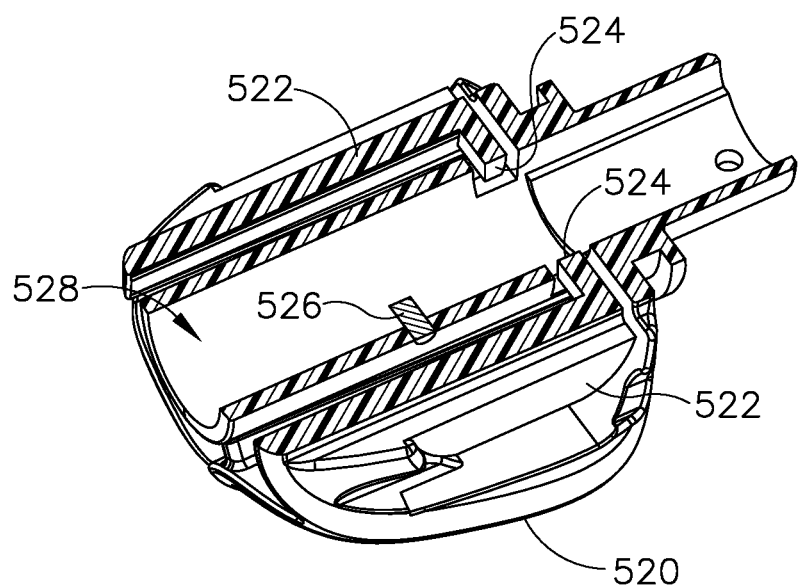
FIG. 29 depicts a cross-sectional perspective view of the knob member of FIG. 28.

Knob member (520) is operable to rotate the shaft assembly that is formed by waveguide (562), inner tube portions (590, 600), outer tube (580), and end effector (550) when first disposable sub-assembly (502) is coupled with second disposable sub-assembly (504). In particular, this shaft assembly is rotatable relative to partial handle assembly (510). As best seen in FIGS. 28-29, knob member (520) includes a pair of cantilevered buttons (522). Each cantilevered button (522) includes an inwardly projecting prong (524). Buttons (522) are operable to be pressed inwardly to thereby drive prongs (524) inwardly, though buttons (522) are resiliently biased to maintain the position of prongs (524) as shown in FIG. 29. As also seen in FIG. 29, a guide pin (526) projects inwardly within a bore (528) defined in knob member (520). Guide pin (526) is fixedly secured in knob member (520) and is configured to interact with guide slot (620) of outer tube (580) during assembly and disassembly of sub-assemblies (502, 504) as will be described in greater detail below.

Figure 30:
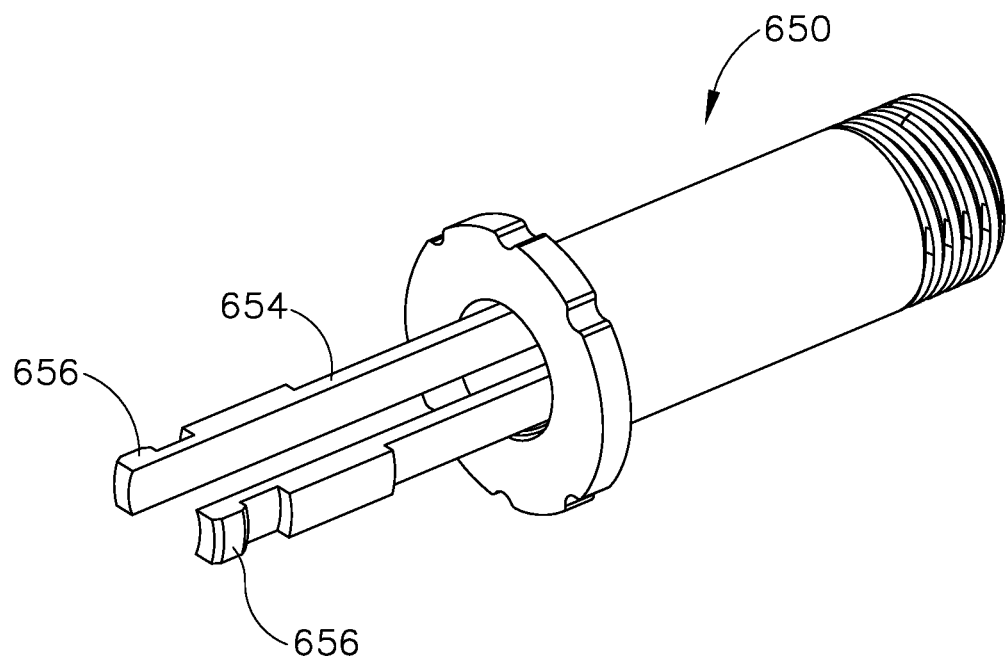
FIG. 30 depicts a perspective view of an outer tube actuator of the second disposable sub-assembly of FIG. 11.
Figure 31:
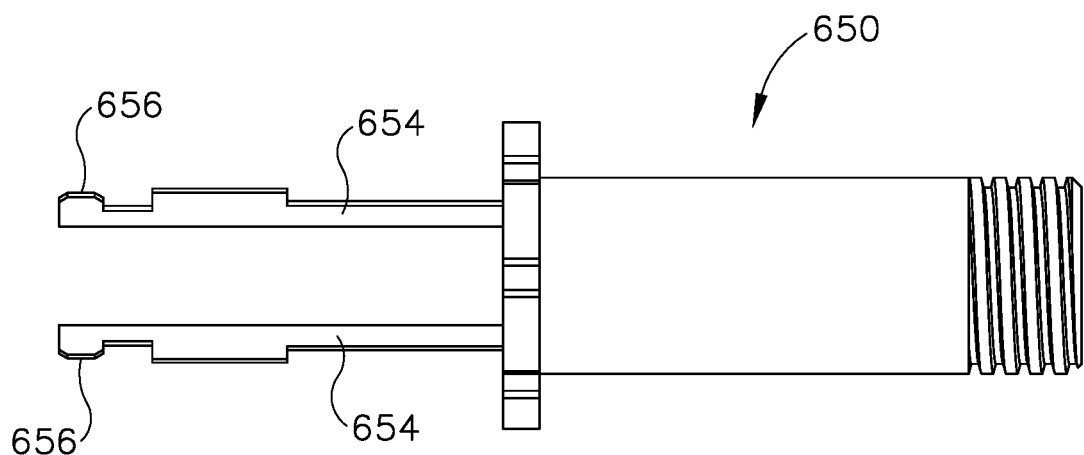
FIG. 31 depicts a top plan view of the outer tube actuator of FIG. 30.

As noted above, tube actuator (650) is configured to removably couple with outer tube (580) and thereby drive outer tube (580) longitudinally in response to pivotal motion of trigger (512). As best seen in FIGS. 30-31, tube actuator (650) comprises a pair of distally projecting arms (654). Each arm (654) includes an outwardly projecting prong (656). Each prong (656) has chamfered distal and proximal edges, which promote entry and exit of prongs (656) into and out of corresponding openings (630) of outer tube (580) during assembly and disassembly of sub-assemblies (502, 504) as will be described in greater detail below. Arms (654) are resiliently biased to assume a parallel relationship with each other as shown in FIG. 31. However, arms (654) are configured to deform inwardly to enable entry and exit of prongs (656) into and out of corresponding openings (630) of outer tube (580) during assembly and disassembly of sub-assemblies (502, 504) as will be described in greater detail below.

C. Exemplary Assembly of First Disposable Sub-Assembly with Second Disposable Sub-Assembly FIGS. 33A-34F show various stages of assembling first disposable sub-assembly (502) with second disposable sub-assembly (504). In particular, FIGS. 33A-33D show various stages occurring at the proximal end of first disposable sub-assembly (502) during a process of assembling first disposable sub-assembly (502) with second disposable sub-assembly (504); while FIGS. 34A-34F show various stages occurring at the proximal end of first disposable sub-assembly (502) during a process of assembling first disposable sub-assembly (502) with second disposable sub-assembly (504).

Figure 32:
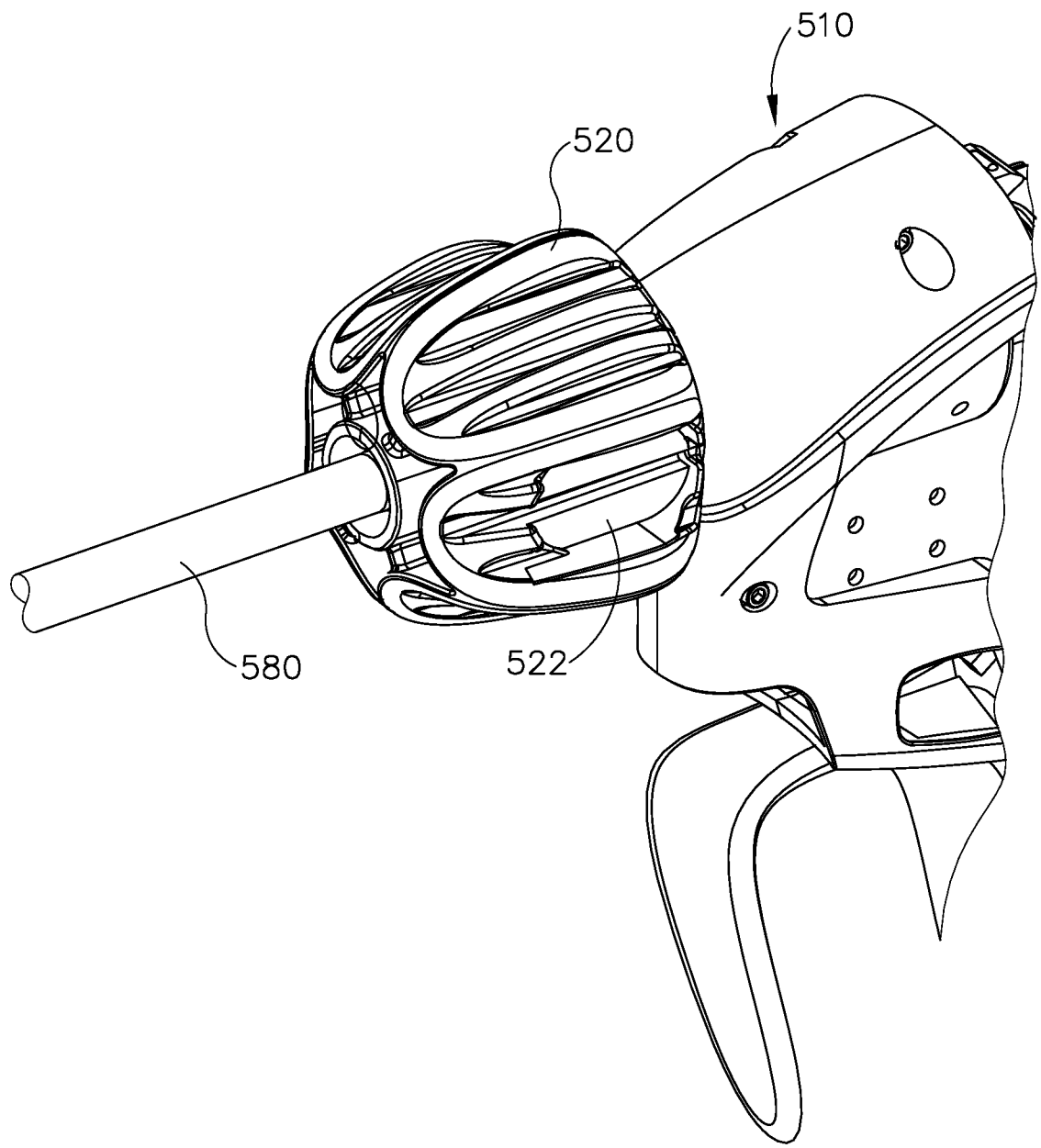
FIG. 32 depicts a partial view of the disposable portion of FIG. 8, showing the outer tube of FIG. 19 extending from the knob member of FIG. 28.
Figure 33A:
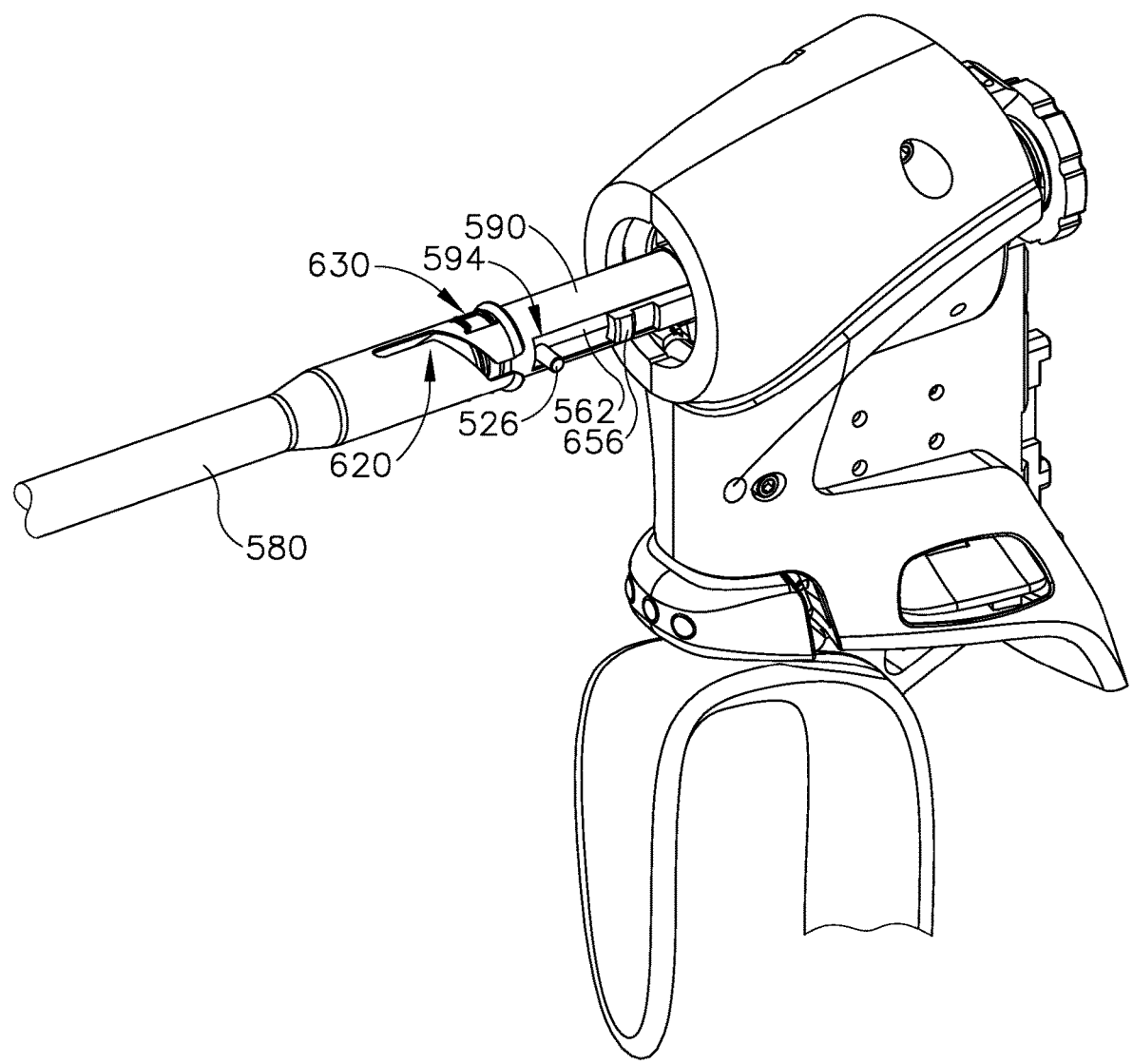
FIG. 33A depicts a partial view of the disposable portion of FIG. 8, showing the same components depicted in FIG. 32 but with the knob member omitted to reveal internal components, with the first disposable sub-assembly in a distal position before a guide slot of the outer tube has engaged a guide pin of the knob member during the process of assembly.

FIG. 32 shows the same initial stage of assembly as is shown in FIG. 33A.

However, knob member (522) is omitted from FIGS. 33A-33D in order to enable visualization of the components that would otherwise be obscured by knob member (522). It should be understood that during the process shown in FIGS. 33A-34F, an operator may grasp first disposable sub-assembly (502) in one hand, grasp second disposable sub-assembly (504) in the other hand, and then move first disposable sub-assembly (502) relative to second disposable sub-assembly (504) (while holding knob member (520) stationary) in order to accomplish the process. As shown in FIG. 33A, first disposable sub-assembly (502) is at a distal position. At this stage, the proximal end of outer tube (580) is distal to guide pin (526). It should be noted that FIG. 33A also shows how the proximal end of proximal inner tube member (590) includes longitudinally extending slots (594) that accommodates inwardly projecting features of second disposable sub-assembly (504), such as guide pin (526) and the distal ends of arms (654).

Figure 33B:
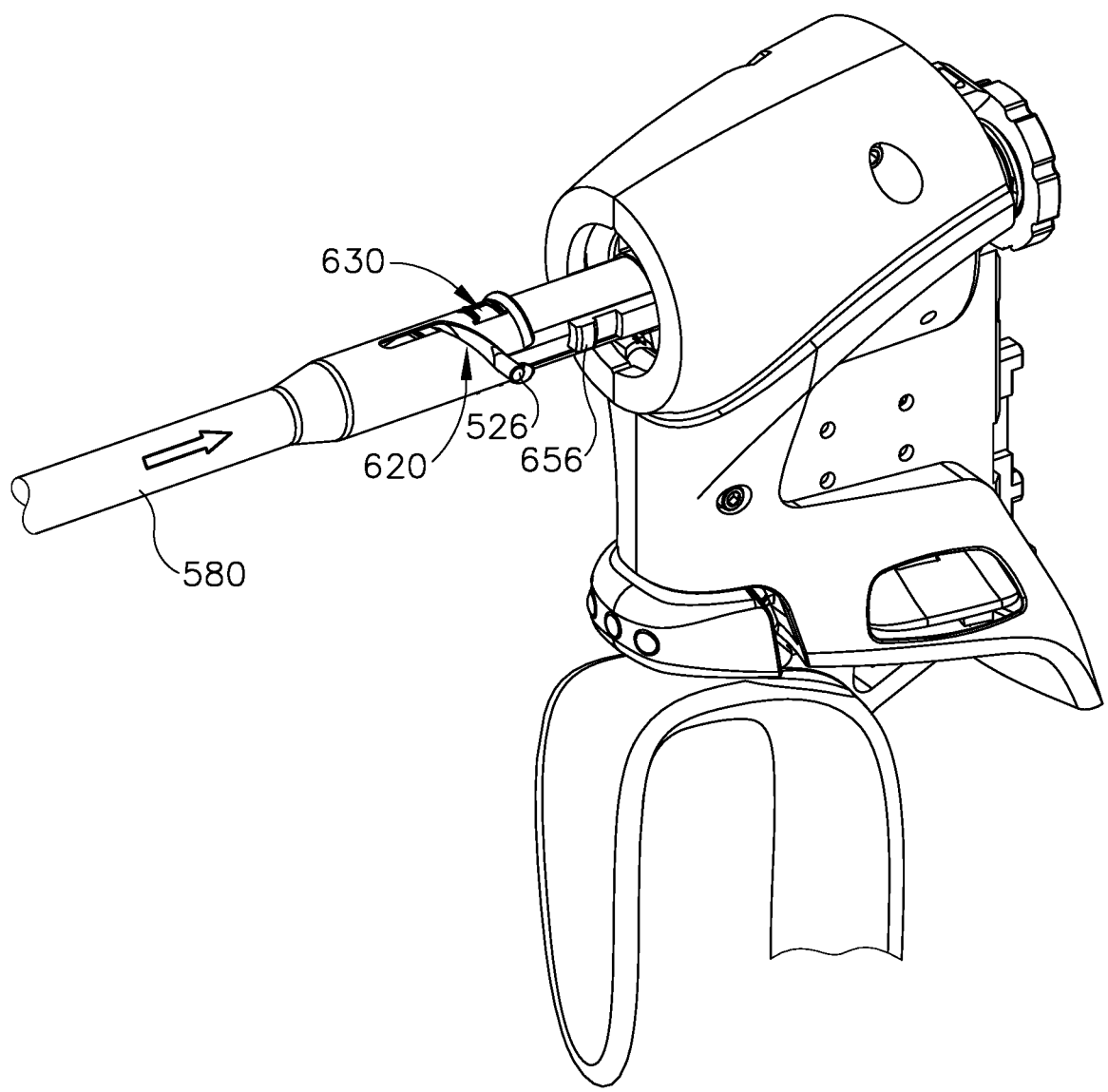
FIG. 33B depicts a partial view of the disposable portion of FIG. 8, showing the same components depicted in FIG. 32 but with the knob member omitted to reveal internal components, with the first disposable sub-assembly in a first proximal position whereby the guide pin has traversed a first portion of a guide slot in the outer tube during the process of assembly.

FIG. 33B shows a stage where first disposable sub-assembly (502) has been translated proximally to a point where guide pin (526) has traversed first portion (622) of guide channel (620) in outer tube (580). It should be understood that features at the distal ends of sub-assemblies (502, 504) may provide the angular alignment of first disposable sub-assembly (502) relative to second disposable sub-assembly (504) that would be required in order for guide pin (526) to successfully enter first portion (622) of guide channel (620) during the transition to the state shown in FIG. 33B. In particular, interaction between the distal end of blade (560) and one or more bearing surfaces (607, 608, 609) of distal inner tube member (600) may ensure that first disposable sub-assembly (502) has an appropriate angular alignment relative to second disposable sub-assembly (504) in order for guide pin (526) to successfully enter first portion (622) of guide channel (620) during the transition to the state shown in FIG. 33B. At the stage shown in FIG. 33B, openings (630) area still distal to prongs (656).

Figure 33C:
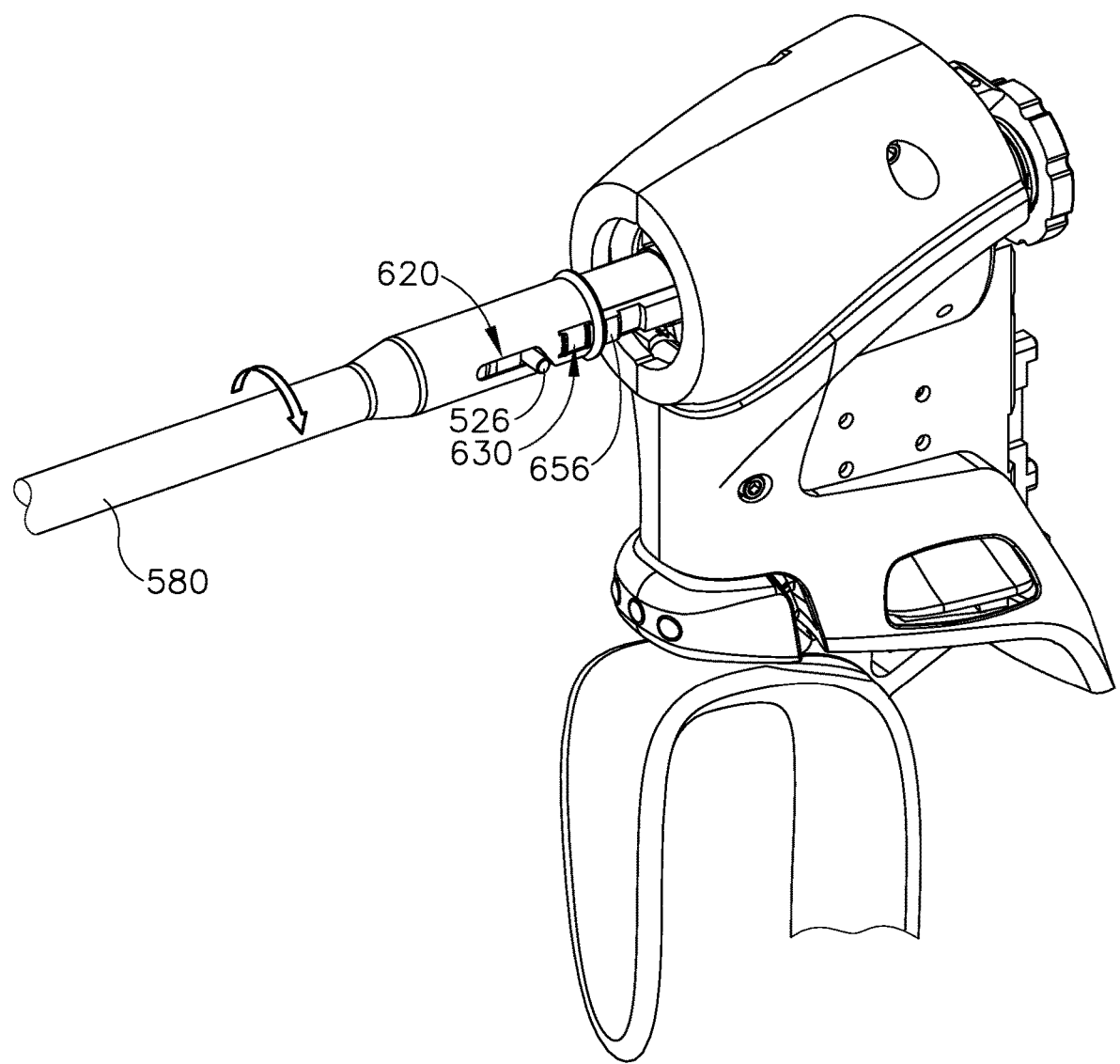
FIG. 33C depicts a partial view of the disposable portion of FIG. 8, showing the same components depicted in FIG. 32 but with the knob member omitted to reveal internal components, with the first disposable sub-assembly in a second proximal position whereby the guide pin has traversed a second portion of a guide slot in the outer tube during the process of assembly.

FIG. 33C shows a stage where first disposable sub-assembly (502) has been translated proximally and rotated about the longitudinal axis to a point where guide pin (526) has traversed second portion (624) of guide channel (620) in outer tube (580). During the transition from the state shown in FIG. 33B to the state shown in FIG. 33C, first disposable sub-assembly (502) has rotated 90° relative to second disposable sub-assembly (504), about the longitudinal axis of outer tube (580). At the stage shown in FIG. 33C, openings (630) area still distal to prongs (656). However, the flared proximal end of outer tube (580) has just engaged the distal edges of prongs (656).

Figure 33D:
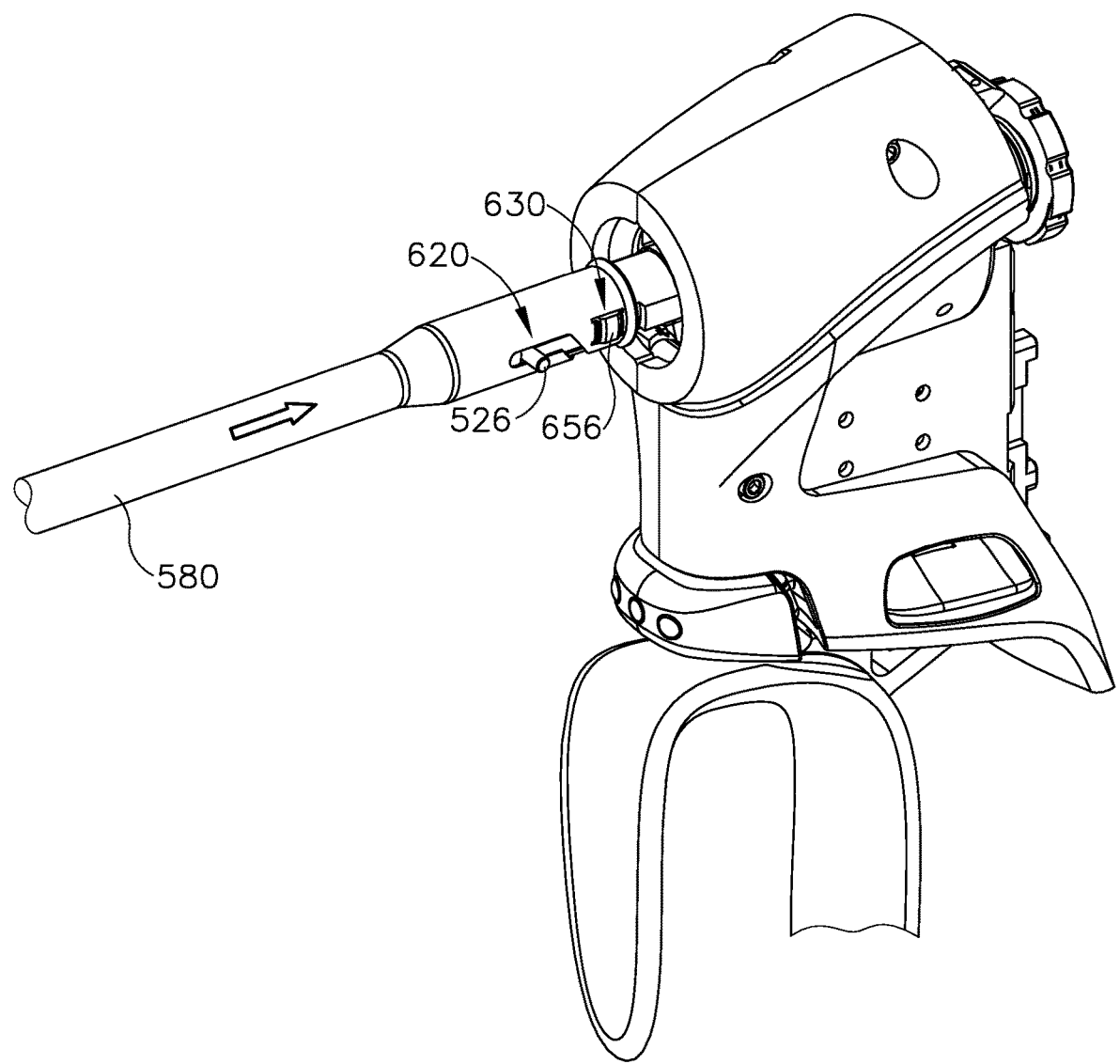
FIG. 33D depicts a partial view of the disposable portion of FIG. 8, showing the same components depicted in FIG. 32 but with the knob member omitted to reveal internal components, with the first disposable sub-assembly in a fully coupled third proximal position upon completion of the process of assembly.

FIG. 33D shows a stage where first disposable sub-assembly (502) has been translated proximally to a point where guide pin (526) has traversed third portion (626) of guide channel (620) in outer tube (580). During the transition from the state shown in FIG. 33C to the state shown in FIG. 33D, the proximal end of outer tube (580) has deflected the distal ends of arms (654) inwardly, thereby driving prongs (656) inwardly. As noted above, this deflection is accommodated by longitudinally extending slots (594) of proximal inner tube member (590). When outer tube (580) reaches the longitudinal position where prongs (656) are aligned with openings, the resilience of arms (654) drives prongs (656) outwardly such that prongs (656) snap into place in openings (630). Thus, at this stage outer tube (580) is coupled with tube actuator (650) such that outer tube (580) will translate longitudinally with tube actuator (650). Flange features (632) reinforce the coupling between prongs (656) and the edges of openings (630).

With assembly completed as shown in FIG. 33D, third portion (626) is dimensioned to enable outer tube (580) to translate relative to guide pin (526) during the translation of outer tube (580) that would be required to pivot clamp arm (570) toward and away from blade (560) as described above. Third portion (626) is also dimensioned to provide enough clearance for knob member (520) and guide pin (526) to be translated distally relative to outer tube (580) to initiate disassembly of first disposable sub-assembly (502) from second disposable sub-assembly (504) as described in greater detail below.

Figure 34A:
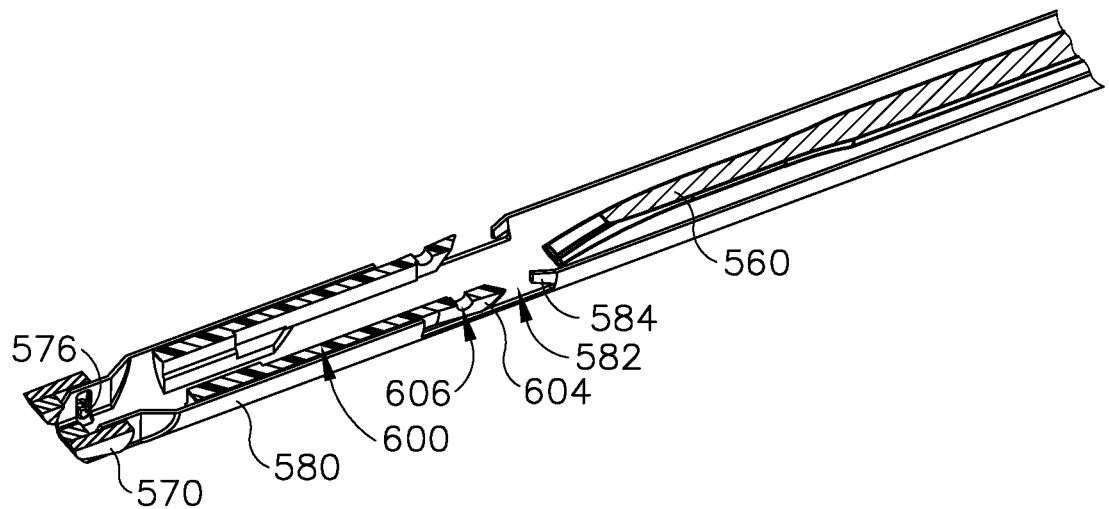
FIG. 34A depicts a cross-sectional perspective view of the distal end of the disposable portion of FIG. 8, with the first disposable sub-assembly in a distal position and at a first angular orientation during the process of assembly.
Figure 34B:
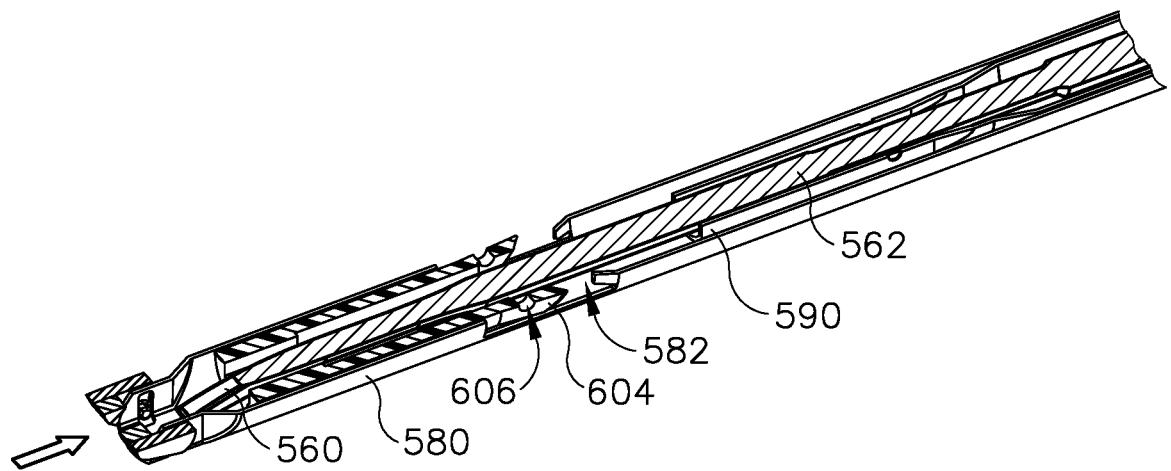
FIG. 34B depicts a cross-sectional perspective view of the distal end of the disposable portion of FIG. 8, with the first disposable sub-assembly in a first proximal position and at the first angular orientation during the process of assembly.
Figure 34C:
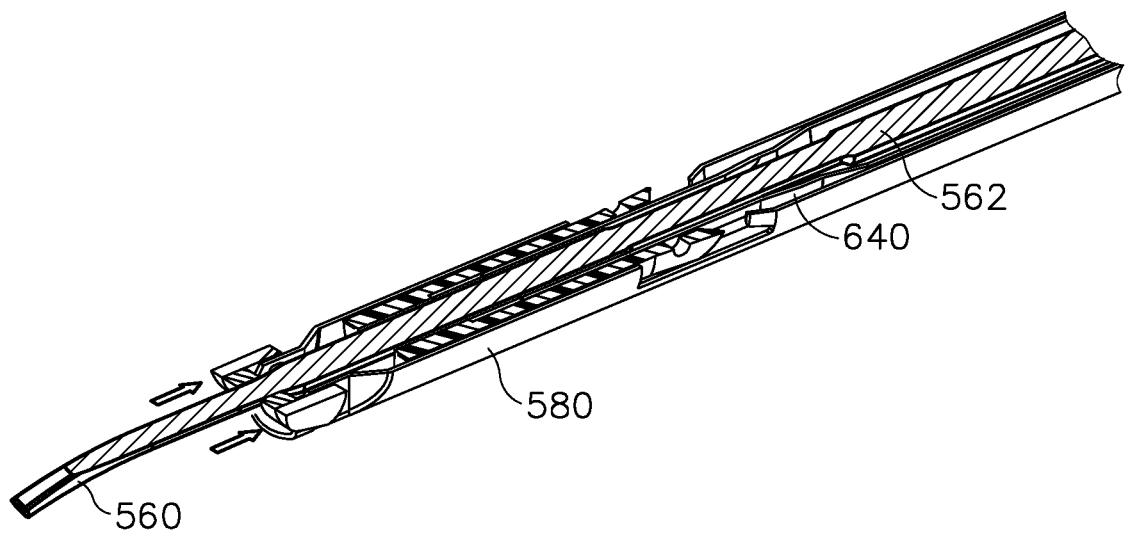
FIG. 34C depicts a cross-sectional perspective view of the distal end of the disposable portion of FIG. 8, with the first disposable sub-assembly in a second proximal position and at the first angular orientation during the process of assembly.

In the series shown in FIGS. 34A-34F, first disposable sub-assembly (502) appears to remain fixed in place while second disposable sub-assembly (504) moves. However, it should be understood that an operator may in fact hold second disposable sub-assembly (504) stationary and move first disposable sub-assembly (502) in order to transition through the stages shown in FIGS. 34A-34G. As shown in FIG. 34A, sub-assemblies (502, 504) are initially positioned such that the curved distal tip of blade (560) is oriented downwardly as outer tube (580) is slid proximally along blade (560), waveguide (562), and proximal inner tube portion (590). This angular positioning may be the same as that shown in FIGS. 33A-33B.

In the event that outer tube (580) is slid proximally along blade (560), waveguide (562), and proximal inner tube portion (590) at a different angular orientation, the distal end of blade (560) will eventually engage one or more bearing surfaces (607, 608, 609). When the operator continues to retract outer tube first disposable sub-assembly (502) proximally, a camming engagement between the distal end of blade (560) and the one or more bearing surfaces (607, 608, 609) will urge first disposable sub-assembly (502) to rotate about the longitudinal axis of outer tube (580) until the angular relationship shown in FIGS. 33A-33B and 34A-34C is achieved. It should be understood that this angular relationship may be necessary in order for the distal end of blade (560) to traverse gap (601). It should also be understood that during the stages shown in FIGS. 34A-34C, studs (592) of proximal inner tube member (590) are oriented along an axis that is perpendicular to an axis passing through the centers of openings (582) of outer tube (580).

Figure 34D:
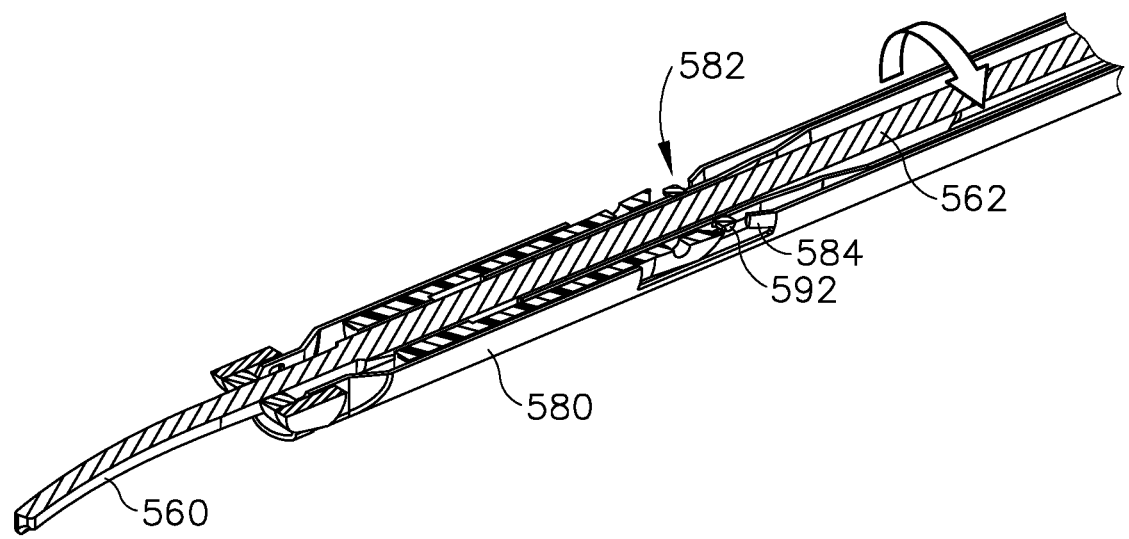
FIG. 34D depicts a cross-sectional perspective view of the distal end of the disposable portion of FIG. 8, with the first disposable sub-assembly in a third proximal position and at a second angular orientation during the process of assembly.

As first disposable sub-assembly (502) translates proximally through the range of motion where guide pin (526) traverses second portion (624) of guide channel (620), the engagement between guide pin (526) and guide channel (620) causes first disposable sub-assembly (502) to rotate 90° about the longitudinal axis of outer tube (580) as noted above. This rotation is also shown in FIG. 34D. At this stage, studs (592) of proximal inner tube member (590) are oriented along an axis that is parallel to an axis passing through the centers of openings (582) of outer tube (580). In addition, blade (560) is now at the orientation shown in FIGS. 8-9, such that the laterally oriented curve of blade (560) complements the laterally oriented curve of clamp arm (570).

Figure 34E:
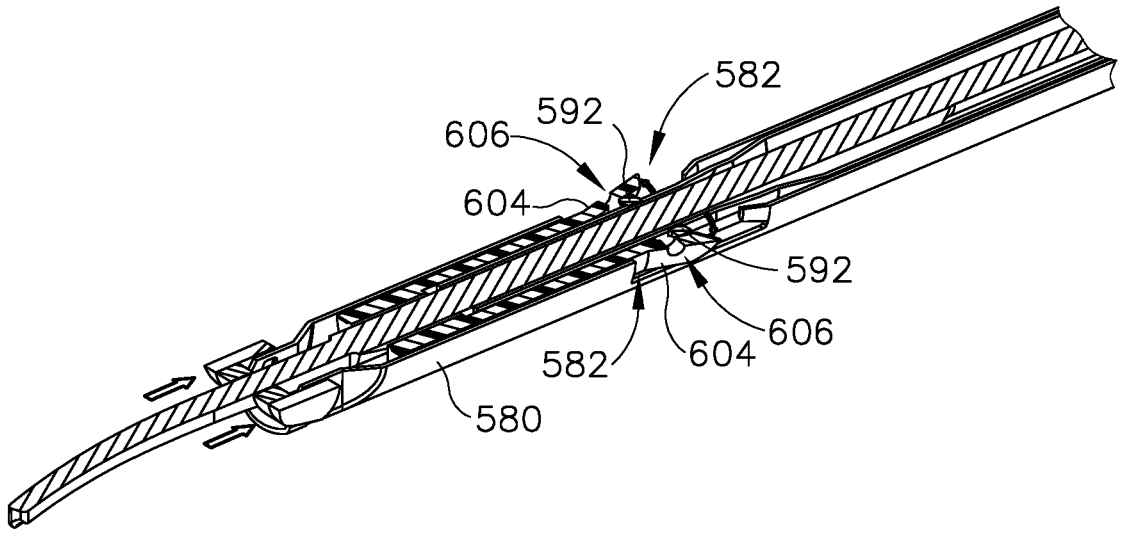
FIG. 34E depicts a cross-sectional perspective view of the distal end of the disposable portion of FIG. 8, with the first disposable sub-assembly in a fourth proximal position and at the second angular orientation during the process of assembly.
Figure 34F:
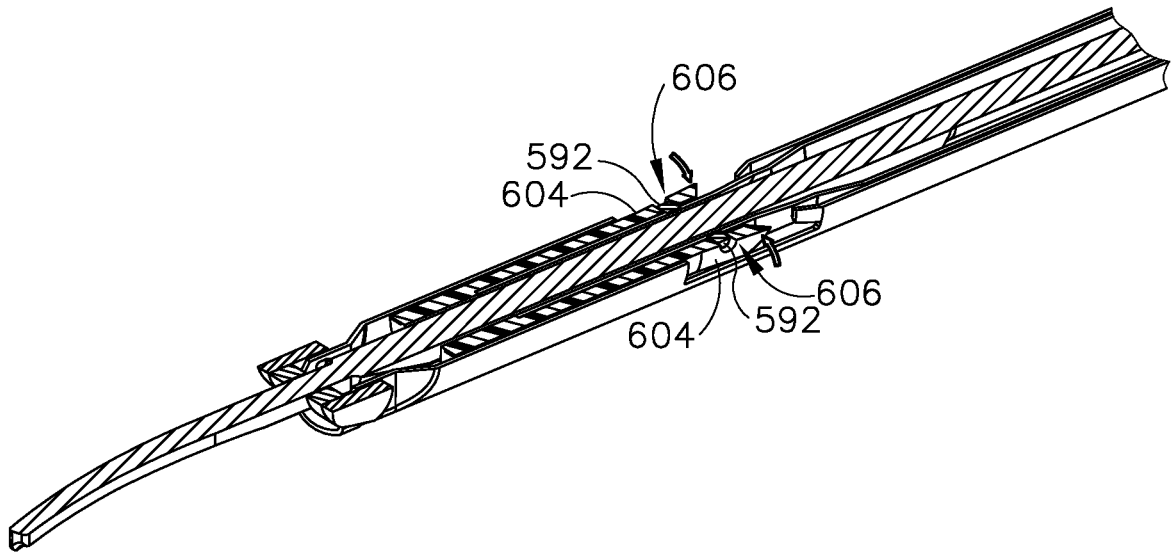
FIG. 34F depicts cross-sectional perspective view of the distal end of the disposable portion of FIG. 8, with the first disposable sub-assembly in a fully coupled fifth proximal position and at the second angular orientation upon completion of the process of assembly.

As the operator continues to retract first disposable sub-assembly (502) proximally relative to second disposable sub-assembly (504), studs (592) of proximal inner tube member (590) engage bearing surfaces (607) of arms (604) of distal inner tube member (600). As the operator continues to retract first disposable sub-assembly (502) proximally relative to second disposable sub-assembly (504), this engagement causes the proximal ends of arms (604) to deflect outwardly as shown in FIG. 34E. Openings (582) of outer tube (580) accommodate this deflection. As the operator continues to retract first disposable sub-assembly (502) proximally relative to second disposable sub-assembly (504), studs (592) eventually reach openings (606) in arms (504). At this stage, the resilience of arms (504) drives the proximal ends of arms (504) back inwardly, such that studs (592) snap into place in openings (606) as shown in FIG. 34F. At this stage, sub-assemblies (502, 504) are coupled together such that disposable assembly (500) is ready for assembly with the variation of reusable assembly (200). It should be understood that the state shown in FIG. 34F corresponds with the state shown in FIG. 33D.

D. Exemplary Disassembly of First Disposable Sub-Assembly from Second Disposable Sub-Assembly As noted above, first disposable sub-assembly (502) may be configured for just one single use while second disposable sub-assembly (504) may be configured for 2 to 20 uses (or any other suitable number of uses). It may therefore be desirable to enable an operator to disassemble first disposable sub-assembly (502) from second disposable sub-assembly (504) without destroying second disposable sub-assembly (504). To that end, FIGS. 35A-36B show various stages of disassembling first disposable sub-assembly (502) with second disposable sub-assembly (504). In particular, FIGS. 35A-35E show various stages occurring at the proximal end of first disposable sub-assembly (502) during a process of disassembling first disposable sub-assembly (502) from second disposable sub-assembly (504); while FIGS. 36A-36B show various stages occurring at the proximal end of first disposable sub-assembly (502) during a process of disassembling first disposable sub-assembly (502) from second disposable sub-assembly (504).

Figure 35A:
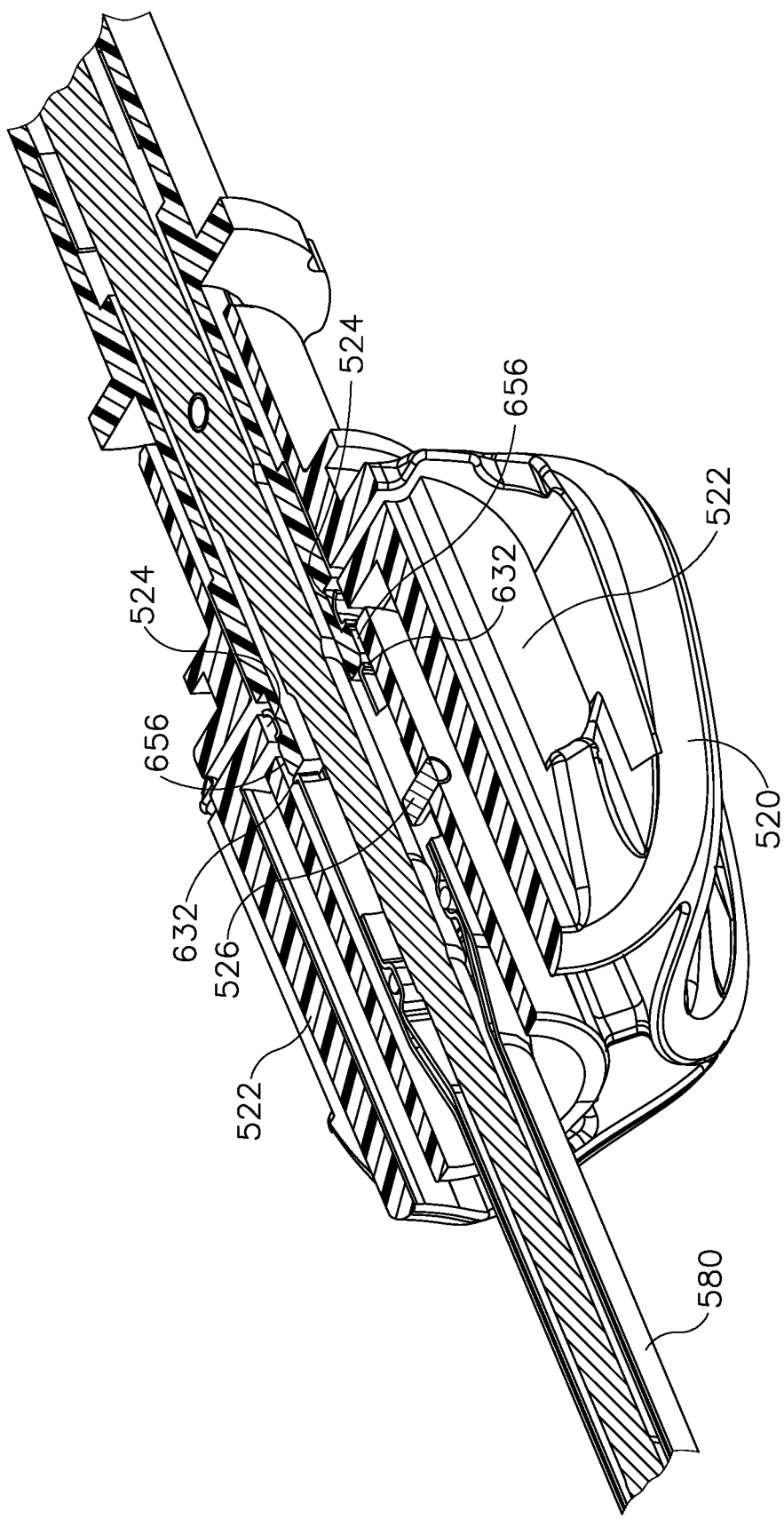
FIG. 35A depicts a cross-sectional perspective view of the disposable portion of FIG. 8, with the knob member at a proximal position before a process of disassembly.
Figure 35B:
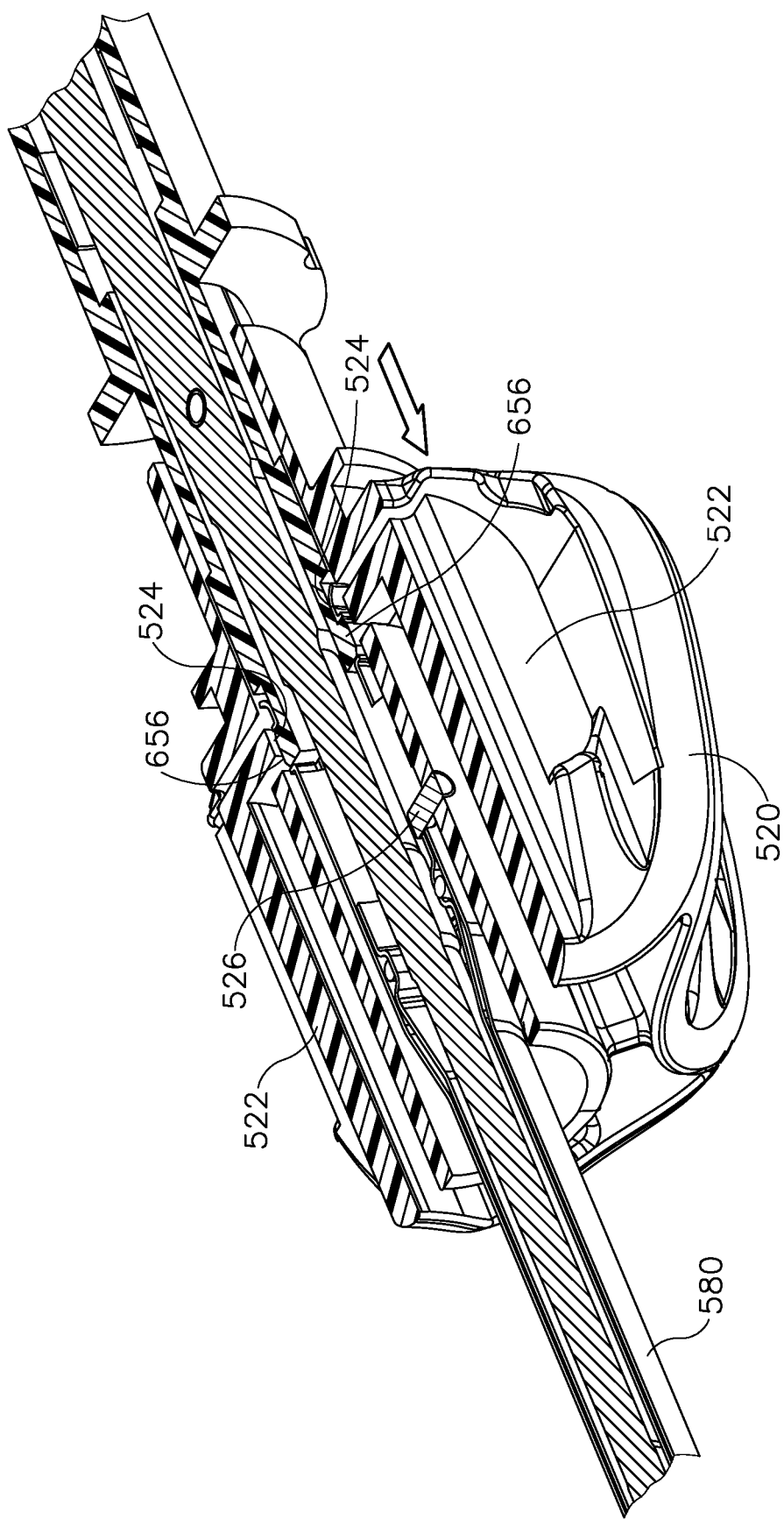
FIG. 35B depicts a cross-sectional perspective view of the disposable portion of FIG. 8, with the knob member at a distal position to initiate the process of disassembly.
Figure 36A:
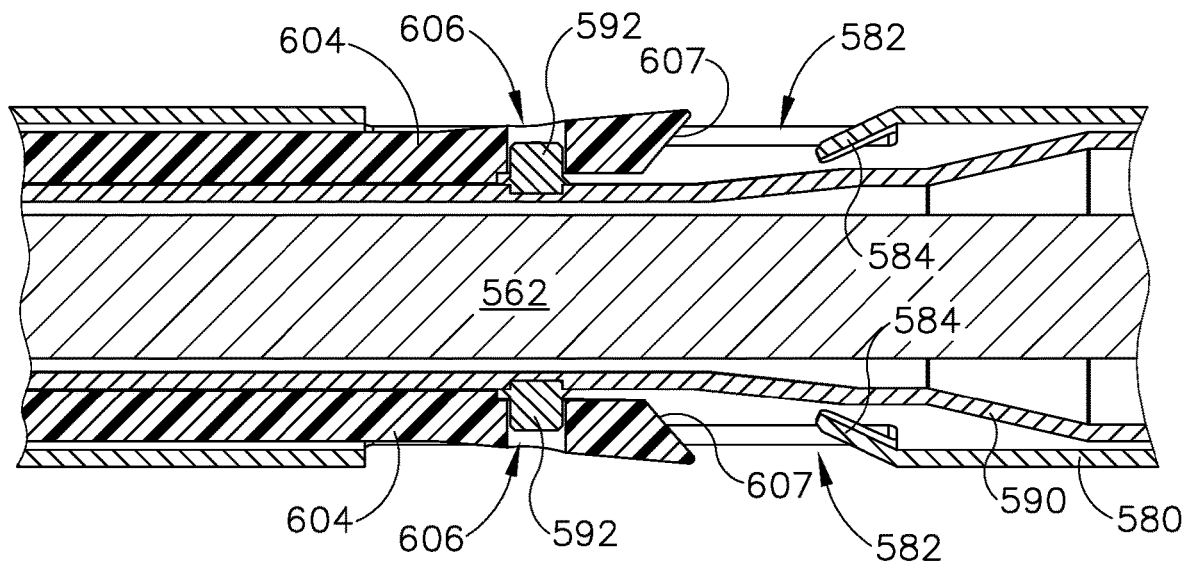
FIG. 36A depicts a cross-sectional top view of portions of the shaft assembly of the disposable portion of FIG. 8, with the outer tube in a proximal position before the process of disassembly.
Figure 36B:
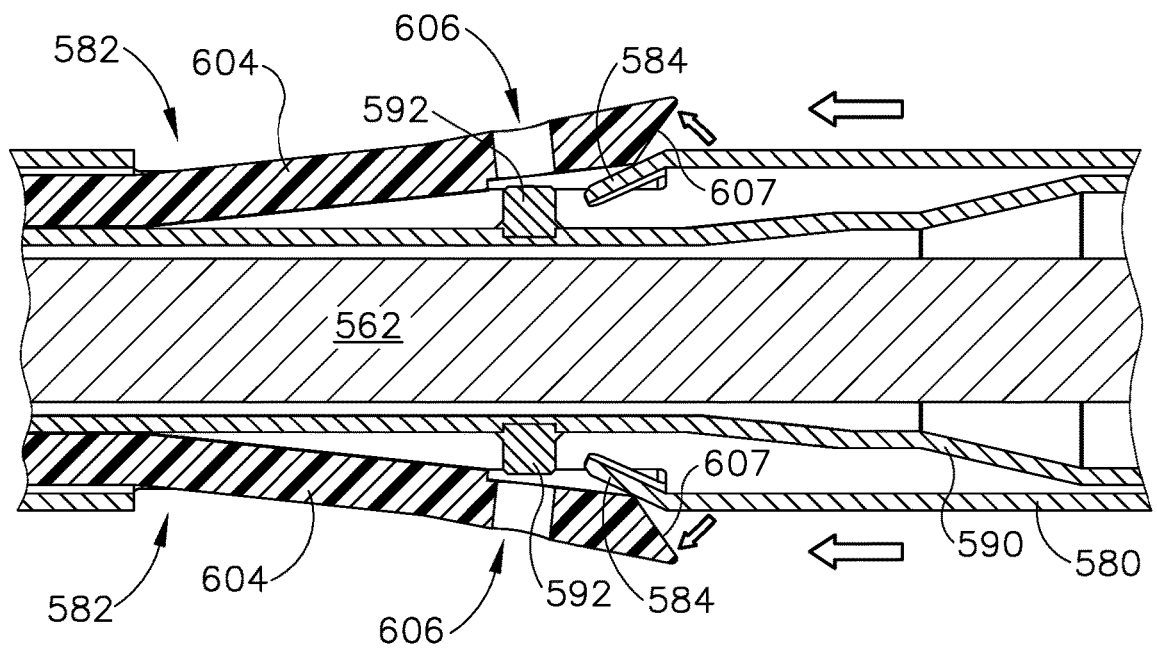
FIG. 36B depicts a cross-sectional top view of portions of the shaft assembly of the disposable portion of FIG. 8, with the outer tube in a distal position during the process of disassembly.

As shown in FIG. 35A, prongs (524) of knob member (520) are initially located at positions that are proximal in relation to the positions of prongs (656) of tube actuator (650). This longitudinal offset may prevent an operator from inadvertently disengaging prongs (656) from outer tube (580) during use of disposable assembly (500) in a fully assembled instrument. In order to initiate disassembly, the operator may need to first translate knob member (520) distally relative to the other components, as shown in FIG. 35B. In some versions, knob member (520) is resiliently biased to maintain the proximal positioning as shown in FIG. 35A. Once knob member (520) has been translated distally to the position shown in FIG. 35B, prongs (524) of knob member (520) are aligned with prongs (656) of tube actuator (650), though prongs (524) of knob member (520) are laterally spaced form prongs (656) of tube actuator (650). In some variations, knob member (520) is not translatable, such that prongs (524) of knob member (520) are aligned with prongs (656) of tube actuator (650) during normal use of disposable assembly (500) in a fully assembled instrument.

Figure 35C:
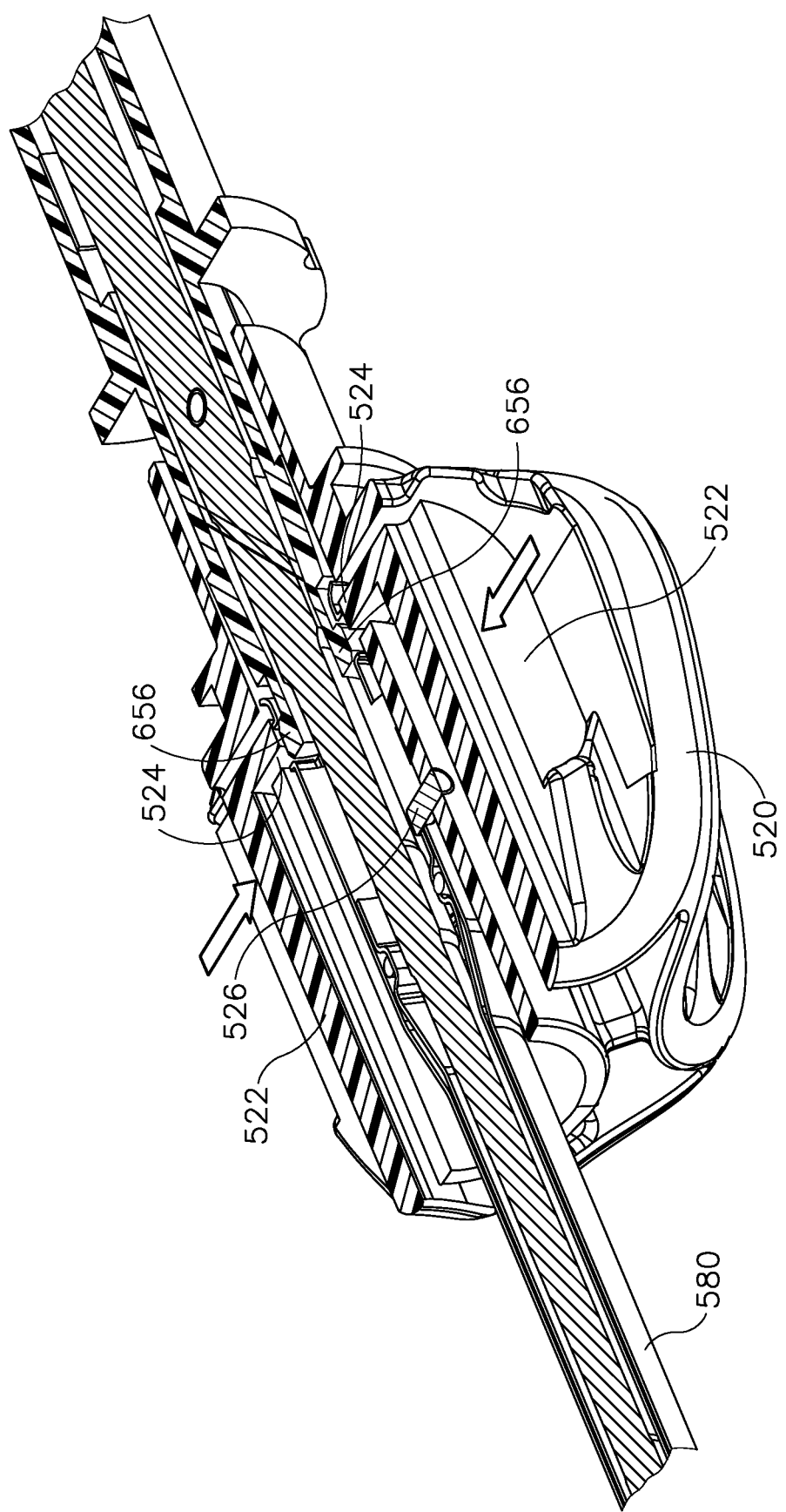
FIG. 35C depicts a cross-sectional perspective view of the disposable portion of FIG. 8, with cantilevered buttons of the knob member pressed inwardly during the process of disassembly.
Figure 35D:
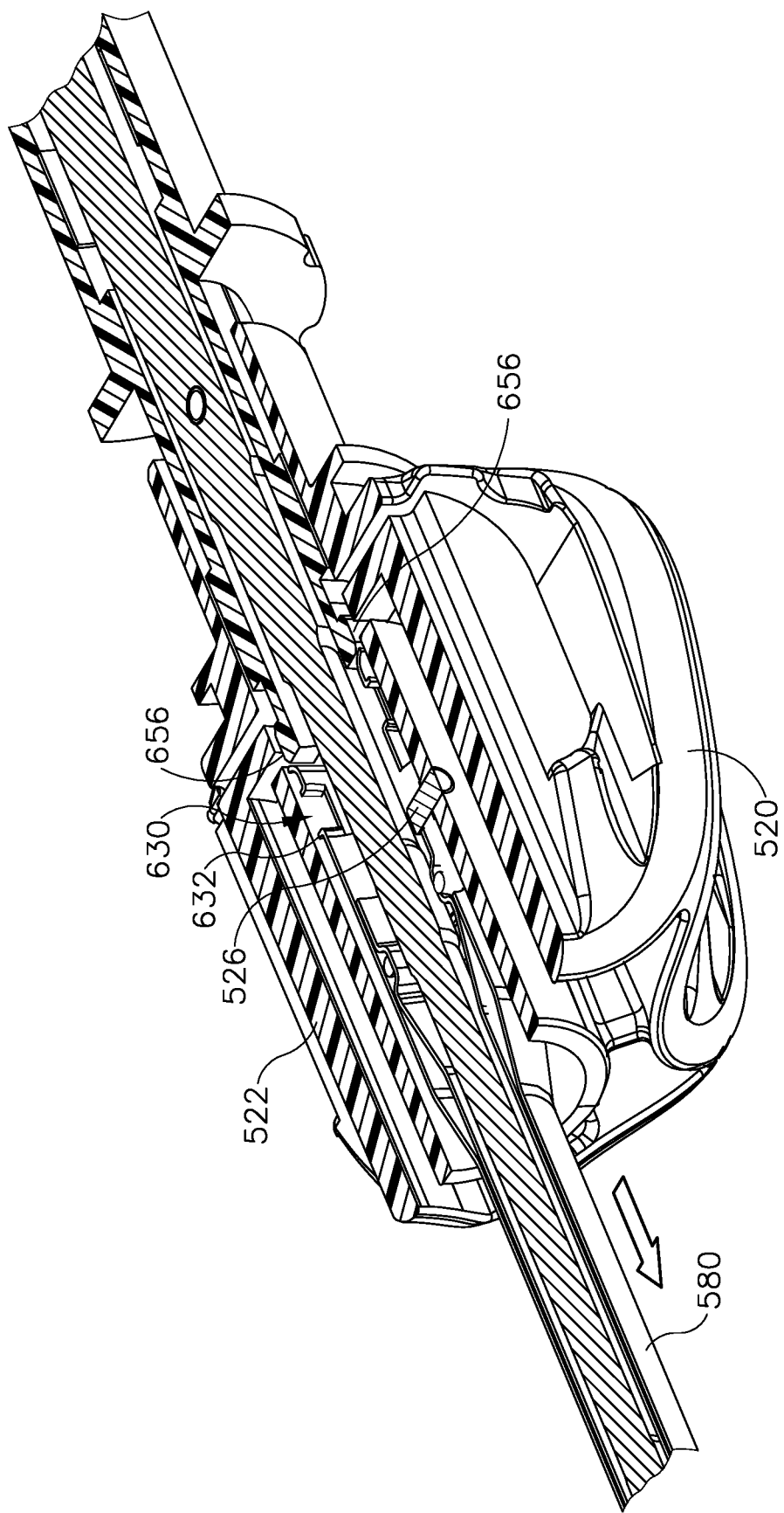
FIG. 35D depicts a cross-sectional perspective view of the disposable portion of FIG. 8, with the first disposable sub-assembly slid distally during the process of disassembly.

After translating knob member (520) distally to the position shown in FIG. 35B, the operator may press cantilevered buttons (522) inwardly as shown in FIG. 35C. In this example, both buttons (522) are pressed inwardly simultaneously. This drives prongs (524) inwardly. As prongs (524) move inwardly, prongs (524) bear against prongs (656), thereby deflecting the distal ends of arms (654) inwardly. This deflection at least partially unseats prongs (656) from openings (630) in outer tube (580). With prongs (656) at least partially unseated from openings (630) in outer tube (580), the operator may pull distally on first disposable sub-assembly (502) while holding second disposable sub-assembly (504) stationary (while still pressing cantilevered buttons (522) inwardly). This will ultimately result in the proximal end of outer tube (580) clearing prongs (524) of tube actuator as shown in FIG. 35D. As noted above, the cantilevered edges of prongs (524) may further promote this clearing. With outer tube (580) clear of prongs (524), arms (654) may resiliently transition back to the straight, parallel orientations as shown in FIG. 35D. In addition, with outer tube (580) clear of prongs (524), the operator is free to pull first disposable sub-assembly (502) clear from the remainder of second disposable sub-assembly (504). The operator may then dispose of first disposable sub-assembly (502); and clean, sterilize, and re-use second disposable sub-assembly (504) if appropriate.

It should be understood that during the process of disassembly shown in FIGS. 35A-35D, first disposable sub-assembly (502) may rotate relative to second disposable sub-assembly (504), about the longitudinal axis of outer tube (580), due to interaction between guide pin (526) and guide slot (620) as described above.

It should also be understood that, since distal inner tube member (600) is longitudinally secured to proximal inner tube member (590) via arms (604) and studs (592), there will be some degree of relative movement between outer tube member (580) and distal inner tube member (600) during the disassembly of first disposable sub-assembly (502) from second disposable sub-assembly (504). This relative movement is shown in FIGS. 36A-36B. When the operator begins the disassembly process and pulls distally on outer tube (580), the inwardly directed tabs (584) of outer tube (580) will eventually engage bearing surfaces (607) of arms (604). This will provide a camming action that eventually causes the proximal ends of arms (604) to deflect outwardly as shown in FIG. 36B. As noted above, openings (582) of outer tube (580) accommodate this outward deflection of the proximal ends of arms (604). Arms (604) will deflect to the point where studs (592) are no longer located in openings (606) of arms (604). This disengagement of studs (592) from arms (604) will decouple distal inner tube member (600) from proximal inner tube member (590), thereby enabling distal inner tube member (600) to travel distally with outer tube (580) as the operator continues to pull outer tube (580) distally to complete the disassembly of first disposable sub-assembly (502) from second disposable sub-assembly (504).

III. EXEMPLARY ALTERNATIVE DISPOSABLE ASSEMBLY FOR ULTRASONIC SURGICAL INSTRUMENT WITH REMOVABLE ACOUSTIC WAVEGUIDE AND MULTIPURPOSE ASSEMBLY TOOL

In some instances, it may be desirable to have an assembly tool that may be utilized to properly couple first disposable sub-assembly (502, 1502) with second disposable sub-assembly (504, 1504); and also be utilized to properly couple ultrasonic blade (560, 1560) with reusable assembly (200). Having a single tool that may be used to properly couple multiple assemblies and sub-assemblies may save time and simplify the assembly process.

Figure 37:
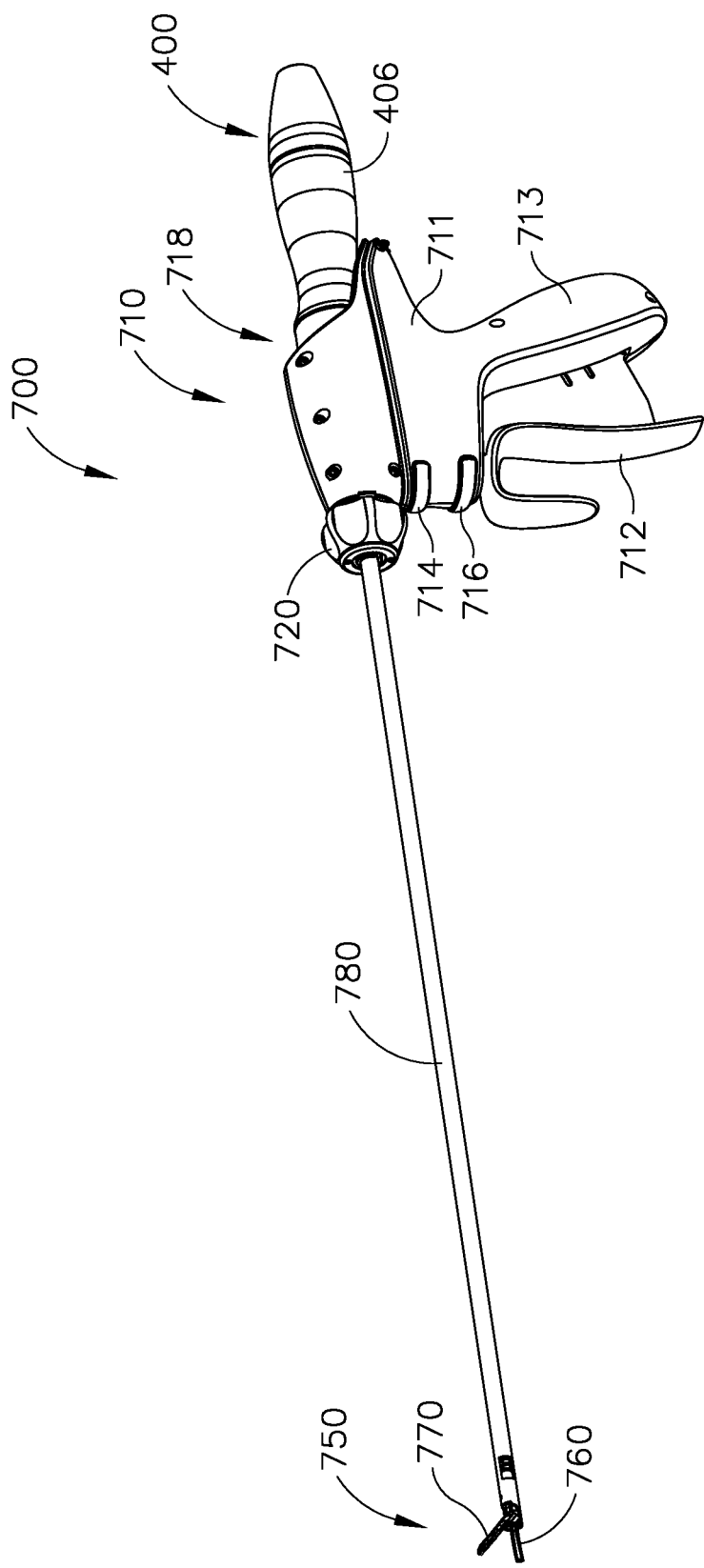
FIG. 37 depicts a perspective view of an alternative ultrasonic surgical instrument having a disposable assembly and a reusable assembly.
Figure 38:
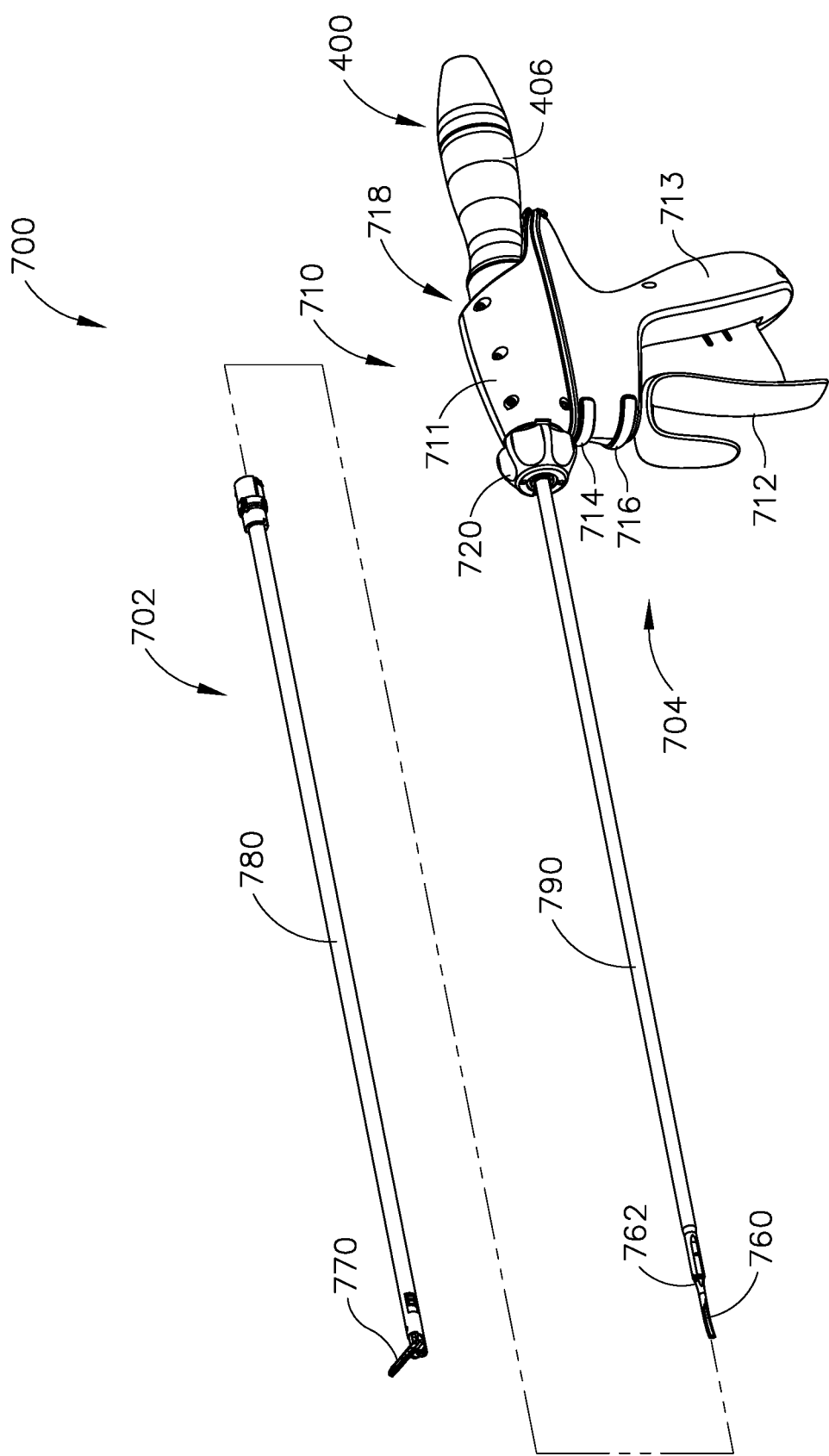
FIG. 38 depicts a partially exploded view of the ultrasonic surgical instrument of FIG. 37, with a first disposable sub-assembly separated from a second disposable sub-assembly.

FIGS. 37-38 show an exemplary alternative disposable assembly (700) that is coupled to alternative reusable assembly (400). To the extent that the following discussion omits various details of disposable assembly (700), it should be understood that disposable assembly (700) may incorporate the various details described above and/or details described in any of the various references that are cited herein. Other suitable details will be apparent to those of ordinary skill in the art in view of the teachings herein.

Figure 63A:
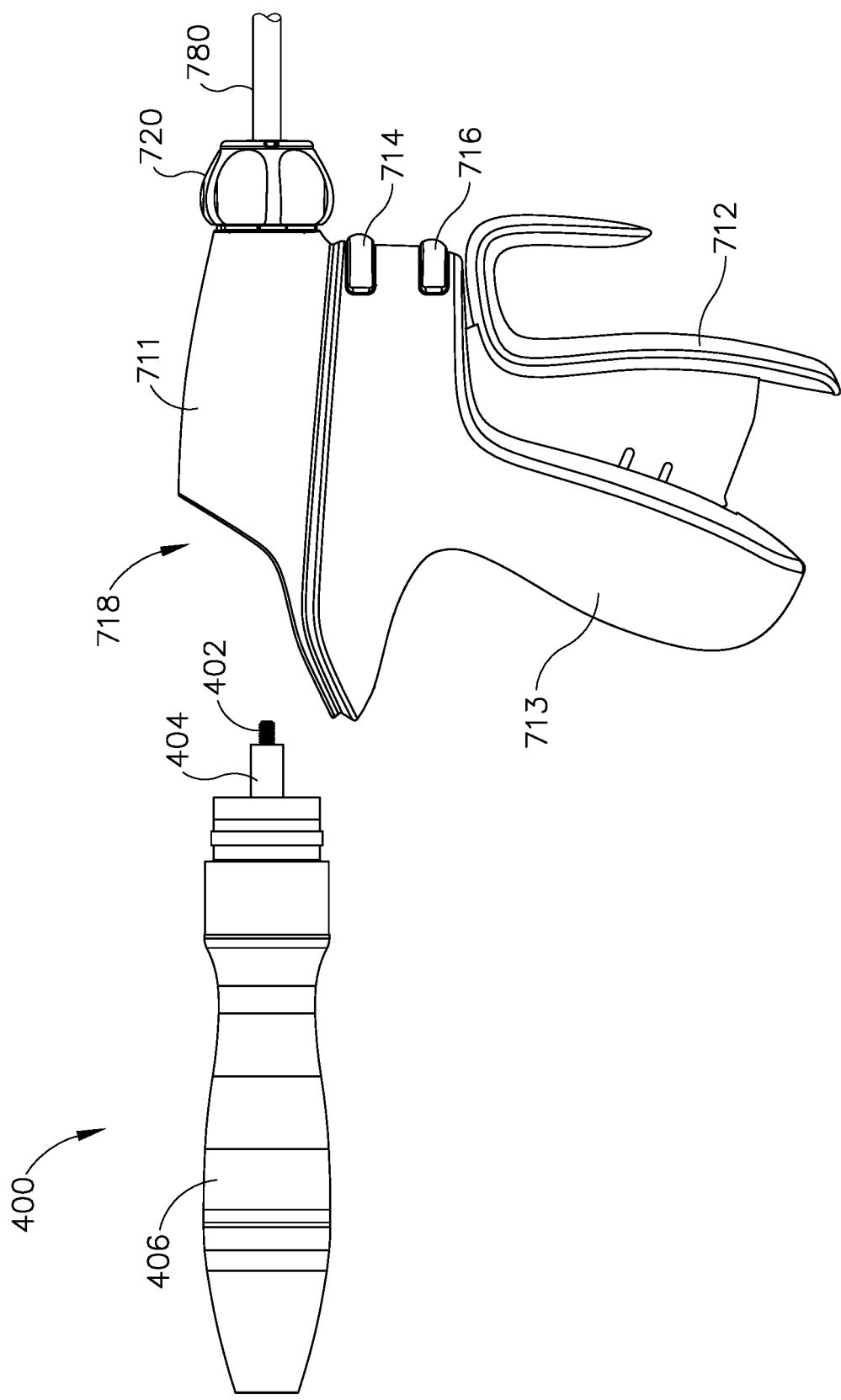
FIG. 63A depicts a side elevation view of the reusable assembly of FIG. 37 decoupled from the disposable assembly of FIG. 37.
Figure 64A:
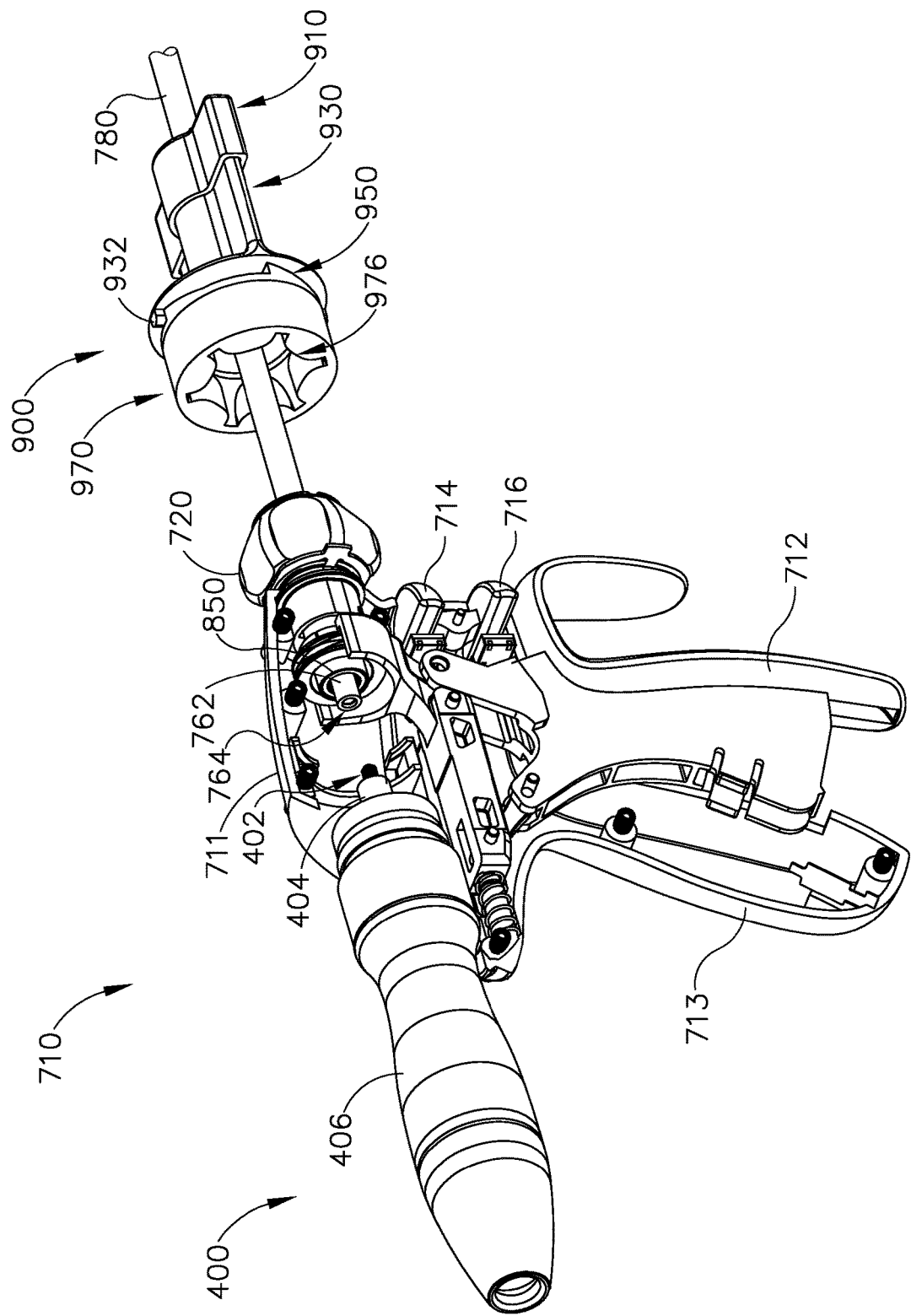
FIG. 64A depicts a perspective view of the assembly tool of FIG. 51 utilized to couple the reusable assembly of FIG. 37 with the disposable assembly of FIG. 37, where the reusable assembly is decoupled with the disposable assembly, where the assembly tool is distal in relation to the knob member of the second sub-assembly of FIG. 38.
Figure 64B:
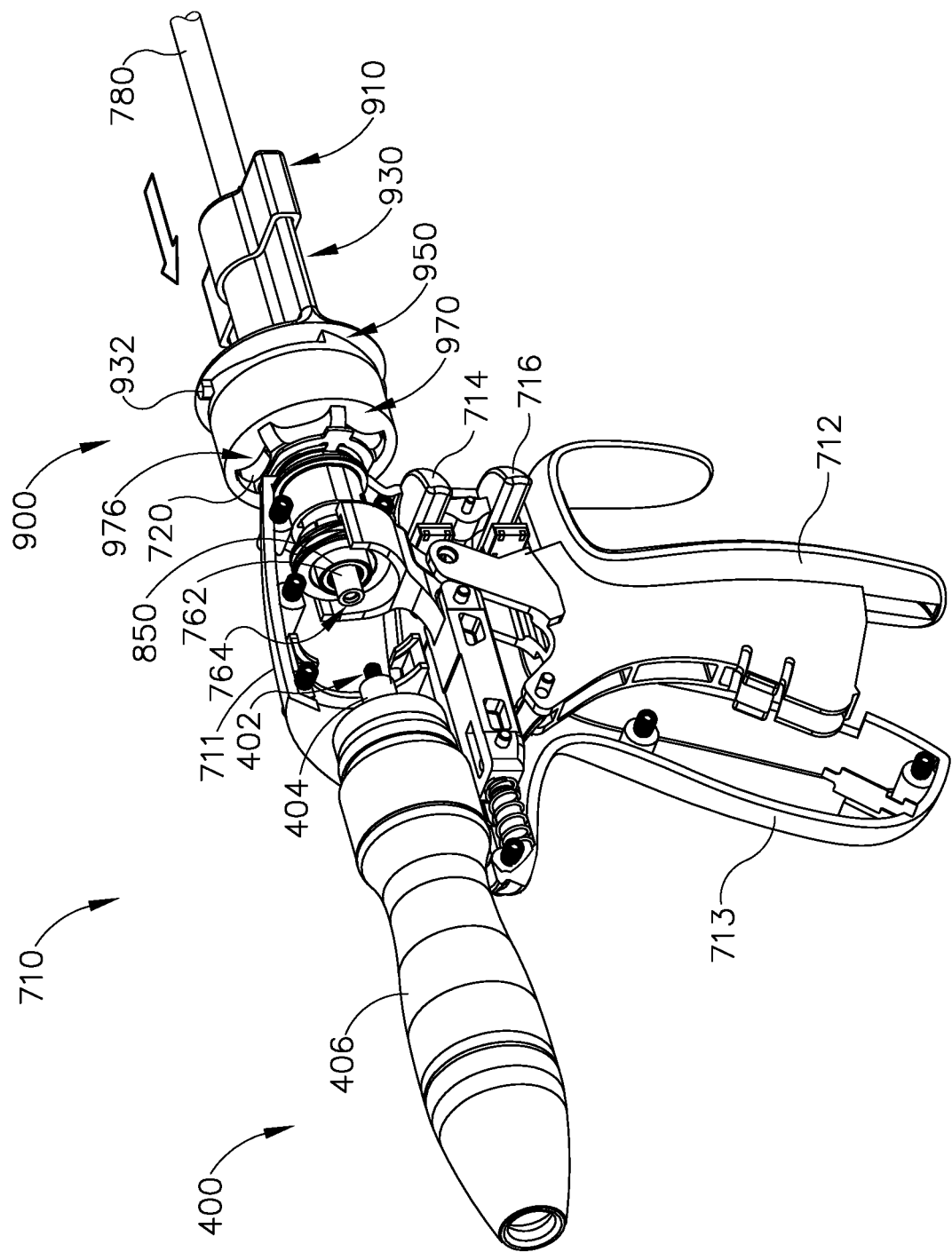
FIG. 64B depicts a perspective view of the assembly tool of FIG. 51 utilized to couple the reusable assembly of FIG. 37 with the disposable assembly of FIG. 37, where the reusable assembly is decoupled with the disposable assembly, where the assembly tool is rotationally secured to the knob member of the second sub-assembly of FIG. 38.

It should be understood that reusable assembly (400) may be substantially similar to reusable assembly (200) described above, with differences described below. Therefore, reusable assembly (400) comprises various features that are operable to activate an ultrasonic blade (760), including an ultrasonic transducer (406). Reusable assembly (400) may include a battery or may be connected to a generator via wires in order to activate ultrasonic transducer (406). As best seen in FIGS. 63A and 64A-64B, reusable assembly (400) includes a coupling shaft (404) rotationally fixed to a distally extending threaded stud (402) of transducer (406). As will be described in greater detail below, reusable assembly (400) may be rotated relative to disposable assembly (700) in order to couple disposable assembly (700) with reusable assembly (400).

Disposable assembly (700) of the present example comprises a first disposable sub-assembly (702) and a second disposable sub-assembly (704). Sub-assemblies (702, 704) are configured to be coupled together in order to form disposable assembly (700), which may then be coupled with a variation of reusable assembly (400) for form a complete ultrasonic surgical instrument. After the ultrasonic surgical instrument is used in a surgical procedure, disposable assembly (700) may be removed from the variation of reusable assembly (400); and then first disposable sub-assembly (702) may be removed from second disposable sub-assembly (704). In some such instances, the variation of reusable assembly (400) may be cleaned, sterilized, and re-used up to 100 times (by way of example only). First disposable sub-assembly (702) may be disposed of, such that first disposable sub-assembly (702) is only used one single time. Second disposable sub-assembly (704) may be cleaned, sterilized, and re-used between 2 to 20 times (by way of example only). Of course, these re-use scenarios are merely illustrative examples. It should nevertheless be understood that the configuration of disposable assembly (700) may minimize the amount of single-use material that is disposed of after each surgical procedure. This may reduce cost and overall waste as compared to conventional instrumentation.

A. Exemplary First Disposable Sub-Assembly

Figure 39:
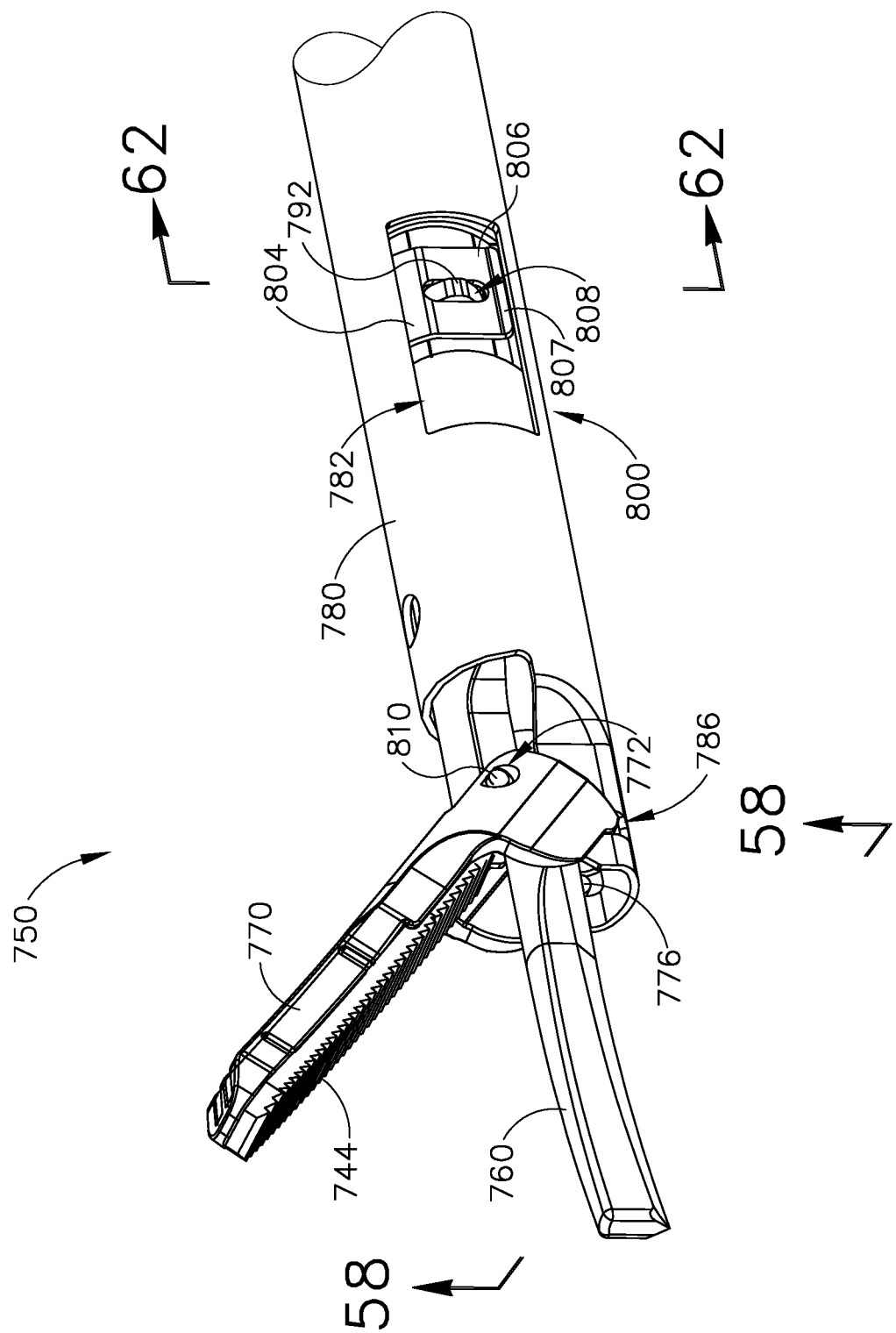
FIG. 39 depicts a perspective view of an end effector of the ultrasonic surgical instrument of FIG. 37, in an open configuration.

As shown in FIGS. 37-40, first disposable sub-assembly (702) of the present example comprises an outer tube (780), a clamp arm (770), and a distal inner tube member (800). Clamp arm (770) is configured to form an end effector (750), as shown in FIG. 39, with an ultrasonic blade (760), which is part of second disposable sub-assembly (704) as will be described in greater detail below. Clamp arm (770) is pivotably coupled with outer tube (780) and with distal inner tube member (800). Outer tube (780) is configured to translate longitudinally while distal inner tube member (800) remains stationary, which drives clamp arm (770) to pivot between an open position and a closed position. In the closed position, clamp arm (770) is operable to clamp tissue against blade (760), which may then be ultrasonically activated to sever and/or seal the tissue as described herein and in various references cited herein.

Figure 40:
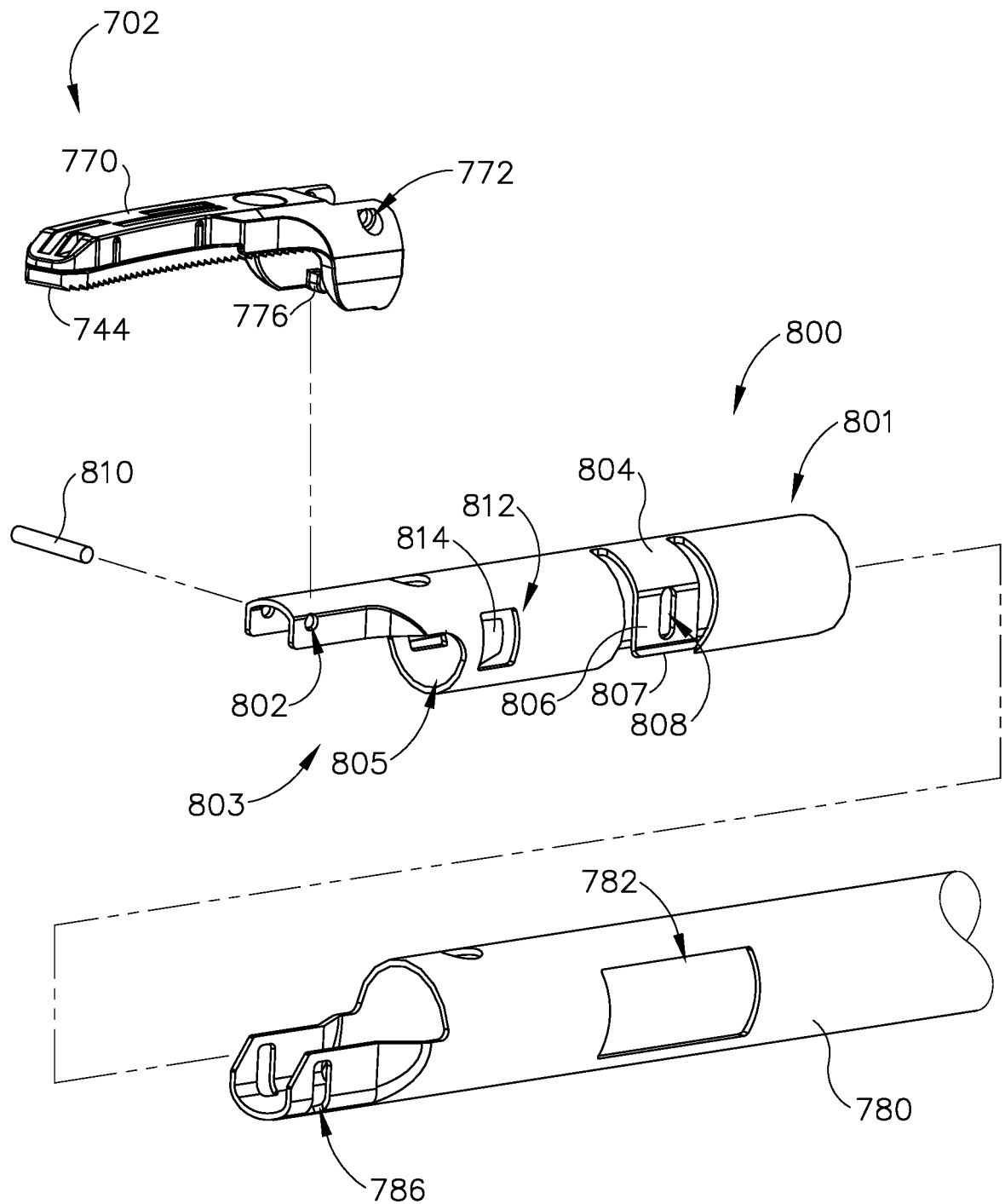
FIG. 40 depicts a perspective exploded view of the distal end of the first disposable sub-assembly of FIG. 38.
Figure 41:
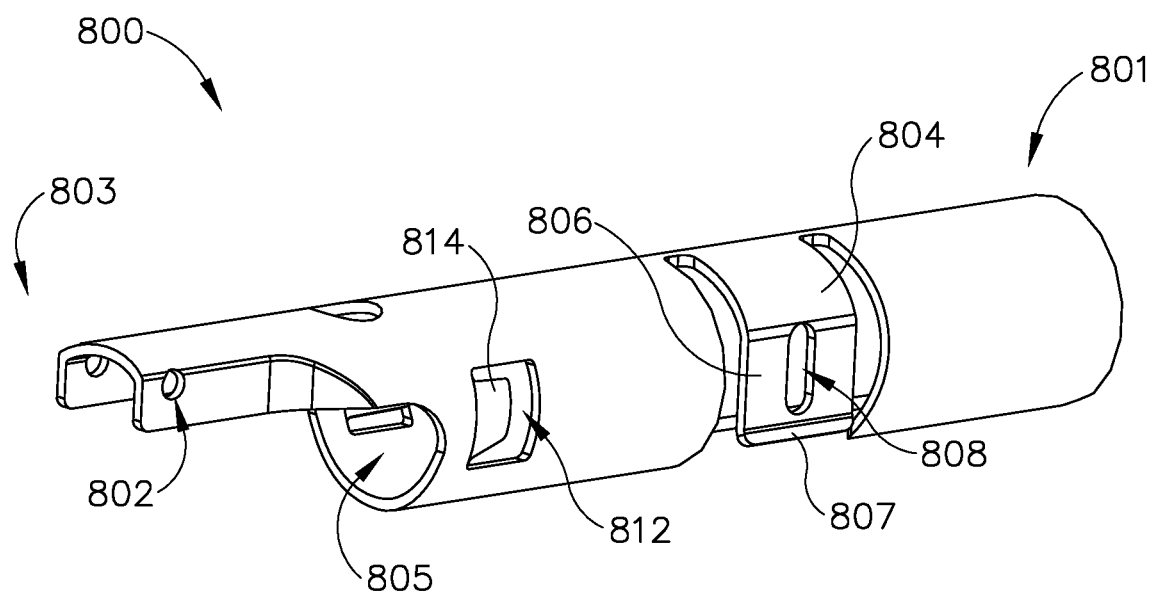
FIG. 41 depicts a perspective view of a distal inner tube member of the first disposable sub-assembly of FIG. 38.

As shown in FIG. 40, clamp arm (770) of the present example comprises a pair of pin openings (772), a clamp pad (774), and a pair of pivot studs (776). Pin openings (772) are configured to receive a pin (810), which is also disposed in a pin opening (802) of distal inner tube member (800). Clamp pad (774) of the present example comprises polytetrafluoroethylene (PTFE) and includes surface features (e.g., teeth or ridges, etc.) that are configured to promote gripping of tissue. Various suitable materials and configurations that may be used to form clamp pad (774) will be apparent to those of ordinary skill in the art in view of the teachings herein. Pivot studs (776) are received in openings (786) of outer tube (780). Clamp arm (770) is pivotable about axes defined by pivot studs (776) and by pin (810), which enables clamp arm (770) to transition between the open position and the closed position in response to translation of outer tube (780) relative to distal inner tube member (800).

Figure 42:
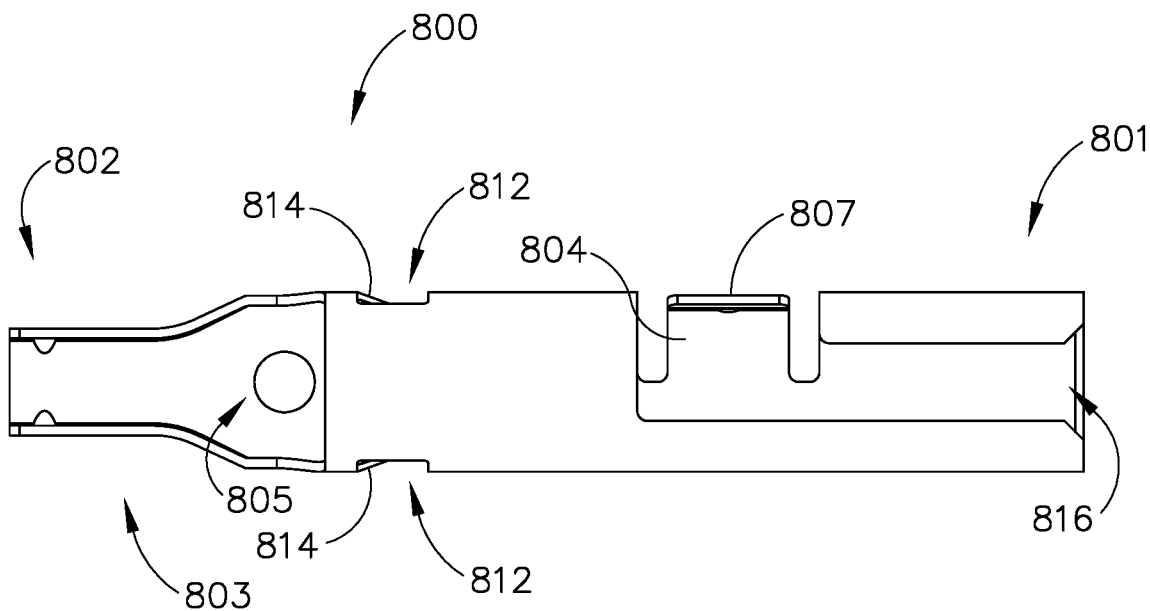
FIG. 42 depicts a bottom plan view of the distal inner tube member of FIG. 41.

As shown in FIGS. 40-43, distal inner tube (800) of the present example comprises a distal portion (803) defining a pair of lateral openings (812), a pair of proximally presented tabs (812), a proximal portion (801), pin opening (802), and a circumferential tab (804) extending into a flat member (806) terminating into an outwardly extending lip (807). Circumferential tab (804) and flat member (806) are resiliently flexible and are in a relaxed position as shown in FIGS. 40-43. Each proximally presented tab (812) extends inwardly from a respective lateral opening (812). Flat member (806) defines a slot (808). As best seen in FIG. 42, proximal portion (801) defines a pathway (816) extending words circumferential tab (805) and flat member (806). A gap (805) extends from proximal portion (801) through distal portion (803). This gap (805) is configured to accommodate longitudinal travel of the distal end of ultrasonic blade (760) during assembly of first disposable sub-assembly (602) with second disposable sub-assembly (604), as will be described in greater detail below.

As will also be described in greater detail below, distal inner tube member (800) is configured to be removably secured to a proximal inner tube member (790) during assembly of first disposable sub-assembly (702) with second disposable sub-assembly (704). This coupling provides a longitudinal mechanical grounding for distal inner tube member (800), such that distal inner tube member (800) does not translate longitudinally relative to other components of disposable assembly (700) when inner tube members (790, 800) are coupled together.

As shown in FIG. 40, the distal end of outer tube (780) of the present example comprises openings (786) that pivotally receive pivot studs (776) as noted above. The distal end of outer tube (780) further includes an elongate lateral opening (782) that is located proximal to openings (786). Outer tube (780) is slidably disposed about distal inner tube member (800), such that outer tube (780) is operable to translate longitudinally relative to distal inner tube member (800).

Figure 43:
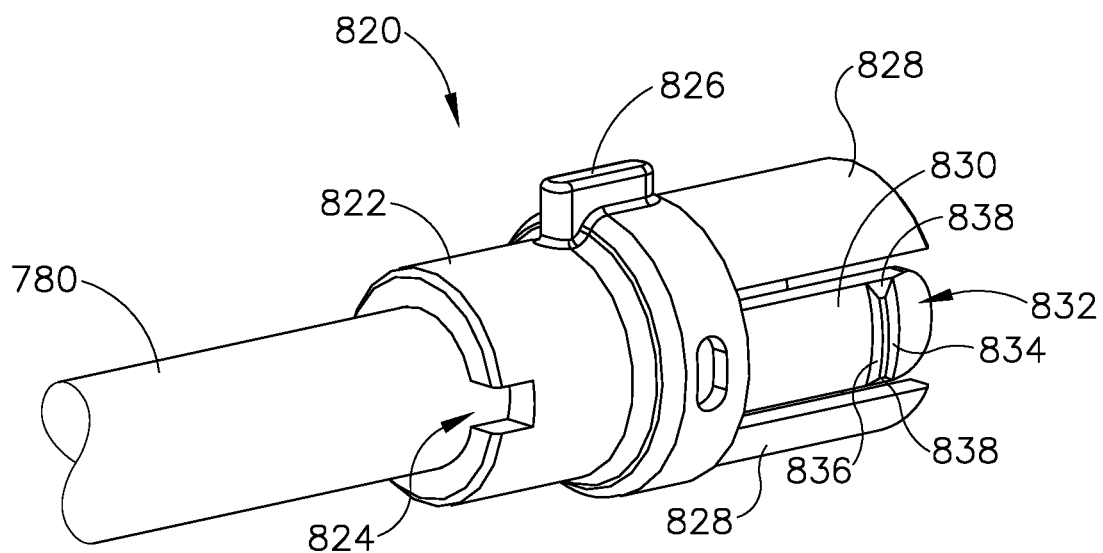
FIG. 43 depicts a perspective front view of the proximal end of the first disposable sub-assembly of FIG. 38.
Figure 44:
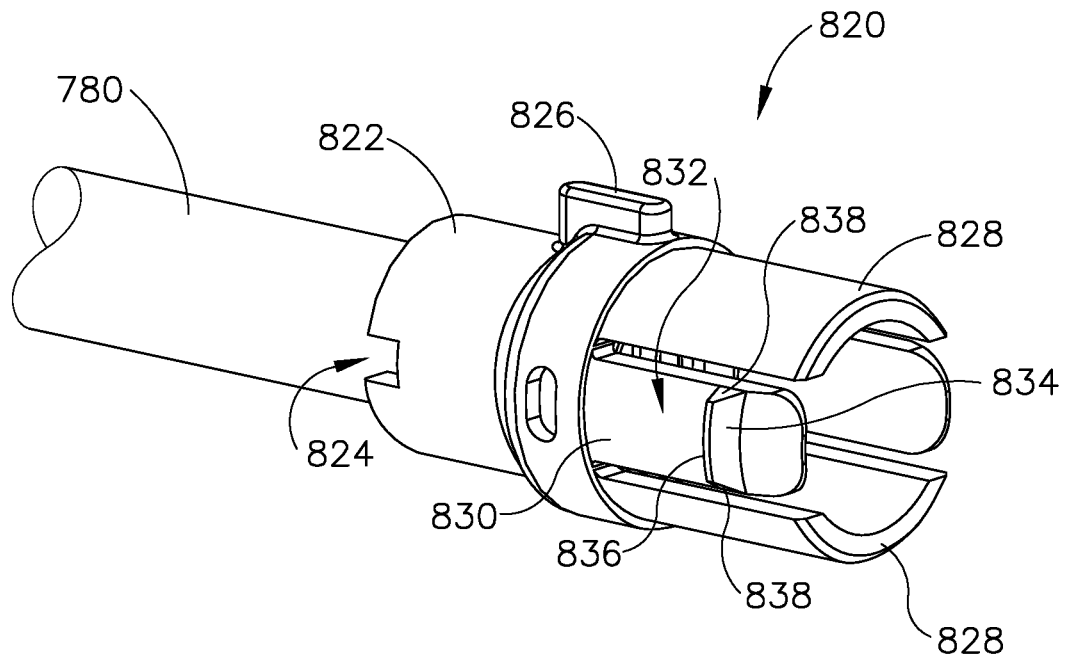
FIG. 44 depicts a perspective rear view of the proximal end of the first disposable sub-assembly of FIG. 38.

As shown in FIGS. 43-44, the proximal end of outer tube (780) of the present example comprises a coupling feature (820). Coupling feature (820) comprises an overmolded portion (822) fixed relative to the rest of outer tube (780), a guide projection (826) extending radially from overmolded portion (822), a pair of proximally presented sleeves (828) spaced 180° relative from each other, and a pair resilient tabs (830) extending proximally relative to overmolded portion (822) and between proximally presented sleeves (828). Overmolded portion (822) defines a pair of notches (824) presented in the distal direction. As will be described in greater detail below, notches (824) are dimensioned to mate with an end of assembly tool (900) to promote attaching coupling feature (820) to a tube actuator (850) of second disposable sub-assembly (704). Each resilient tab (830) includes an outwardly extending protrusion (832). Each outwardly extending protrusion (832) includes a sloped assembly surface (834), a sloped disassembly surface (838) and a locking surface (836). As will be described in greater detail below, sloped assembly surface (834) is configured to promote deflection of resilient tabs (830) during assembly of coupling feature (820) with tube actuator (850), while sloped disassembly surface (836) is configured to promote deflection of resilient tabs (830) during disassembly of coupling feature (820) with tube actuator (850), and locking surface (836) is configured to promote unitary translation of coupling feature (820) with tube actuator (850).

As will be described in further detail below, outer tube (780) is configured to couple with a tube actuator (850) of second disposable sub-assembly (704) when first disposable sub-assembly (702) is coupled with second disposable sub-assembly (704). Tube actuator (850) is configured to drive outer tube (780) longitudinally, to thereby drive clamp arm (770) toward and away from blade (760) as described above.

B. Exemplary Second Disposable Sub-Assembly

As shown in FIGS. 37-38, second disposable sub-assembly (704) of the present example comprises a handle assembly (510) having body (711), a pistol grip (713), a pivoting trigger (712) pivotally coupled to the body (711) and pistol grip (713), and a set of buttons (714, 716). Body (711) defines an opening (718) configured to selectively receive reusable assembly (400), as will be described in greater detail below. As best seen in FIG. 38 proximal inner tube member (790) extends distally from handle assembly (710). An acoustic waveguide (762) is coaxially disposed in proximal inner tube member (790) and distally terminates into ultrasonic blade (760). Waveguide (762) and blade (760) may be configured and operable just like waveguide (192, 592) and blade (190, 590) described above; and/or as described in any of the various references cited herein.

Pistol grip (713) is operable to be grasped by an operator while trigger (712) is operable to drive tube actuator (850) longitudinally in response to pivoting trigger (712) toward and away from pistol grip (713). Pivoting trigger (712) toward and away pistol grip (713) thereby drives outer tube (780) longitudinally, to thereby drive clamp arm (770) toward and away from blade (760), when first disposable sub-assembly (702) is coupled with second disposable sub-assembly (704). Structural features of tube actuator (850) will be described in greater detail below. Various suitable components that may be used to provide longitudinal movement of tube actuator (850) in response to pivotal movement of trigger (712) will be apparent to those of ordinary skill in the art in view of the teachings herein. By way of example only, trigger (712) may be operatively coupled with tube actuator (850) in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition, or in the alternative, trigger (712) may be operatively coupled with tube actuator (850) in accordance with at least some of the teachings of U.S. Patent Pub. No. 2016/0015419, entitled "Ultrasonic Surgical Instrument with Removable Handle Assembly," Published Jan. 21, 2016, issued as U.S. Pat. No. 10,349,967 on Jul 16, 2019, the disclosure of which is incorporated by reference herein.

Buttons (714, 716) are operable to activate ultrasonic blade (760). In particular, buttons (714, 716) are operable to activate the ultrasonic transducer (406) in the variation of reusable assembly (400), which in turn generates ultrasonic vibrations, which are communicated along waveguide (762) to reach blade (760). In some versions, button (714) activates ultrasonic blade (760) with ultrasonic energy at a first set of parameters (e.g., high power); while button (716) activates ultrasonic blade (760) with ultrasonic energy at a second set of parameters (e.g., low power). As another merely illustrative alternative, button (714) may activate ultrasonic blade (760) with ultrasonic energy; while button (716) activates end effector (750) to apply RF electrosurgical energy. Various suitable ways in which this may be carried out, as well as various other suitable ways in which buttons (714, 716) may be configured, arranged, and operable will be apparent to those of ordinary skill in the art in view of the teachings herein.

Figure 45:
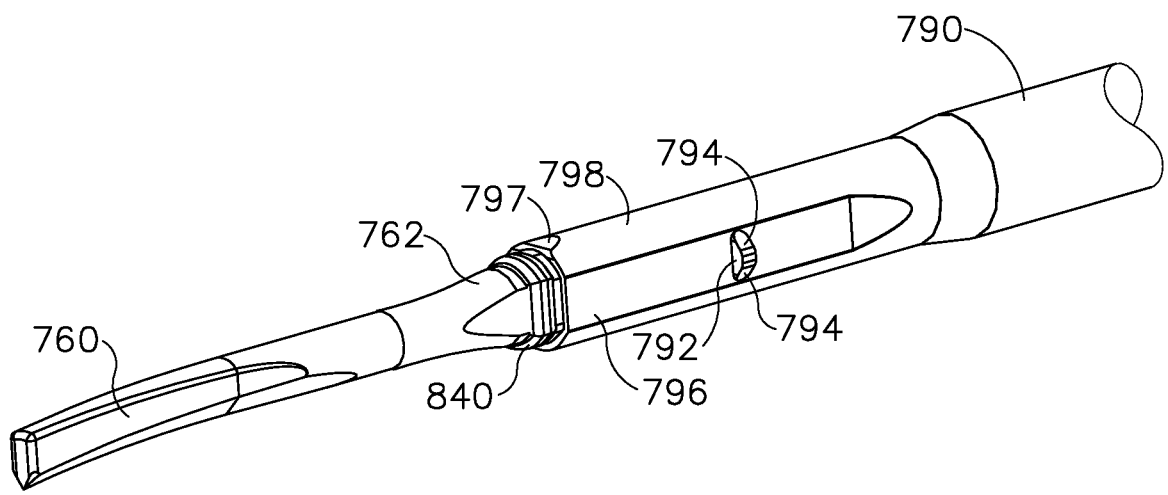
FIG. 45 depicts a perspective view of the distal end of the second disposable sub-assembly of FIG. 38.
Figure 46:
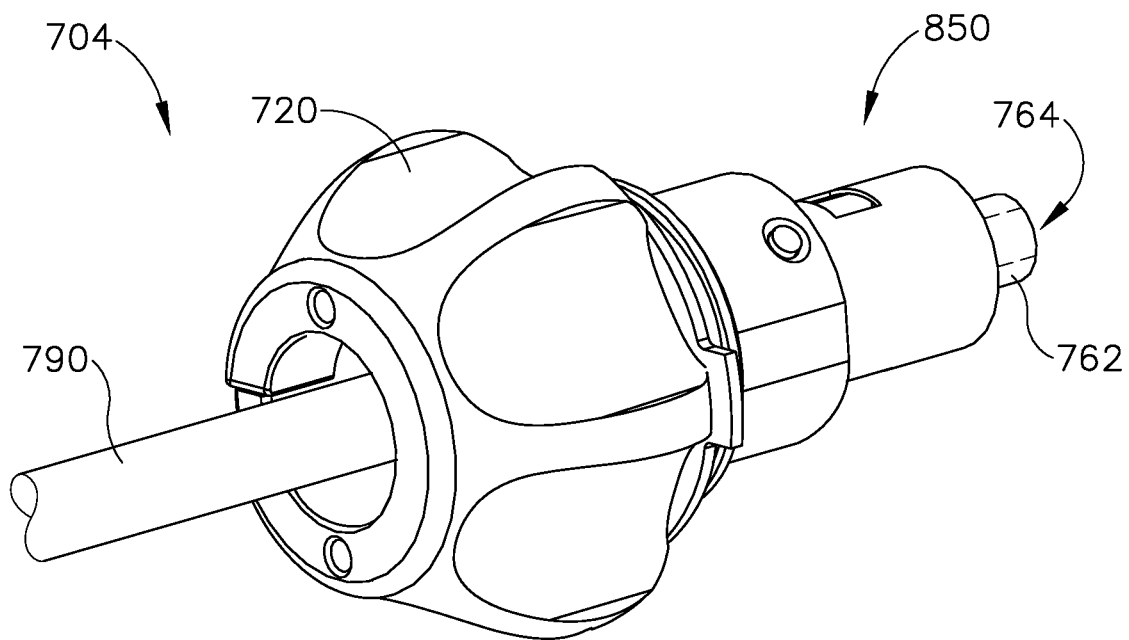
FIG. 46 depicts a perspective view of the proximal end of the second disposable sub-assembly of FIG. 38.
Figure 47:
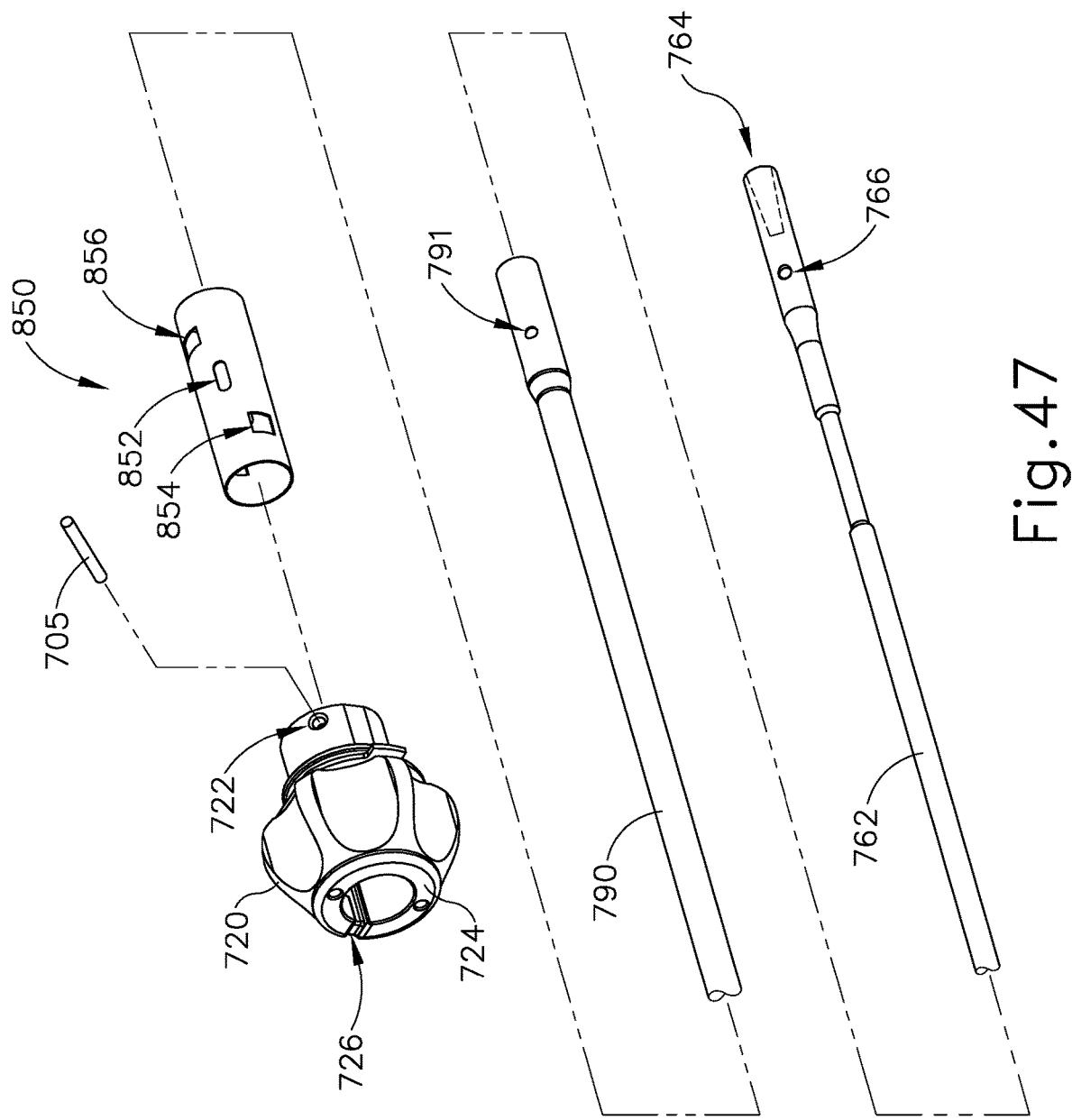
FIG. 47 depicts an exploded perspective view of the proximal end of the second disposable sub-assembly of FIG. 38.

As best seen in FIGS. 45 and 47, proximal inner tube member (790) is disposed coaxially about waveguide (762) yet is radially spaced apart from waveguide (762) such that inner tube member (790) does not contact waveguide (762). As best seen in FIG. 45, a seal member (840) is disposed around waveguide (792) just distal relative to proximal inner tube member (590). As will be described in greater detail below, seal member is configured to interact with proximally presented tabs (814) of distal inner tube (800) to promote correct lateral alignment of distal inner tube (800) relative to waveguide (762).

Seal member (840) may have any suitable geometry known to know in the art in view of the teachings herein. For example, seal member (840) may be substantially like seal member (640) described above. Seal member (840) is formed of an elastomeric material and is located on waveguide (762) at a longitudinal position corresponding to a node associated with resonant ultrasonic vibrations communicated through waveguide (762). Seal member (840) thus provides structural support between waveguide (762) and proximal inner tube member (790) without substantially interfering with ultrasonic vibrations through waveguide (762). Seal member (840) also prevents the ingress of fluids into the gap that is defined between proximal inner tube member (790) and waveguide (762). It should be understood that a series of elastomeric members may be interposed between proximal inner tube member (790) and waveguide (762), at longitudinal positions corresponding to a nodes associated with resonant ultrasonic vibrations communicated through waveguide (762), though such elastomeric members may be configured differently from seal member (840).

The distal end of proximal inner tube member (790) comprises a longitudinally extending flat surface (796) extending adjacent to a longitudinally extending arched surface (798). The distal end of arched surface (797) terminates into a chamfered distal end (797). Proximal inner tube member (790) also comprises an integral, outwardly projecting stud (792) extending away from flat surface (796). Stud (792) is configured to fit in slot (808) of distal inner tube member (800), to thereby couple inner tube members (790, 800) together as will be described in greater detail below.

Figure 69:
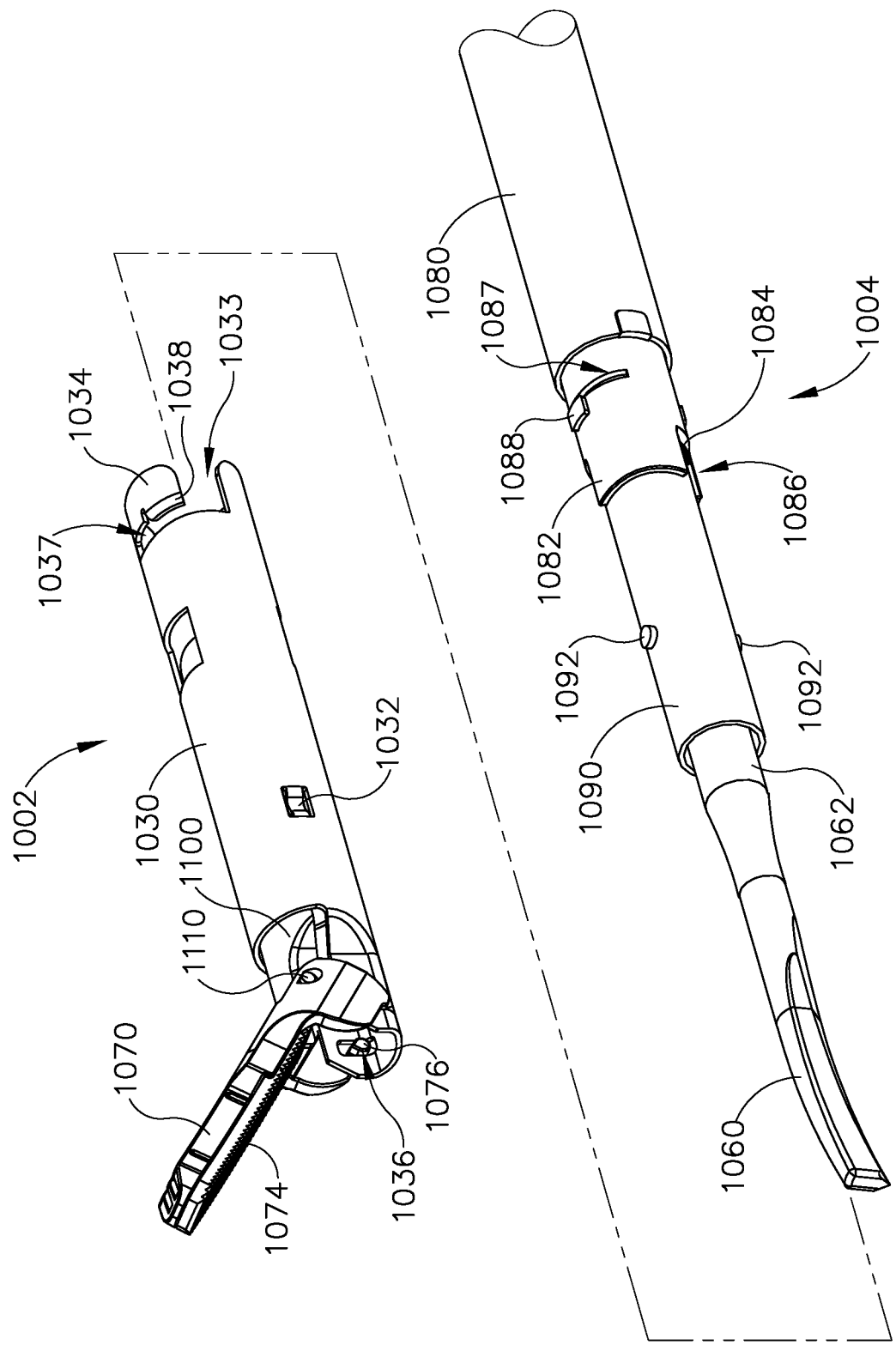
FIG. 69 depicts a perspective exploded view of the first disposable sub-assembly of FIG. 67 and the distal end of the second disposable sub-assembly of FIG. 67.
Figure 70:
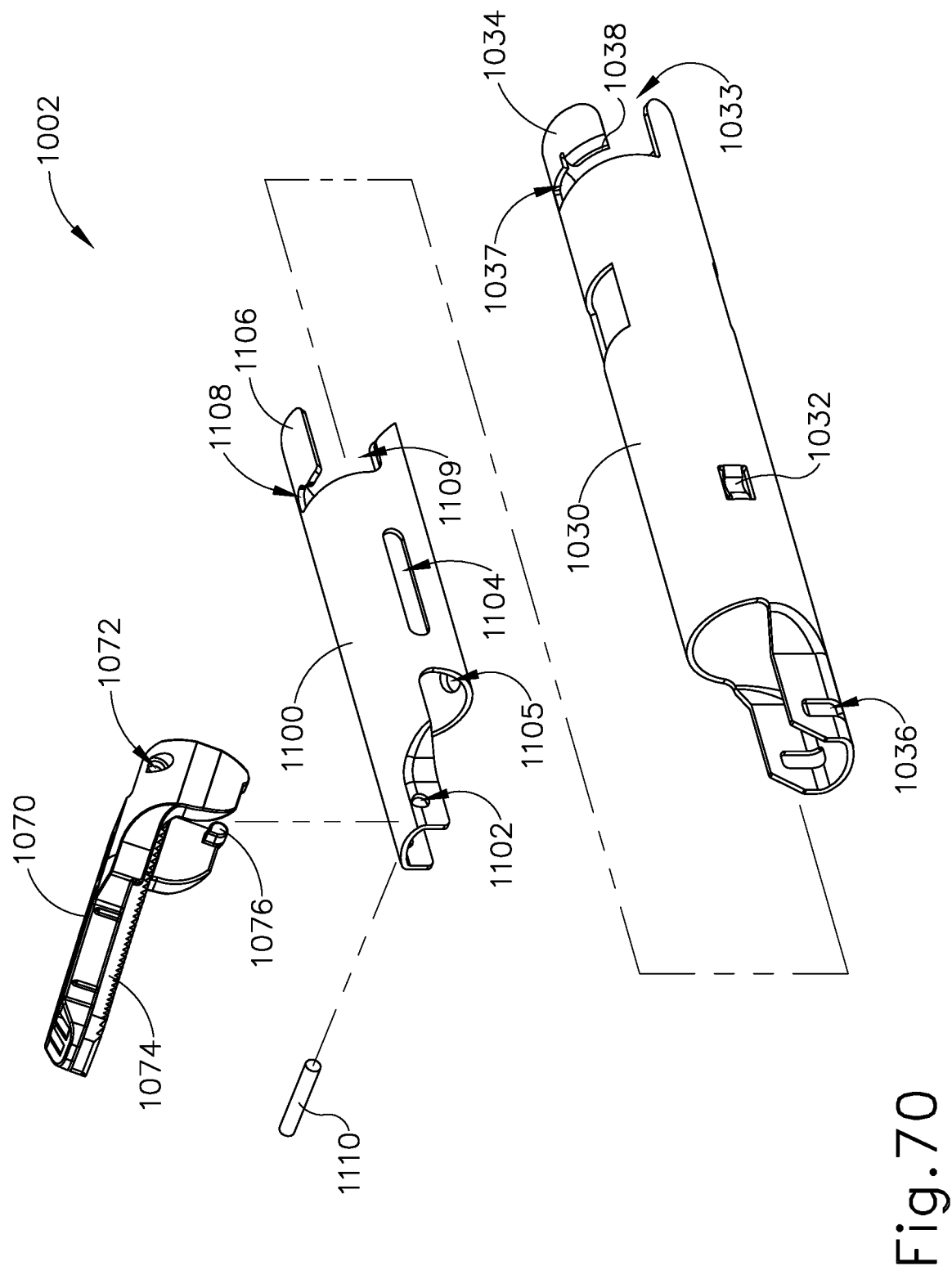
FIG. 70 depicts a perspective exploded view of the first disposable sub-assembly of FIG. 67.
Figure 71:
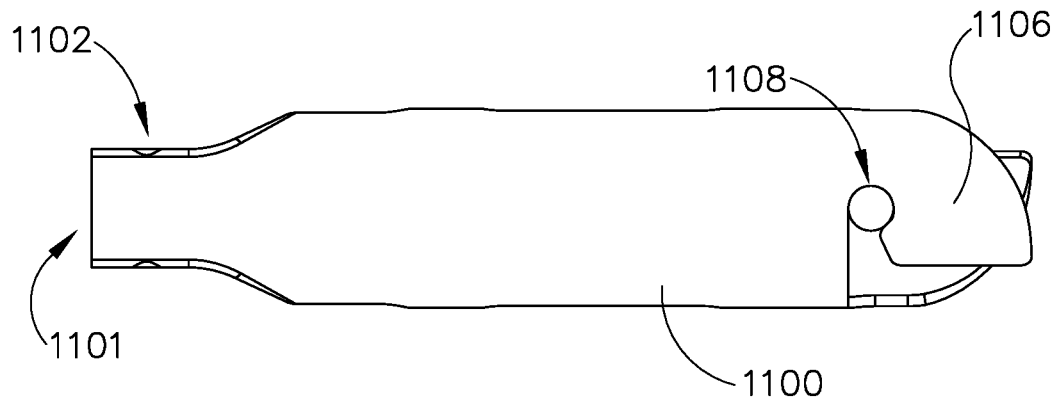
FIG. 71 depicts a top plan view of a distal inner tube member of the first disposable sub-assembly of FIG. 67.
Figure 72:
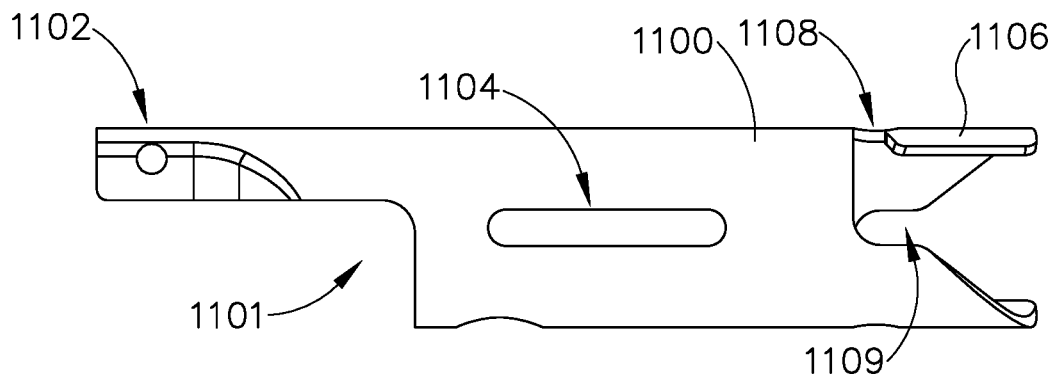
FIG. 72 depicts a side elevational view of the distal inner tube member of FIG. 71.
Figure 73:
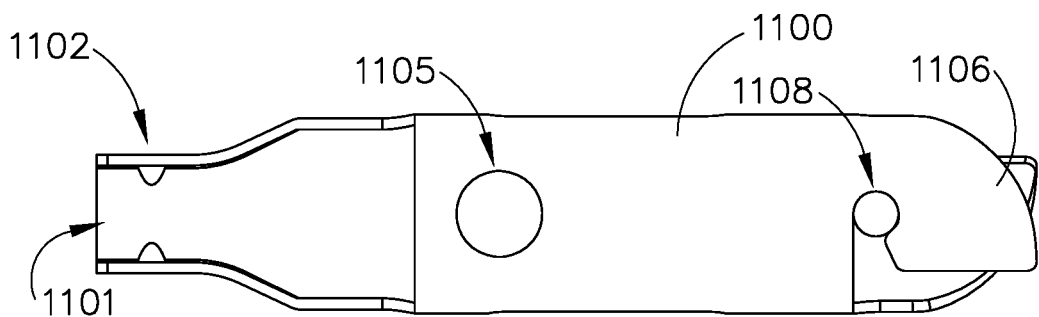
FIG. 73 depicts a bottom plan view of the distal inner tube member of FIG. 71.
Figure 74:
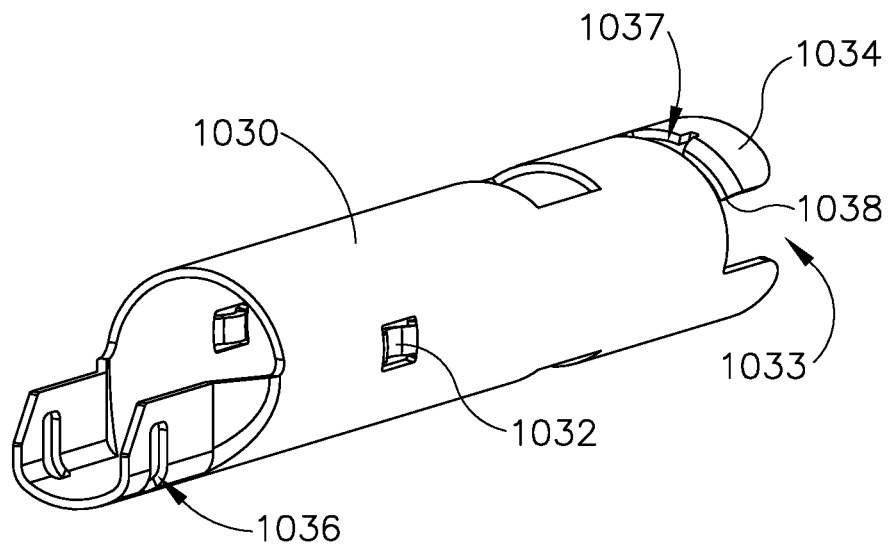
FIG. 74 depicts a perspective view of a distal outer tube member of the first disposable sub-assembly of FIG. 67.
Figure 75:
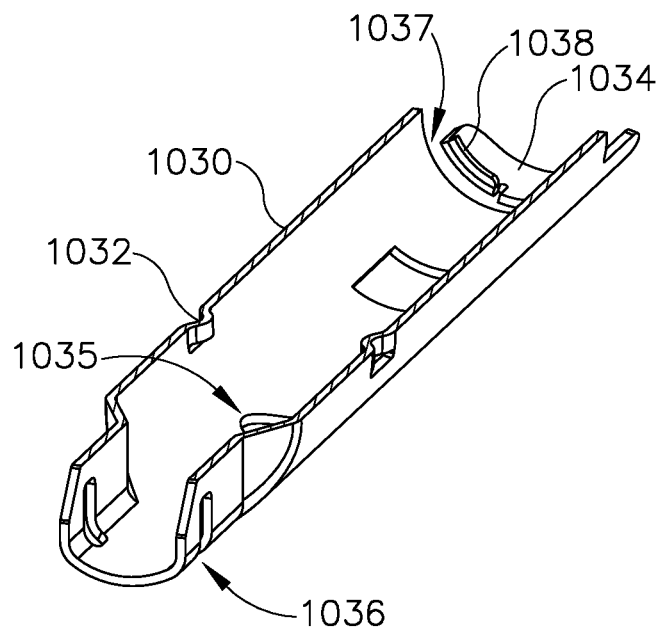
FIG. 75 depicts cross-sectional perspective view of the distal outer tube member of FIG. 74.

Knob member (720) is operable to rotate the shaft assembly that is formed by waveguide (762), inner tube portions (790, 800), outer tube (780), and end effector (750) when first disposable sub-assembly (702) is coupled with second disposable sub-assembly (704). In particular, this shaft assembly is rotatable relative to handle assembly (710). As best seen in FIGS. 69-70, knob member (720), proximal inner tube member (790), and waveguide (762) each include a pin hole (722, 791, 766) respectively to receive pin (705) while tube actuator (850) includes a pair of translation slots (852) to receive pin (705). Therefore, rotation of knob member (720) rotates waveguide (762), proximal inner tube member (790), and tube actuator (850) unitarily. The dimension of translation slots (852) promotes translation of tube actuator (850) and outer tube (780) relative to knob member (720) when first disposable sub-assembly (702) is connected to second disposable sub-assembly (704).

Figure 48:
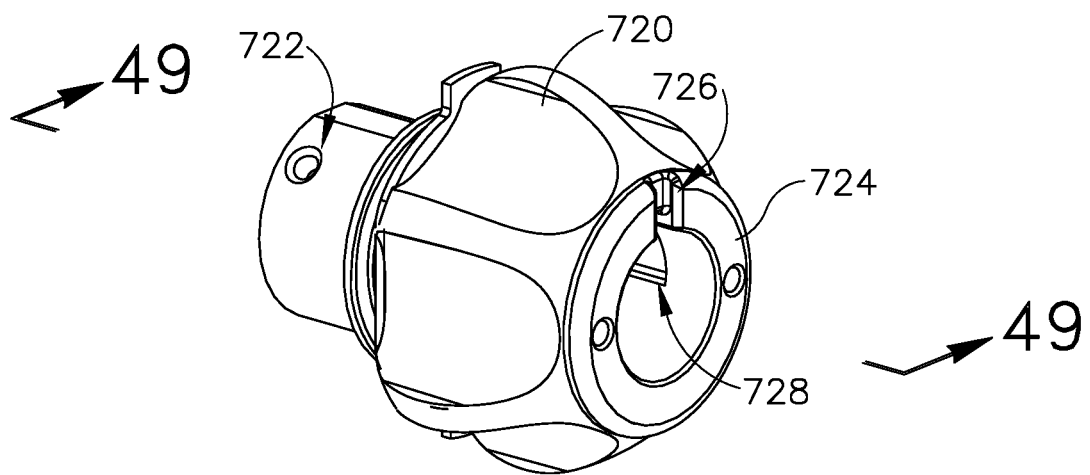
FIG. 48 depicts a perspective view of a knob member of the second disposable sub-assembly of FIG. 38.
Figure 49:
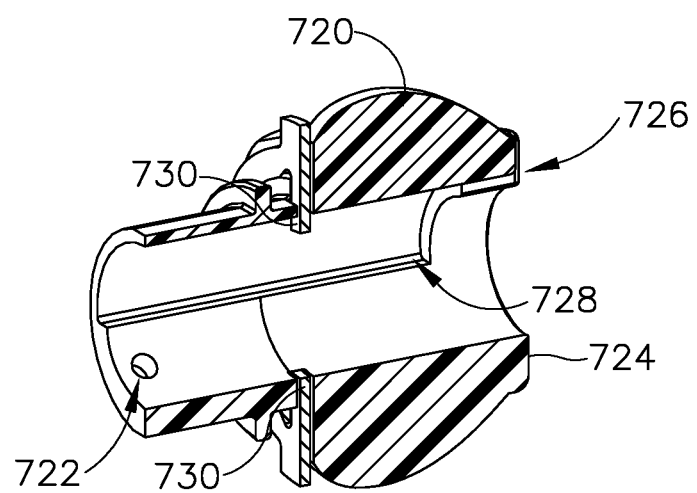
FIG. 49 depicts a cross-sectional perspective view of the knob member of FIG. 48, taken along line 49-49 of FIG. 48.

As best seen in FIGS. 48-49, knob member (720) includes a distal face (724) defining a keyway (726) extending into knob member (720). Keyway (726) terminates into a rotating path (728). Rotating path (728) increases the inner diameter of knob member (720) for a selected circumferential portion of knob member (720). As will be described in greater detail below, keyway (726) and rotating path (728) are dimensioned to accept guide projection (826) of coupling feature (820) such that outer tube (780) may only couple with tube actuator (850) in one angular orientation about the longitudinal axis. Knob member (720) also includes a pair of guide tabs (730). As will be discussed in greater detail below, guide tabs (730) may help promote proper lateral alignment of outer tube (780) relative to tube actuator (850). It should be understood that guide tabs (730) are merely optional. Some versions of knob member (720) may omit guide tabs (730).

Figure 50:
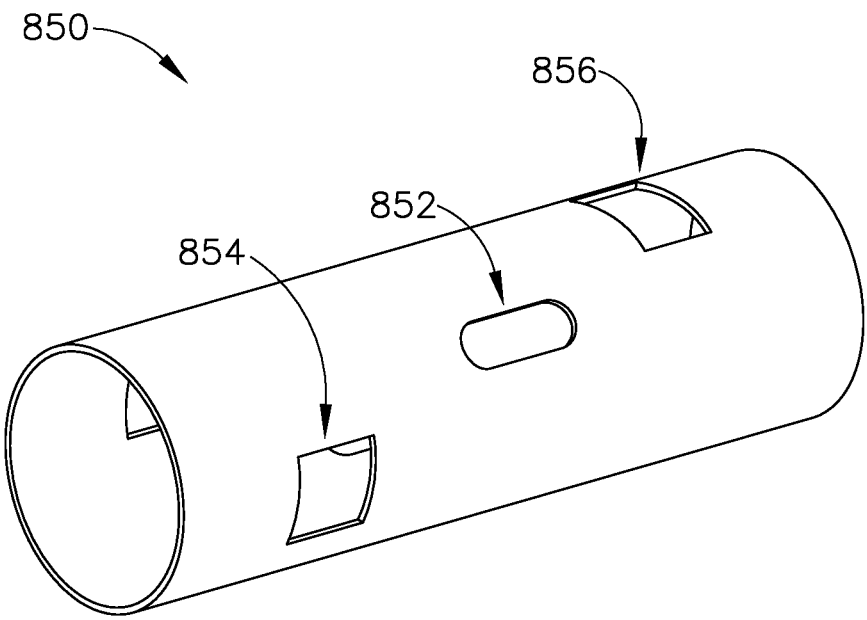
FIG. 50 depicts a perspective view of a tube actuator of the second disposable sub-assembly of FIG. 38.
Figure 51:
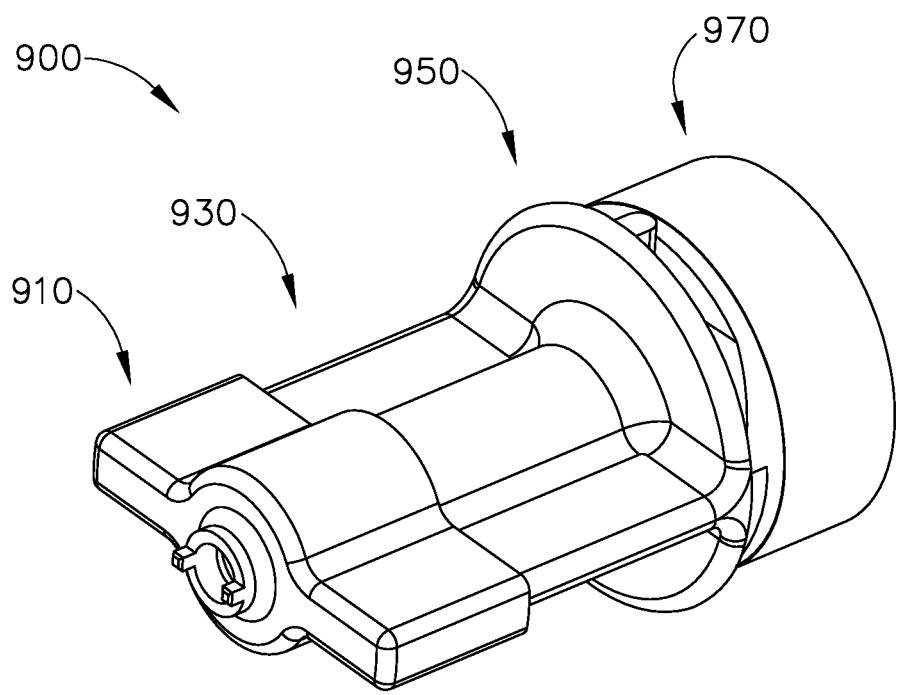
FIG. 51 depicts a perspective front view of an assembly tool that may be utilized to assemble the reusable assembly of FIG. 37 with the disposable assembly of FIG. 37, as well as assemble the first disposable sub-assembly of FIG. 38 with the second disposable sub-assembly of FIG. 38.

As best seen in FIGS. 47 and 50, tube actuator (850) includes translation slot (852), a first pair of coupling windows (854), and a second pair of coupling windows (856). As will be described in greater detail below, first pair of coupling windows are configured to promote coupling between tube actuator (850) and outer tube (780). Second coupling windows (856) may be used to promote coupling of tube actuator (850) with various suitable components that may be used to provide longitudinal movement of tube actuator (850) in response to pivotal movement of trigger (712). While coupling windows (856) are currently shown to promote coupling of tube actuator (850) with various suitable components that may be used to provide longitudinal movement of tube actuator (850) in response to pivotal movement of trigger (712), a threaded portion or any other suitable coupling mechanism may be used as would be apparent to one having ordinary skill in the art in view of the teachings herein.

C. Exemplary Assembly Tool

FIGS. 51-54 show an exemplary assembly tool (900) that may be utilized to couple first disposable sub-assembly (702) with second disposable sub-assembly (704); and also to couple second disposable sub-assembly (704) with reusable assembly (400). Assembly tool (900) includes a spanner wrench portion (910), a hand grip portion (930), a torque slip portion (950), and a knob grip portion (970). Spanner wrench portion (910) and knob grip portion (970) are located on opposite ends of assembly tool (900). Spanner wrench portion (910), hand grip portion (930), torque slip portion (950), and knob grip portion (970) each define a pathway (918, 938, 958, 978) respectively. Assembly tool (900) is dimensioned such that distal end of outer tube (780) may be inserted through pathway (918, 938, 958, 978). As will be described in greater detail below, assembly tool (900) may be inserted to abut against coupling feature (820) or knob member (720), depending on whether spanner wrench portion (910) or knob grip portion (970) is inserted over distal end of outer tube (780) first.

Figure 54:
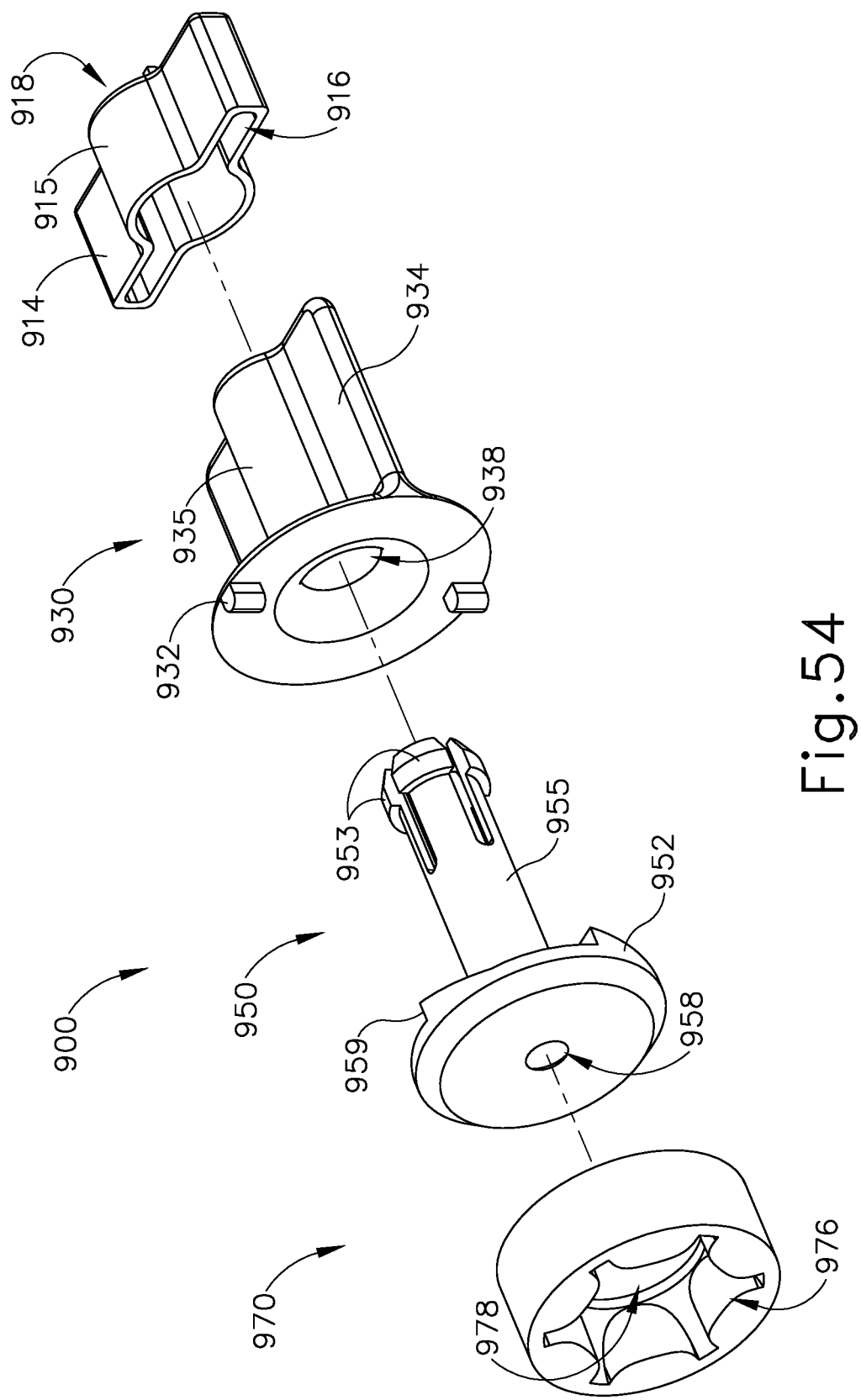
FIG. 54 depicts an exploded rear perspective view of the assembly tool of FIG. 51.

As best seen in FIGS. 53-54, spanner wrench portion (910) includes a pair of prongs (912) extending distally from a central body (915), and a pair of wings (914) extending laterally from central body (915). As best seen in FIG. 54, central body (915) and wings (914) define a cavity (916) dimensioned to be inserted over hand grip portion (930). Cavity (916) may be dimensioned such that spanner wrench portion (910) is coupled to hand grip portion (930) with an interference fit. Of course, any other suitable method of coupling spanner wrench portion (910) with hand grip portion (930) may be utilized as would be apparent to one having ordinary skill in the art in view of the teachings herein, such as adhesives. As mentioned above, spanner wrench portion (910) also defines a pathway (918) for receiving the distal end of outer tube (780).

Hand grip portion (930) includes a central body portion (935) with a pair of grips (934) laterally extending from central body portion (935), and a pair of contact protrusions (932). Contact protrusions (932) are dimensioned to face towards torque slip portion (950).

Torque slip portion (950) includes a disc member (952) unitarily connected to a shaft member (953). Disc member includes a circular pattern of flat surfaces (954), sloped surfaces (956), and vertical surfaces (959). Shaft member (953) includes a plurality of resilient tabs (953). Shaft member (953) is dimensioned to fit within pathway (938) of hand grip portion (930). Additionally, resilient tabs (953) are configured to abut against the inner circumference of pathway (938) in order to provide a predetermined biasing force such that contact protrusions (932) are encouraged to abut against flat surfaces (954) and sloped surfaces (956) of disc member (952). While in the current example, resilient tabs (953) are used to provide a biasing force, any other suitable means of providing a biasing force may be used as would be apparent to one having ordinary skill in the art, such as springs.

Knob gripping portion (970) defines pathway (978) and a gripping surface (976). Gripping surface (976) is dimensioned to cover the surface of knob member (720) such that knob member (720) is rotationally fixed to knob gripping portion (970). Additionally, knob gripping portion (970) is unitary connected to torque slip portion (950).

Torque slip portion (950) is rotatably disposed within hand grip portion (930). However, the biasing force encouraging contact between contact protrusions (932) and surfaces (954, 956) promotes a predetermined frictional braking force. The frictional braking force between torque slip portion (950) and hand grip portion (930) may be great enough to encourage hand grip portion (930) and torque slip portion (950) to rotate unitarily. However, torque slip portion (950) may slip relative to hand grip portion (930) if assembly tool (900) experiences a force great enough to overcome the frictional braking force, such as a predetermined amount of torque.

D. Exemplary Assembly of First Disposable Sub-Assembly with Second Disposable Sub-Assembly FIGS. 55A-60B show various stages of assembling first disposable sub-assembly (702) with second disposable sub-assembly (704). In particular, FIGS. 55A-57B show various stages occurring at the proximal end of first disposable sub-assembly (702) with second disposable sub-assembly (704); while FIGS. 58A-59C show various stages occurring at the distal end of first deposable sub-assembly (702) during a process of assembling first disposable sub-assembly (702) with second disposable sub-assembly (704). Additionally, FIGS. 60A-60B show how assembly tool (900) may be utilized to install first disposable sub-assembly (702) with second disposable sub-assembly (704).

It should be understood that during the process shown in FIGS. 55A-83B, an operator may grasp first disposable sub-assembly (702) in one hand, grasp second disposable sub-assembly (704) in the other hand, and then move first disposable sub-assembly (702) relative to second disposable sub-assembly (704) (while holding knob member (720) stationary) in order to accomplish the process. Alternatively, as shown in FIGS. 60A-60B, an operator may insert assembly tool (900), spanner wrench portion (910) first, over the distal end of first disposable sub-assembly (702) and manipulate first disposable sub-assembly (702) with assembly tool (900)

Figure 55A:
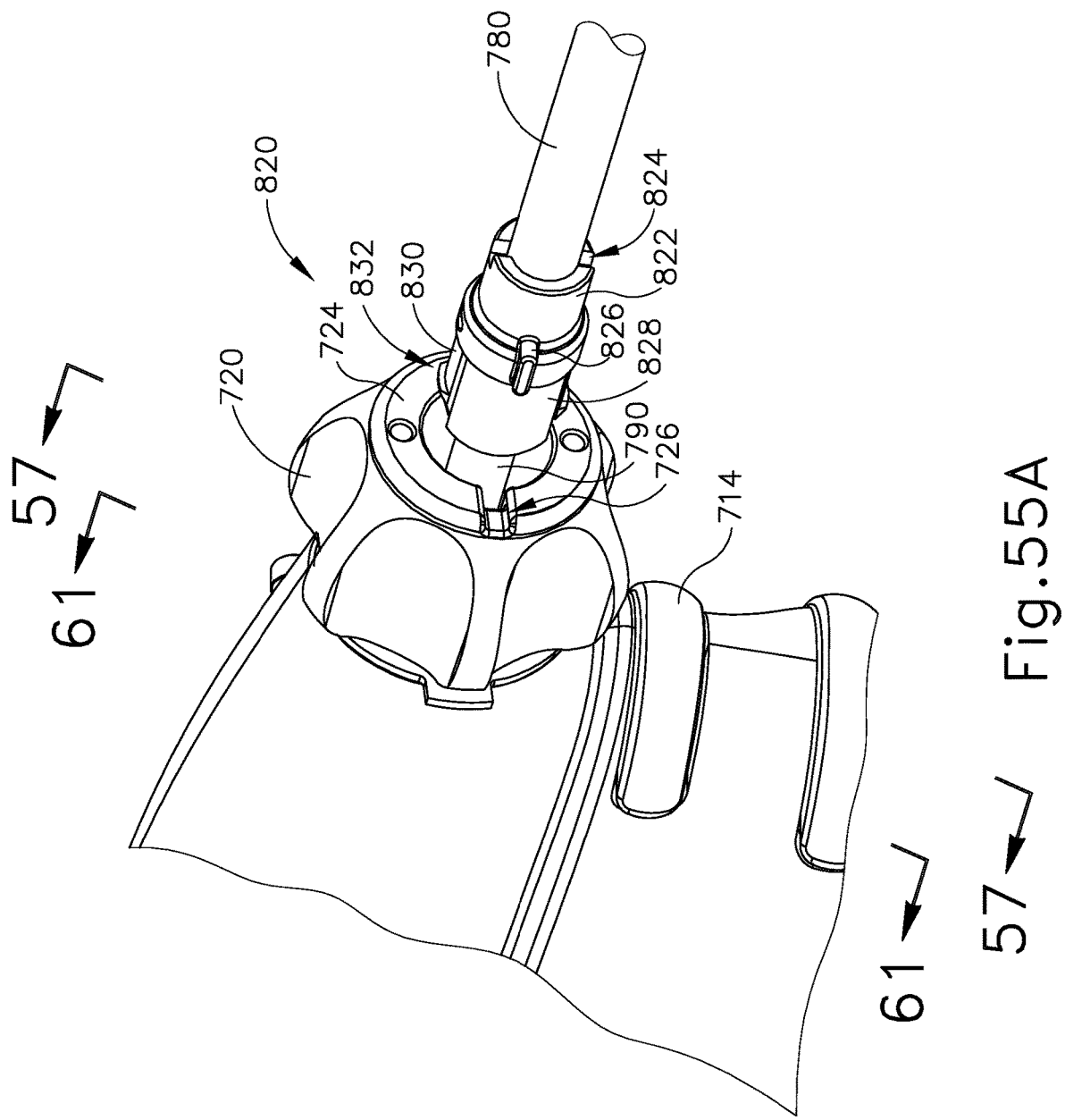
FIG. 55A depicts a perspective view of the proximal end of the first sub-assembly of FIG. 38 being coupled with the proximal end of the second sub-assembly of FIG. 38, where the proximal end of the first sub-assembly is distal in relation to the knob member of the second sub-assembly.
Figure 55B:
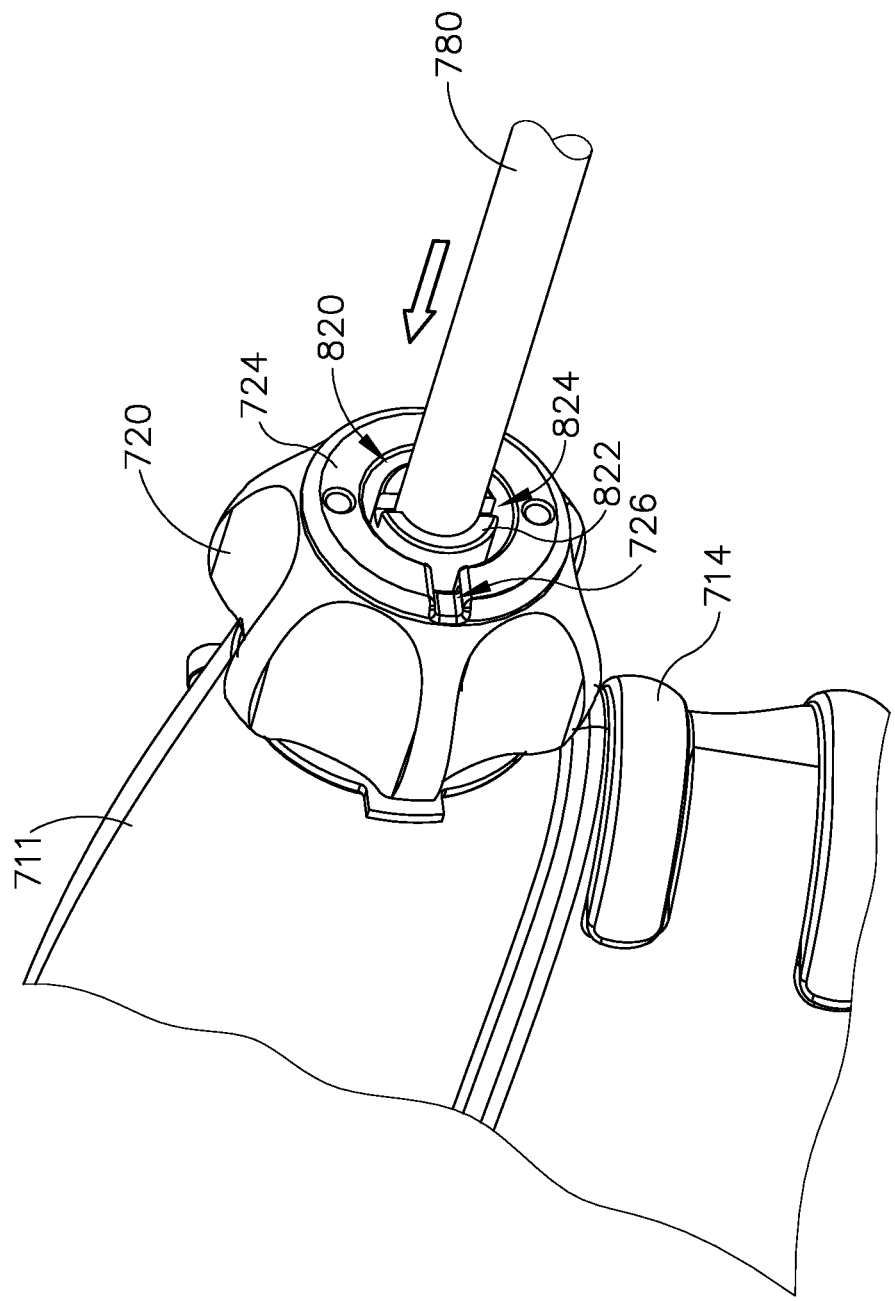
FIG. 55B depicts a perspective view of the proximal end of the first sub-assembly of FIG. 38 being coupled with the proximal end of the second sub-assembly of FIG. 38, where the proximal end of the first sub-assembly is placed within the knob member of the second sub-assembly.
Figure 56A:
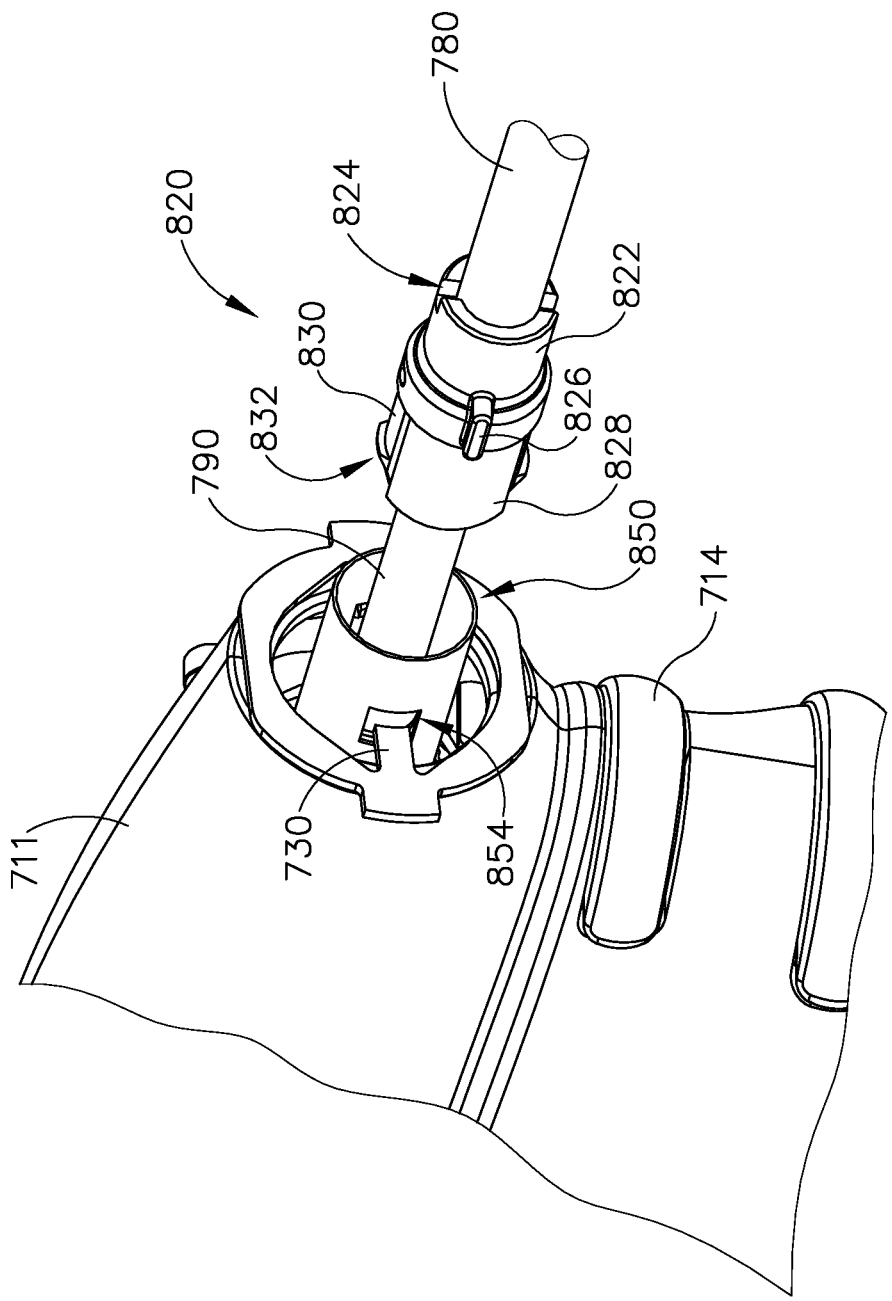
FIG. 56A depicts a perspective view of the proximal end of the first sub-assembly of FIG. 38 being coupled with the proximal end of the second sub-assembly of FIG. 38 with the knob member omitted for clarity, where the proximal end of the first sub-assembly is distal in relation to the knob member of the second sub-assembly.
Figure 56B:
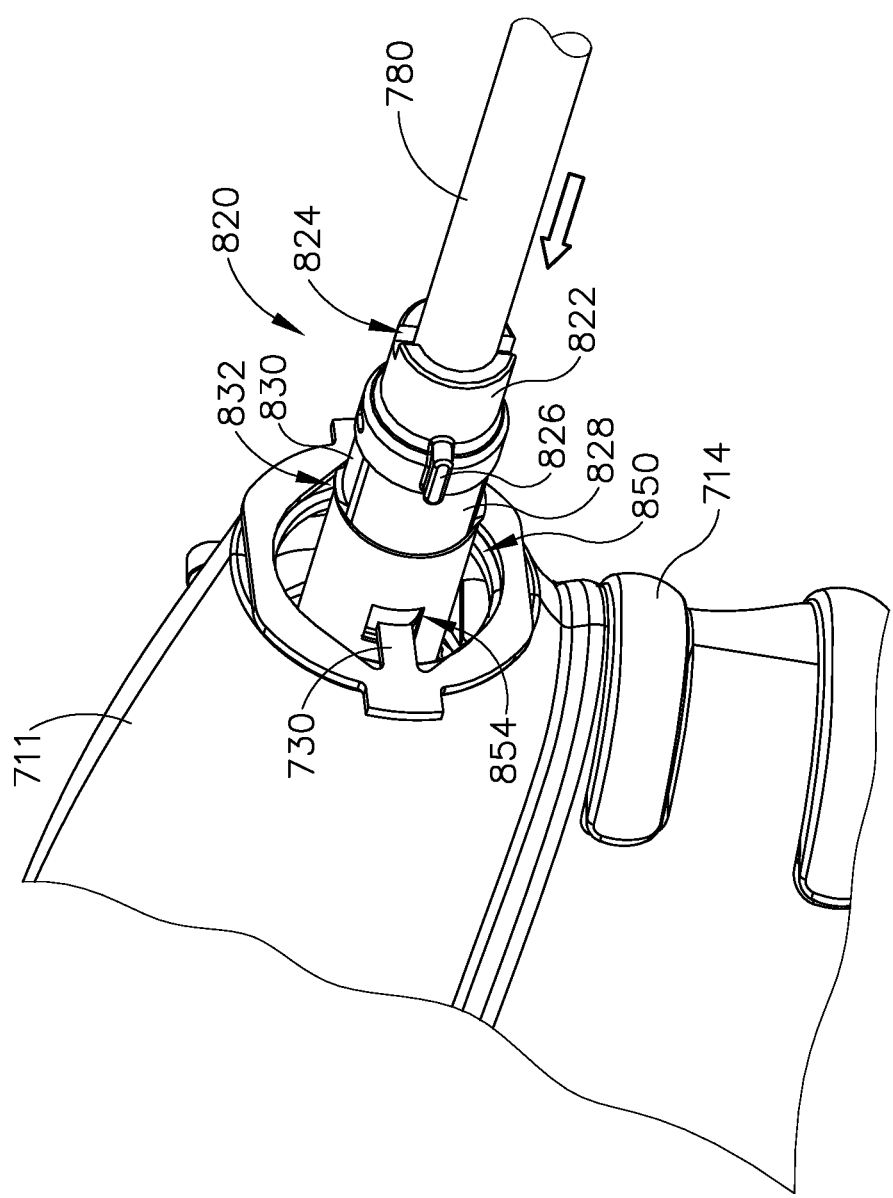
FIG. 56B depicts a perspective view of the proximal end of the first sub-assembly of FIG. 38 being coupled with the proximal end of the second sub-assembly of FIG. 38 with the knob member omitted for clarity, where the proximal end of the first sub-assembly abuts against the distal end of the tube actuator of the second sub-assembly.
Figure 56C:
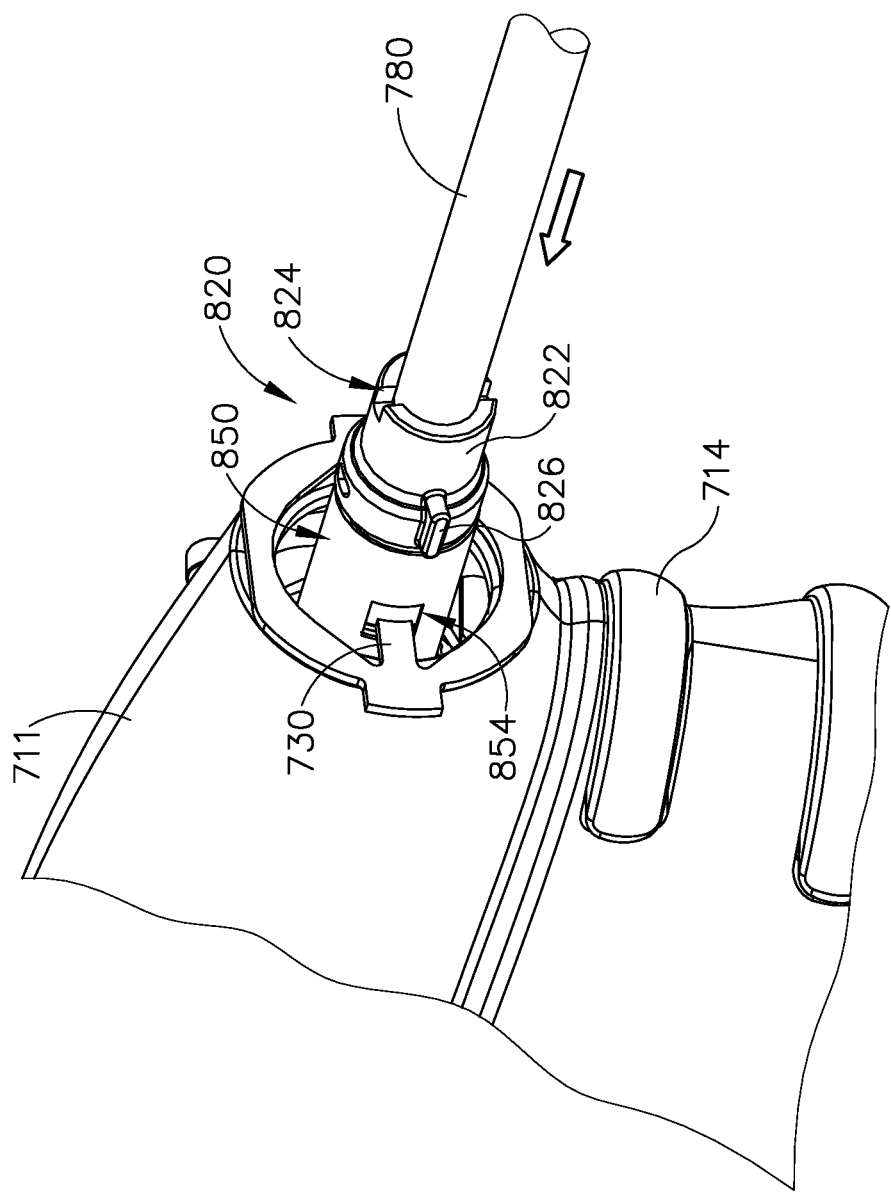
FIG. 56C depicts a perspective view of the proximal end of first sub-assembly of FIG. 38 being coupled with the proximal end of the second sub-assembly of FIG. 38 with the knob member omitted for clarity, where the proximal end of the first sub-assembly is within the tube actuator of the second sub-assembly without being coupled with the tube actuator of the second sub-assembly.

FIGS. 55A-55B show the same movement as shown in FIGS. 56A-56C. However, knob member (720) is omitted from FIGS. 56A-56D in order to enable visualization of the components that would otherwise be obscured by knob member (720). FIGS. 55A-55B show that as the proximal end of outer tube (780) is being inserted within knob member (720), keyway (726) and guide projection (826) must be aligned so that coupling feature (820) may be inserted into knob member (720). As shown in FIG. 56A, first disposable sub-assembly (7020 is at a distal position. At this stage, the proximal end of outer tube (780) is distal relative to the distal end of tube actuator (850). As shown in FIG. 56B, the proximal end of outer tube (780) may be advanced proximally such that the proximal end of resilient tabs (830) and proximally presented sleeves (828) initially enter the distal end of tube actuator (850). It should be understood that at this point, outwardly extending protrusions (832) are not within tub actuator (850). Additionally, it should be understood that outwardly extending protrusions (832) are dimensioned to radially extend past the diameter of tube actuator (850) when resilient tabs (830) are in a relaxed position.

As shown in FIG. 56C, the proximal end of outer tube (780) may be further advanced in the proximal direction such that proximally presented sleeves (828) and resilient tabs (830) are within the confines of tube actuator (850). It should be understood that as the proximal end of outer tube (780) is advanced within tube actuator (850), the distal edge of tube actuator (850) abuts against sloped assembly surface (834) of outwardly extending protrusions (832) to drive resilient tabs (830) from a relaxed position to an inwardly flexed position. Additionally, when resilient tabs (830) are within the confines of tube actuator (850) as shown in FIG. 56C, the inner diameter of tube actuator (850) makes contact with outwardly extending protrusions (832) to keep resilient tabs (930) in the inwardly flexed position.

Figure 56D:
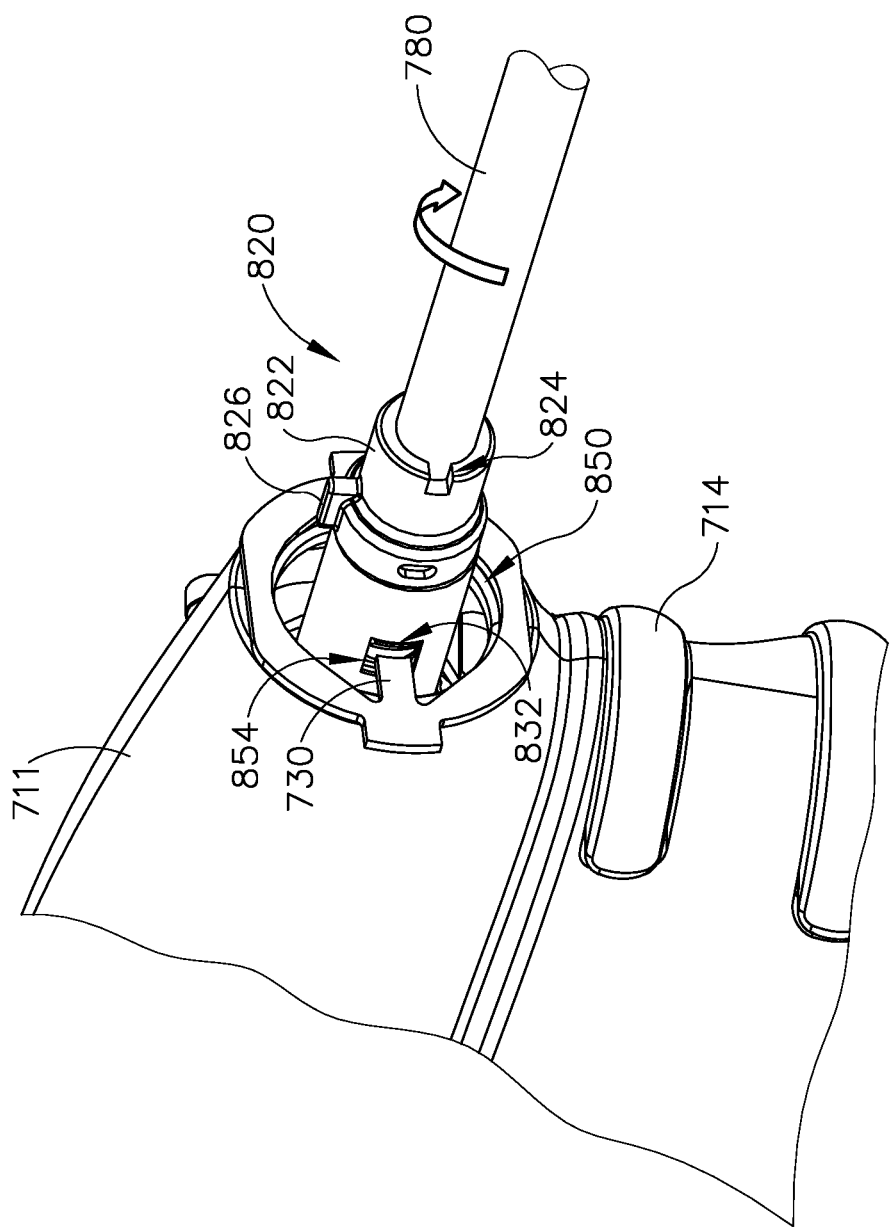
FIG. 56D depicts a perspective view of the proximal end of the first sub-assembly of FIG. 38 being coupled with the proximal end of the second sub-assembly of FIG. 38 with the knob member omitted for clarity, where the proximal end of the first sub-assembly is fully coupled with the tube actuator of the second sub-assembly.

As shown in FIG. 56D, an operator may then rotate outer tube (780) in the clockwise direction (facing proximally) such that proximally presented sleeves (828) and resilient tabs (830) rotate within the confines of tube actuator (850). An operator may rotate outer tube (780) until outwardly extending protrusions (832) align with first coupling windows (854). When outwardly extending protrusions (832) align with first coupling windows (854), the inner diameter of tube actuator (850) no longer makes contact with outwardly extending protrusions (832). Therefore, there is no external force keeping tabs (830) in the inwardly flexed position and the resilient nature of tabs (830) returns tabs (830) to the relaxed position. In the relaxed position, as shown in FIG. 56D, outwardly extending protrusions (832) radially extend past the diameter of tube actuator (850). It should be understood that locking surface (836) and sloped disassembly surfaces (838) may makes contact with a perimeter of first coupling window (854) such that the resilient nature of tabs (830) causes contact between surfaces (836, 838) and perimeter of first coupling window (854), to provide an interface fit between outer tube (780) and tube actuator (850). This inference fit may allow for selectively coupling outer tube (780) and tube actuator (850) such that unitary longitudinal translation of tube actuator (850) and outer tube (780) are achieved. Of course, any other suitable means of providing unitary longitudinal translation can be used as would be apparent to one having ordinary skill in the art in view of the teachings herein. For example, first coupling window (854) may be dimensioned to contact portions of locking surface (836) and sloped assembly surface (834) when coupling tube actuator (850) and outer tube (780).

Figure 57A:
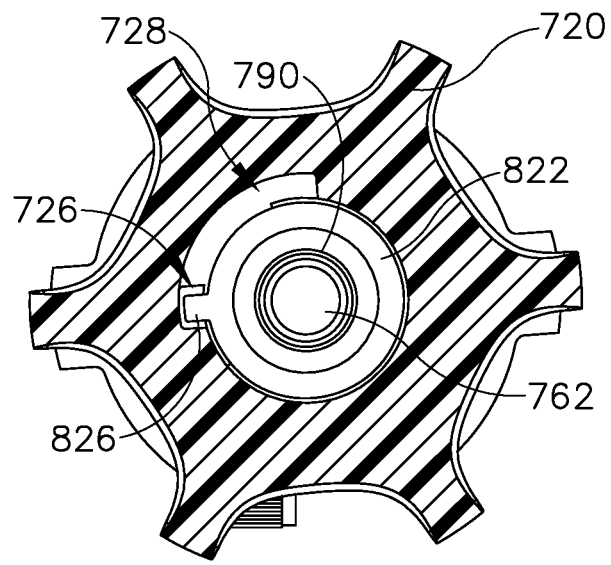
FIG. 57A depicts a cross-sectional front view of the proximal end of the first sub-assembly of FIG. 38 being coupled with the proximal end of the second sub-assembly of FIG. 38, corresponding with the view shown in FIG. 56C, with the knob member of the second sub-assembly shown, taken along line 57-57 of FIG. 55A.
Figure 57B:
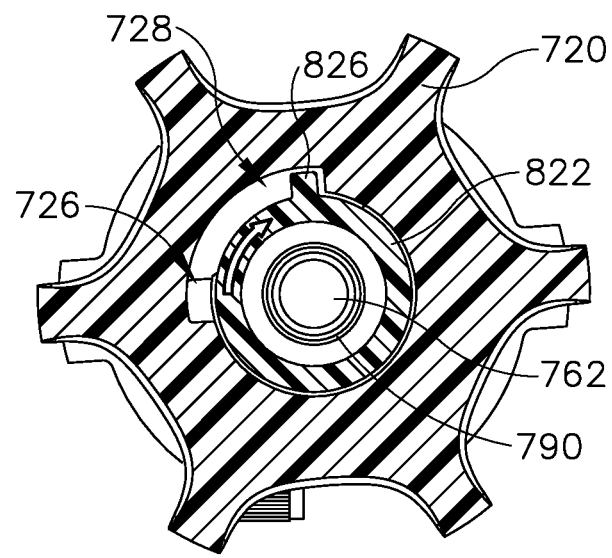
FIG. 57B depicts a cross-sectional front view of the proximal end of first sub-assembly of FIG. 38 being coupled with the proximal end of the second sub-assembly of FIG. 38, corresponding with the view shown in FIG. 56D, with the knob member of the second sub-assembly shown, taken along line 57-57 of FIG. 55A.

FIGS. 57A-57B show that once outer tube (780) is inserted such that guide projection (826) is inserted within keyway (726) of knob member (720) as shown in FIGS. 55B, 56C, and 57A, rotating path (728) restricts rotation of outer tube (780) to a single direction due to interaction between guide projection (826) and rotating path (728). This may help ensure that end effector (750) is has proper rotational alignment when first disposable sub-assembly (702) is coupled with second disposable sub-assembly (704).

Additionally, guide tabs (730) are dimensioned to ensure proper lateral alignment as tube actuator (850) longitudinally translates outwardly extending protrusions (832) past guide tabs (730). This may help ensure that blade (760) has proper lateral alignment compared to clamp arm (770) as clamp arm (770) rotates toward and away from blade (760). However, as noted above, it should be understood that guide tabs (730) are merely optional. Guide tabs (730) are omitted in some versions.

In the series shown in FIGS. 58A-58E, first disposable sub-assembly (702) appears to remain fixed in place while second disposable sub-assembly (704) moves. However, it should be understood that an operator may in fact hold second disposable sub-assembly (704) stationary and move first disposable sub-assembly (702) in order to transition through the stages shown in FIGS. 58A-58E. Additionally, FIGS. 59A-59C show coupling of distal inner tube (800) with proximal inner tube member (790) without outer tube (780) for purposes of clarity.

Figure 58A:
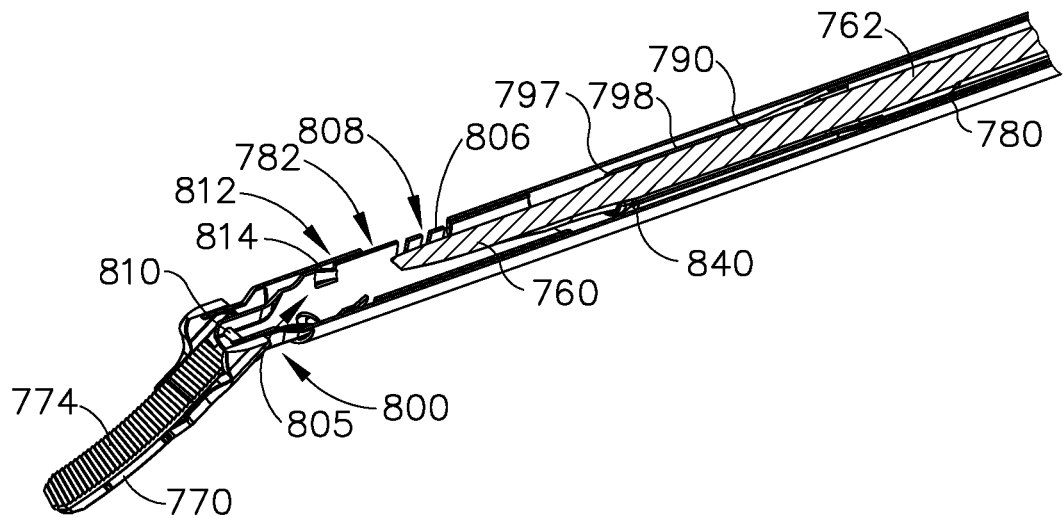
FIG. 58A depicts a cross-sectional perspective view of the distal end of the first sub-assembly of FIG. 38 being coupled with the distal end of the second sub-assembly of FIG. 38, where the first sub-assembly is inserted over the second sub-assembly in the proximal direction, taken along line 58-58 of FIG. 39.
Figure 59A:
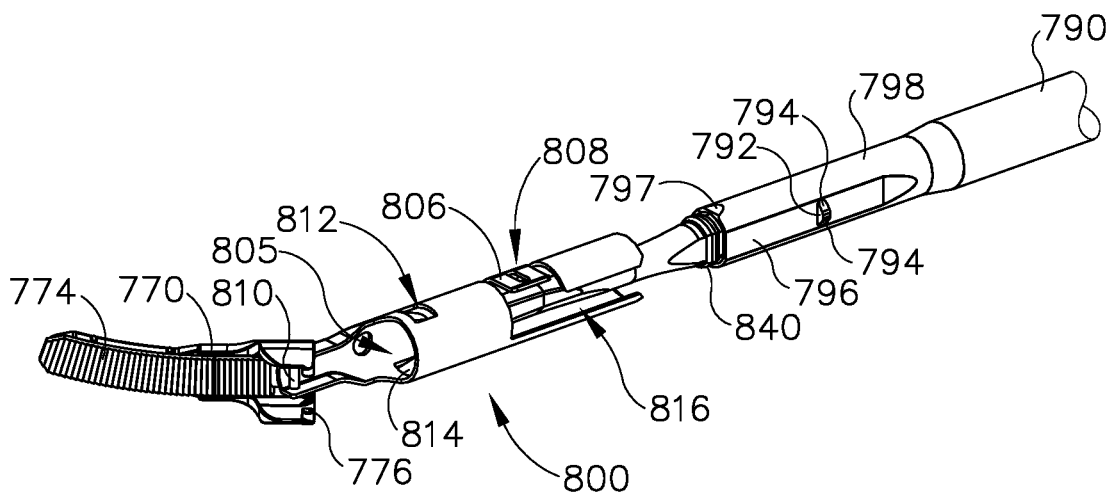
FIG. 59A depicts a perspective view of the distal end of the first sub-assembly of FIG. 38 being coupled with the distal end of the second sub-assembly of FIG. 38 with an outer tube of the first sub-assembly omitted for clarity, where the first sub-assembly is inserted over the second sub-assembly in the proximal direction.
Figure 59B:
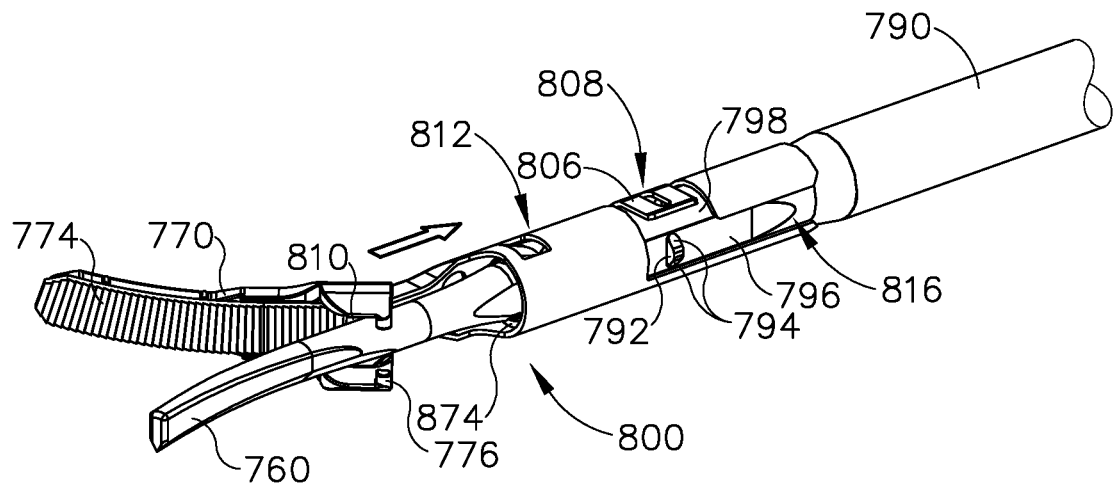
FIG. 59B depicts a perspective view of the distal end of the first sub-assembly of FIG. 38 being coupled with the distal end of the second sub-assembly of FIG. 38 with an outer tube of the first sub-assembly omitted for clarity, where the first sub-assembly is further inserted over the second sub-assembly in the proximal direction.
Figure 60A:
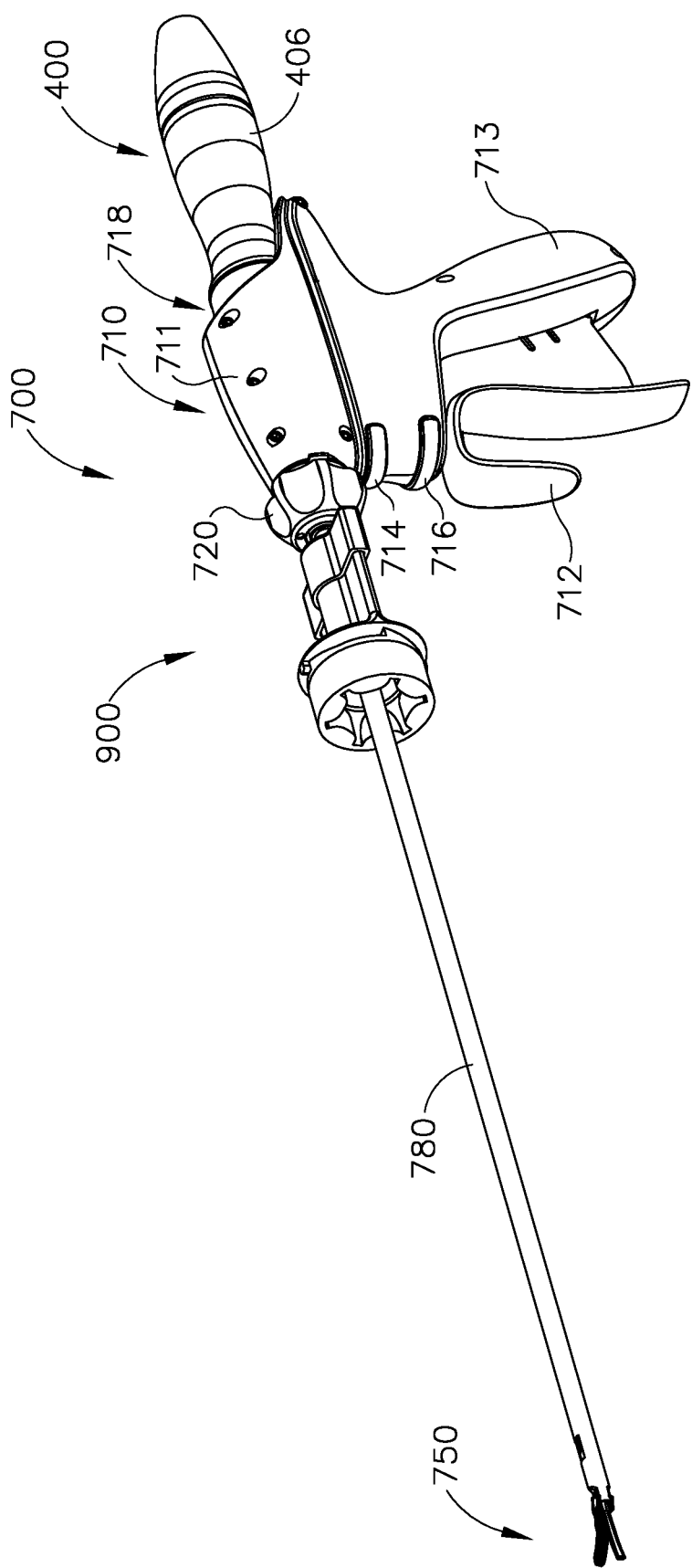
FIG. 60A depicts a perspective view of the first sub-assembly of FIG. 38 being coupled with the second sub-assembly of FIG. 38 utilizing the assembly tool of FIG. 51, with the first sub-assembly and the assembly tool being positioned at a first angular orientation.
Figure 60B:
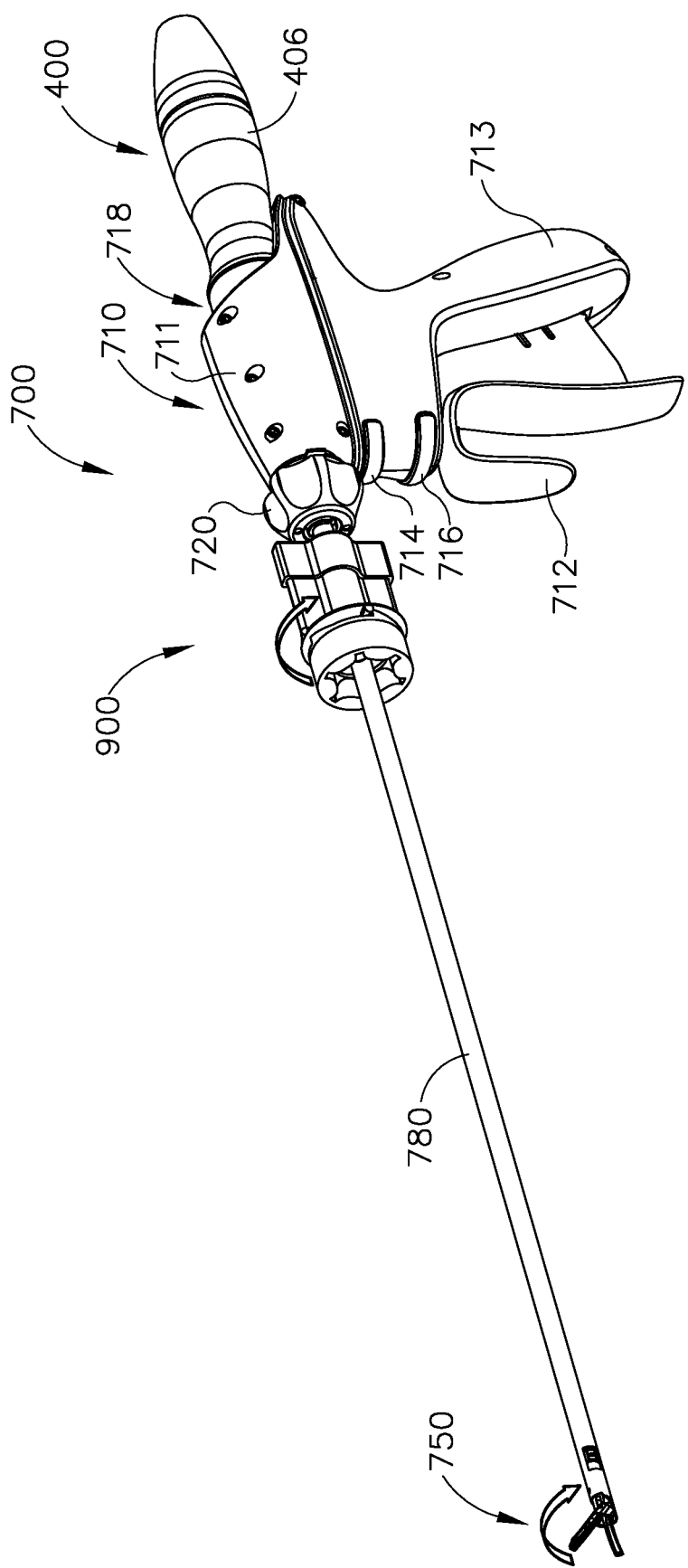
FIG. 60B depicts a perspective view of the first sub-assembly of FIG. 38 being coupled with the second sub-assembly of FIG. 38 utilizing the assembly tool of FIG. 51, with the first sub-assembly and the assembly tool being positioned at a second angular orientation to fully couple the first sub-assembly tool with the tube actuator of the second sub-assembly.

As shown in FIGS. 58A and 59A, sub-assemblies (702, 704) are initially positioned such that the curved distal tip of blade (760) is oriented downwardly as outer tube (780) is slid proximally along blade (760), waveguide (762), and proximal inner tube portion (790). This angular positioning may be the same as that shown in FIGS. 56A-56C.

Figure 58B:
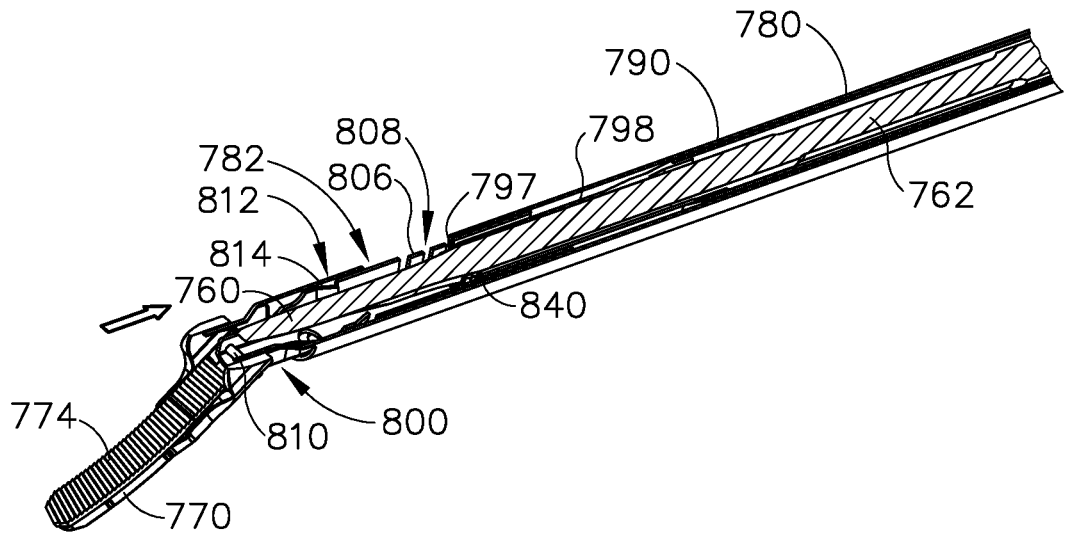
FIG. 58B depicts a cross-sectional perspective view of the distal end of the first sub-assembly of FIG. 38 being coupled with the distal end of the second sub-assembly of FIG. 38, where the first sub-assembly is further inserted over the second sub-assembly in the proximal direction, taken along line 58-58 of FIG. 39.
Figure 58C:
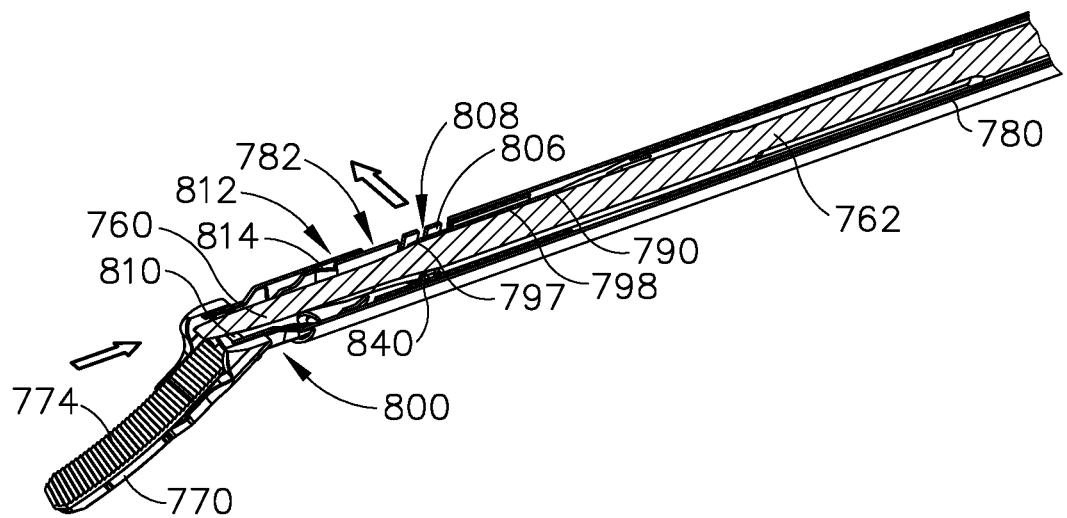
FIG. 58C depicts a cross-sectional perspective view of the distal end of the first sub-assembly of FIG. 38 being coupled with the distal end of the second sub-assembly of FIG. 38, where the first sub-assembly is further inserted over the second sub-assembly in the proximal direction, taken along line 58-58 of FIG. 39.
Figure 58D:
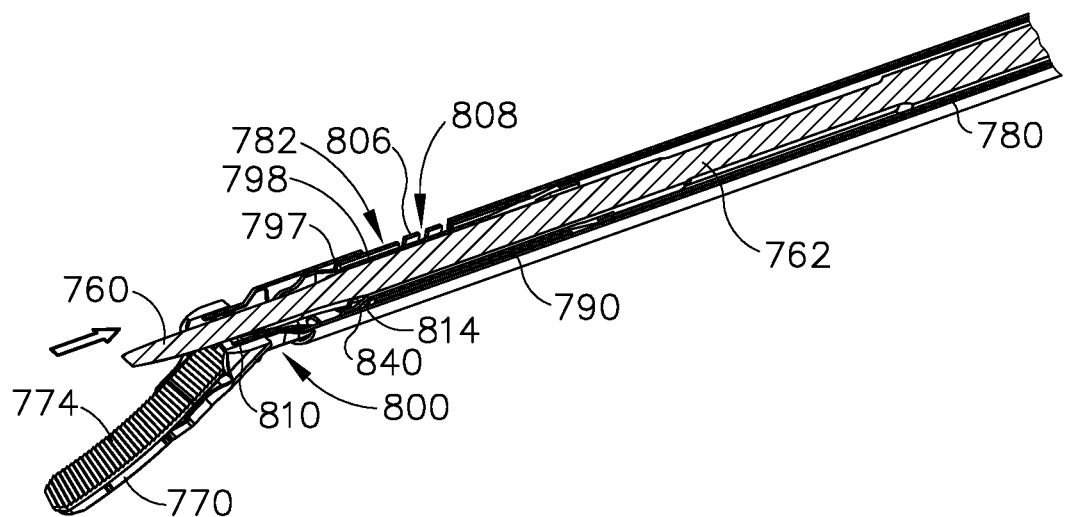
FIG. 58D depicts a cross-sectional perspective view of the distal end of the first sub-assembly of FIG. 38 being coupled with the distal end of the second sub-assembly of FIG. 38, where the first sub-assembly is in the most proximal position, taken along 58-58 of FIG. 39.

An operator may then slide first disposable sub-assembly (702) in the proximal direction to the position shown in FIG. 58B so that blade (760) is inserted within gap (805). At this position, flat member (806) is directly adjacent to chamfered distal end (797) of arched surface (798). As can be seen from FIGS. 58B to 58C, chamfered distal end (797) is dimensioned such that further proximal movement of disposable assembly (702) causes flat member (806) to deform outwardly relative to the relaxed position of flat member (806). This deformation is due to contact with arched surface (798). An operator may then further slide first disposable assembly (702) proximally to the position shown in FIGS. 58D and 59B. It should be understood, as shown in FIG. 59B, that stud (792) slides within pathway (816). It should also be understood that the position shown in FIGS. 81D and 82B correlates with the position shown in FIGS. 55B and 79C. At this stage, flat member (806) is still in an outwardly deformed position due to contact with arched surface (798). Also at this stage, proximally presented tabs (814) are both in contact with seal member (840). As mentioned above, seal member (840) is elastomeric. Seal member (840) in contact with proximally presented tabs (814) may promote lateral and vertical alignment of distal inner tube (800) relative to waveguide (762).

Figure 58E:
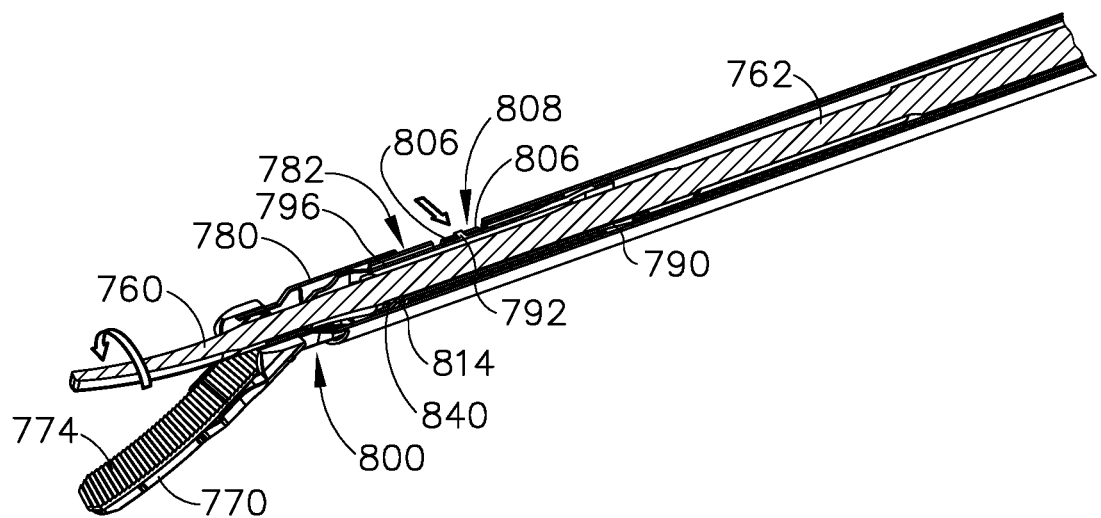
FIG. 58E depicts a cross-sectional perspective view of the distal end of the first sub-assembly of FIG. 38 being coupled with the distal end of the second sub-assembly of FIG. 38, where the second sub-assembly is rotated in order to fully couple with the first sub-assembly.
Figure 59C:
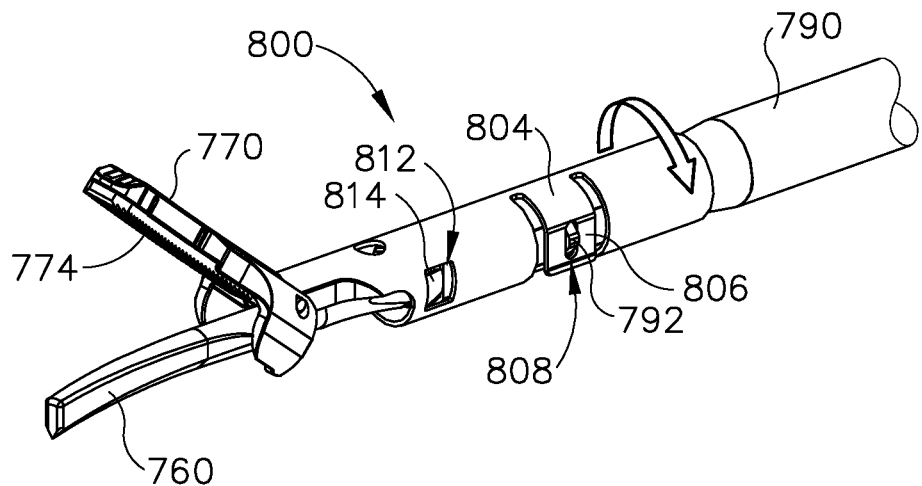
FIG. 59C depicts a perspective view of the distal end of the first sub-assembly of FIG. 38 being coupled with the distal end of the second sub-assembly of FIG. 38 with an outer tube of the first sub-assembly omitted for clarity, where the first sub-assembly is rotated 90 degrees to fully couple with the second sub-assembly.

An operator may then rotate first disposable assembly (702) relative to second disposable assembly (704) to the position shown in FIGS. 58E and 59C, such that flat member (806) is adjacent to flat surface (796). Flat member (806) returns to the relaxed position due to the dimensions of flat surface (796) compared to arched surface (798). Additionally, slot (808) is longitudinally aligned with stud (792) such that rotation, from the position shown in FIGS. 58D to 58E and 59B to 59C, snaps stud (792) into slot (808). Outwardly extending lip (807) of flat member (806) may interface with camming surface (794) of stud (792) in order to promote stud (792) to snap into slot (808). Stud (792) and slot (808) are dimensioned such that proximal inner tube (790) and distal inner tube (800) are coupled and mechanically grounded to one another.

FIGS. 60A-60B show use of assembly tool (900) to rotate first disposable sub-assembly (702) relative to second disposable sub-assembly (702) from the position shown in FIGS. 58D to 58E and 59B to 59C. Prongs (912) may enter notches (824) of overmolded portion (822), thereby enabling an operator to utilize hand grip portion (830) to provide greater leverage when rotating first disposable sub-assembly (702) relative to second disposable sub-assembly (704). This addition of greater leverage may allow for greater resilience of circumferential tab (804) and resilient tabs (830).

Figure 61A:
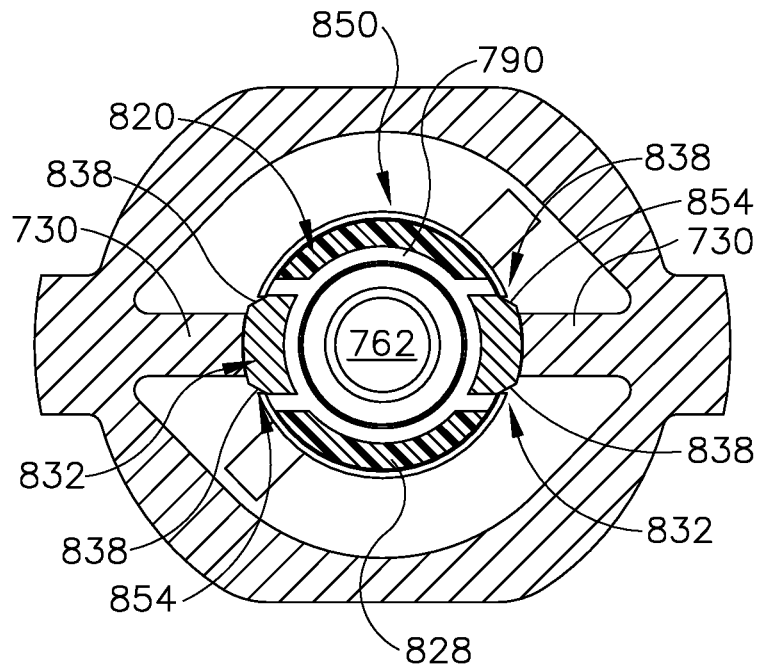
FIG. 61A depicts a front cross-sectional view of the proximal end of the first and second sub-assemblies of FIG. 38, taken along line 61-61 of FIG. 55A.
Figure 61B:
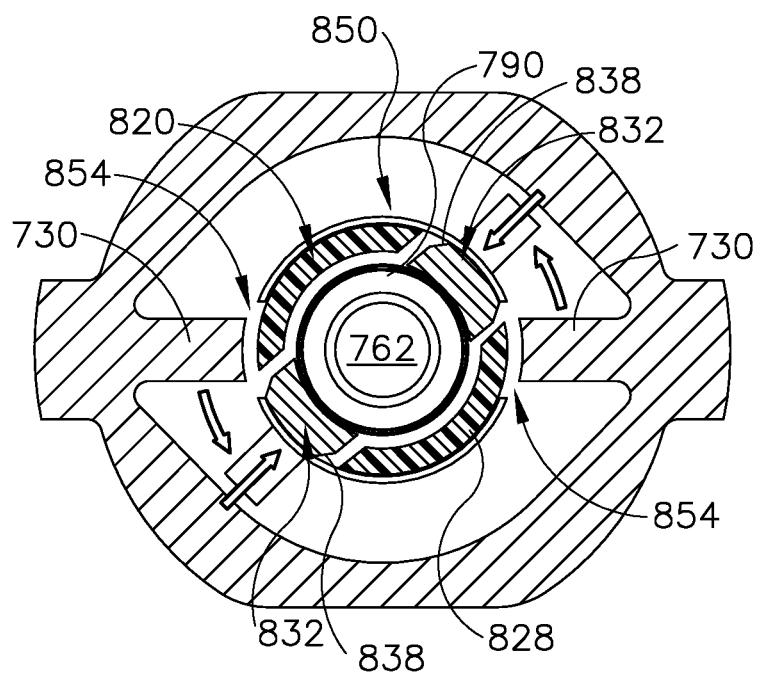
FIG. 61B depicts a front cross-sectional view of the proximal end of the first sub-assembly of FIG. 38 decoupled from the proximal end of the second sub-assembly of FIG. 38, taken along line 61-61 of FIG. 55A.

E. Exemplary Disassembly of First Disposable Sub-Assembly with Second Disposable Sub-Assembly FIGS. 61A-61B shows an exemplary disassembly of the proximal end of first disposable sub-assembly (702) with second disposable sub-assembly (704); while FIGS. 85A-85C show an exemplary disassembly of the distal end of first disposable sub-assembly (702) with second disposable sub-assembly (704).

When an operator desires to uninstall first disposable sub-assembly (702) from second disposable sub-assembly, the operator may reverse the rotation utilized with tool assembly (900) as shown in FIGS. 60A-60B. As shown in FIGS. 61A-61B, this reversed rotation causes the perimeter of first coupling windows (854) to abut against sloped disassembly surfaces (838), pushing outwardly extending protrusions (832) within the confines of tube actuator (850). With outwardly extending protrusions (832) within the confines of tube actuator (850), outer tube (780) is no longer coupled with tube actuator (850), and outer tube (780) may be pulled in the distal direction as shown from FIGS. 57C-57A.

Figure 62A:
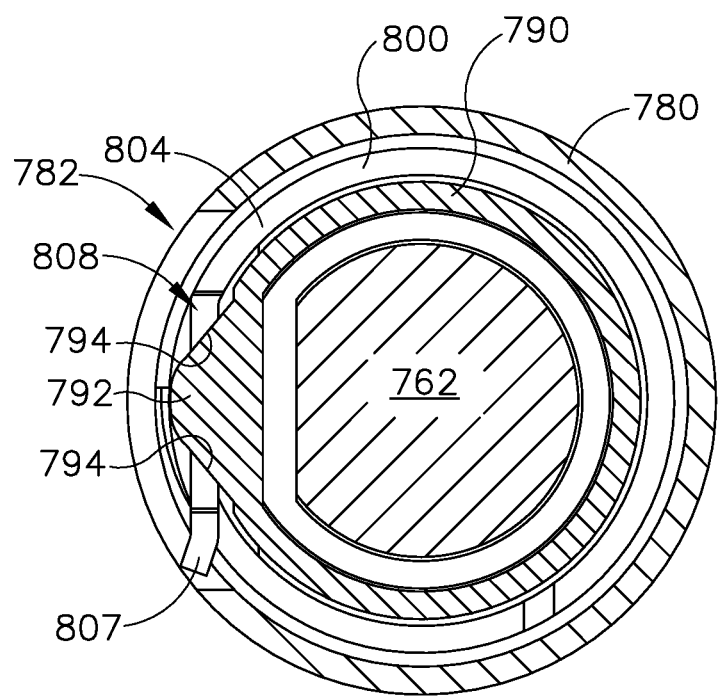
FIG. 62A depicts a front cross-sectional view of the distal end of the first and second sub-assemblies of FIG. 38, taken along line 62-62 of FIG. 39.
Figure 62B:
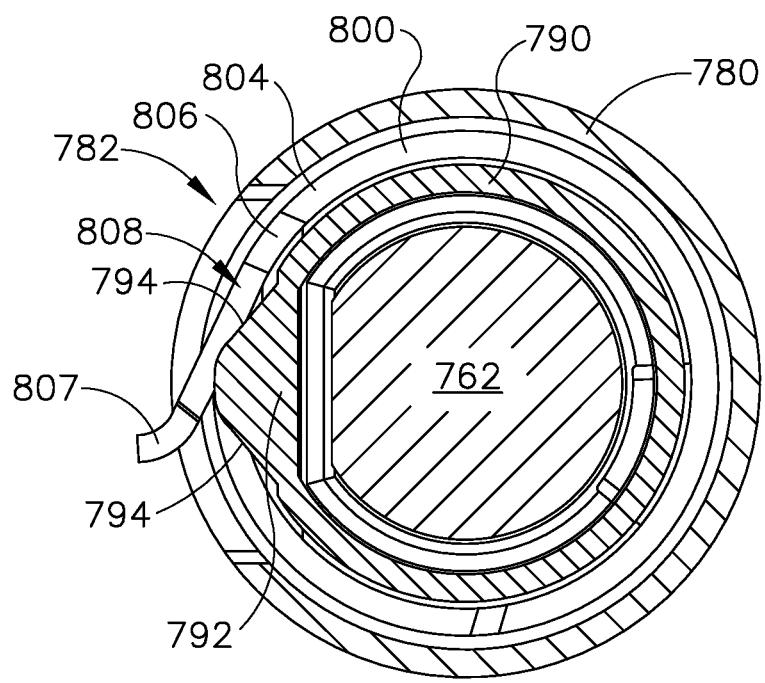
FIG. 62B depicts a front cross-sectional view of the distal end of the first sub-assembly of FIG. 38 rotating relative to the distal end of the second sub-assembly of FIG. 38, taken along line 62-62 of FIG. 39.
Figure 62C:
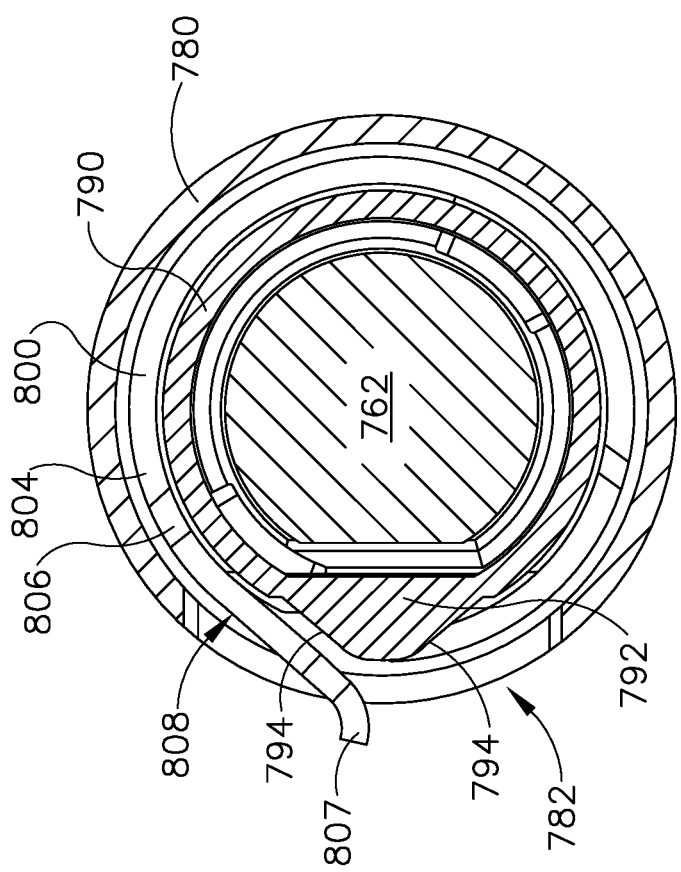
FIG. 62C depicts a front cross-sectional view of the distal end of the first sub-assembly of FIG. 38 decoupled with the distal end of the second sub-assembly of FIG. 38, taken along line 62-62 of FIG. 39.

Simultaneously, as shown in FIGS. 62A-62C, the reverse rotation of tool assembly (900) as shown in FIGS. 60A-60B may cause flat member (806) to deflect and rotate relative to stud (792) due to slot (808) abutting against camming surface (794). The resilient nature of flat member (806) will allow flat member (806) to deform until slot (808) and stud (792) are no longer coupled. Once stud (792) is no longer confined by slot (808) of flat member (806), first disposable sub-assembly may be pulled in the distal direction and removed.

Figure 63B:
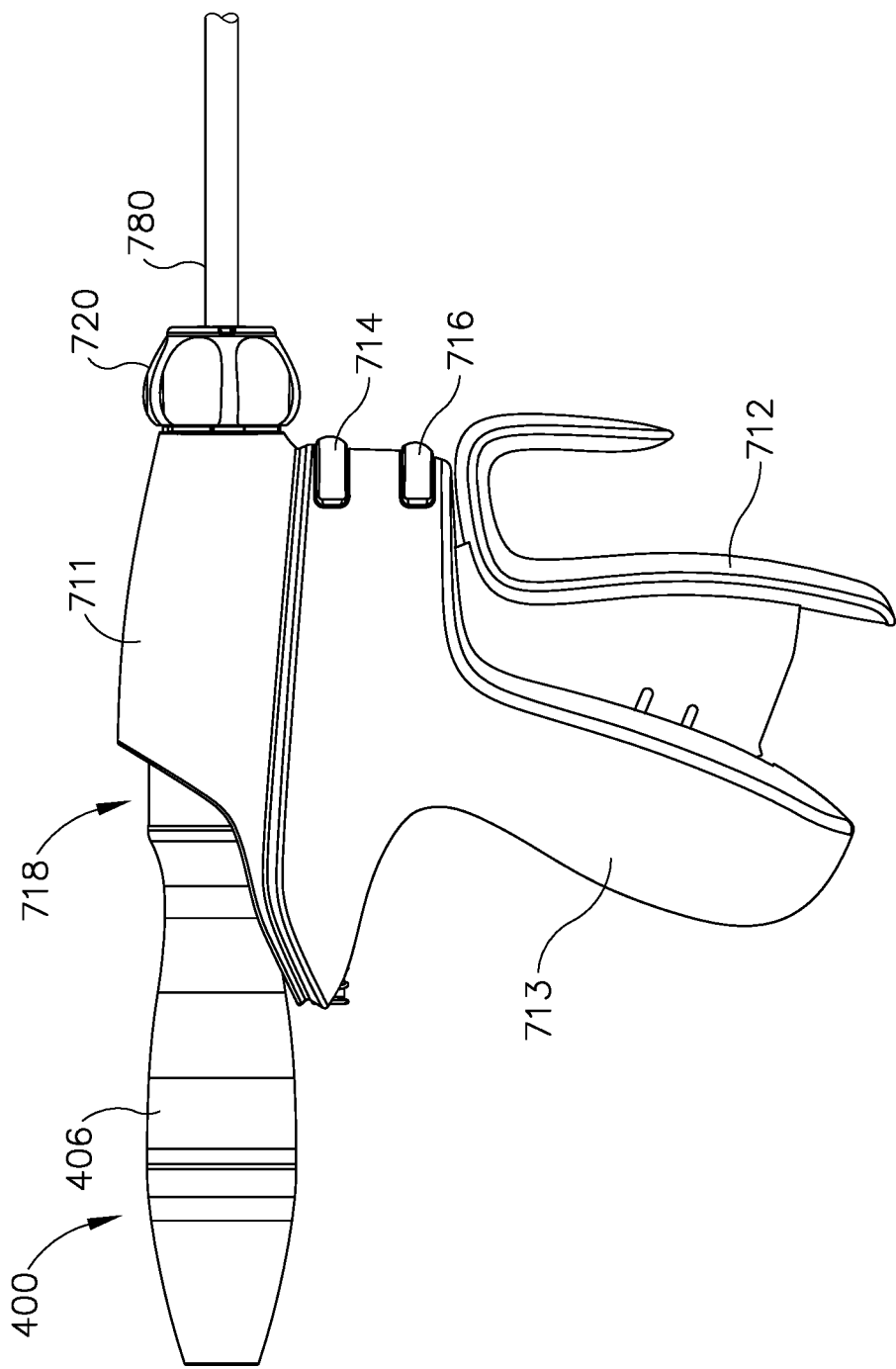
FIG. 63B depicts a side elevation view of the reusable assembly of FIG. 37 coupled with the disposable assembly of FIG. 37.

F. Exemplary Assembly and Disassembly of Reusable Assembly with Second Disposable Sub-Assembly FIGS. 63A-63B show that reusable assembly (400) may be selectively coupled with second disposable sub-assembly (704). In some instances, it may be desirable to couple reusable assembly (400) with second disposable sub-assembly (704) via a threaded stud (402) of transducer (406) and threaded coupling bore (764) of waveguide (762) with a specific torque value. If threaded stud (402) of transducer (406) and threaded coupling bore (764) of waveguide (762) are not coupled with the proper toque value, the complete ultrasonic surgical instrument may not function properly. For example, if the torque value is too low, waveguide (760) may inadvertently decouple from ultrasonic transducer (406) during operation. Alternatively, if the torque value is too high, waveguide (760) or threaded stud (402) of transducer (406) may fracture or otherwise suffer some sort of structural defect. The provision of a predetermined torque value therefore prevents the operator from relying on a torque that is too low; or achieving a torque that is too high. Assembly tool (900) may be utilized to install reusable assembly (400) to second disposable sub-assembly (704) with a predetermined torque value.

Figure 64C:
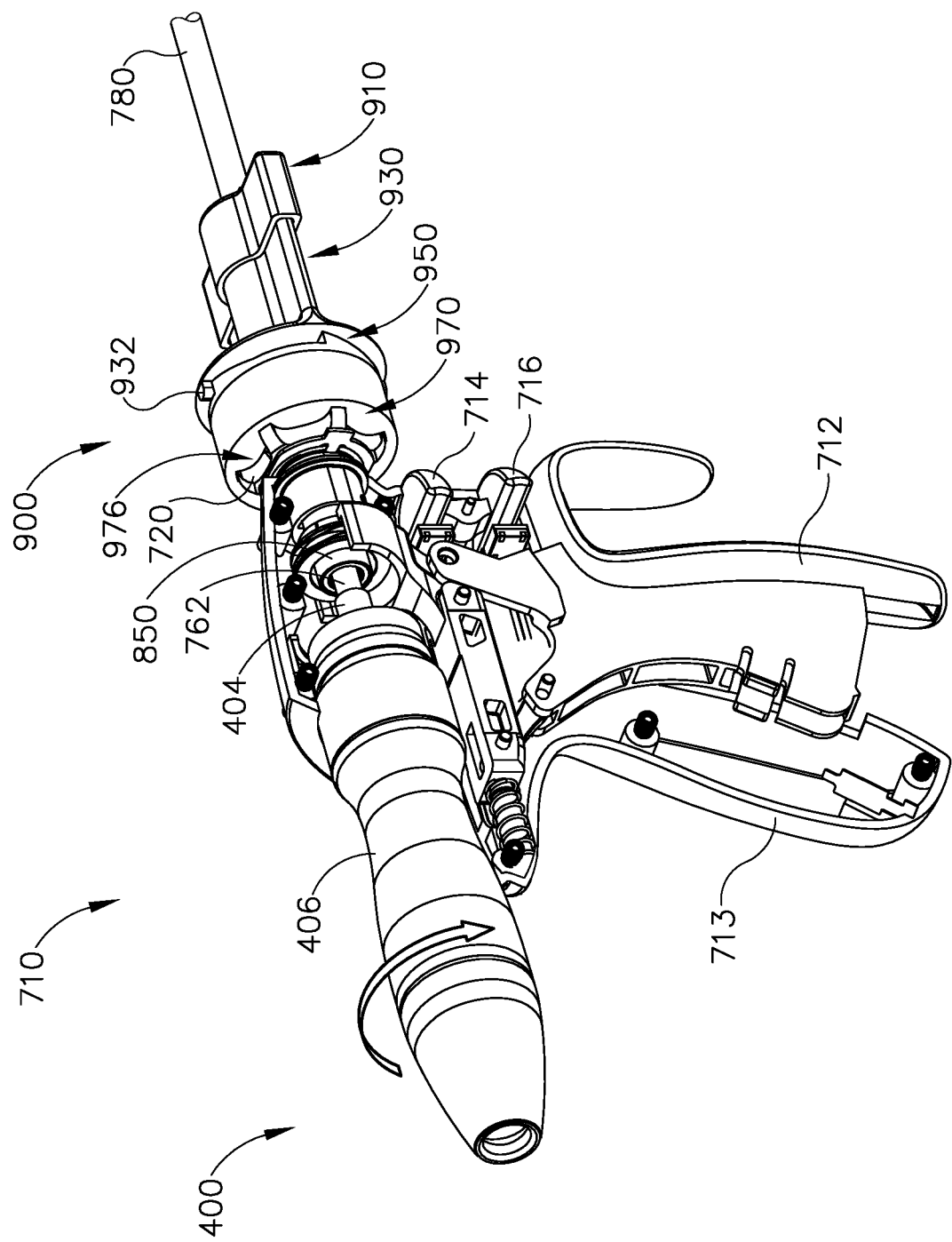
FIG. 64C depicts a perspective view of the assembly tool of FIG. 51 utilized to couple the reusable assembly of FIG. 37 with the disposable assembly of FIG. 37, where the reusable assembly is coupled with the disposable assembly, where the assembly tool is rotationally secured to the knob member of the second sub-assembly of FIG. 38.

FIG. 64A-64C shows assembly tool (900) being utilized during installation of reusable assembly (400) with second disposable sub-assembly (704) without a portion of body (711) for purposes of clarity. FIG. 64A shows assembly tool (900) being inserted over outer tube (780) such that knob gripping member (970) is inserted first. Knob gripping member (970) may be advance in the proximal direction as shown in FIG. 64B such that gripping surface (976) is rotationally coupled with knob member (720). As shown in FIG. 64C, reusable assembly (400) may be inserted distally such that threaded stud (402) of transducer (406) is inserted into threaded coupling bore (764) of waveguide (762) of waveguide (762), thereby coupling reusable member (400) with second disposable sub-assembly (704).

Figure 65C:
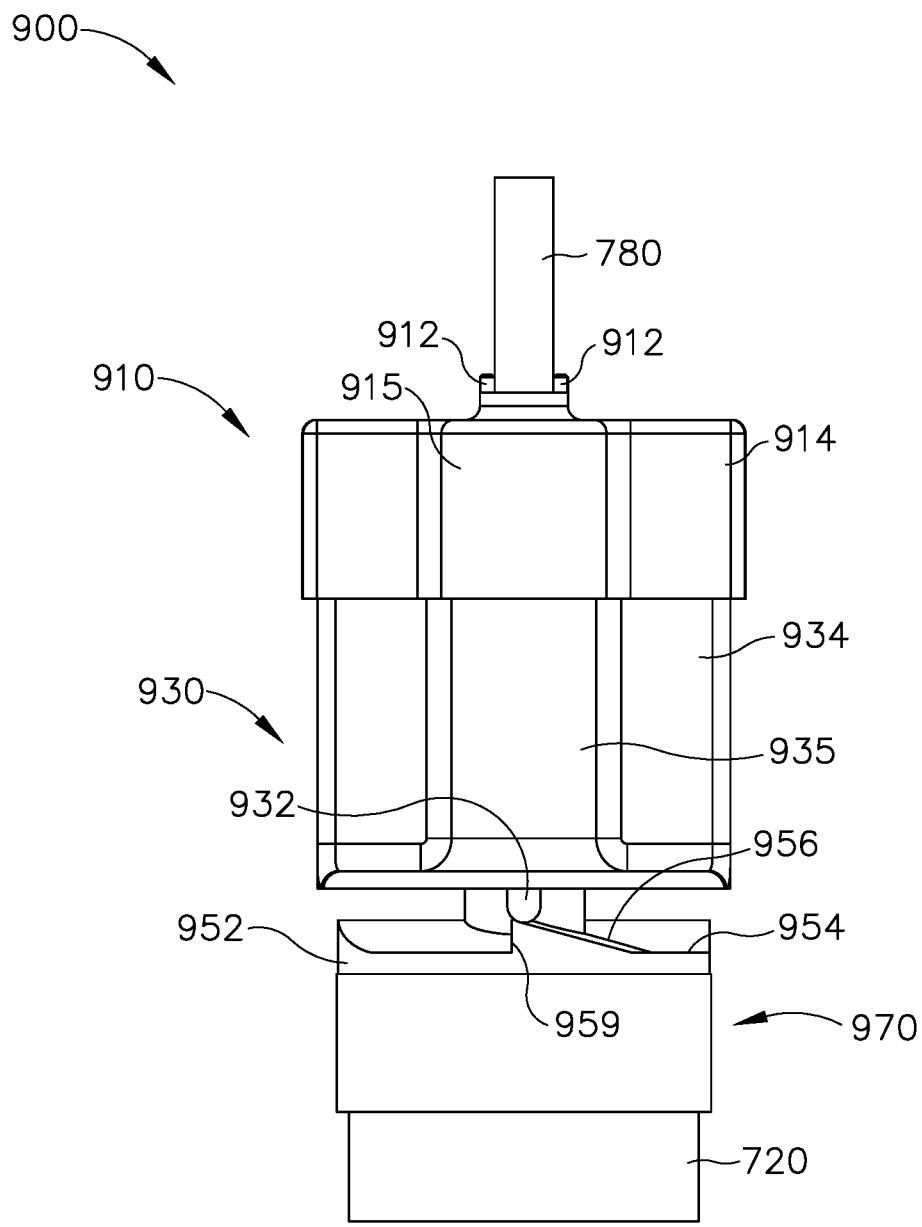
FIG. 65C depicts a top plan view of the assembly tool of FIG. 51 rotationally secured to the knob member of the second sub-assembly of FIG. 38, where the reusable assembly of FIG. 37 is sufficiently coupled with the disposable assembly of FIG. 37 and the reusable assembly is further rotated relative to the disposable assembly.

FIGS. 65A-65C show what happens when threaded stud (402) of transducer (406) and threaded coupling bore (764) of waveguide (762) are coupled with sufficient torque. With the predetermined torque level met, the frictional braking force provided by biasing contact protrusions (932) against disc (952) are overcome, and as a result, contact protrusions (932) start slipping on flat surface (952) and sloped surface (956). Because knob gripping member (970) is fixed to torque slip portion (950), and an operator provides reactionary torsion by gripping hand grip portion (930), further rotation of reusable assembly (400) rotates unitarily with second disposable sub-assembly (704), and no more torque is provided between threaded stud (402) of transducer (406) and threaded coupling bore (764).

If an operator desires to decouple reusable assembly (400) with second disposable sub-assembly (704), the operator simply rotates reusable assembly (400) in the opposite direction while holding hand grip portion (930) causing contact protrusion (932) to interact with flat surface (954), which prevents slipping between hand grip portion (930) and knob gripping member (970).

IV. FURTHER EXEMPLARY ALTERNATIVE DISPOSABLE ASSEMBLY FOR ULTRASONIC SURGICAL INSTRUMENT WITH REMOVABLE ACOUSTIC WAVEGUIDE AND MULTIPURPOSE ASSEMBLY TOOL

FIGS. 66-67 show an exemplary alternative disposable assembly (1000) that is coupled to alternative reusable assembly (400). To the extent that the following discussion omits various details of disposable assembly (1000), it should be understood that disposable assembly (1000) may incorporate the various details described above and/or details described in any of the various references that are cited herein. Other suitable details will be apparent to those of ordinary skill in the art in view of the teachings herein.

As best seen in FIGS. 96A-96B, reusable assembly (400) includes a coupling shaft (404) rotationally fixed to a distally extending threaded stud (402) of transducer (406). As will be described in greater detail below, reusable assembly (400) may be rotated relative to disposable assembly (1000) in order to couple disposable assembly (1000) with reusable assembly (400).

Disposable assembly (1000) of the present example comprises a first disposable sub-assembly (1002) and a second disposable sub-assembly (1004). Sub-assemblies (1002, 1004) are configured to be coupled together in order to form disposable assembly (1000), which may then be coupled with a variation of reusable assembly (400) to form a complete ultrasonic surgical instrument. After the ultrasonic surgical instrument is used in a surgical procedure, disposable assembly (1000) may be removed from the variation of reusable assembly (400); and then first disposable sub-assembly (1002) may be removed from second disposable sub-assembly (1004). In some such instances, the variation of reusable assembly (400) may be cleaned, sterilized, and re-used up to 100 times (by way of example only). First disposable sub-assembly (1002) may be disposed of, such that first disposable sub-assembly (1002) is only used one single time. Second disposable sub-assembly (1004) may be cleaned, sterilized, and re-used between 2 to 20 times (by way of example only). Of course, these re-use scenarios are merely illustrative examples. It should nevertheless be understood that the configuration of disposable assembly (1000) may minimize the amount of single-use material that is disposed of after each surgical procedure. This may reduce cost and overall waste as compared to conventional instrumentation.

A. Exemplary First Disposable Sub-Assembly

Figure 68:
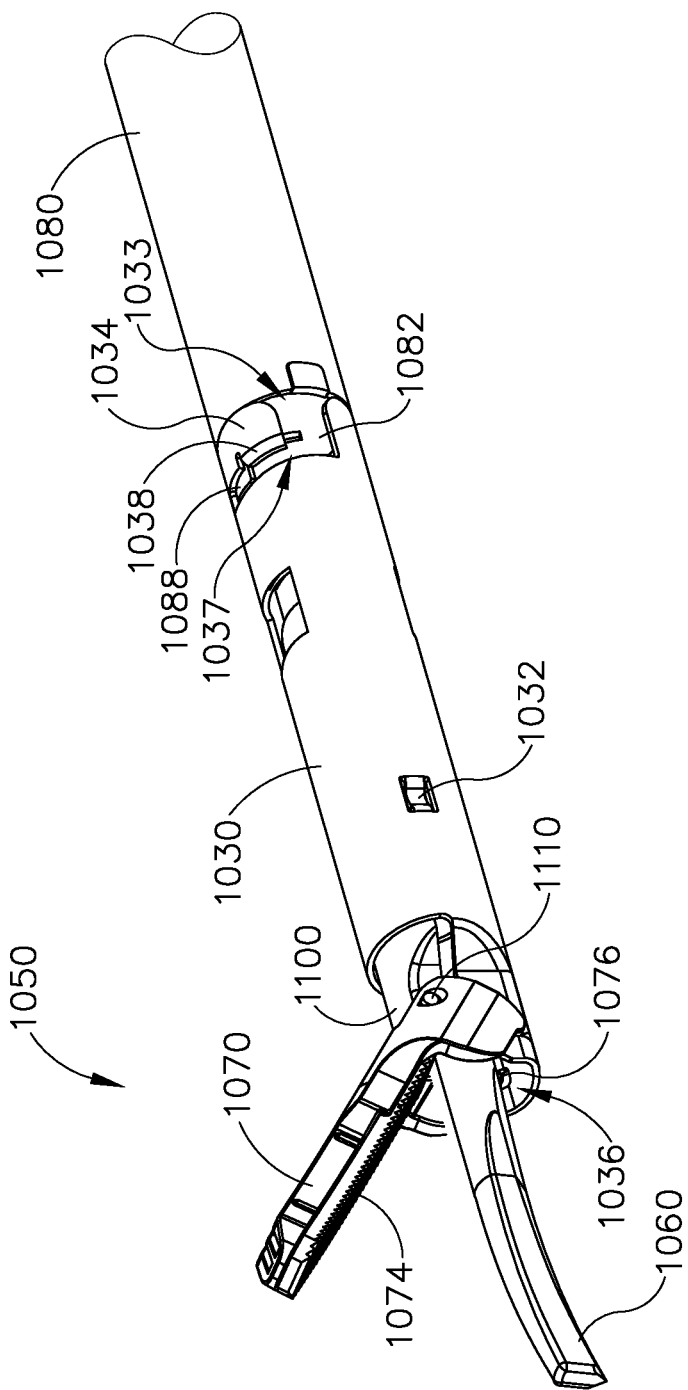
FIG. 68 depicts a perspective view of an end effector of the ultrasonic surgical instrument of FIG. 66.

As shown in FIGS. 66-69, first disposable sub-assembly (1002) of the present example comprises a distal outer tube member (1030), a distal inner tube member (1100), and a clamp arm (1070). Clamp arm (1070) is configured to form an end effector (1050), as shown in FIG. 68, with an ultrasonic blade (1060), which is part of second disposable sub-assembly (1004) as will be described in greater detail below. Clamp arm (1070) is pivotably coupled with distal outer tube member (1030) and with distal inner tube member (1100). Distal outer tube member (1030) is configured to unitarily translate with proximal outer tube member (1080) longitudinally while distal inner tube member (1100) remains stationary, which drives clamp arm (1070) to pivot between an open position and a closed position. In the closed position, clamp arm (1070) is operable to clamp tissue against blade (1060), which may then be ultrasonically activated to sever and/or seal the tissue as described herein and in various references cited herein.

As shown in FIG. 70, clamp arm (1070) of the present example comprises a pair of pin openings (1072), a clamp pad (1074), and a pair of pivot studs (1076). Pin openings (1072) are configured to receive a pin (1110), which is also disposed in a pin opening (1102) of distal inner tube member (1100). Clamp pad (1074) of the present example comprises polytetrafluoroethylene (PTFE) and includes surface features (e.g., teeth or ridges, etc.) that are configured to promote gripping of tissue. Various suitable materials and configurations that may be used to form clamp pad (1074) will be apparent to those of ordinary skill in the art in view of the teachings herein. Pivot studs (1076) are received in openings (1036) of outer tube (1030) Clamp arm (1070) is pivotable about axes defined by pivot studs (1076) and by pin (1110), which enables clamp arm (1070) to transition between the open position and the closed position in response to translation of outer tube (1030) relative to distal inner tube member (1100).

As shown in FIGS. 70-73, distal inner tube (1100) of the present example comprises a pair of proximally presented tabs (1106). Distal inner tube (1100) defines pin opening (1102), a pair of slots (1104), and an alignment hole (1105). Proximally presented tabs (1106) define a stud hole (1108) and an entry channel (1109). Proximally presented tabs (1106) are resilient in that they may flex about stud holes (1108). A gap (1101) extends from proximal portion through distal portion. This gap (1101) is configured to accommodate longitudinal travel of the distal end of ultrasonic blade (1060) during assembly of first disposable sub-assembly (1002) with second disposable sub-assembly (1004), as will be described in greater detail below.

As will also be described in greater detail below, distal inner tube member (1100) is configured to be removably secured to a proximal inner tube member (1090) during assembly of first disposable sub-assembly (1002) with second disposable sub-assembly (1004). This coupling provides a longitudinal mechanical grounding for distal inner tube member (1100), such that distal inner tube member (1100) does not translate longitudinally relative to other components of disposable assembly (1000) when inner tube members (1090, 1100) are coupled together.

As shown in FIGS. 69-70 and 74-75, distal outer tube (1030) includes a pair of crimps (1032), a proximal circumferential tab (1034), and an inwardly extending nub (1038) connected to the distal end of proximal circumferential tab (1034). Distal outer tube (1030) also defines an alignment hole (1035) while proximal circumferential tab (1034) defines a first channel (1033) and a second channel (1037). Crimps (1032) are slidably housed within slots (1104) such that distal outer tube (1030) may translate longitudinally relative to distal inner tube (1100) but distal outer tube (1030) remains laterally and vertically aligned with distal inner tube (1100).

As will be described in greater detail below, the resiliency of proximally presented tabs (1106) and proximal circumferential tabs (1034) are configured to promote snap fitting between first disposable sub-assembly (1002) and second disposable sub-assembly (1004). As will also be described below, alignment holes (1035, 1105) are configured to mate with portions of assembly tool (1200) to fix first disposable sub-assembly (1002) relative to assembly tool (1200) during coupling of the first disposable sub-assembly (1002) and the second disposable sub-assembly (1004).

B. Exemplary Second Disposable Sub-Assembly

As shown in FIGS. 66-67, second disposable sub-assembly (1004) of the present example comprises a handle assembly (1010) having body (1011), a pistol grip (1013), a pivoting trigger (1012) pivotally coupled to the body (1011) and pistol grip (1013), and a set of buttons (1014, 1016). Body (1011) defines an opening (1018) configured to selectively couple to reusable assembly (400), as will be described in greater detail below. As best seen in FIG. 67 a proximal outer tube (1080) extends distally from handle assembly (1100). Proximal outer tube (1080) may include a flush port (1300) substantially similar to flush port (1700) for outer tube (1502) mentioned above. Additionally, a proximal inner tube member (1090) is coaxially disposed in proximal outer tube (1080) and extends past the distal end of proximal outer tube (1080). An acoustic waveguide (1062) is coaxially disposed in proximal inner tube member (1090) and distally terminates in ultrasonic blade (1060). Waveguide (1062) and blade (1060) may be configured and operable just like waveguide (192, 592, 792) and blade (190, 590, 790) described above; and/or as described in any of the various references cited herein.

Pistol grip (1013) is operable to be grasped by an operator while trigger (1012) is operable to drive proximal outer tube (1080) longitudinally relative to proximal inner tube (1090) in response to pivoting trigger (1012) toward and away from pistol grip (1013). Pivoting trigger (1012) toward and away pistol grip (1013) thereby drives outer tube (1080) longitudinally, to thereby drive clamp arm (1070) toward and away from blade (1060), when first disposable sub-assembly (1002) is coupled with second disposable sub-assembly (1004). Structural features of proximal outer tube (1080) will be described in greater detail below. Various suitable components that may be used to provide longitudinal movement of proximal outer tube (1080) in response to pivotal movement of trigger (1012) will be apparent to those of ordinary skill in the art in view of the teachings herein. By way of example only, trigger (1012) may be operatively coupled with proximal outer tube (1080) in accordance with at least some of the teachings of U.S. Pub. No. 2015/0245850, entitled "Ultrasonic Surgical Instrument with Removable Handle Assembly," published Sep. 3, 2015, issued as U.S. Pat. No. 10,010,340 on Jul. 3, 2018, the disclosure of which is incorporated by reference herein. In addition, or in the alternative, trigger (1012) may be operatively coupled with proximal outer tube (1080) in accordance with at least some of the teachings of U.S. Patent Pub. No. 2016/0015419, entitled "Ultrasonic Surgical Instrument with Removable Handle Assembly," published Jan. 21, 2016, issued as U.S. Pat. No. 10,349,967 on Jul. 16, 2019, the disclosure of which is incorporated by reference herein.

Buttons (1014, 1016) are operable to activate ultrasonic blade (1060). In particular, buttons (1014, 1016) are operable to activate the ultrasonic transducer (406) in the variation of reusable assembly (400), which in turn generates ultrasonic vibrations, which are communicated along waveguide (1062) to reach blade (1060). In some versions, button (1014) activates ultrasonic blade (1060) with ultrasonic energy at a first set of parameters (e.g., high power); while button (1016) activates ultrasonic blade (1060) with ultrasonic energy at a second set of parameters (e.g., low power). As another merely illustrative alternative, button (1014) may activate ultrasonic blade (1060) with ultrasonic energy; while button (1016) activates end effector (1050) to apply RF electrosurgical energy. Various suitable ways in which this may be carried out, as well as various other suitable ways in which buttons (1014, 1016) may be configured, arranged, and operable will be apparent to those of ordinary skill in the art in view of the teachings herein.

Figure 76:
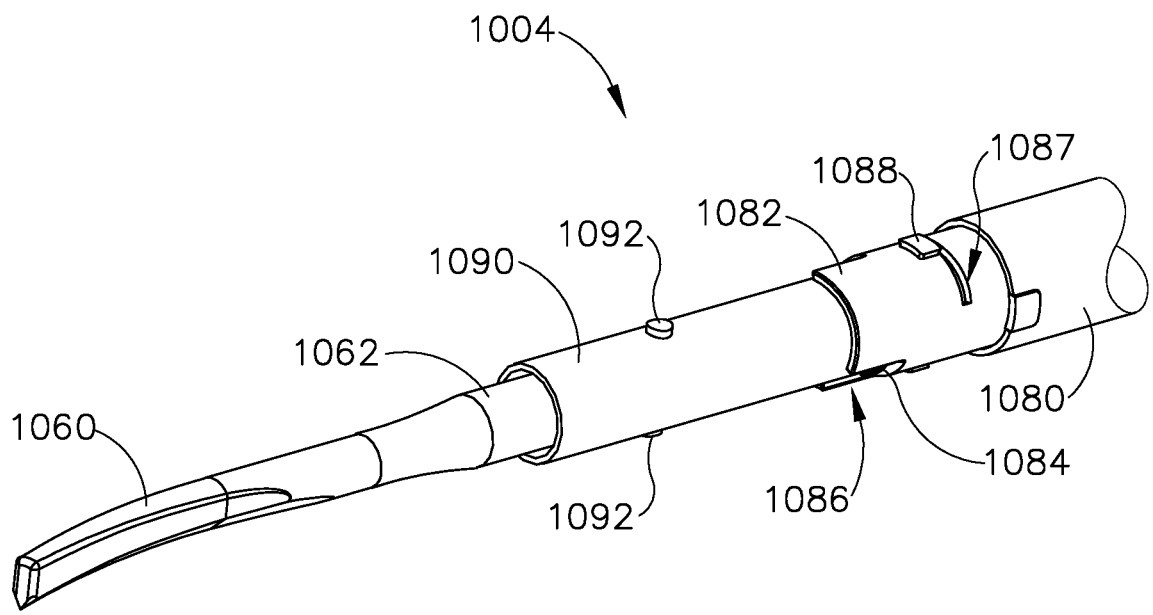
FIG. 76 depicts a perspective view of the distal end of the second disposable sub-assembly of FIG. 67.

As best seen in FIG. 76, proximal inner tube member (1090) is disposed coaxially about waveguide (1062) yet is radially spaced apart from waveguide (1062) such that inner tube member (1090) does not contact waveguide (1062). A seal member, similar to seal member (640, 840), may be disposed around waveguide (1092) in similar locations to seal member (640, 840) described above.

The distal end of proximal inner tube member (1090) includes two integral, outwardly projecting studs (1092) spaced 180° apart about the longitudinal axis defined by proximal inner tube (1090). As will be described in greater detail below, outwardly projecting studs (1092) are configured to snap fit within stud holes (1108) defined by proximally presented tabs (1106).

Figure 77:
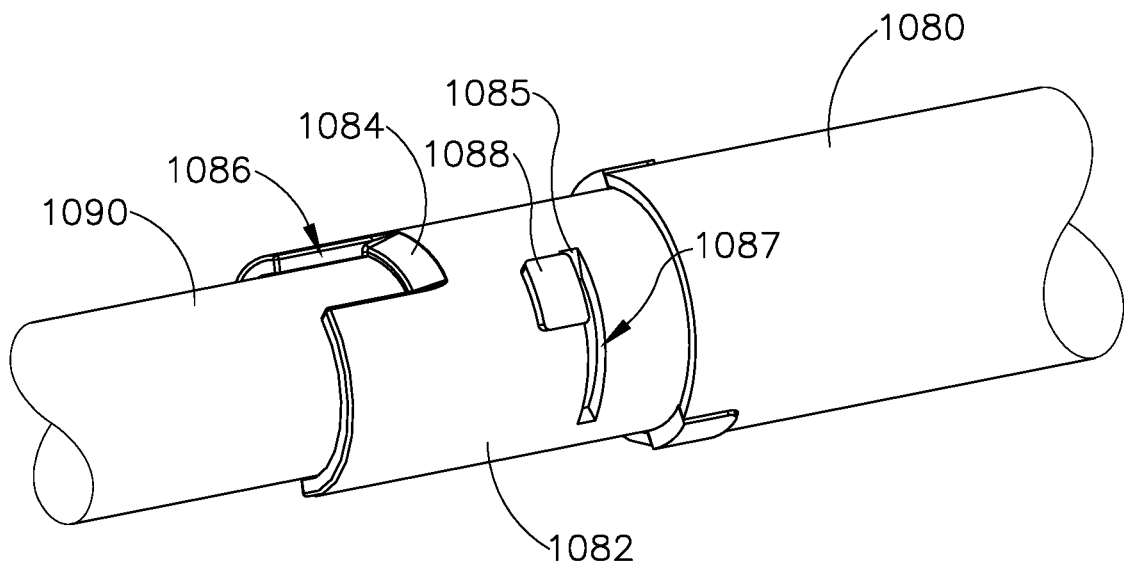
FIG. 77 depicts a perspective view of a coupling feature of the distal end of the second disposable subassembly of FIG. 67.

As best seen in FIGS. 76-77, the distal end of proximal outer tube member (1080) includes a distal coupling feature (1082). Distal coupling feature (1082) may be fixed to proximal outer tube member (1080) through an interference fit, integral connection, or any other suitable means known to a person having ordinary skill in the art in view of the teachings herein. Therefore, distal coupling feature (1082) may unitarily translate with proximal outer tube member (1080) in response to trigger (1012) pivoting toward and away from body (1011).

Distal coupling feature (1082) includes a pair distally facing slants (1084) and a pair of protrusions (1088). Distally facing slants (1084) are spaced 180° apart from one another about the longitudinal axis defined by proximal outer tube member (1080). Additionally, protrusions (1088) are spaced 180° apart from one another about the longitudinal axis defined by proximal outer tube member (1080). Coupling feature (1082) defines a pair of tab guide channels (1086) extending from the distal end of coupling feature (1082) and terminating into distally facing slants (1084). Coupling feature also includes a pair of unlocking slanted surfaces (1085) which partially define locking channels (1087) that are adjacent to protrusions (1088). As will be described in greater detail below, distally facing slants (1084) are configured to raise circumferential tabs (1034) onto the surface of coupling feature (1082) while distal outer tube member (1030) is advanced proximally towards proximal outer tube member (1080).

Additionally, locking channels (1087) are configured to provide a snap fitting with nubs (1038) such that distal outer tube member (1030) may couple with proximal outer tube member (1080). As will also be described in further detail below, unlocking slanted surfaces (1085) are configured to provide a camming surface to aid circumferential tabs (1034) in disassembling with locking channels (1087).

C. Exemplary Assembly Tool

FIGS. 78A-80 show an exemplary assembly tool (1200) that may be utilized to couple first disposable sub-assembly (1002) with second disposable sub-assembly (1004) and also couple second disposable sub-assembly (1004) with reusable assembly (400). Assembly tool (1200) includes a base member (1210) pivotally coupled with a top member (1230) via hinges (1222), a locating member (1250) housed within base member (1210), and a rotating member (1270) rotatably housed within a recess (1215) of base member (1210).

Base member (1210) includes a tubular surface (1212) extending from a first end (1211) towards a second end (1213), a deck (1214), a clamp arm surface (1216), an exterior surface (1218), and hinges (1222). Base member (1210) defines a pathway (1202) extending through first end (1211) and second end (1213) in communication with tubular surface (1212). Pathway (1202) is dimensioned to accept distal outer tube member (1030) and proximal outer tube member (1080) such that second end (1213) of base member (1210) may be adjacent to knob member (1020), as shown in FIG. 96A-115C. Additionally, pathway (1202) at first end (1211) is dimensioned to receive a portion of second disposable sub-assembly (1004) while first disposable sub-assembly (1002) is fixed within assembly tool (1200) in order to couple or decouple first disposable sub-assembly (1002) with second disposable sub-assembly (1004).

Figure 82:
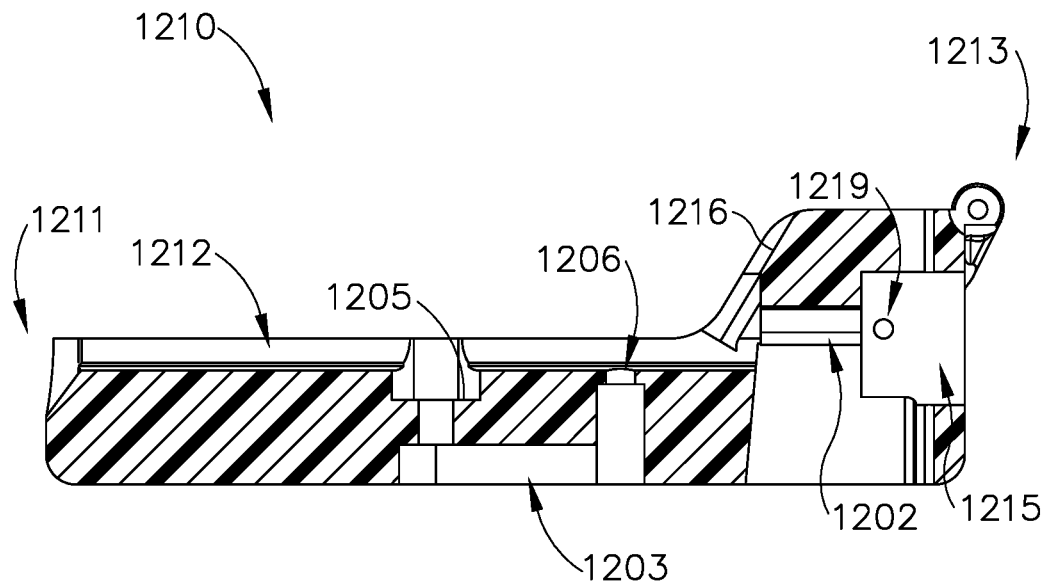
FIG. 82 depicts a cross-sectional side view of the base member of FIG. 81, taken along line 82-82 of FIG. 81.
Figure 83:
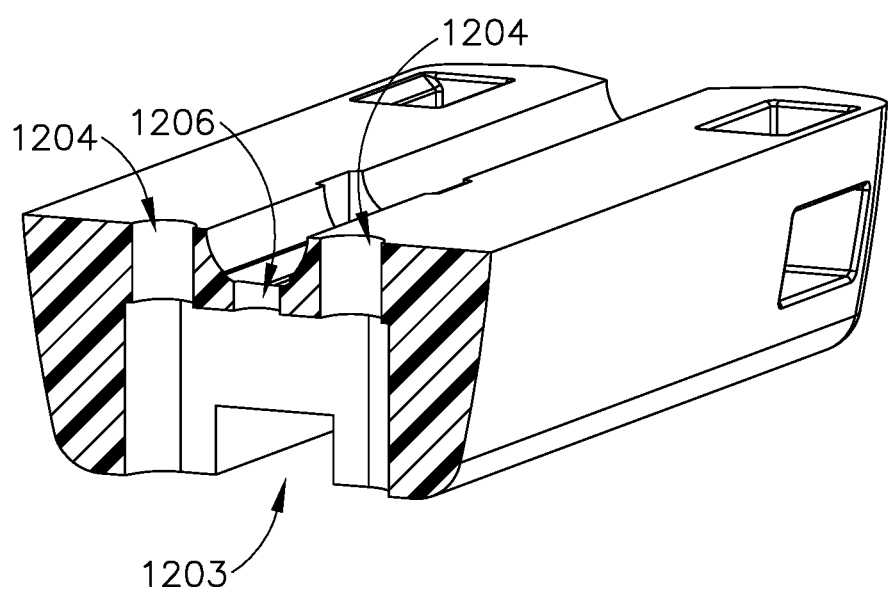
FIG. 83 depicts cross-sectional perspective view of the base member of FIG. 81, taken along line 83-83 of FIG. 81.

Base member (1210) also defines a pair of locking apertures (1220) extending from deck (1214) through exterior surfaces (1218). Base member (1210) also defines a cavity (1203) as seen in FIGS. 82-83. Cavity (1203) is in communication with bore (1206) extending from tubular surface (1212) and two bores (1204) extending from deck (1214). As will be discussed below, bores (1204, 1206) and cavity (1203) promote translation of locating member (1250) as top member (1230) pivots toward and away from base member (1210). Cavity is also defined by an annular surface (1205) dimensioned to house nut (1260) and bolt (1252).

Figure 84:
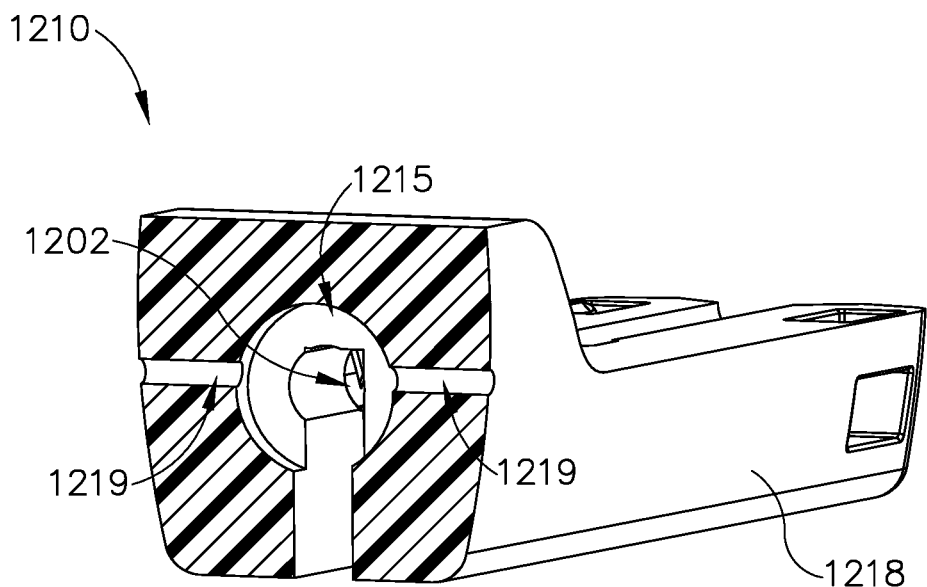

As seen in FIGS. 82 and 84, second end (1213) of base member (1210) defines recess (1215). Additionally, side bores (1219) extend from recess (1215) to exterior surface (1218) of base member (1210). As described above, rotating member (1270) is rotatably housed within cavity (1215). Side bores (1219) each house a plug (1286), plunger (1287), and a spring (1288). Plug (1286) is fixed within side bore (1219), while spring (1288) attaches plug (1286) with plunger (1287). As will be described in greater detail below, plunger (1287) and spring (1288) are dimensioned to impart a frictional braking force on selective portions of rotating member (1270) such that rotating member (1270) may rotate unitarily with the rest of assembly tool (1200) until the frictional braking force is overcome and rotating member (1270) begins to slip relative to plunger (1287), spring (1288), and therefore base member (1210).

Top member (1230) includes a hinge (1222), exterior casing (1238), a pair of resilient legs (1240) each having a latch (1242) extending towards a respective locking aperture (1220), and a transverse wall (1236) including a downwardly presented surface (1232) and an arched surface (1234).

Locking apertures (1220) are dimensioned to force latches (1242) inwardly as latches (1242) enter locking aperture (1220) through deck (1214). Additionally, locking apertures (1220) are dimensioned to release latches (1242) outwardly as latches (1242) exit locking aperture (1220) through exterior surface (1218). As shown in FIG. 78B, with latches (1242) released outwardly while within the portion of locking aperture (1220) defined by exterior surface (1218), top member (1230) is locked relative to base member (1210). Resilient legs (1240) are sufficiently flexible that an operator may push inwardly on resilient legs (1240) to unlock latches (1242) from locking aperture (1220).

Figure 89A:
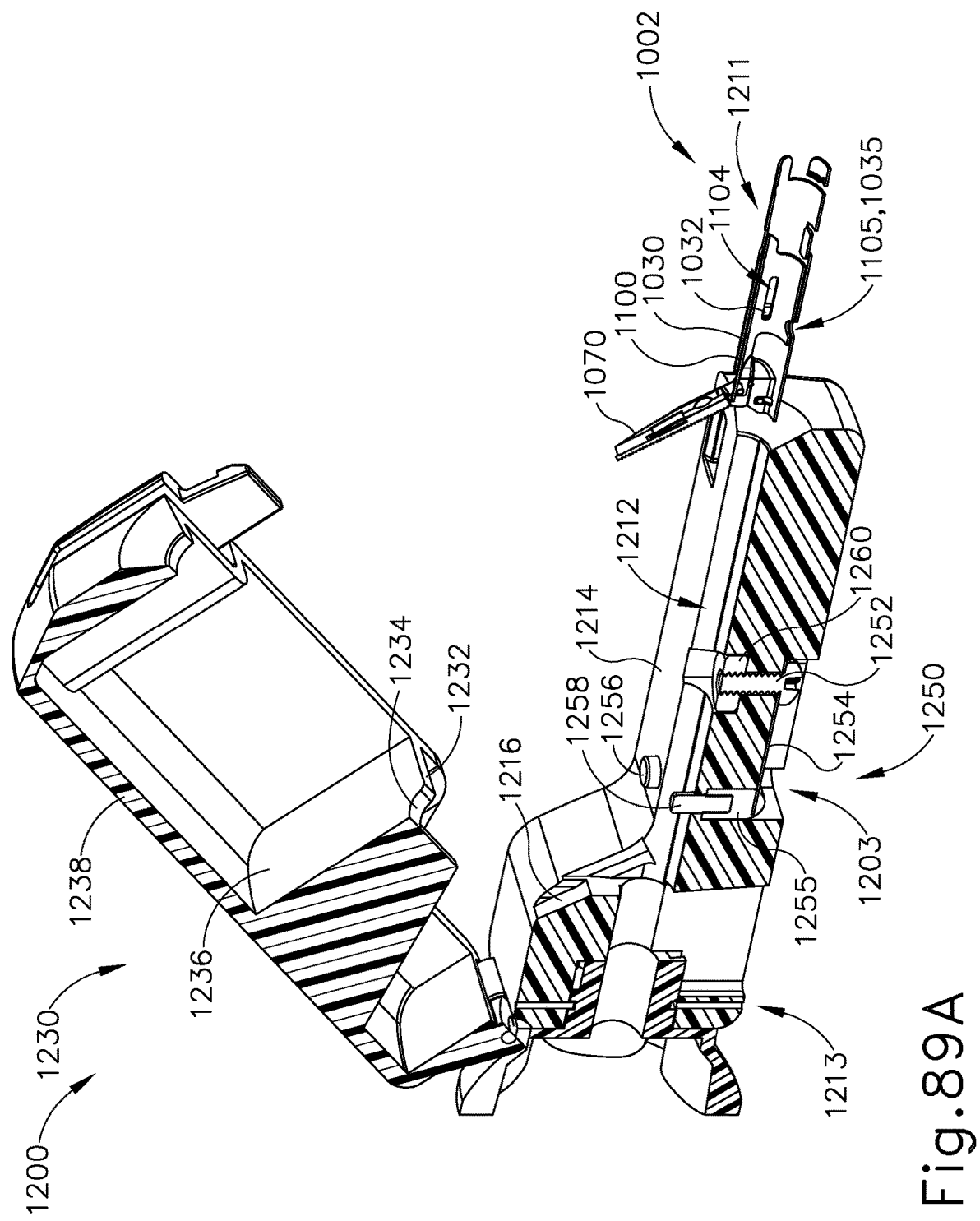
Figure 89B:
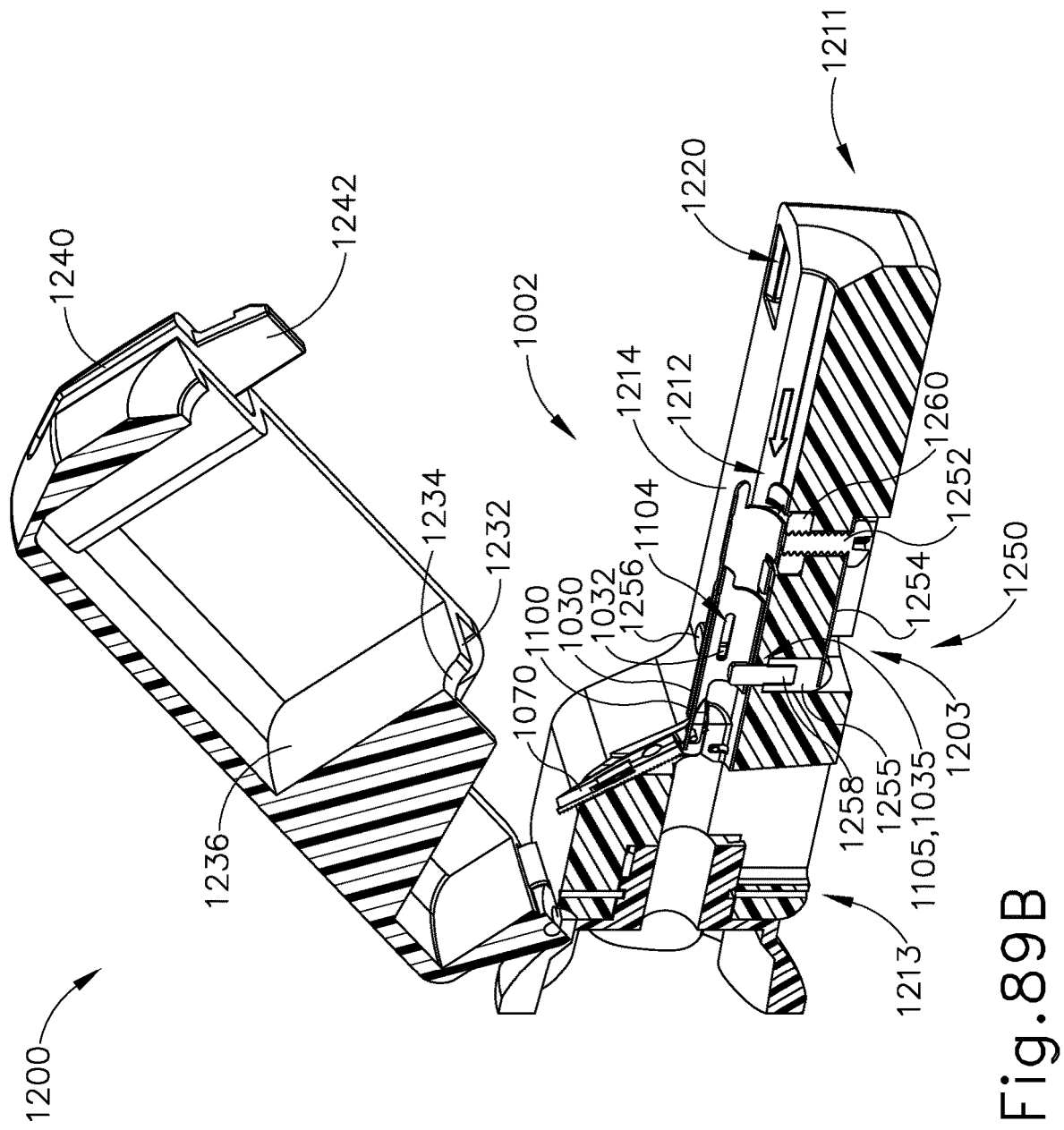
Figure 89C:
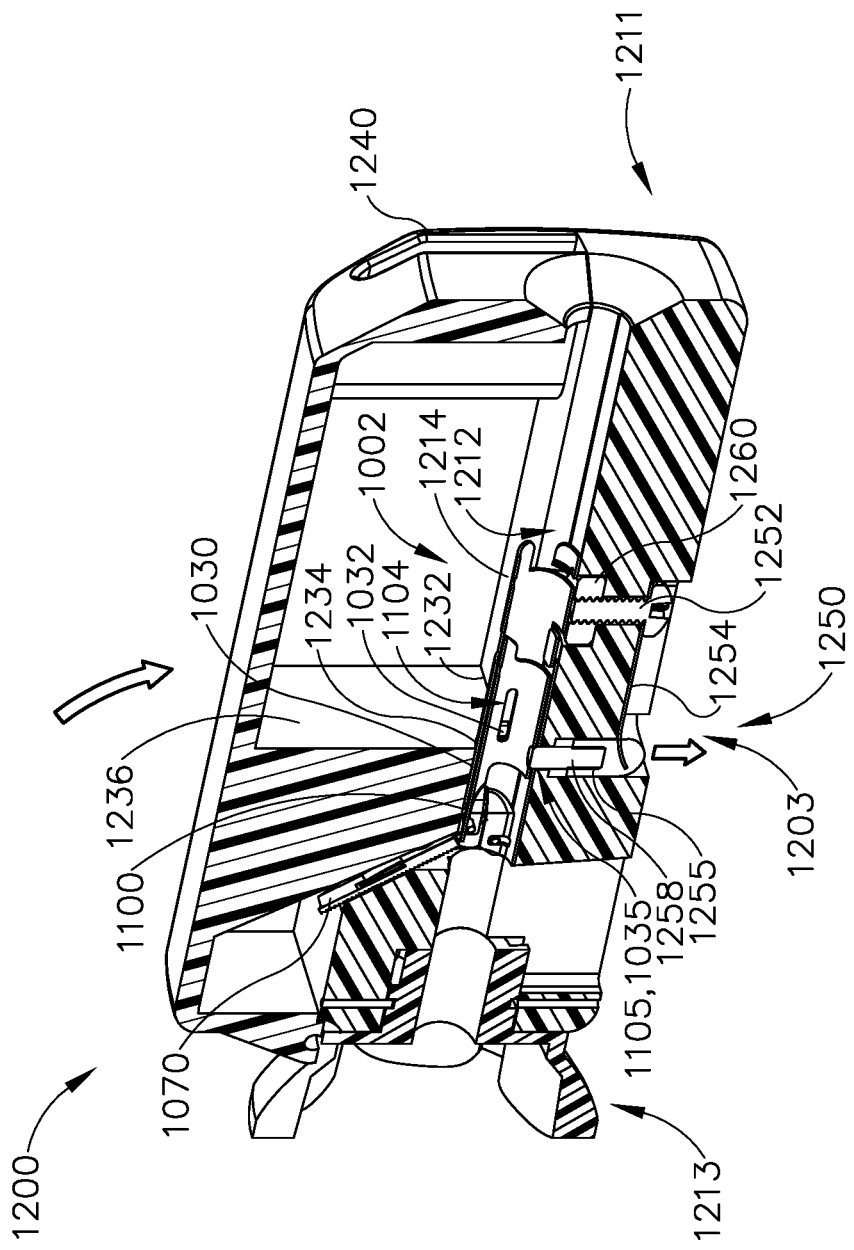

Additionally, as will be described in greater detail below, arched surface (1234) is configured to press against a portion of distal outer tube member (1230) in order to restrict vertical movement of first disposable sub-assembly (1002) when assembly tool (1200) is grasping first disposable sub-assembly (1002) in the closed position (as shown in FIG. 89C).

Figure 80:
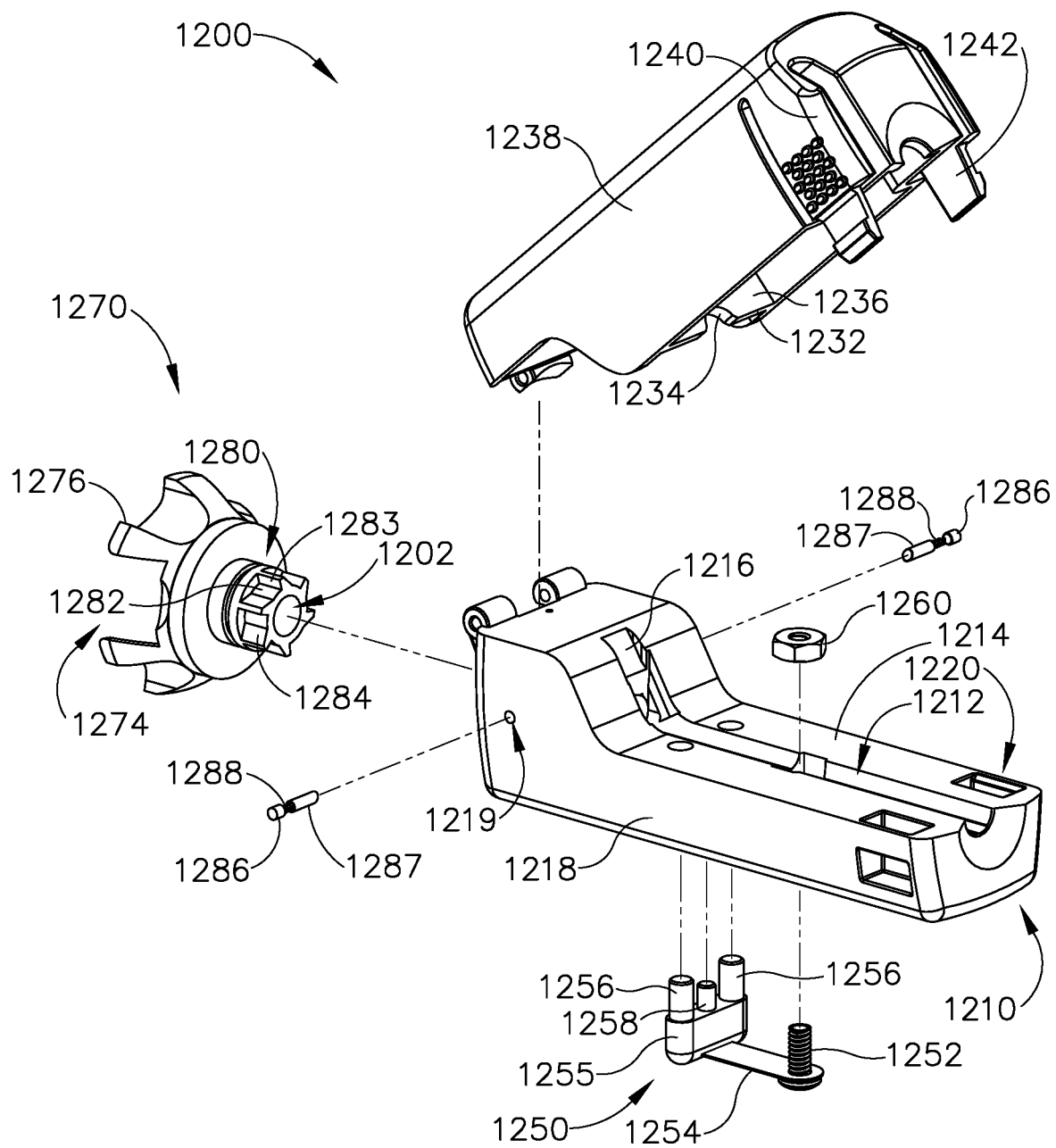
FIG. 80 depicts a perspective exploded view of the assembly tool of FIG. 78A.
Figure 81:
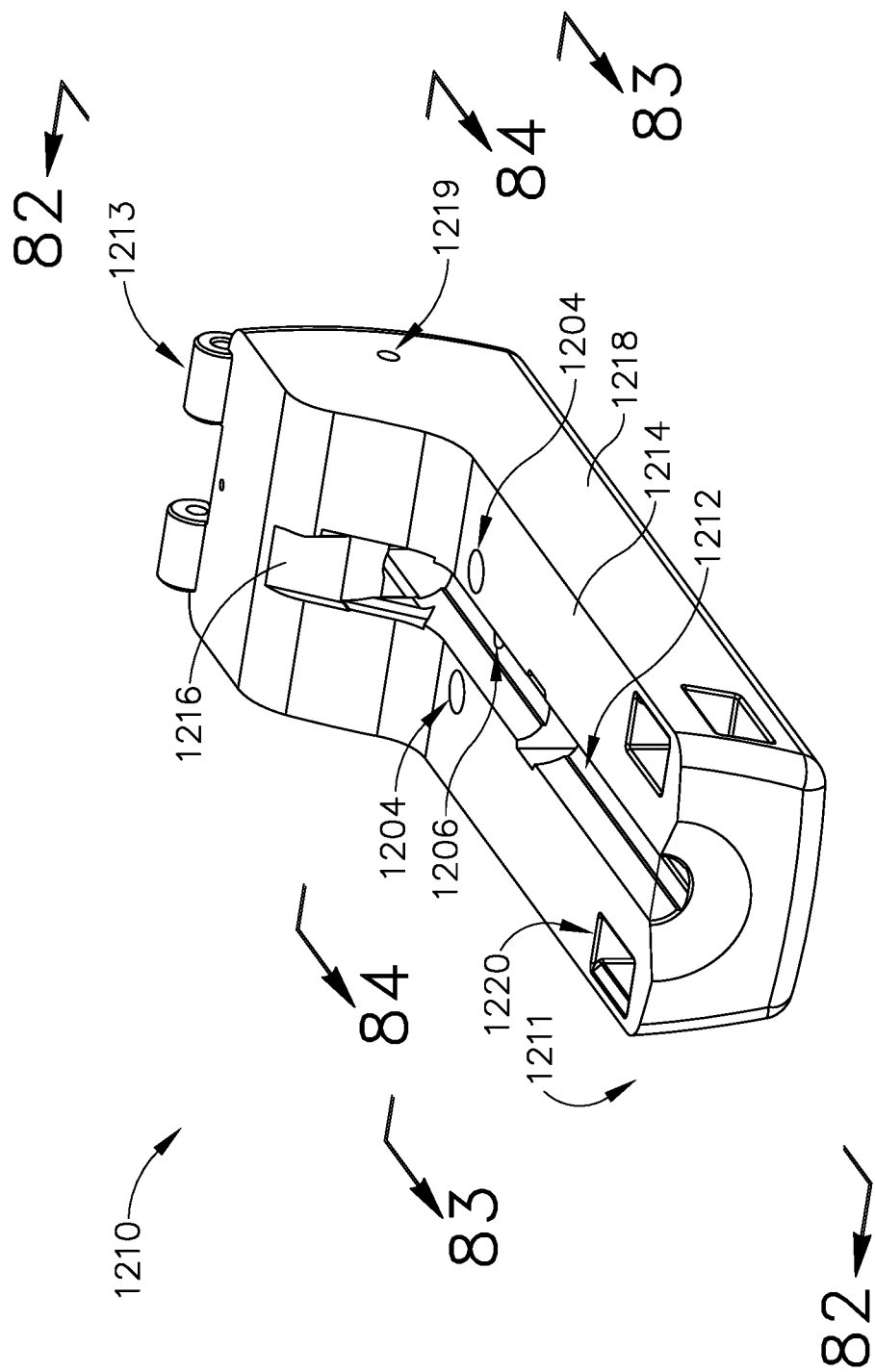
FIG. 81 depicts a perspective view of a base member of the assembly tool of FIG. 78A.
Figure 87A:
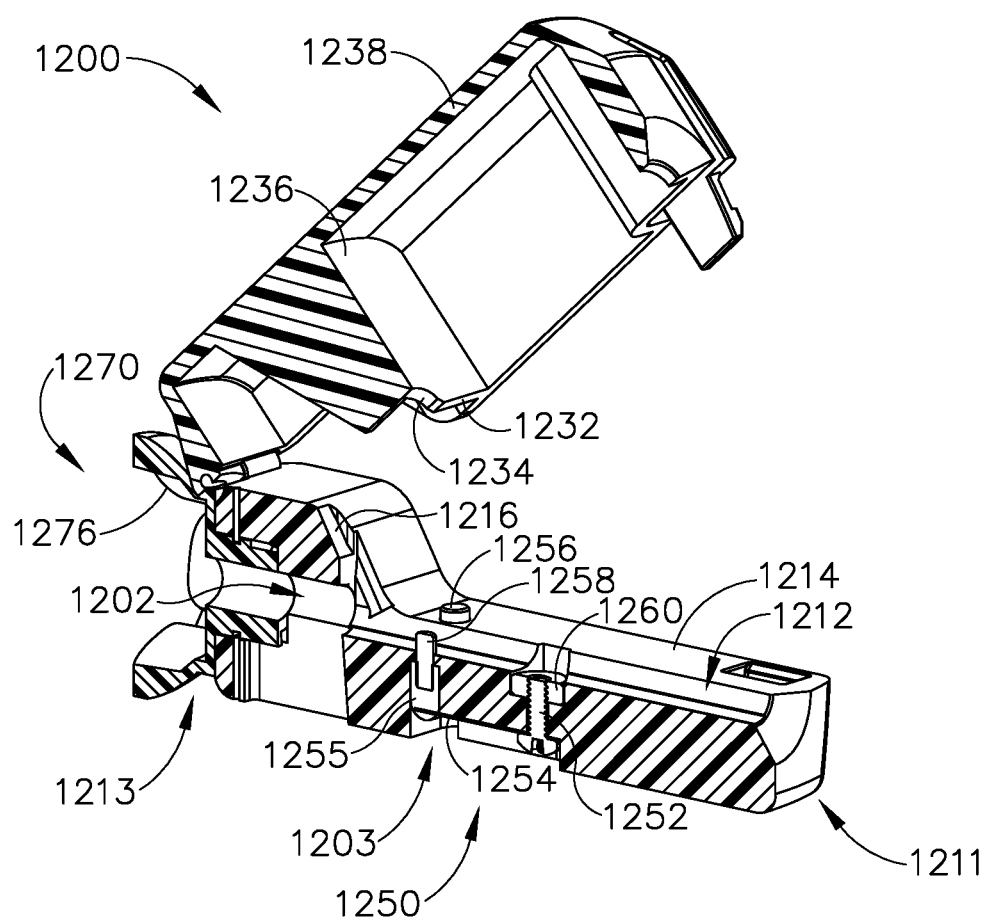
Figure 87B:
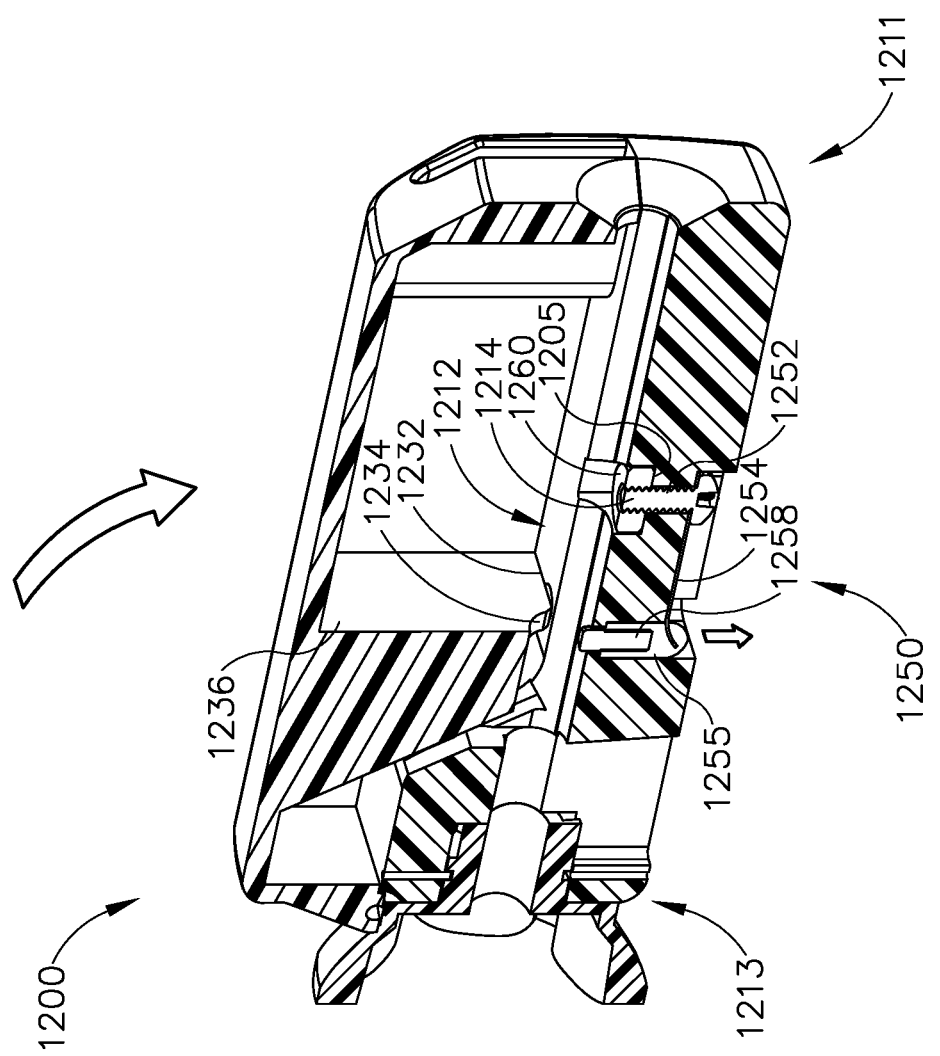

As shown in FIG. 80, locating member (1250) includes a leaf spring (1254) attached to bolt (1253) on one end and attached to connecting member (1255) on the other end. Connecting member (1255) unitarily couples two actuating pins (1256) and a locator pin (1258). Each actuating pin (1256) is slidably housed within a respective bore (1204) while locating pin (1258) is slidably housed within bore (1206). Leaf spring (1254) biases connecting member (1255) so that actuating pins (1256) and locating pin (1258) are biased toward the position shown in FIGS. 78A and 87A. As shown in FIGS. 87A-87B, downwardly presented surface (1232) of transverse wall (1236) is dimensioned to contact actuating pins (1256) when top member (1230) pivots from an open position (FIG. 87A) to a closed position (FIG. 87B). This contact between downwardly presented surface (1232) and actuating pins (1256) actuates connecting member (1255) and locator pin (1258) in the downward direction and also deforms leaf spring (1254). When top member (1230) pivots from the closed position (FIG. 87B) to the open position (FIG. 87A), downwardly presented surface (1232) releases from actuating pins (1256), and leaf spring (1254) returns connecting member (1255), actuating pins (1256) and locating pin (1258) to the position shown in FIGS. 78A and 87A.

Figure 85:
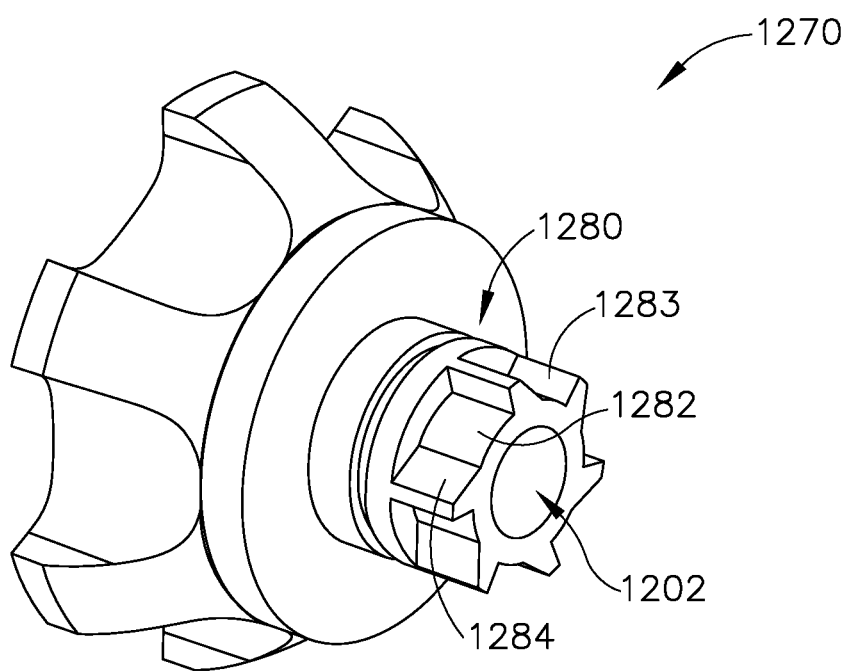
Figure 86:
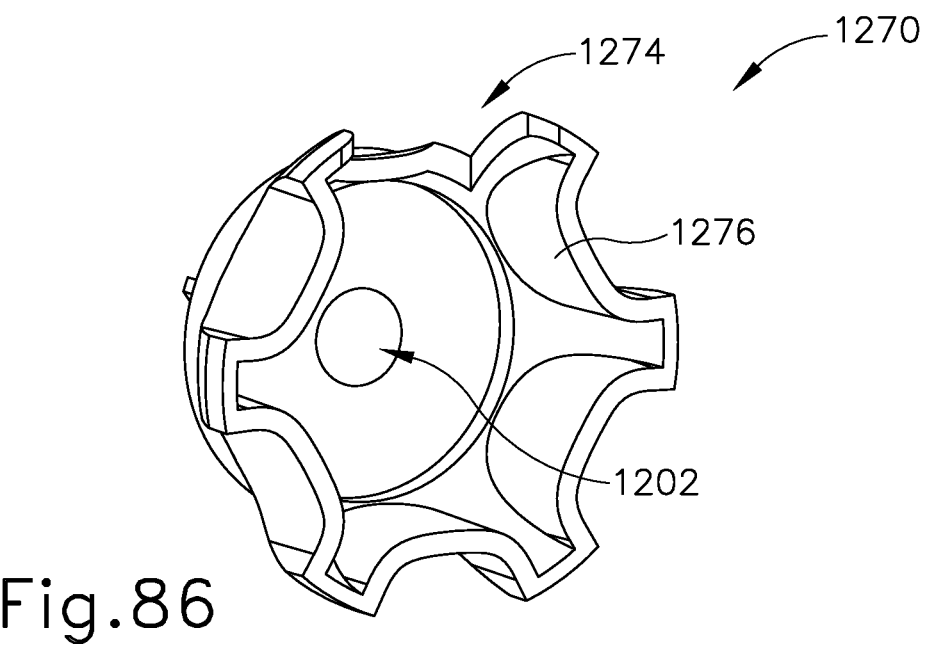

As best seen in FIGS. 85-86, rotating member (1270) includes a torque gear (1280) unitarily connected to a knob gripping member (1276). Knob gripping member defines a cutout (1274) to accommodate flush port (1300). Torque gear (1280) is rotatably housed within recess (1215) while knob gripping member (1276) is housed outside of recess (1215). Rotating member (1270) also helps define pathway (1202) for insertion over distal outer tube member (1030) and proximal outer tube member (1080). Torque gear (1280) includes a plurality of arched surfaces (1282), slanted surfaces (1284) and locking surfaces (1283) repeating in an annular pattern. Each surface (1282, 1283, 1284) is configured to interact with plunger (1287) as will be described in greater detail below.

FIGS. 88A-88C and FIGS. 89A-89C each show how first disposable sub-assembly may be fixed within assembly tool (1200). First, as shown between FIGS. 88A-88B and 89A-89B, first disposable sub-assembly (1002) may be placed on tubular surface (1212) while assembly tool (1200) is in the open configuration. Distal outer tube (1030) and distal inner tube (1100) may be positioned relative to each other that that alignment holes (1105, 1035) are longitudinally aligned. Additionally, locating pin (1258) is dimensioned to insert within alignment holes (1035, 1105) such that distal inner tube member (1100) and distal outer tube member (1030) are longitudinally fixed relative to base member (1210). Because clamp arm (1070) is pivotally coupled to both inner distal tube (1100) and outer distal tube (1030), and inner distal tube (1100) and outer distal tube (1030) may only translate relative to each other longitudinally, the longitudinal position of distal inner tube member (1100) relative to distal outer tube member (1030) determines the angular position of clamp arm (1070). Therefore, clamp arm (1070) will be in a uniform position when locator pin (1258) is within alignment holes (1035, 1105).

Figure 88A:
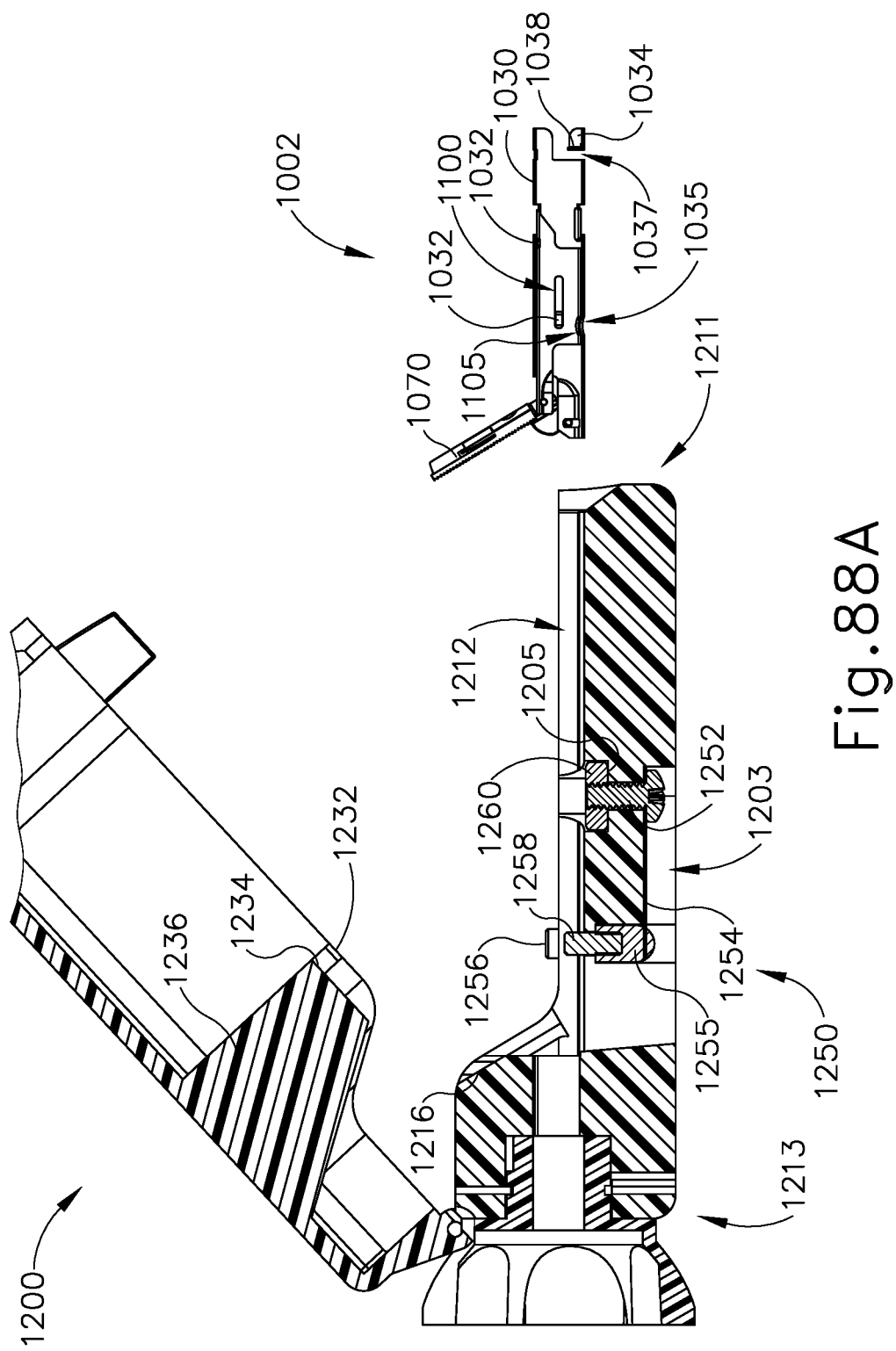
Figure 88B:
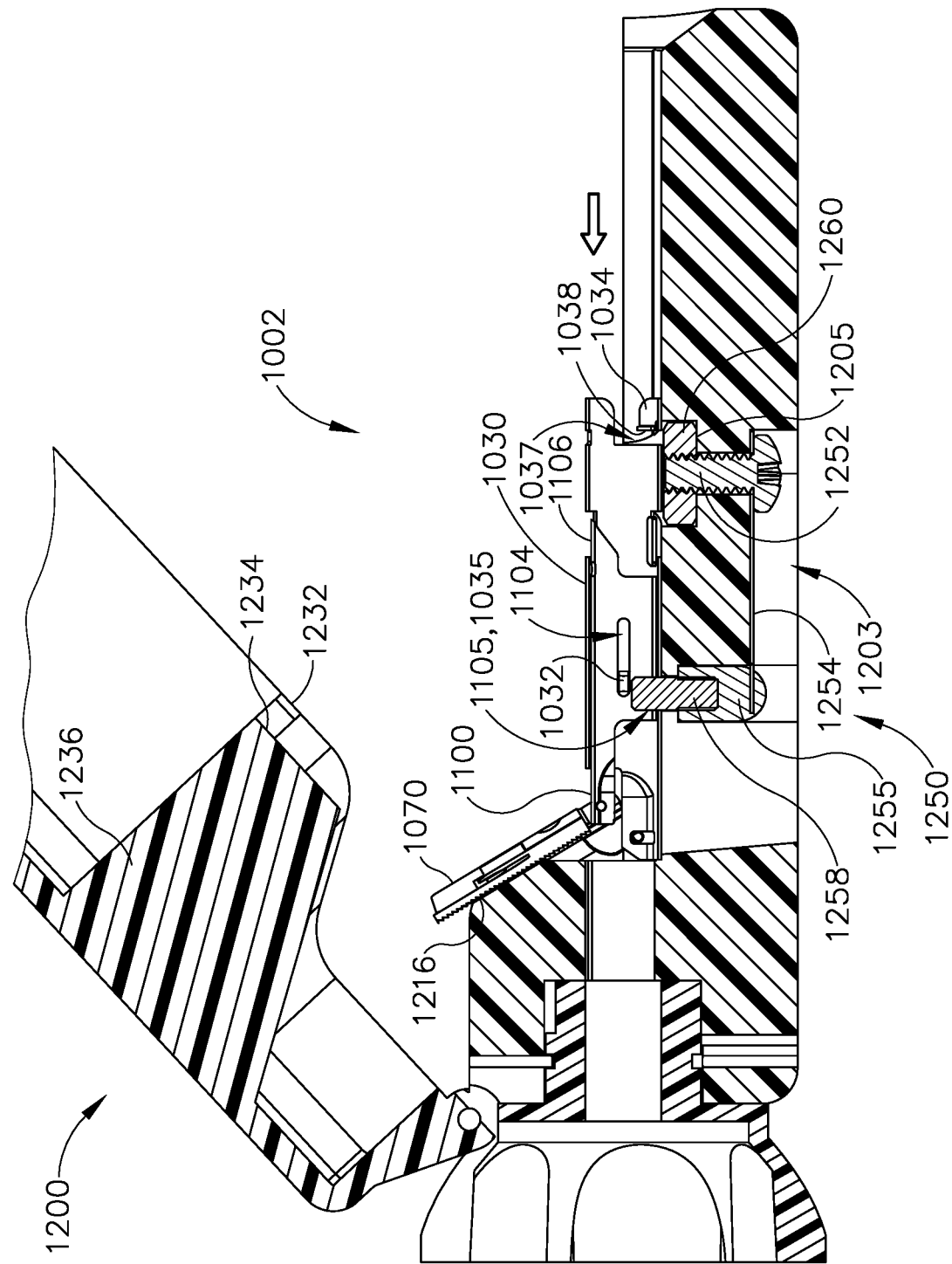
Figure 88C:
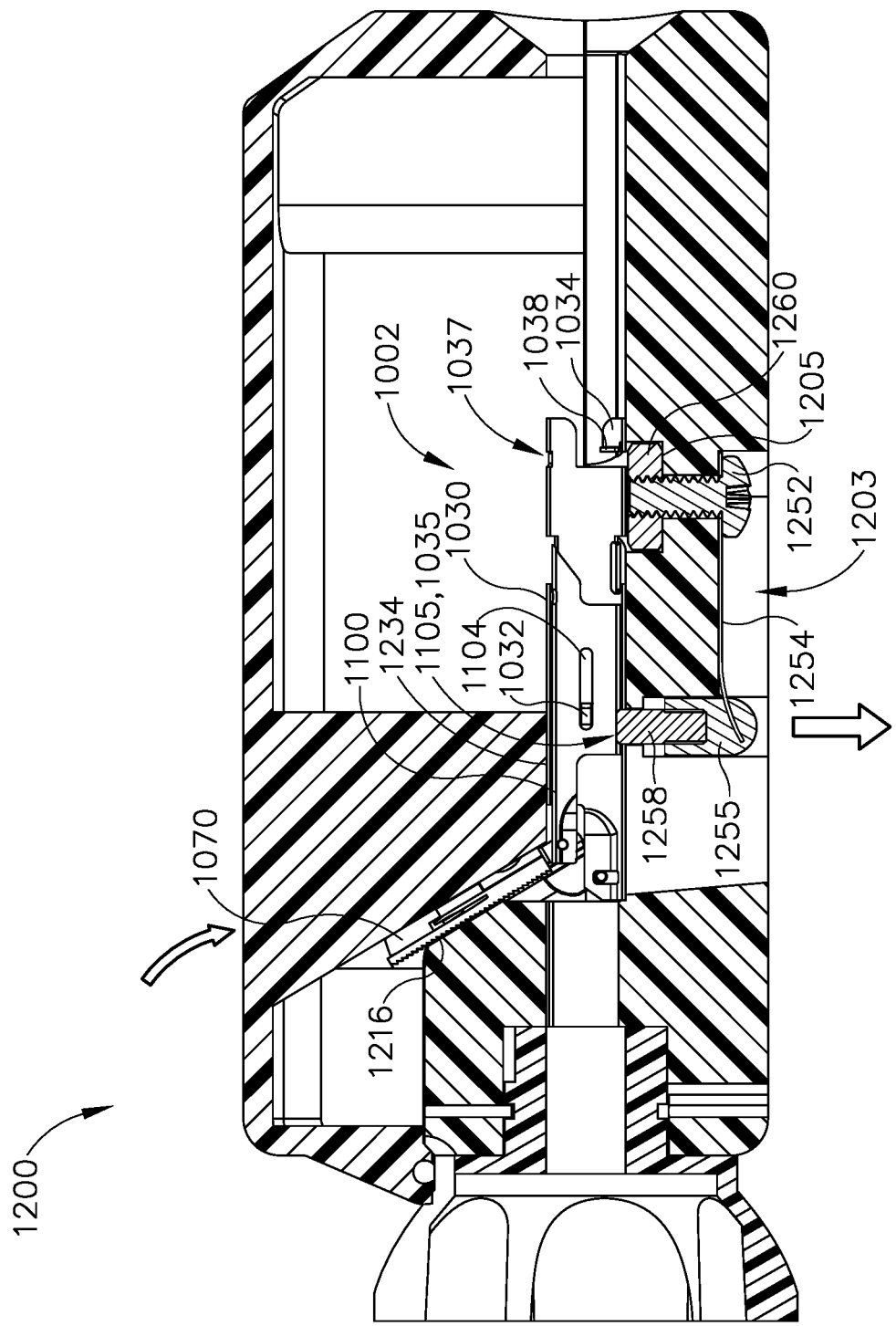

Clamp arm surface (1216) is dimensioned such that clamp pad (1074) rests on clamp arm surface (1216) when locator pin (1258) is within alignment holes (1035, 1105). An operator may then close assembly tool (1200), which as discussed above, drives locator pin (1258) toward the bottom of tubular surface (1212) as shown in FIGS. 88C and 89C It should be understood that locator pin (1258) fixes distal outer tube member (1030) and distal inner tube member (1100) in the longitudinal direction while tubular surface (1212) and arched surface (1234) fix distal outer tube member (1030) and distal inner tube member (1100) in the vertical and lateral directions. It should also be understood that locator pin (1258) is in a position not to interfere with gap (1101) accepting blade (1060). First disposable sub-assembly (1002) is now fixed relative to assembly tool (1200) at the stage shown in FIGS. 88C and 89C. With latches (1242) locking top member (1230) relative to base member (1210), an operator may grasp assembly tool (1200) to manipulate first disposable sub-assembly (1002) in order to rotate first disposable sub-assembly (1002) relative to second disposable sub-assembly (1004) with relative ease.

D. Alternative Exemplary Assembly Tool

FIGS. 90-93 show an alternative exemplary assembly tool (2000) that may be utilized to couple first disposable sub-assembly (1002) with second disposable sub-assembly (1004). Assembly tool (2000) includes a first half (2010) pivotally coupled to a second half (2020) via a living hinge (2030). As best seen in FIG. 91, first half (2010) and second half (2020) are almost entirely symmetrical, with the exception of snap fit features (2016, 2026).

As can be seen between FIGS. 90 and 91, first half (2010) and second half (2020) may collapse from a closed position (FIG. 90) to an open position (FIG. 91). As will be described in greater detail below, first disposable sub-assembly (1002) may be inserted between first half (2010) and second half (2020) in the open position, and then first disposable sub-assembly (1002) may be fixed to assembly tool (2000) when first half (2010) and second half (2020) pivot to the closed position. While in the current example, first half (2010) is pivotally coupled to second half (2020) with a living hinge (2030), it should be understood that any suitable type of pivotal coupling may be utilized as will be apparent to one having ordinary skill in the art in view of the teachings herein.

As best seen in FIG. 91, first half (2010) includes a first mating surface (2014) and a first valley (2018). A snap fit feature (2016) extends from first mating surface (2014) while a flat (2012) extends from first valley (2018). Similarly, second half (2020) includes a second mating surface (2024) and a second valley (2028). A snap fit feature (2026) extends from second mating surface (2024) while a flat (2022) extends from second valley (2028). Flats (2012, 2022) are longitudinally aligned.

First valley (2018) and second valley (2028) are symmetrical such that when first half (2010) and second half (2020) are closed, valleys (2018, 2028) define a disposable assembly channel (2036), a blade channel (2032), and a clamp arm channel (2034). Disposable assembly channel (2036) is dimensioned to receive distal outer tube (1030) and distal inner tube (1100) of first disposable subassembly (1002). Blade channel (2032) is dimensioned to receive ultrasonic blade (1060) when second disposable sub-assembly (1004) is being coupled with first disposable sub-assembly (1002). As best seen in FIG. 92, clamp arm channel (2034) is dimensioned to receive clamp arm (1070) at a specified angle relative to the rest of first disposable sub-assembly (1002).

As mentioned above, because clamp arm (1070) is pivotally coupled to both inner distal tube (1100) and outer distal tube (1030) while inner distal tube (1100) and outer distal tube (1030) may only translate relative to each other longitudinally, the longitudinal position of distal inner tube member (1100) relative to distal outer tube member (1030) determines the angular position of clamp arm (1070). Conversely, the angular position of clamp arm (1070) relative to both outer distal tube member (1030) and inner distal tube member (1100) may determine the longitudinal position of both outer distal tube (1030) and inner distal tube (1100).

Therefore, when clamp arm (1070) is inserted into clamp arm channel (2034) and distal outer tube (1030) is inserted into disposable assembly channel (2036), distal outer tube (1030) may be located at the same longitudinal location every time due to the constant angle made by clamp arm (1070) housed in clamp arm channel (2034).

In order to fix first disposable sub-assembly (1002) to assembly tool (2000) an operator may insert clamp arm (1070) into a portion of clamp arm channel (2034) defined by first half (2010) while assembly tool (2000) is in the open position. Additionally, an operator may insert distal outer tube (1030) and distal inner tube (1100) into disposable assembly channel (2036) defined by first half (2010). While in the current example, first disposable sub-assembly (1002) is being initially inserted into portions of first half (2010), it should be understood first disposable sub-assembly (1002) may be alternatively inserted into portions of second half (2020). As best seen in FIG. 92, an operator may then close assembly tool (2000) to fix first disposable sub-assembly (1002) to assembly tool (2000), as will be described in more detail below.

At best seen in FIG. 93, flats (2012, 2022) are positioned within valleys (2018, 2028) to be inserted within the portion slots (1104) of distal inner tube (1100) accommodating crimps (1032) of distal outer tube (1030). The force provided from flats (2012, 2022) interfacing with crimps (1032) inhibits unwanted movement of first disposable sub-assembly (1002) relative to assembly tool (2000). Therefore, first disposable sub-assembly (1002) may be considered fixed relative to assembly tool (2000).

Snap fit features (2016, 2026) are dimensioned for an interference fit to couple first half (2010) with second half (2020) when assembly tool (2000) pivots to the closed position (as shown in FIG. 90). Snap fit features (2016, 2026) sufficiently couple first half (2010) with second half (2020) so that an operator may fix first disposable sub-assembly (1002) within assembly tool (2000) in order to assemble or disassemble first sub-assembly (1002) with second sub-assembly (1004). However, snap fit features (2016, 2026) may be pulled apart such that an operator may willingly pivot first half (2010) and second half (2020) from the closed position to the open position. Therefore, an operator may selectively fix first disposable assembly (1002) with assembly tool (2000) or selectively release first disposable assembly (1002) from assembly tool (2000).

E. Exemplary Assembly and Disassembly of First Disposable Sub-Assembly with Second Disposable Sub-Assembly FIGS. 94A-95D show an exemplary assembly of first disposable sub-assembly (1002) with second disposable sub-assembly (1004). It should be understood that assembly tool (1200, 2000) may be used to grasp first disposable sub-assembly as shown in FIGS. 88C and 89C while assembling and disassembling disposable assembly (1000), but is left out for purposes of clarity.

In particular FIGS. 94A-94D show distal outer tube (1030) coupling with proximal outer tube (1080) while FIGS. 95A-95D show distal inner tube (1110) coupling with proximal inner tube (1090). FIGS. 94A-94B and 95A-95B show blade (1060) being inserted into gap (1101) with the arch of blade (1060) facing downward.

FIG. 94B shows distal outer tube (1030) being inserted over second disposable sub-assembly (1004) so that circumferential tab (1034) is inserted within tab guide channel (1086) of distal coupling feature (1082). In particular, inwardly extending nub (1038) is directly adjacent to distally facing slant (1084) such that circumferential tab (1034) is still in the relaxed position. FIG. 94C shows distal outer tube (1030) being further translated in the proximal direction such that inwardly extending nub (1038) climbs up distally facing slant (1084), causing circumferential tab (1034) to bend upwardly. Additionally, protrusion (1088) travels within first channel (1033) defined by circumferential tab (1034) while inwardly extending nub (1038) is longitudinally aligned with locking channel (1087). As shown in FIG. 94D, second disposable sub-assembly (1002) is then rotated such that projection travels within the confines of second channel (1037) and inwardly extending nub (1038) snaps into locking channel (1087). Distal outer tube (1030) is now coupled with proximal outer tube member (1080). Therefore, longitudinal translation of proximal outer tube member (1080) will also translate distal outer tube member (1030) in order to pivot clamp arm (1070) relative to blade (1060).

FIG. 95B shows distal inner tube (1100) being inserted over proximal inner tube (1090) such that stud (1092) travels within entry channel (1109). It should be understood that the position shown in FIG. 95B corresponds with the position shown in FIG. 94C. FIG. 95C shows first disposable assembly (1002) being rotated such that stud (1092) flexes proximally presented tab (1106) about stud hole (1108). FIG. 95D shows first disposable assembly (1002) being further rotated such that stud (1092) snaps into stud hole (1108) and proximally presented tab (1106) returns to its relaxed position. The position of inner distal tube (1100) corresponds with the position shown in FIG. 94D. Distal inner tube (1100) is not mechanically grounded with proximal inner tube (1090).

If an operator desires to disassemble first disposable sub-assembly (1002) from second disposable sub-assembly (1004), an operator must follow the steps in reverse order. It should be understood that unlocking slanted surface (1085) is dimensions to allow inwardly extending nub (1038) to raise circumferential tab (1034) such that distal outer tube member (1080) is no longer coupled with proximal outer tube member (1080). It should also be understood that an operator may fix first disposable sub-assembly (1002) with assembly tool (1200) in order to obtain the desired amount of leverage to disassemble first disposable sub-assembly (1002) from second disposable sub-assembly (1004).

F. Exemplary Assembly and Disassembly of Reusable Assembly with Second Disposable Sub-Assembly As discussed above, reusable assembly (400) may be selectively coupled with second disposable sub-assembly (1004) in a similar fashion that reusable assembly (400) may selectively couple with second disposable sub-assembly (704) discussed above. In some instances, it may be desirable to install reusable assembly (400) with second disposable sub-assembly (1004) with a specific torque value. Assembly tool (1200) may be utilized to install reusable assembly (400) to second disposable sub-assembly (1204) with a predetermined torque value.

FIG. 96A-96C shows assembly tool (1200) being utilized during installation of reusable assembly (400) with second disposable sub-assembly (1004), with a portion of body (1011) being omitted for purposes of clarity. FIG. 96A shows assembly tool (1200) being inserted over outer tube (1080) such that knob gripping member (1276) is inserted first. Knob gripping member (1276) may be advanced in the proximal direction as shown in FIG. 96B such that rotating member (1270) is rotationally coupled with knob member (1020). As shown in FIG. 96C, reusable assembly (400) may be inserted distally such that threaded stud (402) of transducer (406) is inserted into threaded coupling bore (1064) of waveguide (1062), thereby coupling reusable member (400) with second disposable sub-assembly (1004).

FIGS. 97A-97D show what happens when threaded stud (402) of transducer (406) and threaded coupling bore (1064) are coupled with sufficient torque. With the predetermined torque level met, the frictional braking force provided by plunger (1287) and spring (1288) against torque gear (1280) are overcome, and as a result, plungers (1287) start slipping on arched surface (1282) and slanted surface (1284). Because knob gripping member (1276) is fixed to torque gear (1280), and an operator provides reactionary torsion by gripping base member (1210) and/or top member (1230), further rotation of reusable assembly (400) rotates unitarily with rotating member (1270), and no more torque is provided between threaded stud (402) of transducer (406) and threaded coupling bore (1064).

If an operator desires to decouple reusable assembly (400) with second disposable sub-assembly (1004), the operator simply rotates reusable assembly (400) in the opposite direction while holding base member (1210) and/or top member (1230), causing plunger (1287) to interact with vertical surface (1283), which prevents slipping between base member (1210) and rotating member (1270).

While in the current example, four first disposable sub-assemblies (702) are used, it should be understood any suitable number of first disposable sub-assemblies (702) may be used as would be apparent to one having ordinary skill in the art in view of the teachings herein.

V. EXEMPLARY ALTERNATIVE ULTRASONIC SURGICAL INSTRUMENT WITH REMOVABLE SHAFT ASSEMBLY PORTION

FIGS. 98-114 show another exemplary ultrasonic surgical instrument (3000) that may be readily broken down into disposable and reusable components. In particular, surgical instrument (3000) of this example comprises a reusable assembly (3400) and a disposable assembly (3700). To the extent that the following discussion omits various details of reusable assembly (3400) and disposable assembly (3700), it should be understood that reusable assembly (3400) and disposable assembly (700) may incorporate the various details described above and/or details described in any of the various references that are cited herein. Other suitable details will be apparent to those of ordinary skill in the art in view of the teachings herein.

When fully assembled, ultrasonic surgical instrument provides an end effector (3750) that includes an ultrasonic blade (3760) and a clamp arm (3770), which is pivotable toward and away from ultrasonic blade (3760). End effector (3750) is thus operable to grasp, ultrasonically seal, and ultrasonically sever tissue as described herein and as described in various references cited herein. Reusable assembly (3400) comprises an ultrasonic transducer (3406), which is operable to convert electrical power into ultrasonic vibrations, also as described herein and as described in various references cited herein. Ultrasonic transducer (3406) is acoustically coupled with ultrasonic blade (3760) via an acoustic waveguide (3762), portions of which are shown in FIGS. 99, 108, and 114. It should be understood that ultrasonic transducer (3406), ultrasonic blade (3760), and acoustic waveguide (3762) may be configured in accordance with the teachings of any of the various references cited herein; or in any other suitable fashion.

Disposable assembly (3700) of the present example comprises a first disposable sub-assembly (3702) and a second disposable sub-assembly (3704). Sub-assemblies (3702, 3704) are configured to be coupled together in order to form disposable assembly (3700), which may then be coupled with reusable assembly (3400) for form a complete ultrasonic surgical instrument (3000). After ultrasonic surgical instrument (3000) is used in a surgical procedure, disposable assembly (3700) may be removed from reusable assembly (3400); and then first disposable sub-assembly (3702) may be removed from second disposable sub-assembly (3704). In some such instances, reusable assembly (3400) may be cleaned, sterilized, and re-used up to 100 times (by way of example only). First disposable sub-assembly (3702) may be disposed of, such that first disposable sub-assembly (3702) is only used one single time. Second disposable sub-assembly (3704) may be cleaned, sterilized, and re-used between 2 to 20 times (by way of example only). Of course, these re-use scenarios are merely illustrative examples. It should nevertheless be understood that the configuration of disposable assembly (3700) may minimize the amount of single-use material that is disposed of after each surgical procedure. This may reduce cost and overall waste as compared to conventional instrumentation.

As shown in FIGS. 98-99, first disposable sub-assembly (3702) comprises an outer tube (3780). As best seen in FIGS. 108-109, clamp arm (3770) is pivotally coupled with a distally projecting tongue (3782) of outer tube (3780). A coupling member (3010) is fixedly secured to the proximal end of outer tube (3780). As shown in FIGS. 108-109, first disposable sub-assembly (3702) further comprises a distal inner tube member (3100). As best seen in FIGS. 108-109 and 114, distal inner tube member (3100) is also pivotally coupled with clamp arm (3770) via a distally projecting tongue (3102) of distal inner tube member (3100). Thus, when outer tube (3780) translates longitudinally relative to distal inner tube member (3100) as will be described in greater detail below, clamp arm (3770) will pivot toward and away from ultrasonic blade (3760).

As shown in FIGS. 98-99, second disposable sub-assembly (3704) comprises a handle assembly (3710), a proximal inner tube member (3790), acoustic waveguide (3762), and ultrasonic blade (3760). Handle assembly (3710) comprises a housing (3718) that defines a pistol grip (3713). Handle assembly (3710) further includes a trigger (3712) that is pivotable toward and away from pistol grip (3713); and a pair of buttons (3714, 3716). Buttons (3714, 3716) are operable to activate ultrasonic transducer (3406) to thereby activate ultrasonic blade (3760). In particular, one button (3714) will provide activation of ultrasonic blade (3760) at one power level or profile; while the other button (3716) will provide activation of ultrasonic blade (3760) at another power level or profile. Of course, any other suitable user input feature(s) may be used.

Trigger (3712) is operable to actuate clamp arm (3770), such that clamp arm (3770) will pivot toward ultrasonic blade (3760) when trigger (3712) us pivoted toward pistol grip (3713); and such that clamp arm (3770) will pivot away from ultrasonic blade (3760) when trigger (3712) us pivoted away from pistol grip (3713). In the present example, this movement is provided by translating outer tube (3780) longitudinally in response to pivotal movement of trigger (3712), while inner tube members (3790, 3100) remain longitudinally stationary. Various suitable ways in which outer tube (3780) may be translated longitudinally in response to pivotal movement of trigger (3712) will be apparent to those of ordinary skill in the art in view of the teachings herein. It should also be understood that, in some alternative versions, clamp arm (3770) is pivoted by translating inner tube members (3790, 3100) longitudinally while outer tube (3780) remains longitudinally stationary.

As shown in FIGS. 99-100, handle assembly (3710) of the present example further includes a knob member (3720). Knob member (3720) is rotatable relative to housing (3718). When instrument (3000) is fully assembled, knob member (3720) is coupled with acoustic waveguide (3762), inner tube members (3790, 3100), and outer tube (3780) such that all of these components will rotate together unitarily relative to housing (3718). Knob member (3720) also provides guidance to first disposable sub-assembly (3702) when first disposable sub-assembly (3702) is being coupled with second disposable sub-assembly (3704). To accomplish this, and as best seen in FIG. 101, knob member (3720) includes a guide channel (3724) that receives a guide tab (3012) of coupling member (3010) as will be described in greater detail below. As best seen in FIG. 102, guide channel (3724) is in communication with a recess (3726) formed in a sidewall defining a central bore (3722) of knob member (3720). Recess (3726) is configured to accommodate angular movement of guide tab (3012) relative to knob member (3720) after guide tab (3012) has cleared guide channel (3724) upon sufficient insertion of coupling member (3010) in bore (3722), as will also be described in greater detail below.

A. Exemplary Bayonet Mount with Detents

FIGS. 103-104 show coupling member (3010) in greater detail. As shown, coupling member (3010) includes guide tab (3012), which extends transversely from an outer sidewall of coupling member (3010). Coupling member (3010) also includes a pair of bayonet mount tabs (3014) that extend transversely from the proximal end of coupling member (3010). In the present example, bayonet mount tabs (3014) are angularly positioned 180° apart from each other, with guide tab (3012) being angularly positioned 90° apart from bayonet mount tabs (3014). Alternatively, other suitable angular relationships may be provided. As best seen in FIG. 104, coupling member (3010) also includes a pair of detent protrusions (3016) that extend proximally away from a central shoulder formed in the body of coupling member (3010). Detent protrusions (3016) are at the same angular positions as bayonet mount tabs (3014), though detent protrusions (3016) are longitudinally positioned at an intermediate region of coupling member (3010) in this example. Again, any other suitable positioning may be used for detent protrusions (3016).

FIGS. 105-106 show a coupling member (3730) that is part of handle assembly (3710). Coupling member (3730) is configured to couple with coupling member (3710) to thereby couple first and second disposable sub-assemblies (3702, 3704) together. Coupling member (3730) is also coupled with trigger (3712), such that pivotal movement of trigger (3712) will cause pivotal movement of coupling member (3730). Coupling member (3730) is also coupled with knob member (3720) such that coupling member (3730) will rotate unitarily with knob member (3720). However, the coupling between coupling member (3730) and knob member (3720) is configured to enable coupling member (3730) to translate relative to knob member (3720). This will in turn accommodate translation of outer tube (3780), thereby enabling pivotal movement of clamp arm (3770).

Coupling member (3730) of the present example includes a pair of bayonet slots (3732) and a pair of detent recesses (3742). Each bayonet slot (3732) includes an entry opening (3734) leading to a longitudinally extending portion (3736), which then leads to an angularly extending portion (3738). Bayonet slots (3734) are angularly offset from each other by 180°. Each detent recess (3742) includes an adjacent ridge (3740) with a lead-up ramp (3744). Detent recesses (37420 are also angularly offset from each other by 180°.

FIGS. 107A-107E show various stages of assembling first disposable sub-assembly (3702) with second disposable sub-assembly (3704). It should be understood that knob member (3720) is omitted from FIGS. 107A-107E in order to depict features that would otherwise be obscured by knob member (3720). In the stage shown in FIG. 107A, the operator has inserted the shaft assembly portion formed by proximal inner tube member (3790) and acoustic waveguide (3762) into the bore defined by coupling member (3010) and outer tube (3780). While holding handle assembly (3710) stationary, the operator moves first disposable sub-assembly (3702) proximally to the position shown in FIG. 107B. At this stage, bayonet mount tabs (3014) have just entered entry openings (3734) of bayonet slots (3732). It should be understood that guide channel (3724) of knob member (3720) and guide tab (3012) of coupling member (3010) are configured such that bayonet mount tabs (3014) will not reach entry openings (3734) of bayonet slots (3732) unless first disposable sub-assembly (3702) is at a particular angular relationship with second disposable sub-assembly (3704). Thus, when the operator retracts first disposable sub-assembly (3702) proximally, the operator may rotate first disposable sub-assembly (3702) as needed in order for guide tab (3012) of coupling member (3010) to enter guide channel (3724) of knob member (3720).

After reaching the stage shown in FIG. 107B, the operator may continue to move first disposable sub-assembly (3702) proximally while holding handle assembly (3710) stationary, until reaching the stage shown in FIG. 107C. At this stage, bayonet mount tabs (3014) have reached the proximal ends of the corresponding longitudinally extending portions (3736) of bayonet slots (3732). The operator may detect this positioning via tactile feedback indicated from the hard stop preventing further proximal movement of first disposable sub-assembly (3702) relative to handle assembly (3710). At this stage, the operator may grasp knob member (3720) and hold knob member (3720) stationary while rotating first disposable sub-assembly (3702). During this rotation, bayonet mount tabs (3014) traverse the corresponding angularly extending portions (3738) of bayonet slots (3732). As noted above, the configuration of recess (3726) in knob member (3720) will accommodate the corresponding angular movement of guide tab (3012) relative to knob member (3720) during this rotation of first disposable sub-assembly (3702).

As the operator rotates first disposable sub-assembly (3702) relative to knob member (3720) and thus relative to coupling member (3730), detent protrusions (3016) of coupling member (3710) will eventually encounter corresponding lead-up ramps (3744) as shown in FIG. 107D. While the operator will feel some degree of resistance to further rotation of first disposable sub-assembly (3702) relative to knob member (3720), the operator may continue rotating first disposable sub-assembly (3702) relative to knob member (3720) and thus relative to coupling member (3730). Detent protrusions (3016) will ride up corresponding lead-up ramps (3744) and along the corresponding adjacent ridges (3740), eventually reaching detent recesses (3742) as shown in FIG. 107E. Once detent protrusions (3016) are seated in corresponding detent recesses (3742), bayonet mount tabs (3014) will have completed their travel through corresponding bayonet slots (3732), and first disposable sub-assembly (3702) will be fully coupled with second disposable sub-assembly (3704).

After reaching the stage shown in FIG. 107E, the cooperation between detent protrusions (3016) and detent recesses (3742) will maintain the coupling of first disposable sub-assembly (3702) with second disposable sub-assembly (3704) during normal use of instrument (3000). However, the configuration of detent protrusions (3016) and detent recesses (3742) will still enable the operator to disassemble first disposable sub-assembly (3702) from second disposable sub-assembly (3704) after completing a surgical procedure. The operator may then dispose of first disposable sub-assembly (3702) and reprocess second disposable sub-assembly (3704), if appropriate, for subsequent use. In order to disassemble first disposable sub-assembly (3702) from second disposable sub-assembly (3704), the operator may simply grasp knob member (3720) and rotate first disposable sub-assembly (3702) to re-traverse angularly extending portions (3738) of bayonet recesses (3732), then pull first disposable sub-assembly (3702) distally away from second disposable sub-assembly (3704) once bayonet mount tabs (3014) reach longitudinally extending portions (3736) of bayonet recesses (3732).

B. Exemplary Stop Member for Inner Tube Assembly

FIGS. 110-112 show distal inner tube member (3100) in greater detail. As shown, distal inner tube member (3100) includes distally projecting tongue (3102), a resilient latch arm (3104), and a lateral opening (3110). As noted above, distally projecting tongue (3102) is pivotably coupled with clamp arm (3770). As best seen in FIG. 112, resilient latch arm (3014) includes an inwardly projecting tab (3016). As also best seen in FIG. 112, distal inner tube member (3100) includes an inwardly projecting stop member (3112) adjacent to lateral opening (3110).

FIG. 113 shows the distal end of proximal inner tube member (3790) in greater detail. As shown, proximal inner tube member (3790) includes a distally projecting tongue (3792), a lateral opening (3794), and a distally presented edge (3796). As will be described in greater detail below, lateral opening (3794) is configured to cooperate with inwardly projecting tab (3016), while edge (3796) is configured to cooperate with stop member (3112).

FIG. 108 shows distal inner tube member (3100) decoupled from proximal inner tube member (3790). It should therefore be understood that first disposable sub-assembly (3702) and second disposable sub-assembly (3704) are not coupled together at this stage. FIGS. 109 and 114 show distal inner tube member (3100) fully coupled with proximal inner tube member (3790). At this stage, inwardly projecting tab (3016) is positioned in lateral opening (3794), thereby securing distal inner tube member (3100) with proximal inner tube member (3790). It should be understood that the positioning of components shown in FIGS. 109 and 114 corresponds with the positioning of components shown in FIG. 107E.

It should also be understood that, during the transition from the state shown in FIG. 108 to the state shown in FIG. 109, resilient latch arm (3014) will deflect outwardly as inwardly projecting tab (3016) rides along the exterior of proximal inner tube member (3790), until inwardly projecting tab (3016) snaps into place in lateral opening (3794). The distal end of outer tube (3780) includes a lateral opening (3784) that is sized and positioned to accommodate this outward deflection of resilient latch arm (3014) during the transition from the state shown in FIG. 108 to the state shown in FIG. 109.

As shown in FIG. 114, stop member (3112) will abut edge (3796) when distal inner tube member (3100) is fully coupled with proximal inner tube member (3790). It should be understood that this abutment may prevent distal inner tube member (3100) from inadvertently decoupling from proximal inner tube member (3790). For instance, when the operator drives clamp arm (3770) to clamp on tissue with substantial force, this may provide a substantial, proximally oriented load on distal inner tube member (3100). If this occurred without a stop member (3112) engaging edge (3796), the substantial, proximally oriented load on distal inner tube member (3100) may eventually cause inwardly projecting tab (3016) to pop out of lateral opening (3794), thereby decoupling distal inner tube member (3100) from proximal inner tube member (3790). Thus, with stop member (3112) abutting edge (3796), stop member (3112) and edge (3796) cooperate to transfer the substantial, proximally oriented load from distal inner tube member (3100) to proximal inner tube member (3790). In other words, stop member (3112) and edge (3796) prevent inwardly projecting tab (3016) from having to bear any of the substantial, proximally oriented load that would result from clamp arm (3770) clamping on tissue with substantial force. Stop member (3112) and edge (3796) may thereby reduce the likelihood of distal inner tube member (3100) inadvertently decoupling from proximal inner tube member (3790).

VI. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a reusable assembly comprising an ultrasonic transducer; (b) a first disposable sub-assembly comprising a clamp arm; (c) a second disposable sub-assembly comprising: (i) a pivotable trigger, and (ii) an ultrasonic waveguide, wherein the second disposable sub-assembly is configured to removably coupled with the reusable assembly; wherein the first disposable sub-assembly is configured to removably coupled with the second disposable sub-assembly, wherein the pivotable trigger is configured to rotate the clamp arm relative to the ultrasonic waveguide when the first disposable sub-assembly is coupled to the second disposable sub-assembly.

Example 2

The surgical instrument of Example 1, wherein the first disposable sub-assembly comprises a first inner tube and a first outer tube, wherein the first outer tube is pivotally coupled to the clamp arm, wherein the first inner tube is pivotally coupled to the clamp arm.

Example 3

The surgical instrument of Example 2, wherein the second disposable sub-assembly comprises a second inner tube having a proximal end and a distal end, wherein the second inner tube is configured to removably couple with the first inner tube at the distal end of the second inner tube.

Example 4

The surgical instrument of any one or more of Example 2 through 3, wherein the second disposable assembly comprises a knob member configured to rotate the ultrasonic waveguide about a longitudinal axis defined by the ultrasonic waveguide, wherein knob member houses a tube actuator, wherein the first outer tube is removable coupled to the tube actuator.

Example 5

The surgical instrument of Example 4, wherein the knob member defines a keyway and a rotation path, wherein the keyway and rotation path are configured to align the first disposable sub-assembly when coupled to the second sub-assembly.

Example 6

The surgical instrument of any one or more of Examples 1 through 5, wherein the second disposable sub-assembly has a counting mechanism to determine how many times the second disposable sub-assembly has been used.

Example 7

An assembly tool for use with any of the surgical instruments of Examples 1 through 6, where the assembly tool comprises a torque wrench configured to properly couple the reusable assembly with the second sub-assembly.

Example 8

The assembly tool of Example 7, wherein the assembly tool also comprises a spanner wrench configured to rotate the first sub-assembly relative to the second sub-assembly.

Example 9

The assembly tool of Example 7, wherein the assembly tool is configured to fix the first sub-assembly relative to the assembly tool.

Example 10

The assembly tool of Example 9, wherein the assembly tool comprises a base member and a top member, wherein the top member is configured to pivot relative to the base member from an open position to a closed position, wherein the assembly tool is configured to fix the first sub-assembly relative to the assembly tool when the top member is in the closed position.

Example 11

The assembly tool of Example 10, wherein the assembly tool is configured to selectively lock when the top member is in the closed position

Example 12

The assembly tool of any one or more of Examples 9 through 11, wherein the assembly tool further has a locator feature configured to fix the first disposable sub-assembly in the same position relative to the assembly tool.

Example 13

The assembly tool of Example 12, wherein the locator feature comprises a locator pin.

Example 14

The assembly tool of Example 13, wherein the locator pin is biased to a first position, wherein the locator pin is configured to translate from the first position to the a second position in response to the top member pivoting from the open position to the closed position.

Example 15

The assembly tool of any one or more of Example 9 through 14, wherein the first inner tube comprises a first alignment hole, wherein the first outer tube each comprises a second alignment hole, wherein the locator pin is configured to insert through the first alignment hole and the second alignment hole.

Example 16

The assembly tool of Example 15, wherein the locator pin and the first inner tube define a gap configured to receive the ultrasonic waveguide when the locator pin is in the second position.

Example 17

The assembly tool of any one or more of Example 9 through 16, wherein the assembly tool comprises a tubular surface configured to conform to at least a portion of first outer tube.

Example 18

The assembly tool of any one or more of Example 9 through 16, wherein the assembly tool is pivotable via a living hinge.

Example 19

The surgical instrument of Example 6, wherein the second disposable sub-assembly further comprises an indicator, wherein the indicator is configured to show whether the second disposable sub-assembly has been used a predetermined number of times.

Example 20

The surgical instrument of Example 19, wherein the indicator is activated by a button.

Example 21

An apparatus, comprising: (a) a body; (b) a shaft assembly, wherein the shaft assembly comprises: (i) an outer tube, (ii) a proximal inner tube member, (iii) a distal inner tube member, and (iv) an acoustic waveguide; and (c) an end effector, wherein the end effector comprises: (i) an ultrasonic blade acoustically coupled with the acoustic waveguide, and (ii) a clamp arm, wherein a first portion of the clamp arm is pivotably coupled with a distal end of the outer tube, wherein a second portion of the clamp arm is pivotably coupled with a distal end of the distal inner tube member; wherein the outer tube is configured to removably couple with the body and the distal inner tube member is configured to removably couple with the proximal inner tube member such that the outer tube, the distal inner tube member, and the clamp arm are configured to removably couple with the body and the remainder of the shaft assembly and end effector as a unit.

Example 22

The apparatus of Example 21, wherein the distal inner tube member comprises a resilient latch feature configured to removably secure the distal inner tube member to the proximal inner tube member.

Example 23

The apparatus of Example 22, wherein the outer tube includes a lateral opening configured to accommodate outward deflection of the resilient latch feature.

Example 24

The apparatus of any one or more of Examples 21 through 23, wherein the distal inner tube member is configured to removably couple with the proximal inner tube member via a snap fitting.

Example 25

The apparatus of any one or more of Examples 21 through 24, wherein the body and the shaft assembly further comprise complementary guide features, wherein the guide features are configured to guide angular positioning of the clamp arm relative to the ultrasonic blade about a longitudinal axis defined by the shaft assembly.

Example 26

The apparatus of Example 25, wherein the guide features comprise a bayonet slot.

Example 27

The apparatus of Example 26, wherein the bayonet slot is formed in a proximal end of the outer tube.

Example 28

The apparatus of Example 26, wherein the body comprises a coupling member, wherein the bayonet slot is formed in the coupling member.

Example 29

The apparatus of any one or more of Examples 21 through 28, wherein the body includes a coupling member, wherein a proximal end of the outer tube is configured to removably couple with the coupling member of the body.

Example 30

The apparatus of Example 29, wherein the coupling member of the body is configured to provide a snap fit with the proximal end of the outer tube.

Example 31

The apparatus of any one or more of Examples 29 through 30, wherein the proximal end of the outer tube comprises a coupling member, wherein the coupling member of the outer tube is configured to engage the coupling member of the body to thereby secure the proximal end of the outer tube to the body.

Example 32

The apparatus of Example 31, wherein the coupling member of the outer tube and the coupling member of the body comprise complementary detent features, wherein the detent features are configured to removably secure the proximal end of the outer tube to the body.

Example 33

The apparatus of any one or more of Examples 21 through 32, wherein the body comprises a handle assembly.

Example 34

The apparatus of Example 33, wherein the handle assembly comprises a knob, wherein the knob is operable to rotate the shaft assembly and the end effector about a longitudinal axis defined by the shaft assembly.

Example 35

The apparatus of Example 34, wherein the knob defines a guide channel, the shaft assembly further comprises a guide tab, wherein the guide channel and the guide tab are configured to restrict insertion of a proximal end of the outer tube into the body based on an angular orientation of the outer tube about the longitudinal axis.

Example 36

The apparatus of any one or more of Examples 21 through 35, wherein the proximal inner tube member and the acoustic waveguide are secured to the body such that the proximal inner tube member and the acoustic waveguide are prevented from translating longitudinally relative to the body.

Example 37

An apparatus, comprising: (a) a body; (b) a shaft assembly, wherein the shaft assembly comprises: (i) an outer tube, wherein the entire outer tube is configured to be removably coupled with the body, (ii) a proximal inner tube member, wherein the proximal inner tube member is integral with the body, (iii) a distal inner tube member, wherein the distal inner tube member is configured to be removably coupled with the proximal inner tube member, and (iv) an acoustic waveguide, wherein the acoustic waveguide is integral with the body; and (c) an end effector, wherein the end effector comprises: (i) an ultrasonic blade acoustically coupled with the acoustic waveguide, and (ii) a clamp arm, wherein a first portion of the clamp arm is pivotably coupled with a distal end of the outer tube, wherein a second portion of the clamp arm is pivotably coupled with a distal end of the distal inner tube member.

Example 38

The apparatus of Example 37, wherein the outer tube, the distal inner tube member, and the clamp arm are configured to removably couple with the body and the remainder of the shaft assembly and end effector as a unit.

Example 39

A method of assembling a surgical instrument, the method comprising: (a) grasping a first sub-assembly, wherein the first sub-assembly comprises: (i) an outer tube, (ii) a distal inner tube portion, and (iii) a clamp arm, wherein the clamp arm is pivotably coupled with the outer tube, wherein the clamp arm is further pivotably coupled with the distal inner tube portion; (b) grasping a second sub-assembly, wherein the second sub-assembly comprises: (i) a body, (ii) an acoustic waveguide extending distally from the body, (iii) a proximal inner tube portion extending distally from the body, and (iv) an ultrasonic blade positioned at a distal end of the acoustic waveguide; and (c) moving the first sub-assembly relative to the second sub-assembly, thereby securing the outer tube to the body, and thereby securing the distal inner tube portion to the proximal inner tube portion.

Example 40

The method of Example 39, wherein the act of moving the first sub-assembly proximally relative to the second sub-assembly comprises: (i) moving the first sub-assembly proximally relative to the second sub-assembly, and (ii) rotating the first sub-assembly relative to the second sub-assembly.

VII. MISCELLANEOUS

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071; U.S. Pub. No. 2011/0015660, issued as U.S. Pat. No. 8,461,744 on Jun. 11, 2013; U.S. Pub. No. 2012/0112687, issued as U.S. Pat. No. 9,381,058; U.S. Pub. No. 2012/0116265, now abandoned; U.S. Pub. No. 2014/0005701, issued as U.S. Pat. No. 9,393,037; U.S. Pub. No. 2015/0080924, issued as U.S. Pat. No. 10,172,636; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument comprising:
   (a) a first subassembly comprising:
      (i) an ultrasonic waveguide,
      (ii) an ultrasonic blade in acoustic communication with the ultrasonic waveguide,
      (iii) a proximal inner tube disposed about a proximal portion of the ultrasonic waveguide, and
      (iv) a proximal outer tube disposed about the proximal inner tube;
   (b) a second subassembly, the second subassembly comprising:
      (i) a clamp arm,
      (ii) a distal inner tube, wherein the clamp arm is pivotably coupled with the distal inner tube, and
      (iii) a distal outer tube, wherein the distal outer tube and the distal inner tube are slidably attached to each other, wherein the clamp arm is pivotably coupled with the distal outer tube; and
   (c) a snap-fit coupling assembly comprising a resilient feature associated with the second subassembly and a second feature associated with the first subassembly configured to deform the resilient feature;
   wherein the second subassembly is configured to couple and decouple with the first subassembly via the snap-fit coupling assembly such that the clamp arm and the ultrasonic blade form an end effector with the first subassembly coupled with the second subassembly, and wherein the clamp arm is configured to pivot relative to the ultrasonic blade with the second subassembly coupled with the first subassembly.

2. The ultrasonic surgical instrument of claim 1, wherein the distal inner tube is rotationally constrained relative to the distal outer tube about a longitudinal axis.

3. The ultrasonic surgical instrument of claim 2, wherein the distal outer tube comprises a pair of crimps, wherein the distal inner tube defines a pair a slots, wherein the distal outer tube and the distal inner tube are slidably attached via the pair of crimps and the pair of slots.

4. The ultrasonic surgical instrument of claim 1, wherein the distal inner tube is pivotably coupled with the clamp arm via a pin.

5. The ultrasonic surgical instrument of claim 1, wherein the proximal inner tube extends distally past the proximal outer tube.

6. The ultrasonic surgical instrument of claim 5, wherein the proximal inner tube is configured to couple with the distal inner tube with the second subassembly coupled with the first subassembly.

7. The ultrasonic surgical instrument of claim 6, wherein the proximal inner tube comprises a projecting stud configured to selectively couple with the distal inner tube.

8. The ultrasonic surgical instrument of claim 7, wherein the distal inner tube comprises a resilient proximal tab defining a stud hole, wherein the stud hole is dimensioned to selectively receive the projecting stud.

9. The ultrasonic surgical instrument of claim 8, wherein the distal inner tube further defines an entry channel dimensioned to receive the stud hole as the first subassembly and the second subassembly couple together.

10. The ultrasonic surgical instrument of claim 5, wherein the proximal outer tube is configured to couple with the distal outer tube with the second subassembly coupled to the first subassembly.

11. The ultrasonic surgical instrument of claim 10, wherein the proximal outer tube defines a locking channel configured to selectively couple with the distal outer tube.

12. The ultrasonic surgical instrument of claim 11, wherein the proximal outer tube has an outer surface, and wherein the locking channel is circumferentially disposed on the outer surface of the proximal outer tube.

13. The ultrasonic surgical instrument of claim 12, wherein the distal outer tube comprises a resilient proximal tab dimensioned to fit within the locking channel to couple the proximal outer tube and the distal outer tube.

14. The ultrasonic surgical instrument of claim 13, wherein the resilient proximal tab comprises a circumferential portion and an inwardly presented portion.

15. The ultrasonic surgical instrument of claim 14, wherein the resilient proximal tab defines a first channel and a second channel.

16. The ultrasonic surgical instrument of claim 15, wherein the proximal outer tube comprises a protrusion, wherein the protrusion is configured to fit within the second channel with the second subassembly coupled to the first subassembly.

17. The ultrasonic surgical instrument of claim 1, wherein the first subassembly further comprises a handle.

18. The ultrasonic surgical instrument of claim 17, wherein the handle comprises a pivot trigger configured to pivot the clamp arm relative to the ultrasonic blade with the second subassembly coupled to the first subassembly.

19. An ultrasonic surgical instrument comprising:
(a) a first subassembly comprising:
  (i) an ultrasonic waveguide,
  (ii) an ultrasonic blade in acoustic communication with the ultrasonic waveguide,
  (iii) a proximal inner tube disposed about a proximal portion of the ultrasonic waveguide,
  (iv) a proximal outer tube disposed about the proximal inner tube, and
  (v) a first coupling feature fixed relative to either the proximal inner tube or the proximal outer tube; and
(b) a second subassembly configured to removably attach with the first subassembly, the second subassembly comprising:
  (i) a clamp arm,
  (ii) a distal inner tube dimensioned to house at least a portion of the ultrasonic blade and at least a portion of the ultrasonic waveguide, wherein the clamp arm is pivotably coupled with the distal inner tube,
  (iii) a distal outer tube, wherein the distal outer tube and the distal inner tube are slidably attached to each other, wherein the clamp arm is pivotably coupled with the distal outer tube, and
  (iv) a resilient coupling feature attached to either the distal inner tube or the distal outer tube, wherein the resilient coupling feature is configured to deform in order to couple with the first coupling feature to thereby removably attach the second subassembly with the first subassembly.

20. A method of assembling an ultrasonic surgical instrument having a first subassembly and a second subassembly, wherein the first subassembly includes an ultrasonic waveguide, an ultrasonic blade in acoustic communication with the ultrasonic waveguide, a cam surface, a proximal inner tube disposed about a proximal portion of the ultrasonic waveguide, and a proximal outer tube disposed about the proximal inner tube, wherein the second subassembly includes a distal inner tube, a clamp arm is pivotably coupled with the distal inner tube, a snap-fit feature, and a distal outer tube slidably attached to the distal inner tube, wherein the clamp arm is pivotably coupled with the distal outer tube, the method comprising:
(a) grasping the first subassembly;
(b) grasping the second subassembly;
(c) aligning the second subassembly with the first subassembly;
(d) deforming the snap-fit feature against the cam surface;
(e) securing the distal inner tube with the proximal inner tube; and
(f) securing the distal outer tube with the proximal outer tube.

* * * * *